(12) United States Patent
Huang et al.

(10) Patent No.: US 6,596,772 B1
(45) Date of Patent: Jul. 22, 2003

(54) PHOSPHATE MIMICS AND METHODS OF TREATMENT USING PHOSPHATASE INHIBITORS

(75) Inventors: Ping Huang, Mountain View, CA (US); Chung Chen Wei, Foster City, CA (US); Peng Cho Tang, Moraga, CA (US); Chris Liang, Sunnyvale, CA (US); John Ramphal, Union City, CA (US); Bahija Jallal, Menlo Park, CA (US); John Biltz, Newark, CA (US); Sharon Li, Los Altos, CA (US); Matt Mattson, Santa Clara, CA (US); Gerald McMahon, Kenwood, CA (US); Marcel Koenig, Burlingame, CA (US)

(73) Assignee: Sugen, Inc., South San Francisco, CA (US)

( * ) Notice: Subject to any disclaimer, the term of this patent is extended or adjusted under 35 U.S.C. 154(b) by 0 days.

(21) Appl. No.: 09/645,879

(22) Filed: Aug. 25, 2000

Related U.S. Application Data

(60) Provisional application No. 60/150,970, filed on Aug. 27, 1999, and provisional application No. 60/165,365, filed on Nov. 12, 1999.

(51) Int. Cl.[7] ............... A61K 31/05; C07D 265/35; C07D 295/03; C07C 323/00; C07C 303/00
(52) U.S. Cl. ............... 514/602; 514/613; 514/715; 514/730; 544/106; 544/162; 544/170; 564/80; 564/84; 564/100; 564/123; 564/430; 568/21; 568/38; 568/579; 568/608
(58) Field of Search ............... 514/602, 613, 514/715, 730; 568/21, 38, 579, 608, 927, 939; 564/80, 84, 100–123, 430; 544/106, 162, 170

(56) References Cited

U.S. PATENT DOCUMENTS 5,710,173 A    1/1998   Tang et al. ............... 514/447

FOREIGN PATENT DOCUMENTS

| BE | 758241 | * | 4/1971 |
| WO | 9586376 | * | 12/1998 |
| WO | 9856376 | * | 12/1998 |
| WO | 98/56376 |   | 12/1998 |

OTHER PUBLICATIONS

Zhmurova et al;"Zh.OBshch.Khim., 37/8, 1879–83 (1967)"; Phosphazothiole.*
Levchenko et al;"Zh.Org.Khim. 14/9, 1846–51 (1978);"Reaction of disulfides with N,N–dichloroamines.*
PubMed Abstr. 12110500; Lee JU et al,Eur.J.Cancer,"Antiproliferative activ . . . ", 38/11, 1526–34(2002).*
PubMed Abstr. 12049842; Tseng et al,Toxicology,"Microtubule damaging agts . . . ", 175/1–3, 123–42(2002).*
PUbMed Abstr. 12028501;Ukkola et al,J. Intern Med.,"Protein Tyrosine phosphatase . . . ",251/6,467(2002).*
PubMed Abstr. 12134145;Xu et al,Nat Immuno,"Negative regulation of CD 45 . . . ",3/8,764–71(2002).*
PubMed Abstr. 12047178;Jenkind et al,JACS,"Solid–phase synthesis and biochemical studies . . . ", 124/23, 6584–93(2002).*

* cited by examiner

Primary Examiner—Richard L. Raymond
Assistant Examiner—Sudhaker B. Patel
(74) Attorney, Agent, or Firm—Beth A. Burrous; Foley & Lardner

(57) ABSTRACT

The invention relates to trifluoromethyl sulfonyl and trifluoromethyl sulfonamido compounds and the physiologically acceptable salts and the prodrugs thereof. These compounds are expected to modulate the activity of protein tyrosine enzymes which are related to cellular signal transduction, in particular, protein tyrosine phosphatase, and therefore are expected to be useful in the prevention and treatment of disorders associated with abnormal protein tyrosine enzyme related cellular signal transduction such as cancer, diabetes, immuno-modulation, neurologic degenerative diseases, osteoporosis and infectious diseases. The invention also relates to the use of compounds containing fluoromethyl sulfonyl groups as phosphate mimics. These mimics may be used to inhibit, regulate or modulate the activity of a phosphate binding protein in a cell.

20 Claims, 14 Drawing Sheets

Figure 1. Exemplary compounds of the invention.

| EX. | STRUCTURE | NAME |
|---|---|---|
| 1 | 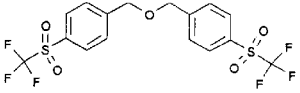 | Bis(4-Trifluoromethylsulfonylbenzyl) ether |
| 2 | 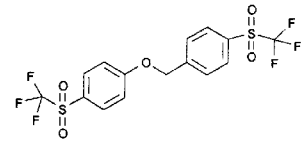 | 4-Trifluoromethylsulfonylbenzyl 4-trifluoromethylsulfonylphenyl ether |
| 3 | 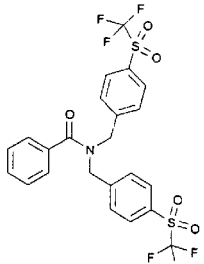 | N,N-Bis(4-trifluoromethylsulfonylbenzyl)benzamide |
| 4 | 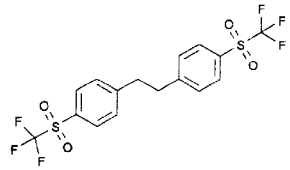 | 1,2-Bis(4-trifluoromethylsulfonylphenyl)ethane |
| 5 | 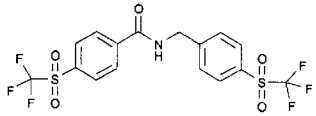 | N-(4-Trifluoromethylsulfonylbenzyl)-4-trifluoromethylsulfonylbenzamide |
| 6 | 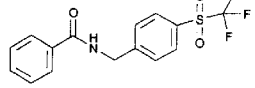 | N-(4-Trifluoromethylsulfonylbenzyl)benzamide |
| 7 | 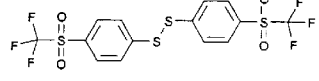 | Bis(4-Trifluoromethylsulfonylphenyl) disulfide |
| 8 | 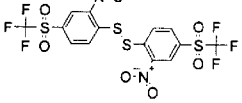 | Bis-(2-Nitro-4-trifluoromethylsulfonylphenyl) disulfide |

FIG. 1-A

| EX. | STRUCTURE | NAME |
|---|---|---|
| 8 | 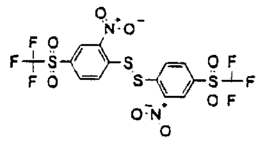 | Bis-(2-Nitro-4-trifluoromethylsulfonylphenyl) disulfide |
| 9 | 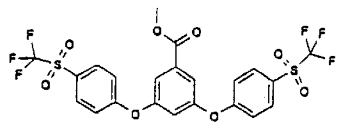 | 3,5-Bis-(4-trifluoromethanesulfonyl-phenoxy)-benzoic acid methyl ester |
| 10 | 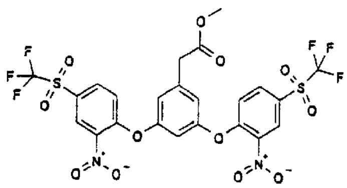 | [3,5-Bis-(2-nitro-4-trifluoromethanesulfonyl-phenoxy)-phenyl]-acetic acid methyl ester |
| 11 | 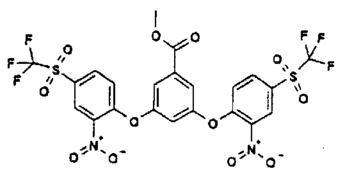 | 3,5-Bis-(2-nitro-4-trifluoromethanesulfonyl-phenoxy)-benzoic acid methyl ester |
| 12 | 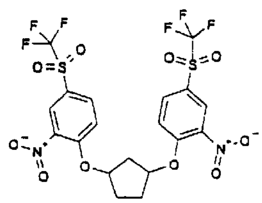 | 1,3-Bis-(2-nitro-4-trifluoromethanesulfonyl-phenoxy)-cyclopentane |
| 13 | 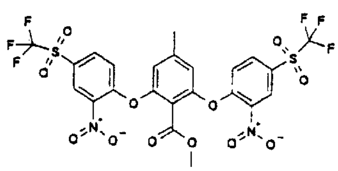 | 4-Methyl-2,6-bis-(2-nitro-4-trifluoromethanesulfonyl-phenoxy)-benzoic acid methyl ester |
| 14 | 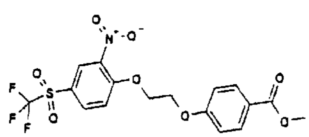 | 4-[2-(2-Nitro-4-trifluoromethanesulfonyl-phenoxy) ethoxy]-benzoic acid methyl ester |
| 15 | 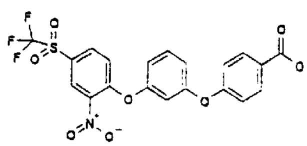 | 4-[3-(2-Nitro-4-trifluoromethanesulfonyl-phenoxy) phenoxy]-benzoic acid |

FIG. 1-B

| EX. | STRUCTURE | NAME |
|---|---|---|
| 16 | 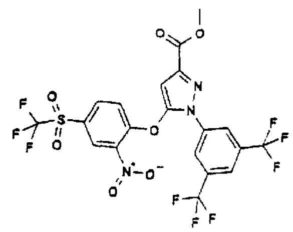 | 1-(3,5-Bis-trifluoromethyl-phenyl)-5-(2-nitro-4-trifluoromethanesulfonyl-phenoxy)-1H-pyrazole-3-carboxylic acid methyl ester |
| 17 | 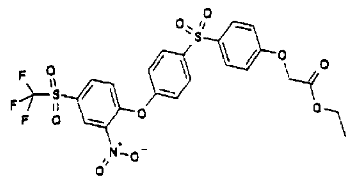 | {4-[4-(2-Nitro-4-trifluoromethanesulfonyl-phenoxy)-benzenesulfonyl]-phenoxy}-acetic acid ethyl ester |
| 18 | 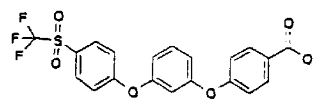 | 4-[3-(4-Trifluoromethanesulfonyl-phenoxy)-phenoxy]-benzoic acid |
| 19 | 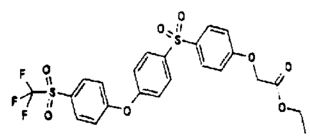 | {4-[4-(4-Trifluoromethanesulfonyl-phenoxy)-benzenesulfonyl]-phenoxy}-acetic acid ethyl ester |
| 20 | 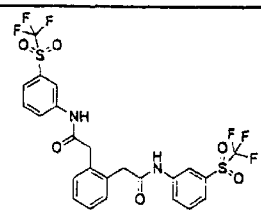 | N-(3-Trifluoromethanesulfonyl-phenyl)-2-{2-[(3-trifluoromethanesulfonyl-phenylcarbamoyl)-methyl]-phenyl}-acetamide |
| 21 | 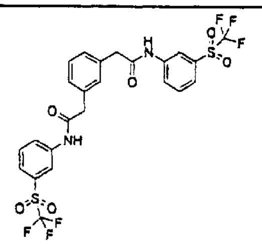 | N-(3-Trifluoromethanesulfonyl-phenyl)-2-{3-[(3-trifluoromethanesulfonyl-phenylcarbamoyl)-methyl]-phenyl}-acetamide |
| 22 | 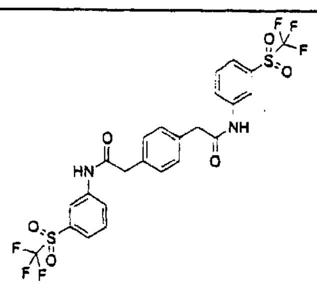 | N-(3-Trifluoromethanesulfonyl-phenyl)-2-{4-[(3-trifluoromethanesulfonyl-phenylcarbamoyl)-methyl]-phenyl}-acetamide |

FIG. 1-C

| EX. | STRUCTURE | NAME |
|---|---|---|
| 23 | 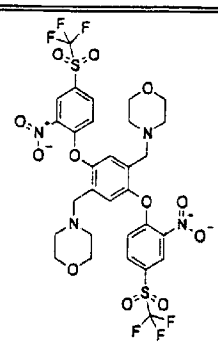 | 3,6-Bis-(morpholin-4-ylmethyl)-2,5-bis-(2-nitro-4-trifluoromethanesulfonyl-phenoxy)-benzene |
| 24 | 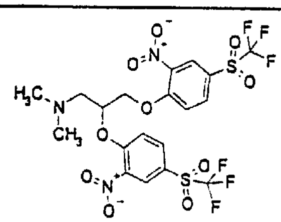 | [2,3-Bis-(2-nitro-4-trifluoromethanesulfonyl-phenoxy)-propyl]-dimethyl-amine |
| 25 | 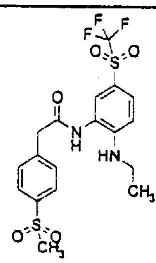 | N-(2-Ethylamino-5-trifluoromethanesulfonyl-phenyl)-2-(4-methanesulfonyl-phenyl)-acetamide |
| 26 | 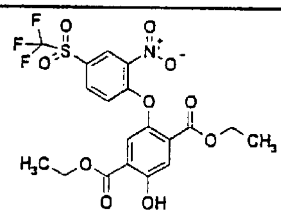 | 2-Hydroxy-5-(2-nitro-4-trifluoromethanesulfonyl-phenoxy)-terephthalic acid diethyl ester |
| 27 | 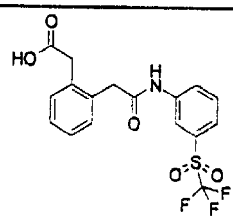 | {2-[(3-Trifluoromethanesulfonyl-phenylcarbamoyl)methyl]-phenyl}-acetic acid |
| 28 | 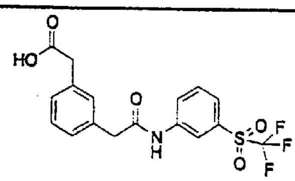 | {3-[(3-Trifluoromethanesulfonyl-phenylcarbamoyl)methyl]-phenyl}-acetic acid |

FIG. 1-D

| EX. | STRUCTURE | NAME |
|---|---|---|
| 29 | 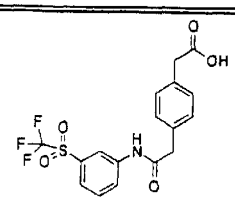 | {4-[(3-Trifluoromethanesulfonyl-phenylcarbamoyl) methyl]-phenyl}-acetic acid |
| 30 | 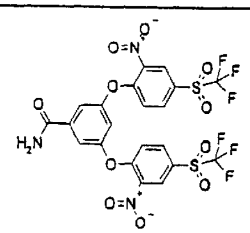 | 3,5-Bis-(2-nitro-4-trifluoromethanesulfonyl-phenoxy)-benzamide |
| 31 | 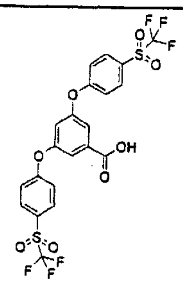 | 3,5-Bis-(4-trifluoromethanesulfonyl-phenoxy)-benzoic acid |
| 32 | 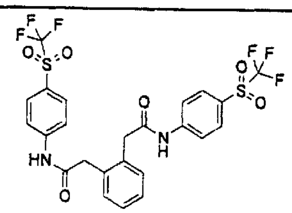 | N-(4-Trifluoromethanesulfonyl-phenyl)-2-{2-[(4-trifluoromethanesulfonyl-phenylcarbamoyl)-methyl]-phenyl}-acetamide |
| 33 | 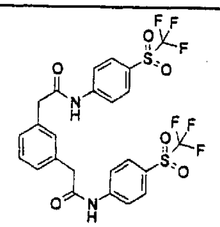 | N-(4-Trifluoromethanesulfonyl-phenyl)-2-{3-[(4-trifluoromethanesulfonyl-phenylcarbamoyl)-methyl]-phenyl}-acetamide |
| 34 | 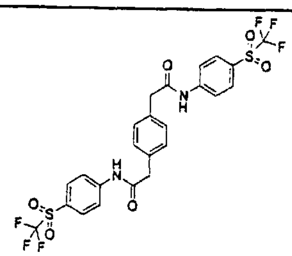 | N-(4-Trifluoromethanesulfonyl-phenyl)-2-{4-[(4-trifluoromethanesulfonyl-phenylcarbamoyl)-methyl]-phenyl}-acetamide |

FIG. 1-E

| EX. | STRUCTURE | NAME |
|---|---|---|
| 35 | 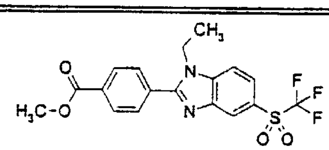 | 4-(1-Ethyl-5-trifluoromethanesulfonyl-1H-benzoimidazol-2-yl)-benzoic acid methyl ester |
| 36 | 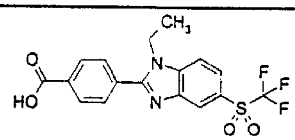 | 4-(1-Ethyl-5-trifluoromethanesulfonyl-1H-benzoimidazol-2-yl)-benzoic acid |
| 37 | 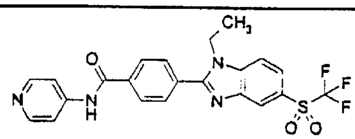 | 4-(1-Ethyl-5-trifluoromethanesulfonyl-1H-benzoimidazol-2-yl)-N-pyridin-4-yl-benzamide |
| 38 | 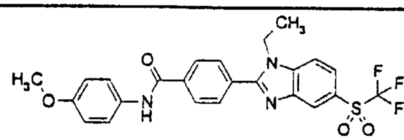 | 4-(1-Ethyl-5-trifluoromethanesulfonyl-1H-benzoimidazol-2-yl)-N-(4-methoxy-phenyl)-benzamide |
| 39 | 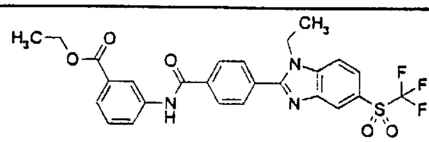 | 3-[4-(1-Ethyl-5-trifluoromethanesulfonyl-1H-benzoimidazol-2-yl)-benzoylamino]-benzoic acid ethyl ester |
| 40 | 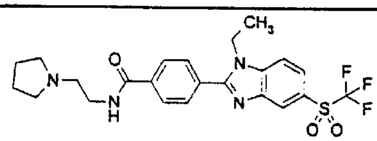 | 4-(1-Ethyl-5-trifluoromethanesulfonyl-1H-benzoimidazol-2-yl)-N-(2-pyrrolidin-1-yl-ethyl)-benzamide |
| 41 | 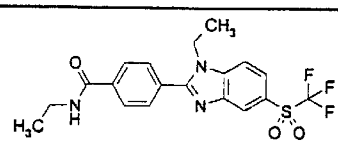 | N-Ethyl-4-(1-ethyl-5-trifluoromethanesulfonyl-1H-benzoimidazol-2-yl)-benzamide |
| 42 | 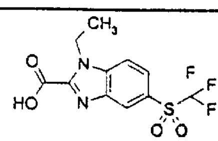 | 1-Ethyl-5-trifluoromethanesulfonyl-1H-benzoimidazole-2-carboxylic acid |
| 43 | 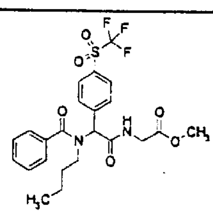 | [2-(Benzoyl-butyl-amino)-2-(4-trifluoromethanesulfonyl-phenyl)-acetylamino]-acetic acid methyl ester |

FIG. 1-F

| EX. | STRUCTURE | NAME |
|---|---|---|
| 44 | 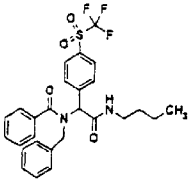 | N-Benzyl-N-[butylcarbamoyl-(4-trifluoromethanesulfonyl-phenyl)-methyl]-benzamide |
| 45 | 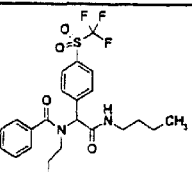 | N-[Butylcarbamoyl-(4-trifluoromethanesulfonyl-phenyl)-methyl]-N-(2-hydroxy-ethyl)-benzamide |
| 46 | 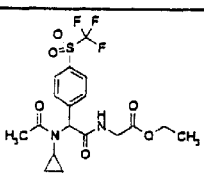 | [2-(Acetyl-cyclopropyl-amino)-2-(4-trifluoromethanesulfonyl-phenyl)-acetylamino]-acetic acid ethyl ester |
| 47 | 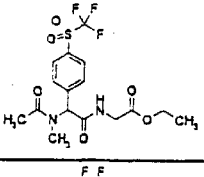 | [2-(Acetyl-methyl-amino)-2-(4-trifluoromethanesulfonyl-phenyl)-acetylamino]-acetic acid ethyl ester |
| 48 | 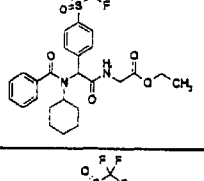 | [2-(Benzoyl-cyclohexyl-amino)-2-(4-trifluoromethanesulfonyl-phenyl)-acetylamino]-acetic acid ethyl ester |
| 49 | 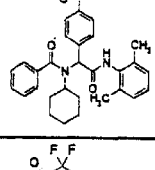 | N-Cyclohexyl-N-[(2,6-dimethyl-phenylcarbamoyl)(4-trifluoromethanesulfonyl-phenyl)-methyl]-benzamide |
| 50 | 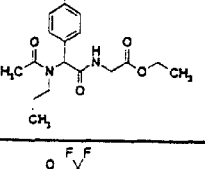 | [2-(Acetyl-propyl-amino)-2-(4-trifluoromethanesulfonyl-phenyl)-acetylamino]-acetic acid ethyl ester |
| 51 | 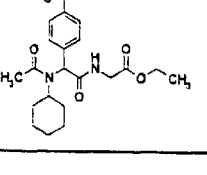 | [2-(Acetyl-cyclohexyl-amino)-2-(4-trifluoromethanesulfonyl-phenyl)-acetylamino]-acetic acid ethyl ester |

FIG. 1-G

| EX. | STRUCTURE | NAME |
|---|---|---|
| 52 | 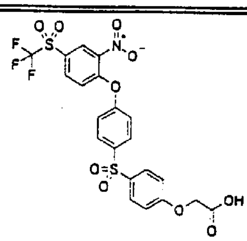 | {4-[4-(2-Nitro-4-trifluoromethanesulfonyl-phenoxy)-benzenesulfonyl]-phenoxy}-acetic acid |
| 53 | 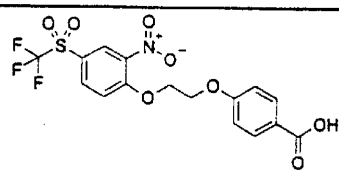 | 4-[2-(2-Nitro-4-trifluoromethanesulfonyl-phenoxy)ethoxy]-benzoic acid |
| 54 | 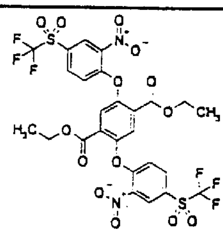 | 2,5-Bis-(2-nitro-4-trifluoromethanesulfonyl-phenoxy)-terephthalic acid diethyl ester |
| 55 | 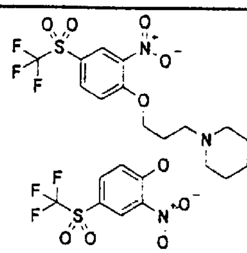 | 1-[2,3-Bis-(2-nitro-4-trifluoromethanesulfonyl-phenoxy)-propyl]-piperidine |
| 56 | 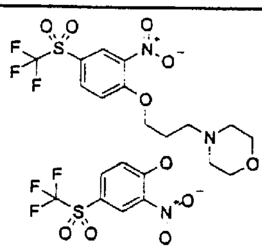 | 4-[2,3-Bis-(2-nitro-4-trifluoromethanesulfonyl-phenoxy)-propyl]-morpholine |
| 57 | 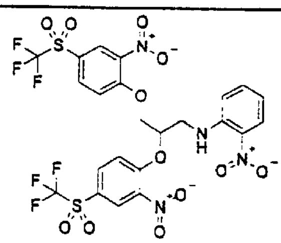 | [2,3-Bis-(2-nitro-4-trifluoromethanesulfonyl-phenoxy)-propyl]-(2-nitro-phenyl)-amine |

FIG. 1-H

| EX. | STRUCTURE | NAME |
|---|---|---|
| 58 | 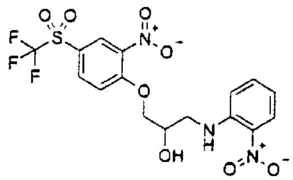 | 1-(2-Nitro-phenylamino)-3-(2-nitro-4-trifluoromethanesulfonyl-phenoxy)-propan-2-ol |
| 59 | 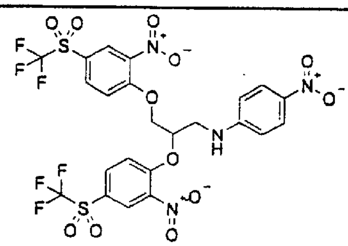 | [2,3-Bis-(2-nitro-4-trifluoromethanesulfonyl-phenoxy)-propyl]-(4-nitro-phenyl)-amine |
| 60 | 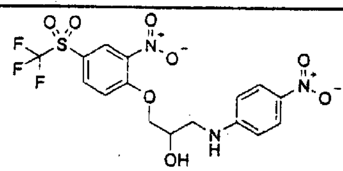 | 1-(4-Nitro-phenylamino)-3-(2-nitro-4-trifluoromethanesulfonyl-phenoxy)-propan-2-ol |
| 61 | 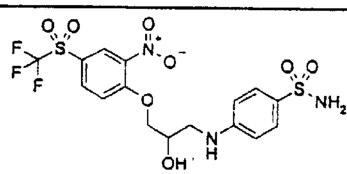 | 4-[2-Hydroxy-3-(2-nitro-4-trifluoromethanesulfonyl-phenoxy)-propylamino]-benzenesulfonamide |
| 62 | 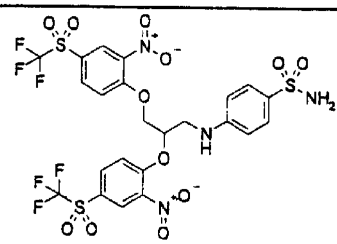 | 4-[2,3-Bis-(2-nitro-4-trifluoromethanesulfonyl-phenoxy)-propylamino]-benzenesulfonamide |
| 63 | 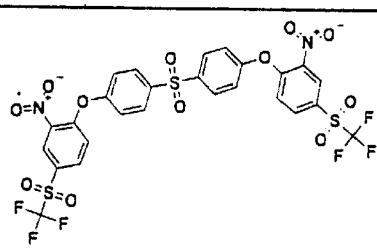 | Bis-{[4-(2-nitro-4-trifluoromethanesulfonyl)-phenoxy]-phenyl}sulfone |
| 64 | 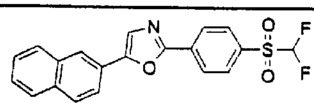 | 2-[4-(Difluoro-methanesulfonyl)-phenyl]-5-naphthalen-2-yl-oxazole |

FIG. 1-I

| EX. | STRUCTURE | NAME |
|---|---|---|
| 65 | 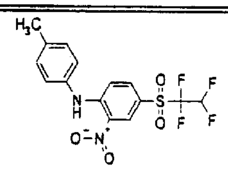 | [2-Nitro-4-(1,1,2,2-tetrafluoro-ethanesulfonyl)-phenyl]-*p*-tolyl-amine |
| 66 | 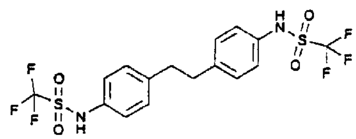 | 1,2-Bis(4-trifluoromethylsulfonamidophenyl)ethane |
| 67 | 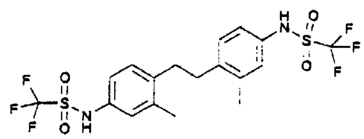 | 1,2-Bis(2-methyl-4-trifluoromethylsulfonamidophenyl)ethane |
| 68 | 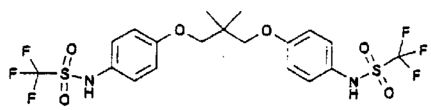 | 1,3-Bis(4-trifluoromethylsulfonamidophenoxy)-2,2 dimethylpropane |
| 69 | 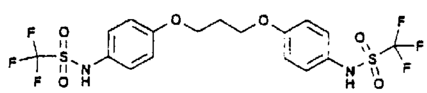 | 1,3-Bis(4-trifluoromethylsulfonamidophenoxy)propane |
| 70 | 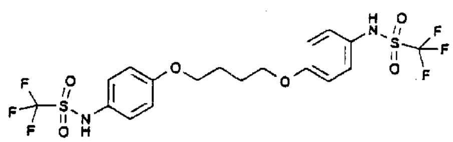 | 1,4-Bis(4-trifluoromethylsulfonamidophenoxy)butane |
| 71 | 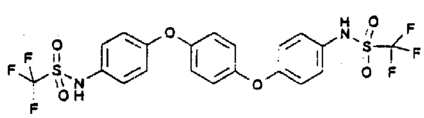 | 1,4-Bis(4-trifluoromethylsulfonamidophenoxy)benzene |
| 72 | 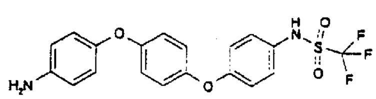 | 1-(4-Aminophenoxy)-4-trifluoromethylsulfonamidophenoxy benzene |
| 73 | 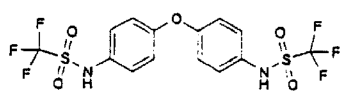 | Bis(4-trifluoromethylsulfonamidophenyl) ether |

FIG. 1-J

| EX. | STRUCTURE | NAME |
|---|---|---|
| 74 | 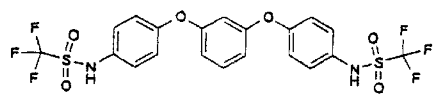 | 1,3-Bis(4-trifluoromethylsulfonamidophenoxy)benzene |
| 75 | 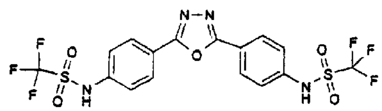 | 2,5-Bis(4-trifluoromethylsulfonamidophenyl)-(1,3,4)oxadiazole |
| 76 | 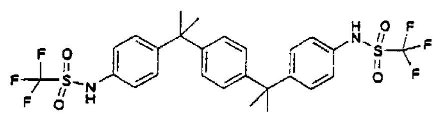 | Bis(4-trifluoromethylsulfonamidophenyl)-1,4-diisopropylbenzene |
| 77 | 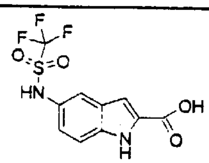 | 5-Trifluoromethanesulfonylamino-1*H*-indole-2-carboxylic acid |
| 78 | 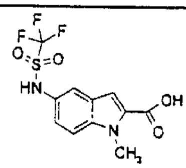 | 1-Methyl-5-trifluoromethanesulfonylamino-1*H*-indole-2-carboxylic acid |
| 79 | 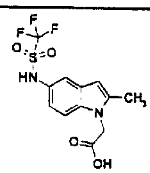 | (2-Methyl-5-trifluoromethanesulfonylamino-indol-1-yl)-acetic acid |
| 80 | 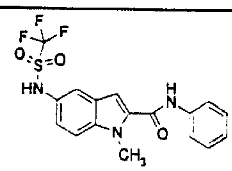 | 1-Methyl-5-trifluoromethanesulfonylamino-1*H*-indole-2-carboxylic acid phenylamide |
| 81 | 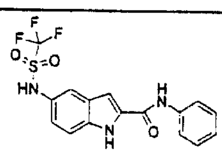 | 5-Trifluoromethanesulfonylamino-1H-indole-2-carboxylic acid phenylamide |
| 82 | 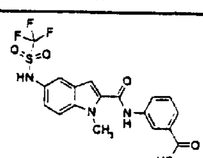 | 3-[(1-Methyl-5-trifluoromethanesulfonylamino-1*H*-indole-2-carbonyl)-amino]-benzoic acid |

FIG. 1-K

| EX. | STRUCTURE | NAME |
|---|---|---|
| 83 | 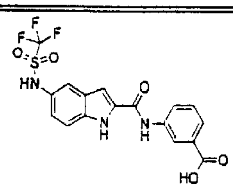 | 3-[(5-Trifluoromethanesulfonylamino-1*H*-indole-2 carbonyl)-amino]-benzoic acid |
| 84 | 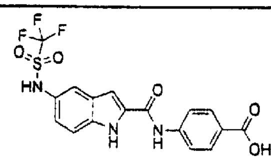 | 4-[(5-Trifluoromethanesulfonylamino-1*H*-indole-2 carbonyl)-amino]-benzoic acid |
| 85 | 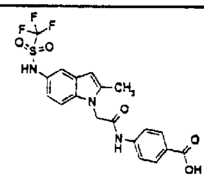 | 4-[2-(2-Methyl-5-trifluoromethanesulfonylamino-indol-1-yl)-acetylamino]-benzoic acid |
| 86 | 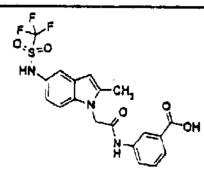 | 3-[2-(2-Methyl-5-trifluoromethanesulfonylamino-indol-1-yl)-acetylamino]-benzoic acid |
| 87 | 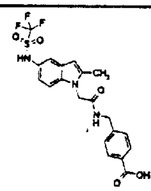 | 4-{[2-(2-Methyl-5-trifluoromethanesulfonylamino-indol-1-yl)-acetylamino]-methyl}-benzoic acid |
| 88 | 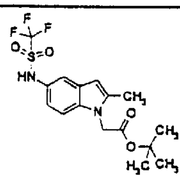 | (2-Methyl-5-trifluoromethanesulfonylamino-indol-1-yl)-acetic acid *tert*-butyl ester |
| 89 | 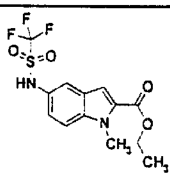 | 1-Methyl-5-trifluoromethanesulfonylamino-1*H*-indole-2-carboxylic acid ethyl ester |
| 90 | 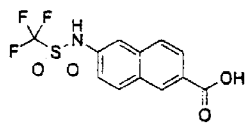 | 6-Trifluoromethanesulfonylamino-naphthalene-2-carboxylic acid |

FIG. 1-L

| EX. | STRUCTURE | NAME |
|---|---|---|
| 91 | 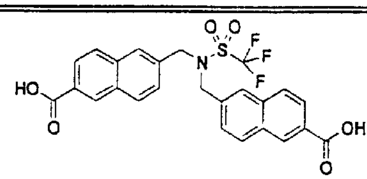 | N,N-Bis[(6-carboxyl-naphthalen-2-yl)methyl]trifluoromethanesulfonamide |
| 92 | 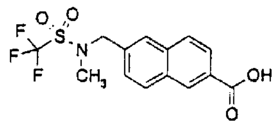 | 6-[(Methyl-trifluoromethanesulfonyl-amino)-methyl]-naphthalene-2-carboxylic acid |
| 93 | 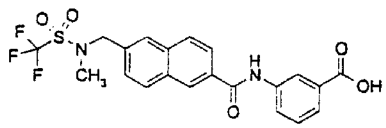 | 3-({6-[(Methyl-trifluoromethanesulfonyl-amino)-methyl]-naphthalene-2-carbonyl}-amino)-benzoic acid |
| 94 | 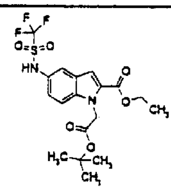 | 1-tert-Butoxycarbonylmethyl-5-trifluoromethanesulfonylamino-1H-indole-2-carboxylic acid ethyl ester |
| 95 | 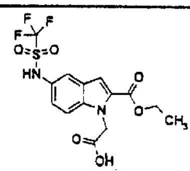 | 1-Carboxymethyl-5-trifluoromethanesulfonylamino-1H-indole-2-carboxylic acid ethyl ester |
| 96 | 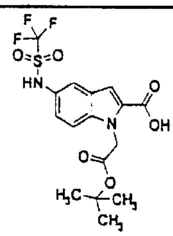 | 1-tert-Butoxycarbonylmethyl-5-trifluoromethanesulfonylamino-1H-indole-2-carboxylic acid |
| 97 | 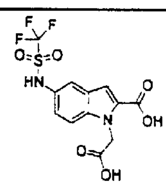 | 1-Carboxymethyl-5-trifluoromethanesulfonylamino-1H-indole-2-carboxylic acid |
| 98 | 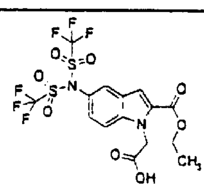 | 1-Carboxymethyl-5-(N,N-ditrifluoromethanesulfonyl)amino-1H-indole-2-carboxylic acid ethyl ester |

FIG. 1-M

| EX. | STRUCTURE | NAME |
|---|---|---|
| 99 | 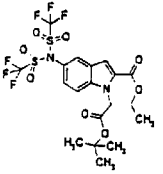 | 1-*tert*-Butoxycarbonylmethyl-5-(*N*,*N*-ditrifluoromethanesulfonyl)amino-1*H*-indole-2-carboxylic acid ethyl ester |
| 100 | 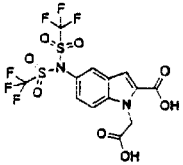 | 1-Carboxymethyl-5-(*N*,*N*-ditrifluoromethanesulfonyl)amino-1*H*-indole-2-carboxylic acid |
| 101 | 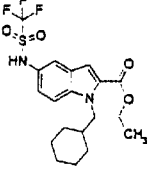 | 1-Cyclohexylmethyl-5-trifluoromethanesulfonylamino-1*H*-indole-2-carboxylic acid ethyl ester |
| 102 | 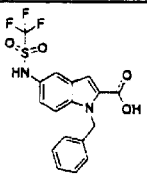 | 1-Benzyl-5-trifluoromethanesulfonylamino-1*H*-indole-2-carboxylic acid |
| 103 | 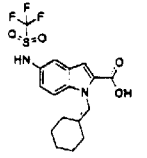 | 1-Cyclohexylmethyl-5-trifluoromethanesulfonylamino-1*H*-indole-2-carboxylic acid |

FIG. 1-N

PHOSPHATE MIMICS AND METHODS OF TREATMENT USING PHOSPHATASE INHIBITORS

RELATED APPLICATIONS

This application is related to U.S. Provisional Application Serial No. 60/150,970, filed Aug. 27, 1999 and U.S. Provisional Application Serial No. 60/165,365, filed Nov. 12, 1999, which are incorporated by reference as if fully set forth herein.

FIELD OF THE INVENTION

The present invention relates to, inter alia, novel trifluoromethyl sulfonyl and trifluoromethyl sulfonamido compounds, their physiologically acceptable salts and prodrugs, which modulate the activity of protein phosphatases and uses thereof. The invention also relates to the use of compounds containing fluoromethyl sulfonyl groups to treat certain diseases. These compounds may be used as phosphate mimics to inhibit, regulate or modulate the activity of a phosphate binding protein in a cell. Thus, these mimics may be particularly useful in the treatment of phosphate binding protein associated disorders.

BACKGROUND OF THE INVENTION

Phosphate derivatives are involved in a wide variety of cellular processes. Common phosphate derivatives include nucleotides (e.g. mono-, di- or tri-phosphate adenosine, guanine, cytosine, thymidine, or uridine, or cyclic derivatives) either naturally occurring or synthetic analogues. Other common cellular phosphate derivatives include co-factors such as thiamine pyrophosphate, NADPH, pyridoxal pyrophosphate, or coenzyme A; compounds involved in sugar metabolism such as glucose 6-phosphate, fructose 6-phosphate, compounds involved in fatty acid metabolism such as glycerol 3-phosphate; compounds involved in lipid biosynthesis such as isopentyl pyrophosphate, geranyl pyrophosphate or farnesyl pyrophosphate.

Signal Transduction

Another area involving phosphate binding proteins is cellular transduction. Cellular signal transduction is a fundamental mechanism whereby external stimuli that regulate diverse cellular processes are relayed to the interior of cells. The biochemical pathways through which signals are transmitted within cells comprise a circuitry of directly or functionally connected interactive proteins. One of the key biochemical mechanisms of signal transduction involves the reversible phosphorylation of residues on proteins. The phosphorylation state of a protein may affect its conformation and/or enzymatic activity as well as its cellular location. The phosphorylation state of a protein is modified through the reciprocal actions of protein kinases and protein phosphatases at various specific residues.

A common mechanism by which receptors regulate cell function is through an inducible kinase or phosphatase activity, including tyrosine kinase activity which is either endogenous to the receptor or is imparted by other proteins that become associated with the receptor. (Darnell et al., 1994, Science, 264:1415–1421; Heldin, 1995, Cell, 80:213–223; Pawson, 1995, Nature, 373:573–580). Protein tyrosine kinases (PTK) comprise a large family of transmembrane receptor and intracellular enzymes with multiple functional domains (Taylor et al., 1992, Ann. Rev. Cell Biol. 8:429–62). The binding of ligand allosterically transduces a signal across the cell membrane where, the cytoplasmic portion of the PTKs initiates a cascade of molecular interactions that disseminate the signal throughout the cell and into the nucleus. Many receptor protein tyrosine kinase (RTKs), such as epidermal growth factor receptor (EGFR) and platelet-derived growth factor receptor (PDGFR) undergo oligomerization upon ligand binding, and the receptors self-phosphorylate (via autophosphorylation or transphosphorylation) on specific tyrosine residues in the cytoplasmic portions of the receptor (Schlessinger and Ullrich, 1992, Neuron, 9:383–91, Heldin, 1995, Cell, 80:213223). Cytoplasmic protein tyrosine kinases (CTKs), such as Janus kinases (e.g., JAK1, JAK2, TYK2) and Src kinases (e.g., src, lck, fyn) are associated with receptors for cytokines (e.g., IL-2, IL-3, IL-6, erythropoietin), interferons and antigens. These associated receptors also undergo oligomerization, and have tyrosine residues that become phosphorylated during activation, but the receptor polypeptides themselves do not possess kinase activity.

Like the PTKS, the protein tyrosine phosphatases (PTPs) comprise a family of transmembrane and cytoplasmic enzymes, possessing at least an approximately 230 amino acid catalytic domain containing a highly conserved active site with the consensus motif [I/V]HCXXXXXR[S/T] (SEQ ID NO: 1). The substrates of PTPs may be PTKs which possess phosphotyrosine residues or the substrates of PTKs. (Hunter, 1989, Cell, 58:1013–16; Fischer et al., 1991, Science, 253:401–6; Saito and Streuli, 1991, Cell Growth and Differentiation, 2:59–65; Pot and Dixon, 1992, Biochem. Biophys. Acta, 1136:35–43).

Transmembrane or receptor-like PTPs (RTPs) possess an extracellular domain, a single transmembrane domain, and one or two catalytic domains followed by a short cytoplasmic tail. The extracellular domains of these RTPs are highly divergent, with small glycosylated segments (e.g., RTPα, RTPε), tandem repeats of immunoglobulin-like and/or fibronectin type III domains (e.g., LAR) or carbonic anhydrase like domains (e.g., RTPα, RTPβ). These extracellular features might suggest that these RTPs function as a receptor on the cell surface, and their enzymatic activity might be modulated by ligands. Intracellular or cytoplasmic PTPs (CTPs), such as PTP1C and PTP1D, typically contain a single catalytic domain flanked by several types of modular conserved domains. For example, PTP1C, a hemopoietic cell CTP, is characterized by two Src homology 2 (SH2) domains that recognize short peptide motifs bearing phosphotyrosine (pTyr).

In general, these modular conserved domains may influence the intracellular localization of the protein. SH2-domain containing proteins are able to bind pTyr sites in activated receptors and cytoplasmic phosphoproteins. Another conserved domain known as SH3 binds to proteins with proline-rich regions. A third type known as the pleckstrin-homology (PH) domain has also been identified. These modular domains have been found in both CTKs and CTPs as well as in noncatalytic adapter molecules, such as Grbs (Growth factor Receptor Bound), which mediate protein-protein interactions between components of the signal transduction pathway (Skolnik et al., 1991, Cell, 65:83–90; Pawson, 1995, Nature, 373:573–580).

Multiprotein signaling complexes comprising receptor subunits, kinases, phosphatases and adapter molecules are assembled in subcellular compartments through the specific and dynamic interactions between these domains and their binding motifs. Such signaling complexes integrate the extracellular signal with the ligand-bound receptor and relay the signal to other downstream signaling proteins or complexes in other locations inside the cell, including the nucleus (Koch et al., 1991, Science, 252:668–674; Pawson, 1994, Nature, 373:573–580; Mauro et al., 1994, Trends Biochem. Sci., 19:151–155; Cohen et al., 1995, Cell, 80:237–248).

The levels of phosphorylation required for normal cell growth and differentiation at any time are achieved through the coordinated action of phosphatases and kinases. Depending on the cellular context, these two types of enzymes may either antagonize or cooperate with each other during signal transduction. An imbalance between these enzymes may impair normal cell functions leading to metabolic disorders and cellular transformation.

For example, insulin binding to the insulin receptor, which is a PTK, triggers a variety of metabolic and growth promoting effects such as glucose transport, biosynthesis of glycogen and fats, DNA synthesis, cell division and differentiation. Diabetes mellitus, which is characterized by insufficient or a lack of insulin signal transduction, can be caused by any abnormality at any step along the insulin signaling pathway. (Olefsky, 1988, "Cecil Textbook of Medicine," 18th Ed., 2:1360–81).

It is also well known, for example, that the overexpression of PTKS, such as HER2, can play a decisive role in the development of cancer (Slamon et al., 1987, Science, 235:77–82) and that antibodies capable of blocking the activity of this enzyme can abrogate tumor growth (Drebin et al., 1988, Oncogene, 2:387–394). Blocking the signal transduction capability of tyrosine kinases such as FlK-1 and the PDGF receptor have been shown to block tumor growth in animal models (Millauer et al., 1994, Nature, 367:577; Ueno et al., 1991, Science, 252:844–848).

Relatively less is known with respect to the direct role of tyrosine phosphatases in signal transduction. However, PTPs have been linked to human diseases. For example, ectopic expression of RTPα produces a transformed phenotype in embryonic fibroblasts (Zheng et al., 1992, Nature, 359:336–339), and overexpression of RTPα in embryonal carcinoma cells causes the cells to differentiate into a cell type with a neuronal phenotype (den Hertog, et al., 1993, EMBO Journal, 12:3789–3798). The gene for human RTPγ has been localized to chromosome 3p21 which is a segment frequently altered in renal and small lung carcinoma. Mutations may occur in the extracellular segment of RTPγ which renders the RTP no longer responsive to external signals (LaForgia et al., 1993, Cancer Res., 53:3118–3124; Wary et al., 1993, Cancer Res., 52:478–482). Mutations in the gene encoding PTP1C (also known as HCP or SHP) are the cause of the moth-eaten phenotype in mice which suffer from severe immunodeficiency, and systemic autoimmune disease accompanied by hyperproliferation of macrophages (Schultz et al., 1993, Cell, 73:1445–1454). PTP1D (also known as Syp, SHP2 or PTP2C) has been shown to bind through SH2 domains to sites of phosphorylation in PDGFR, EGFR and insulin receptor substrate 1 (IRS-1). Reducing the activity of PTP1D by microinjection of anti-PTP1D antibody has been shown to block insulin or EGF-induced mitogenesis (Xiao et al., 1994, J. Biol. Chem., 269:21244–21248).

It has been reported that some of the biological effects of insulin can be mimicked by vanadium salts such as vanadates and pervanadates. Vanadates and pervanadates are known to be non-specific phosphatase inhibitors. However, this class of compounds is toxic because each compound contains a heavy metal (U.S. Pat. No. 5,155,031; Fantus et al., 1989, Biochem., 28:8864–71; Swarup et al., 1982, Biochem. Biophys. Res. Commun., 107:1104–9). Others have reported non-peptidyl inhibitors of protein tyrosine phosphatase 1B. Taylor et al., 1998, Bioorganic & Medicinal Chemistry, 6:1457–1468; For recent reviews, see "Protein-Tyrosine Phosphatases: Structure, Mechanism, and Inhibitor Discovery." Burke, Jr. et al., 1998, Biopolymers (Peptide Science), 47:225–241; and "Phosphotyrosyl-Based Motifs in the Structure-Based Design of Protein-Tyrosine Kinase-Dependent Signal Transduction Inhibitors." Burke, Jr. et al., 1997, Current Pharmaceutical Design, 3:291–304.

Trifluoromethyl Sulfonyl Compounds

Trifluoromethyl sulfonyl compounds have been previously disclosed for uses unrelated to the present invention. For example, Pawloski et al., U.S. Pat. No. 5,480,568 disclose aryl triflouromethyl sulfonyl compounds for use as high temperature lubricants for magnetic recording media. Haug et al., U.S. Pat. No. 5,117,038 disclose triflouromethyl phenoxyphenylpropionic acid derivatives as herbicides. Others, namely Haga et al., U.S. Pat. No. 4,985,449 disclose trifluoromethyl sulfonyl phenoxy compounds for use as pesticides. Markley et al., U.S. Pat. No. 4,349,568, disclose triflouromethyl sulfonyl diphenyl ethers for use as antiviral agents. Reisdorff et al., U.S. Pat. No. 3,966,725, disclose triflouromethyl sulfonyl 1,3,5-triazine derivatives as coccidiostats. Others disclose aryl triflouromethyl sulfonyl compounds with a single nitrogen atom as a linker between the aromatic rings as herbicides. Examples of such compounds include Serban et al., EP 13144; Hartmann et al., U.S. Pat. No. 4,459,304 (insecticides, bactericides and fungicides). Still others have disclosed compounds with a single sulfur atom linker between the aromatic rings as synthetic intermediates to prepare trifluoromethyl sulfonyl substituted piperazinyl-benzothiazepines for use as sedatives, tranquilizers, antidepressants, and antiemetics (Schmutz et al., GB 1411587). Young et al., EP 233763, disclose sulfur linked quinolinyl trifluoromethyl sulfonyl compounds for use as a leukotriene antagonists.

Also, trifluoromethyl sulfonamido compounds have been previously disclosed for uses unrelated to the present invention. Hall et al., U.S. Pat. No. 5,405,871, disclose aryl trifluoromethyl sulfonamido hydrazones for use as pesticides. Takano et al., U.S. Pat. No. 4,954,518, disclose oxygen linked trifluoromethyl sulfonamido compounds for use as anti-inflammatory agents. Similarly, Adams et al., U.S. Pat. No. 5,545,669, disclose single oxygen linked trifluoromethyl sulfonamido compounds for use as phospholipase A2 inhibitors. Landes et al., WO97/10714, disclose sulfone linked aryl trifluoromethyl sulfonamido compounds for use as herbicides. Blaschke et al., WO97/03953, disclose sulfur linked aryl trifluoromethyl sulfonamido compounds for use as cyclo-oxygenase II inhibitors. Matsuo et al., U.S. Pat. No. 5,034,417, disclose alkanesulfonanilides as anti-inflammatory and analgesic agents.

In addition, methylene linked aryl trifluoromethyl sulfonyl compounds have been previously disclosed for uses unrelated to the present invention. Specifically, Fukada et al., WO 97/11050 and Toriyabe et al., 5,728,699, disclose methylene linked trifluoromethyl sulfonyl benzophenone and hydrazone as pesticides.

Although a great deal of information has been described about signal transduction and protein target associated therewith, there remains a need for drugs that effectively interact with these treat disease. Such drugs may be discovered from compounds published in the literature or novel compounds yet to be synthesized.

SUMMARY OF THE INVENTION

One aspect of this invention relates to, inter alia, novel trifluoromethyl sulfonyl and trifluoromethyl sulfonamido compounds and the physiologically acceptable salts and the prodrugs thereof and the use of these compounds to modulate the activity of enzymes associated with cellular signal transduction, and in particular, kinases and phosphatases, and in more particular, protein tyrosine phosphatases. Further, the invention encompasses that use of these compounds in the prevention and treatment of certain disorders including, but not limited to, disorders associated with phosphate binding proteins, including abnormal protein tyrosine enzyme related cellular signal transduction, such as cancer, diabetes, immuno-modulation, neurologic degenerative diseases, osteoporosis and infectious diseases.

Thus, the invention encompasses trifluoromethyl sulfonyl and trifluoromethyl sulfonamido compounds which are useful for the prevention or treatment of neoplastic diseases, diabetes (type I and II), and autoimmune diseases. The compounds of the invention are membrane permeable, easily synthesized using standard materials and potent and selective for inhibiting certain phosphate binding proteins, including phosphatases (e.g. PTP SHP2, 1B, Epsilon, MEG2, Zeta, Sigma, PEST, Alpha, Beta, Mu, DEP1 vide supra). This invention includes salts and prodrugs and other equivalents thereof, pharmaceutical compositions containing these and methods of their use.

The Compounds

In one embodiment, the invention is directed to compounds having the formula:

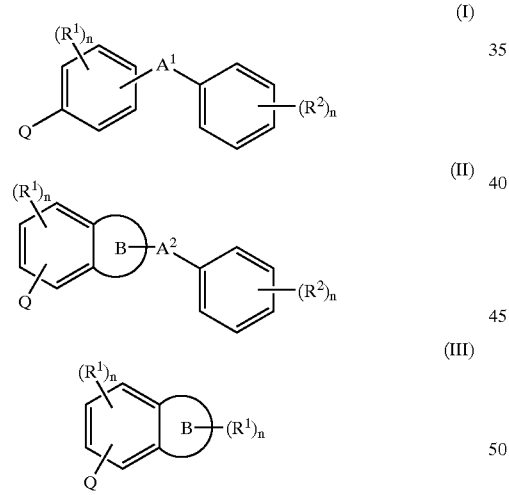

or a pharmaceutically acceptable salt or solvate thereof, wherein:

Q is $CF_3SO_2$, $CF_3SO_2NR^3$, $CF_3SO_2R^4$ or $CF_3SO_2N(R^3)R^4$, wherein $R^3$ is H, alkoxy, acyl or $C_1$–$C_3$ alkyl, each of which may be substituted or unsubstituted, and $R^4$ is methylene which may be substituted or unsubstituted;

each $R^1$ is independently C1–C3 alkyl, C1–C3 haloalkyl (for example, but not limited to, CF3, CC13), CN, (C=O)OR, (C=O)R5, H, halo, O(C=O)R, OR, OH, NHR, NH(C=O)OR, NH(C=O)R5, NO2, NHSO2R5, SO2R5, R4SO2CF3 or tetrazole, wherein R5 is CF3, $C_1$–$C_3$ alkyl, NHR and wherein R is H, C1–C3 alkyl, aryl or heteroaryl, which may be substituted or unsubstituted;

each R2 is independently C1–C3 alkyl, C1–C3 haloalkyl (for example, but not limited to, CF3, CC13), CN, (C=O)OR, (C=O)R5, H, halo, O(C=O)R, OR, OH, NHR, NH(C=O)OR, NH(C=O)R5, NO2, NHSO2R5, SO2R5. tetrazole, or X1-R6-X2 wherein X1 may be present or absent and if present is O, N, (C=O), (C=O)NH, NH(C=O), SO2NH, NHSO2; R6 is C1–3 alkylene which may be substituted or unsubstituted; X2 is CF3, (C=O)OR, (C=O)R5, H, NH(C=O)R5, NH(C=O)OR, NHSO2R5, NRR3, O(C=O)R, OR, SO2R5, tetrazole;

each n is independently from 0 to 3;

Ring B is an aryl, carbocyclic, heteroaryl, heterocyclic or phenyl ring which may be substituted or unsubstituted;

A1 is a linkage in which the shortest path is 2–8 atoms in length wherein the atoms in the linkage are carbon which may be substituted or unsubstituted or the carbon replaced with a single nitrogen or oxygen, or combination of nitrogen, oxygen and sulfur provided no two heteroatoms are adjacently linked in a linear linkage; the linkage may be or may contain an aryl, carbocyclic, heteroaryl, heterocyclic or a phenyl ring, which may be directly in the linkage or appended to the linkage; the linkage may be acylalkyl, alkenylene, alkoxy, alkoxyalkyl, alkoxyamino (—O—R—N—), alkoxyarylalkoxy (—O—R—Ar—R—O—, R is C1), alkoxyarylalkyl (—O—R—Ar—R—, R is C1-2), alkoxyarylamino (—O—R—Ar—N—, R is C1-2), alkoxyaryloxyalkyl (—O—R—Ar—O—R—, R is C1), alkylamino, alkylaminoalkyl, alkylaminoarylaminoalkyl (—R—N—Ar—N—R—, R is C1), alkylaryl, alkylarylalkyl, alkylarylamino (—R—Ar—N—, R is C1-3), alkylaryloxy (—R—Ar—O—, R is C1-3), alkylene, alkylenediamine, alkylenedioxy, alkyloxy (—R—O—), alkyloxyaryl, alkyloxyarylalkyloxy (—R—O—Ar—R—O—, R is C1), alkyloxyaryloxyalkyl (—R—O—Ar—O—R—, R is C1), C1–C6 alkylsulfonylamino, alkylthio, alkylthioalkyl, alkynylene, C1–C6 N-sulfonamido (—N—SO2—R—, R is C1–6), C3–C7 N-amido (—N—(C=O)—R—, R is C2–6), aminoalkyl (—N—R—), aminoalkylamino, aminoalkylarylalkyl (—N—R—Ar—R—, R is C1-2), aminoalkylarylalkylamino (—N—R—Ar—R—N—, R is C1), aminoalkylaryloxy (—N—R—Ar—O—, R is C1-2), aminoalkyloxy (—N—R—O—), aminoaryl (—N—Ar—), aminoarylalkyl (—N—Ar—R—, R is C1-3), aminoarylcarbonyl (—N—Ar—(C=O)—), aminoaryloxy (—N—Ar—O—), aminoaryloxyalkyl (—N—Ar—O—R—, R is C1-2), aminoarylsulfonyl (—N—Ar—SO2-), aryl, arylamino, ortho or para aryldioxy (—O—Ar—O—), substituted meta-aryldioxy, aryldiamine (—N—Ar—N—), aryloxy, aryloxyalkyl (—O—Ar—R—, R is C1-3), aryloxyamino (—O—Ar—N—), aryloxyaminoalkyl (—O—Ar—N—R—, R is C1-2), aryloxycarbonyl (—O—Ar—(C=O)—), aryloxysulfonyl (—O—Ar—SO2-), benzimidazole, benzo[b]furan, benzo[b]thiophene, C3–C7 C-amido (—(C=O)—N—R—, R is C2-7), carbonylarylamino (—(C=O)—Ar—N—), carbonylarylcarbonyl (—(C=O)—Ar—(C=O)—), carbonylaryloxy (—(C=O)—Ar—O—), chromene, cycloalkylene, disulfide, furan, haloalkyl, imidazole, imidazolidine, imidazoline, indole, isothiazole, isoxazole, morpholine, oxadiazole, oxazole, oxirane, parathiazine, phenothiazine, piperazine, piperidine, purine, pyran, pyrazine, pyrazole, pyrazolidine, pyrimidine, pyridine, pyrrole, pyrrolidine, quinoline, C2–C6 S-sulfonamido (—SO2-N—R, R is C2–6), sulfonylalkyl, sulfonylarylamino (—SO2-Ar—N—), sulfonylaryloxy (—SO2-Ar—O—), sulfonylarylsulfonyl (—SO2-Ar—SO2-), thiadiazole, thiazole, thiophene, triazine, triazole, unsubstituted azeridine, C3–C6 ureido (—N—(C=O)—N—R—, R is C2–5), which may be substituted or unsubstituted;

$A^2$ is a linkage in which the shortest path is 0–6 atoms in length wherein the atoms in the linkage are carbon which may be substituted or unsubstituted or the carbon replaced with a single nitrogen, oxygen or sulfur, or combination of nitrogen, oxygen and sulfur; the linkage may be or may contain an aryl, carbocyclic, heteroaryl, heterocyclic or a phenyl ring, which may be directly in the linkage or appended to the linkage; the linkage may be single atom C, O, S or N which may be substituted or unsubstituted; the linkage may be acylalkyl, alkenylene, alkoxy, alkoxyalkyl, alkoxyamino, alkoxyarylalkoxy, alkoxyarylalkyl, alkoxyarylamino, alkoxyaryloxyalkyl, alkylamino, alkylaminoalkyl, alkylaminoarylaminoalkyl, alkylaryl, alkylarylalkyl, alkylarylamino, alkylaryloxy, alkylene, alkylenediamine, alkylenedioxy, alkyloxy, alkyloxyaryl, alkyloxyarylalkyloxy, alkyloxyaryloxyalkyl, alkylsulfonylamino, alkylthio, alkylthioalkyl, alkynylene, N-sulfonamido, N-amido, aminoalkyl, aminoalkylamino, aminoalkylarylalkyl, aminoalkylarylalkylamino, aminoalkylaryloxy, aminoalkyloxy, aminoaryl, aminoarylalkyl, aminoarylcarbonyl, aminoaryloxy, aminoaryloxyalkyl, aminoarylsulfonyl, aryl, arylamino, ortho or para aryldioxy, substituted meta-aryldioxy, aryldiamine, aryloxy, aryloxyalkyl, aryloxyamino, aryloxyaminoalkyl, aryloxycarbonyl, aryloxysulfonyl, benzimidazole, benzo[b]furan, benzo[b]thiophene, C-amido, carbonylarylamino, carbonylarylcarbonyl, carbonylaryloxy, chromene, cycloalkylene, furan, haloalkyl, imidazole, imidazolidine, imidazoline, indole, isothiazole, isoxazole, morpholine, oxadiazole, oxazole, oxirane, parathiazine, phenothiazine, piperazine, piperidine, purine, pyran, pyrazine, pyrazole, pyrazolidine, pyrimidine, pyridine, pyrrole, pyrrolidine, quinoline, sulfonamido, sulfonylalkyl, sulfonylarylamino, sulfonylaryloxy, sulfonylarylsulfonyl, thiadiazole, thiazole, thiophene, triazine, triazole, unsubstituted azeridine, ureido, which may be substituted or unsubstituted.

In another embodiment, the invention is directed to compounds having the formula (I), (II) above or a pharmaceutically acceptable salt or solvate thereof, wherein:

Q is CF3SO2;

each R1 is independently CF3, (C=O)OR, (C=O)R5, H, halo, NHR, NH(C=O)OR, NH(C=O)R5, NHSO2R5, NO2, O(C=O)R, OH, OR, SO2R5 or tetrazole;

each R2 is independently (C=O)OR, (C=O)R5, NH(C=O)OR, NH(C=O)R5, NHR, NHSO2R5, NO2, —R6—(C=O)OR, —R6-NRR3, —R6-tetrazole, or tetrazole;

each n is independently from 0 to 2;

Ring B is phenyl or heteroaryl which may be substituted or unsubstituted; and linkage A1 is C2–C4 alkoxy, C2–C4 alkoxyalkyl, C2–C4 alkylenedioxy, C2–C4 alkylaminoalkyl, C2–C4 alkylenediamine, C3–C4 C-amido, C3–C4 N-amido, C3–C4 ureido, C1–C3 N-sulfonamido, C2–C3 S-sulfonamido, aryldioxy, aryldiamine, aryl, alkylarylalkyl, imidazole, oxazole, oxadiazole, pyrazole, pyrazolidine, pyrrole or triazole.

In another embodiment, the invention is directed to compounds having the formula (I), (II) above or a pharmaceutically acceptable salt or solvate thereof, wherein:

Q is $CF_3SO_2NH$;

each R1 is independently CF3, (C=O)OR, (C=O)R5, H, halo, NHR, NH(C=O)OR, NH(C=O)R5, NHSO2R5, NO2, O(C=O)R, OH, OR, SO2R5 or tetrazole;

each R2 is independently (C=O)OR, (C=O)R5, NH(C=O)OR, NH(C=O)R5, NHR, NHSO2R5, NO2, SO2R5, —R6—(C=O)OR, —R6—NRR3, —R6-tetrazole, or tetrazole;

each n is independently from 0 to 2;

Ring B is phenyl or heteroaryl which may be substituted or unsubstituted; and linkage A1 is C2–C4 alkoxy, C2–C4 alkoxyalkyl, C2–C4 alkylenedioxy, C2–C4 alkylaminoalkyl, C2–C4 alkylenediamine, C3–C4 C-amido, C3–C4 N-amido, C3–C4 ureido, C1–C3 N-sulfonamido, C2–C3 S-sulfonamido, aryldioxy, aryldiamine, aryl, alkylarylalkyl, imidazole, oxazole, oxadiazole, pyrazole, pyrazolidine, pyrrole or triazole.

In another embodiment, the invention is directed to compounds having the formula:

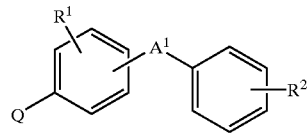

(IV)

or a pharmaceutically acceptable salt or solvate thereof, wherein: Q is CF3SO2 or $CF_3SO_2NH$; R1 is H or NO2; R2 is (C=O)OR, NHSO2R5 or SO2R5; and the linkage A1 is C2–C4 alkoxyalkyl, aryldioxy, aryl, alkylarylalkyl or oxadiazole.

In another embodiment, the A1 linker in the compound having formula I or IV above the linker has the structure:

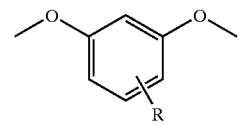

where R is any substituent other than hydrogen.

The invention also includes pharmaceutical compositions comprising a compound of formula (I), (II) or (II). Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically.

Treatment of Disease Using Phosphate Mimics

Based in part upon an investigation of the activity of the above compounds in both biochemical and cellular assays, we have discovered that compounds having a trifluoromethylsulfonyl moiety and its derivative trifluoromethylsulfonamido have a broad spectrum of activity. Presently, without being limited by any specific mechanism of action, such compounds mimic the effects of the phosphate group for a wide variety of phospho-derivatives including proteins such as phosphatases and kinases, e.g., phosphotyrosine, thus providing inhibition of a variety of important therapeutic targets. The compounds of the invention are stable to phosphatase, capable of crossing cell membranes and readily prepared in high purity. Thus, these compounds are uniquely suitable for use as medicaments.

The compounds and pharmaceutical compositions of the invention can be used for treating, alleviating or preventing diseases, including but not limited to, diabetes mellitus; immune disorders in which cytokine signal transduction is deficient specifically anemia and immunodeficiency; rheumatoid arthritis; neurodegenerative diseases; cancer, particularly solid tumors, such as glioma, melanoma, Kaposi's sarcoma, hemangioma and ovarian, breast, lung, pancreatic, liver, prostate, colon and epidermoid cancer, in which the malignant cells proliferate and/or metastasize as a result of uncontrolled signal transduction mediated by growth factors; infectious diseases associated with PTPases; or osteoporosis.

In addition, this invention provides a method for inhibiting, regulating or modulating the activity of a phosphate binding protein in a cell which comprises administering to the cell an effective amount of a compound with a molecular weight less than 2000 daltons, or a pharmaceutically acceptable salt or solvate thereof. The compound contains at least one functional group selected from the group consisting of $C(R^{11})F_aSO_bZ$— and $R^{12}SO_bC(R^{11})F_m$—; wherein a is 1, 2 or 3 and b is 1 or 2 and m is 1 or 2; Z is C or N; wherein R11 may be present or absent and if present is independently H, halo, $C_1$–$C_4$ alkyl, $C_2$–$C_4$ alkenyl or $C_1$–$C_4$ haloalkyl, which may be substituted or unsubstituted; wherein $R^{12}$ is $C_1$–$C_3$ haloalkyl, $C_1$–$C_3$ alkyl which may be substituted or unsubstituted, or N which may be substituted or unsubstituted.

In this embodiment, the compound regulates, inhibits or modulates the activity of the phosphate binding protein.

In one embodiment of the above method the compound has the formula: $C(R^{11})F_aSO_bZR^{13}$ or $R^{12}SO_bC(R^{11})F_mR^3$ $ZR^{13}$ or $R^{13}$ may be an amide, an amine, an ester, an ether, a monocyclic heterocycle, a polycyclic heterocycle, an acyclic hydrocarbon, a monocyclic aliphatic hydrocarbon, a polycyclic aliphatic hydrocarbon, a monocyclic aromatic hydrocarbon, a polycyclic aromatic hydrocarbon, a macrocycle, a nucleoside, a nucleotide, an oligoamide, an oligoamine, an oligoester, an oligoether, an oligonucleotide, an oligosaccharide, an oligourea, an oligourethane, a peptide, a peptide oligomer, a saccharide, a steroid, a urea, a urethane, which may be substituted or unsubstituted.

In a preferred embodiment, the compound contains the formula $CF_3SO_2$—, $CF_3SO_2N$—, $CF_3SO_2C$—, $CF_3SO_2CO$—, $CF_3SO_2CN$—, $CF_3CF_2SO_2$— or $CHF_2SO_2$—.

In another preferred embodiment, $ZR^{13}$ or $R^{13}$ is a monocyclic heterocycle, a polycyclic heterocycle, a monocyclic aromatic hydrocarbon, a polycyclic aromatic hydrocarbon which may be substituted or unsubstituted. Alternatively, Z is methylene which may be substituted or unsubstituted. The molecular weight of the compound maybe less than 1000 daltons, preferably less than 650 daltons.

In the method above, the phosphate binding protein may be a phosphohistidine, phosphoserine, phosphothreonine or phosphotyrosine binding protein. It may also be an enzyme. The enzyme may be a metalloproteinase or an enzyme that forms a covalent phosphocysteine intermediate. The enzyme may be a phosphatase or a kinase such as a histidine kinase, a serine kinase, a threonine kinase or a tyrosine kinase. It may also be associated with protein tyrosine phosphatase signal transduction.

In one embodiment of the method, the phosphate binding protein is a dual-specificity phosphatase, histidine/lysine phosphatase, low-molecular weight phosphatase, a phosphotyrosine binding (PTB) domain, a pleckstrin homology domain, a Ser/Thr phosphatase, a Src homology 2 (SH2) domain, a protein tyrosine phosphatase, or a tyrosine-specific phosphatase. The phosphatase may be Alpha phosphatase, Beta phosphatase, cdc25 phosphatase, cdi phosphatase, CD45 phosphatase, DEPI phosphatase, Epsilon phosphatase, LAR phosphatase, MAP kinase phosphatase, MEG2 phosphatase, Mu phosphatase, 1B phosphatase, PEST phosphatase, PP2β(calcineurin) phosphatase, SHPI phosphatase, SHP2 phosphatase, Sigma phosphatase, T-cell phosphatase, VH1-like phosphatase, VHR phosphatase, Yersinia phosphatase, or Zeta phosphatase.

Preferably, the activity of the phosphate binding protein is determined by an in vitro assay. In addition, preferably the cell is a mammalian cell, more preferably a human cell.

BRIEF DESCRIPTION OF THE DRAWINGS

FIG. 1 shows exemplary compounds of the present invention.

DETAILED DESCRIPTION OF THE INVENTION

Phosphatase Inhibition

The present invention encompasses compounds capable of acting as phosphate mimics, including but not limited to, inhibiting the activity of phosphatases and kinases. More specifically, the present invention encompasses compounds capable of inhibiting phosphatase activity. These compounds will be referred to herein generically as "phosphatase inhibitors", even though these compounds either upregulate or downregulate cellular processes that are controlled by signal transduction. Without being limited by any specific mechanism of action, the small molecules of the invention have activity as phosphate mimics thus may achieve phosphatase inhibition in a cell.

The invention encompasses a method for regulating, inhibiting or modulating protein tyrosine phosphatase signal transduction in a mammalian cell comprising contacting the cell with an effective amount of administration to a mammal of a pharmaceutically effective amount of a compound as described above and a pharmaceutically acceptable carrier or excipient.

The present invention encompasses the use of compounds capable of modulating or regulating signal transduction in normal or diseased cells. The present invention is also directed to the use of compounds capable of inhibiting the activity of enzymes, in particular kinases and phosphatases, to modulate or trigger signal transduction. The invention is further directed to the regulation of cellular processes that are controlled by signal transduction through the inhibition of the activity of these enzymes by the compounds. The compounds of this invention are particularly suited for the prevention or treatment of cancer, diabetes, immunomodulation related disorders, neurologic degenerative disorders or osteoporosis. The invention further provides for the use of such compounds in the treatment of a subject having a disorder caused by dysfunctional signal transduction involving a kinase or a phosphatase.

In one embodiment of the invention, the compounds of the invention are capable of inhibiting the activity of protein tyrosine phosphatases, that are transmembrane or intracellular, and that may have one or more characteristic catalytic domains. The amino acid sequences of the PTPs in the catalytic domains may include but are not limited to [I/V]HCXXXXXR[S/T](SEQ ID NO: 1). In addition, the PTPs may possess one or more modular conserved domains, which include but are not limited to, SH2, SH3 and PH domains. In a specific embodiment of the invention, the compounds of the invention can be used to inhibit the phosphatase activity of PTP1B (Charbonneau, et al., 1989, Proc. Natl. Acad. Sci., USA, 86:5252–5256), T-cell PTP (Cool et al., 1989, Proc. Natl. Acad. Sci., USA, 86:5257–5261), PTPIC (Shen et al., 1991, Nature, 352:736–739), PTP1D (Vogel, et al., 1993, Science, 259:1611–1614), RTPα, RTPβ, RTPγ (Kaplan et al., 1990, Proc. Natl. Acad. Sci., USA, 87:7000–7004), RTPα (Yan, et al., 1993, J. Biol. Chem., 268:24880–24886), RTPΛ (Jiang et al., 1993, Mol. Cell Biol., 13:2942–2951) and CD45 (Charbonneau et al., 1988, Proc. Natl. Acad. Sci. USA, 85: 182–7186). The PTKs and PTPs preferred in the invention are of human origin. Inhibition of phosphatase activity that is substantially specific to a PTP or a set of PTPs in a signaling pathway is preferred. While the inhibition of phosphatase activity is believed to be a mechanism of action of the compounds of the present invention with respect to their ability to modulate and/or regulate signal transduction, applicants do not intend to be limited to a particular mechanism of action.

The term "signal transduction" as used herein is not limited to transmembrane signaling, and includes the multiple pathways that branch off throughout the cell and into the nucleus. Such signaling pathways may include but are not limited to the Ras pathway (Schlessinger, 1994, Curr. Opin. Genet. Dev., 4:25–30), the JAK/STAT pathways (Sadowski et al., 1994, Science, 261:1739–1744), the phosphoinositide 3-kinase pathway and the phospholipase C-γ pathway. As used herein, the term "modulation" or "modulating" shall mean upregulation or downregulation of a signaling pathway. Cellular processes under the control of signal transduction may include, but are not limited to, transcription of specific genes; normal cellular functions, such as metabolism, proliferation, differentiation, adhesion, apoptosis and survival; as well as abnormal processes, such as transformation, blocking of differentiation and metastasis.

A signal may be triggered by the binding of a ligand to its receptor on the cell surface, and the signal is transduced and propagated by the phosphorylation or dephosphorylation of specific tyrosine residues on various substrates inside the cell. The specific interactions between the kinases or phosphatases and their substrates may involve the formation of a transient or stable multimolecular complex on the inner face of the plasma membrane or in other subcellular compartments including the nucleus. A substrate may contain one or more residues that are phosphorylated or dephosphorylated by enzymes in the signaling pathway. Such substrates may include the receptor and its subunits, molecules associated with or recruited to the receptor such as cytoplasmic kinases, cytoplasmic phosphatases, adapter molecules, cytoskeletal proteins and transcription factors.

The term "receptor" as used herein may include, but is not limited to, insulin receptor, members of the insulin-like growth factor receptor family, epidermal growth factor receptor family, fibroblast growth factor receptor family, hepatocyte growth factor receptor family, vascular endothelial growth factor receptor family, neurotrophin receptor (trk) family, the T-cell receptor, the B cell receptor and members of the Type I–IV cytokine receptor families (Heldin, 1995, Cell, 80:213–223; Taniguchi, 1995, Science, 268:251–255). Adapter molecules that are substrates may include the Grb proteins, IRS-1, Zap-70 and Shc (Pawson et al., 1995, Nature, 373:573–580). Cytoskeletal proteins such as actin and transcription factors such as the STAT proteins (Ihle et al., 1994, Trends Biochem. Sci., 19:222–227) may also serve as substrates. As used herein, the term ligand is synonymous with extracellular signaling molecules, and includes but is not limited to growth factors such as insulin, EGF, PDGF, fibroblast growth factors, vascular endothelial growth factor, and neurotrophins; and cytokines such as growth hormone, erythropoietin, tumor necrosis factor, interleukins and interferons. The term ligand is not limited to soluble molecules, and includes, for example, extracellular matrix proteins, cell adhesion molecules as well as antigenic peptides associated with the major histocompatibility complex proteins on the surface of an antigen-presenting cell.

In one embodiment of the invention, the compounds of the invention can be used to trigger or upregulate signal transduction in cells so that the effect of ligand binding to a receptor is enhanced, or mimicked if the ligand is not present. The compounds exert the effect by inhibiting or diminishing the activity of a phosphatase in the signaling pathway which normally acts negatively toward signaling. One mechanism by which phosphatases normally down-regulate signal transduction involves the dephosphorylation of specific phosphotyrosine residues (pTyr) on PTKs and their substrates since many PTKs require phosphorylation of some of its own tyrosine residues in order to become optimally active in the signaling pathway. The compounds of the invention can be used to prevent the dephosphorylation of pTyr residues on receptors or their subunits which normally becomes phosphorylated upon ligand binding, thereby enhancing the extent and duration of phosphorylation. The compounds of the invention can also be used to prevent the dephosphorylation of kinases in which the residues become autophosphorylated or transphosphorylated due to its basal activity. In these kinases, a signal may be triggered by the compounds of the invention in the absence of ligand binding since the basal activity of kinase is sufficient to promote a signal if constitutive phosphatase activity is inhibited or diminished by the compounds.

One embodiment of the invention is directed to a method of triggering, enhancing or sustaining insulin receptor signal transduction by inhibiting the constitutive dephosphorylation of sites on the activated insulin receptor. This would allow the insulin receptor to remain phosphorylated, thus enhancing or sustaining the insulin signal. Furthermore, since it has been shown that insulin receptor is phosphorylated at a low level even in the absence of insulin (Goldstein, 1992, J. Cell Biol., 48:33–42), the compounds of the invention can be used to trigger a signal, even in the absence of insulin, by allowing the tyrosine residues on the receptor to become self-phosphorylated.

Another mechanism by which phosphatases may exert a negative effect on signaling is through the dephosphorylation of specific sites to which SH2-containing molecules bind during signaling. The absence of such sites would prevent the recruitment of SH2-containing molecules to specific subcellular compartments to form multiprotein signaling complexes, thereby, preventing the further propagation of the signal. Thus, the compounds of the invention can be used to upregulate or prolong signal transduction by preventing the dephosphorylation of sites on substrate proteins that normally serve as binding sites for SH2-containing proteins which promote signaling. In another embodiment of the invention, the compounds of the invention may be used to prevent the dephosphorylation of specific residues on any substrate, which residues are essential to the transmissions or propagation of the signal. Furthermore, the compounds of the invention may be used to prevent the dephosphorylation of specific residues on any substrate, which residues are inhibitory to signal transduction.

The compounds of the invention can also be used to suppress or downregulate signal transduction in cells so that the effect of ligand binding to a receptor is abolished or attenuated. The compounds can inhibit a phosphatase in a signaling pathway which normally acts positively toward signaling. For example, phosphatases promote signaling through the activation of members of the Src family of kinases. Src family kinases have an inhibitory site of phosphorylation in their carboxy termini which by dephosphorylation activates kinase activity. Thus, the compounds of the invention can be used to prevent the dephosphorylation of the inhibitory residues in the carboxy termini of kinases which function normally to promote signal transductions. Src family kinases may include Src, Fyn, Lck, Lyn, Blk, Hck, Fgr and Yrk. Other kinases which may be similarly regulated by a phosphatase may include Fak and Csk (Taniguchi, 1995, Science, 268:251–255).

The Compounds

In one embodiment, the invention is directed to compounds having the formula:

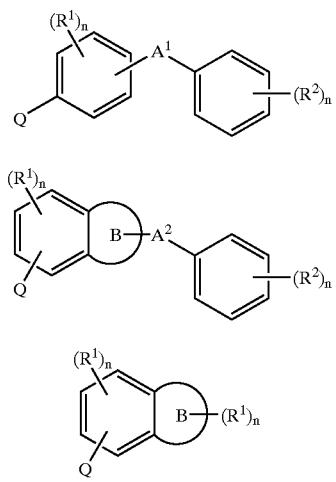

or a pharmaceutically acceptable salt or solvate thereof, wherein:

Q is $CF_3SO_2$, $CF_3SO_2NR^3$, $CF_3SO_2R^4$ or $CF_3SO_2N(R^3)$ $R^4$, where $R^3$ is H, alkoxy, acyl or $C_1-C_3$ alkyl, each of which may be substituted or unsubstituted, and $R^4$ is methylene which may be substituted or unsubstituted;

each R1 is independently C1–C3 alkyl, C1–C3 haloalkyl (for example, but not limited to, CF3, CCl3), CN, (C=O)OR, (C=O)R5, H, halo, NHR, NH(C=O)OR, NH(C=O)R5, NO2, NHSO2R5, O(C=O)R, OH, OR, SO2R5, R4SO2CF3 or tetrazole, wherein R5 is CF3, C1–C1–C3 alkyl, NHR and wherein R is H, C1–C3 alkyl, aryl or heteroaryl, which may be substituted or unsubstituted; each R2 is independently C1–C3 alkyl, C1–C3 haloalkyl (for example, but not limited to, CF3, CC13), CN, (C=O)OR, (C=O)R5, H, halo, O(C=O)R, OR, OH, NHR, NH(C=O)OR, NH(C=O)R5, NO2, NHSO2R5, SO2R5, tetrazole, or X1-R6-X2 wherein X1 may be present or absent and if present is O, N, (C=O), (C=O)NH, NH(C=O), SO2NH, NHSO2; R6 is C1–3 alkylene which may be substituted or unsubstituted; X2 is CF3, (C=O)OR, (C=O)R5, H, NH(C=O)R5, NH(C=O)OR, NHSO2R5, NRR3, O(C=O)R, OR, SO2R5, tetrazole;

each n is independently from 0 to 3;

Ring B is an aryl, carbocyclic, heteroaryl, heterocyclic or phenyl ring which may be substituted or unsubstituted;

A1 is a linkage in which the shortest path is 2–8 atoms in length wherein the atoms in the linkage are carbon which may be substituted or unsubstituted or the carbon replaced with a single nitrogen or oxygen, or combination of nitrogen, oxygen and sulfur provided no two heteroatoms are adjacently linked in a linear linkage; the linkage may be or may contain an aryl, carbocyclic, heteroaryl, heterocyclic or a phenyl ring, which may be directly in the linkage or appended to the linkage; the linkage may be acylalkyl, alkenylene, alkoxy, alkoxyalkyl, alkoxyamino (—O—R—N—), alkoxyarylalkoxy (—O—R—Ar—R—O—, R is C1), alkoxyarylalkyl (—O—R—Ar—R—, R is C1–2), alkoxyarylamino (—O—R—Ar—N—, R is C1–2), alkoxyaryloxyalkyl (—O—R—Ar—O—R—, R is C1), alkylamino, alkylaminoalkyl, alkylaminoarylaminoalkyl (—R—N—Ar—N—R—, R is C1), alkylaryl, alkylarylalkyl, alkylarylamino (—R—Ar—N—, R is C1–3), alkylaryloxy (—R—Ar—O—, R is C1–3), alkylene, alkylenediamine, alkylenedioxy, alkyloxy (—R—O—), alkyloxyaryl, alkyloxyarylalkyloxy (—R—O—Ar—R—O—, R is C1), alkyloxyaryloxyalkyl (—R—O—Ar—O—R—, R is C1), C1–C6 alkylsulfonylamino, alkylthio, alkylthioalkyl, alkynylene, C1–C6 N-sulfonamido (—N—SO2—R—, R is C1–6), C3–C7 N-amido (—N—(C=O)—R—, R is C2–6), aminoalkyl (—N—R—), aminoalkylamino, aminoalkylarylalkyl (—N—R—Ar—R—, R is C1–2), aminoalkylarylalkylamino (—N—R—Ar—R—N—, R is C1), aminoalkylaryloxy (—N—R—Ar—O—, R is C1–2), aminoalkyloxy (—N—R—O—), aminoaryl (—N—Ar—), aminoarylalkyl (—N—Ar—R—, R is C1–3), aminoarylcarbonyl (—N—Ar—(C=O)—), aminoaryloxy (—N—Ar—O—), aminoaryloxyalkyl (—N—Ar—O—R—, R is C1–2), aminoarylsulfonyl (—N—Ar—SO2-), aryl, arylamino, ortho or para aryldioxy (—O—Ar—O—), substituted meta-aryldioxy, aryldiamine (—N—Ar—N—), aryloxy, aryloxyalkyl (—O—Ar—R—, R is C1–3), aryloxyamino (—O—Ar—N—), aryloxyaminoalkyl (—O—Ar—N—R—, R is C1–2), aryloxycarbonyl (—O—Ar—(C=O)—), aryloxysulfonyl (—O—Ar—SO2-), benzimidazole, benzo[b]furan, benzo[b]thiophene, C3–C7C-amido (—(C=O)—N—R—, R is C2–7), carbonylarylamino (—(C=O)—Ar—N—), carbonylarylcarbonyl (—(C=O)—Ar—(C=O)—), carbonylaryloxy (—(C=O)—Ar—O—), chromene, cycloalkylene, disulfide, furan, haloalkyl, imidazole, imidazolidine, imidazoline, indole, isothiazole, isoxazole, morpholine, oxadiazole, oxazole, oxirane, parathiazine, phenothiazine, piperazine, piperidine, purine, pyran, pyrazine, pyrazole, pyrazolidine, pyrimidine, pyridine, pyrrole, pyrrolidine, quinoline, C2–C6 S-sulfonamido (—SO2-N—R, R is C2–6), sulfonylalkyl, sulfonylarylamino (—SO2-Ar—N—), sulfonylaryloxy (—SO2-Ar—O—), sulfonylarylsulfonyl (—SO2-Ar—SO2-), thiadiazolc, thiazole, thiophene, triazine, triazole, unsubstituted azeridine, C3–C6 ureido (—N—(C=O)—N—R—, R is C2–5), which may be substituted or unsubstituted;

A² is a linkage in which the shortest path is 0–6 atoms in length wherein the atoms in the linkage are carbon which may be substituted or unsubstituted or the carbon replaced with a single nitrogen, oxygen or sulfur, or combination of nitrogen, oxygen and sulfur; the linkage may be or may contain an aryl, carbocyclic, heteroaryl, heterocyclic or a phenyl ring, which may be directly in the linkage or appended to the linkage; the linkage may be single atom C, O, S or N which may be substituted or unsubstituted; the linkage may be acylalkyl, alkenylene, alkoxy, alkoxyalkyl, alkoxyamino, alkoxyarylalkoxy, alkoxyarylalkyl, alkoxyarylamino, alkoxyaryloxyalkyl, alkylamino, alkylaminoalkyl, alkylaminoarylaminoalkyl, alkylaryl, alkylarylalkyl, alkylarylamino, alkylaryloxy, alkylene, alkylenediamine, alkylenedioxy, alkyloxy, alkyloxyaryl, alkyloxyarylalkyloxy, alkyloxyaryloxyalkyl, alkylsulfonylamino, alkylthio, alkylthioalkyl, alkynylene, N-sulfonamido, N-amido, aminoalkyl, aminoalkylamino, aminoalkylarylalkyl, aminoalkylarylalkylamino, aminoalkylaryloxy, aminoalkyloxy, aminoaryl, aminoarylalkyl, aminoarylcarbonyl, aminoaryloxy, aminoaryloxyalkyl, aminoarylsulfonyl, aryl, arylamino, ortho or para aryldioxy, substituted meta-aryldioxy, aryldiamine, aryloxy, aryloxyalkyl, aryloxyamino, aryloxyaminoalkyl, aryloxycarbonyl, aryloxysulfonyl, benzimidazole, benzo[b]furan, benzo[b]thiophene, C-amido, carbonylarylamino, carbonylarylcarbonyl, carbonylaryloxy, chromene, cycloalkylene, furan, haloalkyl, imidazole, imidazolidine, imidazoline, indole, isothiazole, isoxazole, morpholine, oxadiazole, oxazole, oxirane, parathiazine, phenothiazine, piperazine, piperidine, purine, pyran, pyrazine, pyrazole, pyrazolidine, pyrimidine, pyridine, pyrrole, pyrrolidine, quinoline, sulfonamido, sulfonylalkyl, sulfonylarylamino, sulfonylaryloxy, sulfonylarylsulfonyl, thiadiazole, thiazole, thiophene, triazine, triazole, unsubstituted azeridine, ureido, which may be substituted or unsubstituted.

In another embodiment, the invention is directed to compounds having the formula (I), (II) above or a pharmaceutically acceptable salt or solvate thereof, wherein:

Q is CF3SO2;

each R1 is independently CF3, (C=O)OR, (C=O)R5, H, halo, NHR, NH(C=O)OR, NH(C=O)R5, NHSO2R5, NO2, O(C=O)R, OR, OH, SO2R5 or tetrazole; each R2 is independently (C=O)OR, (C=O)R5, NH(C=O)OR, NH(C=O)R5, NHR, NHSO2R5, NO2, —R6-(C=O)OR, —R6-NRR3, —R6-tetrazole, or tetrazole;

each n is independently from 0 to 2;

Ring B is phenyl or heteroaryl which may be substituted or unsubstituted; and linkage A1 is C2–C4 alkoxy, C2–C4 alkoxyalkyl, C2–C4 alkylenedioxy, C2–C4 alkylaminoalkyl, C2–C4 alkylenediamine, C3–C4C-amido, C3–C4 N-amido, C3–C4 ureido, C1–C3 N-sulfonamido, C2–C3 S-sulfonamido, aryldioxy, aryldiamine, aryl, alkylarylalkyl, imidazole, oxazole, oxadiazole, pyrazole, pyrazolidine, pyrrole or triazole.

In another embodiment, the invention is directed to compounds having the formula (I), (II) above or a pharmaceutically acceptable salt or solvate thereof, wherein:

Q is CF₃SO₂NH;

each R1 is independently CF3, (C=O)OR, (C=O)R5, H, halo, NHR, NH(C=O)OR, NH(C=O)R5, NHSO2RS, NO2, O(C=O)R, OH, OR, SO2R5 or tetrazole; each R2 is independently (C=O)OR, (C=O)R5, NH(C=O)OR, NH(C=O)R5, NHR, NHSO2R5, NO2, SO2R5, —R6—(C=O)OR, —R6—NRR3, —R6-tetrazole, or tetrazole;

each n is independently from 0 to 2;

Ring B is phenyl or heteroaryl which may be substituted or unsubstituted; and linkage A1 is C2–C4 alkoxy, C2–C4 alkoxyalkyl, C2–C4 alkylenedioxy, C2–C4 alkylaminoalkyl, C2–C4 alkylenediamine, C3–C4C-amido, C3–C4 N-amido, C3–C4 ureido, C1–C3 N-sulfonamido, C2–C3 S-sulfonamido, aryldioxy, aryldiamine, aryl, alkylarylalkyl, imidazole, oxazole, oxadiazole, pyrazole, pyrazolidine, pyrrole or triazole.

Alternatively, Q is CF3SO2 each R1 is independently H, NHR, NO2, or OR; each R2 is independently (C=O)OR, or NHSO2R5 or SO2R5; each n is independently from 0 to 2; and the linkage A1 is alkylarylalkyl, C2–C4 alkoxyalkyl, C2–C4 alkylenedioxy, aryl, aryldiamine, aryldioxy, or oxadiazole which may be substituted or unsubstituted or A1 is unsubstituted or monosubstituted C2–C4 N-amido.

In another embodiment, the invention is directed to compounds having the formula:

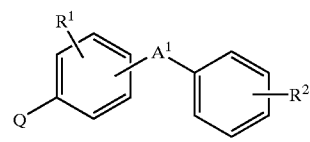

(IV)

or a pharmaceutically acceptable salt or solvate thereof, wherein: Q is CF3SO2 or CF₃SO₂NH; R1 is H or NO2; R2 is (C=O)OR, NHSO2R5 or SO2R5; and the linkage A1 is C2–C4 alkoxyalkyl, aryldioxy, aryl, alkylarylalkyl or oxadiazole.

In another embodiment, the A1 linker in the compound having formula I or IV above the linker has the structure:

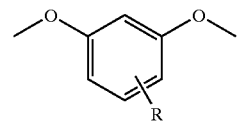

where R is any substituent other than hydrogen.

In one preferred embodiment, Q is CF₃SO₂ and the compound is: Bis(4-Trifluoromethylsulfonylbenzyl)ether, 4-Trifluoromethylsulfonylbenzyl 4-trifluoromethylsulfonylphenyl ether, N,N-Bis(4-trifluoromethylsulfonylbenzyl)benzamide, 1,2-Bis(4-trifluoromethylsullfonylphenyl)ethane, N-(4-Trifluoromethylsulfonylbenzyl)-4-trifluoromethylsulfonylbenzamide, N-(4-Trifluoromethylsulfonylbenzyl)benzamide, 3,5-Bis-(4-trifluoromethanesulfonyl-phenoxy)-benzoic acid methyl ester, [3,5-Bis-(2-nitro-4-trifluoromethanesulfonyl-phenoxy)-phenyl]-acetic acid methyl ester, 3,5-Bis-(2-nitro-4-trifluoromethanesulfonyl-phenoxy)-benzoic acid methyl ester, 1,3-Bis-(2-nitro-4-trifluoromethanesulfonyl-phenoxy)-cyclopentane, 4-Methyl-2,6-Bis-(2-nitro-4-trifluoromethanesulfonyl-phenoxy)-benzoic acid methyl ester, 4-[2-(2-Nitro-4-trifluoromethanesulfonyl-phenoxy)-ethoxy]-benzoic acid methyl ester, 4-[3-(2-Nitro-4-trifluoromethanesulfonyl-phenoxy)-phenoxy]-benzoic acid, 1-(3,5-Bis-trifluoromethyl-phenyl)-5-(2-nitro-4- trifluoromethanesulfonyl-phenoxy)-1H-pyrazole-3-carboxylic acid methyl ester, {4-[4-(2-Nitro-4-trifluoromethanesulfonyl-phenoxy)-benzenesulfonyl]-phenoxy}-acetic acid ethyl ester, 4-[3-(4-Trifluoromethanesulfonyl-phenoxy)-phenoxy]-benzoic acid, {4-[4-(4-Trifluoromethanesulfonyl-phenoxy)-benzenesulfonyl]-phenoxy}-acetic acid ethyl ester, N-(3-Trifluoromethanesulfonyl-phenyl)-2-{2-[(3-trifluoromethanesulfonyl-phenylcarbamoyl)-methyl]-phenyl}-acetamide, N-(3-Trifluoromethanesulfonyl-phenyl)-2-{3-[(3-trifluoromethanesulfonyl-phenylcarbamoyl)-methyl]-phenyl}-acetamide, N-(3-Trifluoromethanesulfonyl-phenyl)-2-{4-[(3-trifluoromethanesulfonyl-phenylcarbamoyl)-methyl]-phenyl}-acetamide, 3,6-Bis-(morpholin-4-ylmethyl)-2,5-bis-(2-nitro-4-trifluoromethanesulfonyl-phenoxy)-benzene, [2,3-Bis-(2-nitro-4-trifluoromethanesulfonyl-phenoxy)-propyl]-dimethyl-amine, N-(2-Ethylamino-5-trifluoromethanesulfonyl-phenyl)-2-(4-methanesulfonyl-phenyl)-acetamide, 2-Hydroxy-5-(2-nitro-4-trifluoromethanesulfonyl-phenoxy)-terephthalic acid diethyl ester, {2-[(3-Trifluoromethanesulfonyl-phenylcarbamoyl)-methyl]-phenyl}-acetic acid, {3-[(3-Trifluoromethanesulfonyl-phenylcarbamoyl)-methyl]-phenyl}-acetic acid, {4-[(3-Trifluoromethanesulfonyl-phenylcarbamoyl)-methyl]-phenyl}-acetic acid, 3,5-Bis-(2-nitro-4-trifluoromethanesulfonyl-phenoxy)-benzamide, 3,5-Bis-(4-trifluoromethanesulfonyl-phenoxy)-benzoic acid, N-(4-Trifluoromethanesulfonyl-phenyl)-2-{2-[(4-trifluoromethanesulfonyl-phenylcarbamoyl)-methyl]-phenyl}-acetamide, N-(4-Trifluoromethancsulfonyl-phenyl)-2-{3-[(4-trifluoromethanesulfonyl-phenylcarbamoyl)-methyl]-phenyl}-acetamide, N-(4-Trifluoromethanesulfonyl-phenyl)-2-{4-[(4-trifluoromethanesulfonyl-phenylcarbamoyl)-methyl]-phenyl}-acetamide, 4-(1-Ethyl-5-trifluoromethanesulfonyl-1H-benzoimidazol-2-yl)-benzoic acid methyl ester, 4-(1-Ethyl-5-trifluoromethanesulfonyl-1H-benzoimidazol-2-yl)-benzoic acid, 4-(1-Ethyl-5-trifluoromethanesulfonyl-1H-benzoimidazol-2-yl)-N-pyridin-4-yl-benzamide, 4-(1-Ethyl-5-trifluoromethanesulfonyl-1H-benzoimidazol-2-yl)-N-(4-methoxy-phenyl)-benzamide, 3-[4-(1-Ethyl-5-trifluoromethanesulfonyl-1H-benzoimidazol-2-yl)-benzoylamino]-benzoic acid ethyl ester, 4-(1-Ethyl-5-trifluoromethanesulfonyl-1-benzoimidazol-2-yl)-N-(2-pyrrolidin-1-yl-ethyl)-benzamide, N-Ethyl-4-(1-ethyl-5-trifluoromethanesulfonyl-1H-benzoimidazol-2-yl)-benzamide, 1-Ethyl-5-trifluoromethanesulfonyl-1H-benzoimidazole-2-carboxylic acid, [2-(Benzoyl-butyl-amino)-2-(4-trifluoromethanesulfonyl-phenyl)-acetylamino]-acetic acid methyl ester, N-Benzyl-N-[butylcarbamoyl-(4-trifluoromethanesulfonyl-phenyl)-methyl]-benzamide, N-[Butylcarbamoyl-(4-trifluoromethanesulfonyl-phenyl)-methyl]-N-(2-hydroxy-ethyl)-benzamide, [2-(Acetyl-cyclopropyl-amino)-2-(4-trifluoromethanesulfonyl-phenyl)-acetylamino]-acetic acid ethyl ester, [2-(Acetyl-methyl-amino)-2-(4-trifluoromethanesulfonyl-phenyl)-acetylamino]-acetic acid ethyl ester, [2-(Benzoyl-cyclohexyl-amino)-2-(4-trifluoromethanesulfonyl-phenyl)-acetylamino]-acetic acid ethyl ester, N-Cyclohexyl-N-[(2,6-dimethyl-phenylcarbamoyl)-(4-trifluoromethanesulfonyl-phenyl)-methyl]-benzamide, [2-(Acetyl-propyl-amino)-2-(4-trifluoromethanesulfonyl-phenyl)-acetylamino]-acetic acid ethyl ester, [2-(Acetyl-cyclohexyl-amino)-2-(4-trifluoromethanesulfonyl-phenyl)-acetylamino]-acetic acid ethyl ester, {4-[4-(2-Nitro-4-trifluoromethanesulfonyl-phenoxy)-benzenesulfonyl]-phenoxy}-acetic acid, 4-[2-(2-Nitro-4-trifluoromethanesulfonyl-phenoxy)-ethoxy]-benzoic acid, 2,5-Bis-(2-nitro-4-trifluoromethanesulfonyl-phenoxy)-terephthalic acid diethyl ester, 1-[2,3-Bis-(2-nitro-4-trifluoromethanesulfonyl-phenoxy)-propyl]-piperidine, 4-[2,3-Bis-(2-nitro-4-trifluoromethanesulfonyl-phenoxy)-propyl]-morpholine, [2,3-Bis-(2-nitro-4-trifluoromethanesulfonyl-phenoxy)-propyl]-(2-nitro-phenyl)-amine, 1-(2-Nitro-phenylamino)-3-(2-nitro-4-trifluoromethanesulfonyl-phenoxy)-propan-2-ol, [2,3-Bis-(2-nitro-4-trifluoromethanesulfonyl-phenoxy)-propyl]-(4-nitro-phenyl)-amine, 1-(4-Nitro-phenylamino)-3-(2-nitro-4-trifluoromethanesulfonyl-phenoxy)-propan-2-ol, 4-[2-Hydroxy-3-(2-nitro-4-trifluoromethanesulfonyl-phenoxy)-propylamino]-benzenesulfonamide or 4-[2,3-Bis-(2-nitro-4-trifluoromethanesulfonyl-phenoxy)-propylamino]-benzenesulfonamide.

In another preferred embodiment, Q is $CF_3SO_2NR^3$, R3 is H, and the compound is: 1,2-Bis(4-trifluoromethylsulfonamidophenyl)ethane, 1,2-Bis(2-methyl-4-trifluoromethylsulfonamidophenyl)ethane, 1,3-Bis(4-trifluoromethylsulfonamidophenoxy)-2,2-dimethylpropane, 1,3-Bis(4-trifluoromethylsulfonamidophenoxy)propane, 1,4-Bis(4-trifluoromethylsulfonamidophenoxy)butane, 1,4-Bis(4-trifluoromethylsulfonamidophenoxy)benzene, 1-(4-Aminophenoxy)-4-trifluoromethylsulfonamidophenoxy benzene, Bis(4-trifluoromethylsulfonamidophenyl) ether, 1,3-Bis(4-trifluoromethylsulfonamidophenoxy)benzene, 2,5-Bis(4-trifluoromethylsulfonamidophenyl)-(1,3,4) oxadiazole, Bis(4-trifluoromethylsulfonamidophenyl)-1,4-diisopropylbenzene, 5-Trifluoromethanesulfonylamino-1H-indole-2-carboxylic acid, 1-Methyl-5-trifluoromethanesulfonylamino-1H-indole-2-carboxylic acid, (2-Methyl-5-trifluoromethanesulfonylamino-indol-1-yl)-acetic acid, 1-Methyl-5-trifluoromethanesulfonylamino-1H-indole-2-carboxylic acid phenylamide, 5-Trifluoromethanesulfonylamino-1H-indole-2-carboxylic acid phenylamide, 3-[(1-Methyl-5-trifluoromethanesulfonylamino-1H-indole-2-carbonyl)-amino]-benzoic acid, 3-[(5-Trifluoromethanesulfonylamino-1H-indole-2-carbonyl)-amino]-benzoic acid, 4-[(5-Trifluoromethanesulfonylamino-1H-indole-2-carbonyl)-amino]-benzoic acid, 4-[2-(2-Methyl-5-trifluoromethanesulfonylamino-indol-1-yl)-acetylamino]-benzoic acid, 3-[2-(2-Methyl-5-trifluoromethanesulfonylamino-indol-1-yl)-acetylamino]-benzoic acid, 4-{[2-(2-Methyl-5-trifluoromethanesulfonylamino-indol-1-yl)-acetylamino]-methyl}-benzoic acid, (2-Methyl-5-trifluoromethanesulfonylamino-indol-1-yl)-acetic acid tert-butyl ester, 1-Methyl-5-trifluoromethanesulfonylamino-1H-indole-2-carboxylic acid ethyl ester, 6-Trifluoromethanesulfonylamino-naphthalene-2-carboxylic acid, N,N-Bis[(6-carboxyl-naphthalen-2-yl) methyl]trifluoromethanesulfonamide, 6-[(Methyl-trifluoromethanesulfonyl-amino)-methyl]-naphthalene-2-carboxylic acid, 3-({6-[(Methyl-trifluoromethanesulfony-amino)-benzoic acid, 1-tert-Butoxycarbonylmethyl-5-trifluoromethanesulfonylamino-1H-indole-2-carboxylic acid ethyl ester, 1-Carboxymethyl-5-trifluoromethanesulfonylamino-1H-indole-2-carboxylic acid ethyl ester, 1-tert-Butoxycarbonylmethyl-5-trifluoromethanesulfonylamino-1H-indole-2-carboxylic acid, 1-Carboxymethyl-5-trifluoromethanesulfonylamino-1H-indole-2-carboxylic acid, 1-Carboxymethyl-5-(N,N- ditrifluoromethanesulfonyl)amino-1H-indole-2-carboxylic acid ethyl ester, 1-tert-Butoxycarbonylmethyl-5-(N,N-ditrifluoromethanesulfonyl)amino-1H-indole-2-carboxylic acid ethyl ester, 1-Carboxymethyl-5-(N,N-ditrifluoromethanesulfonyl)amino-1H-indole-2-carboxylic acid, 1-Cyclohexylmethyl-5-trifluoromethanesulfonylamino-1H-indole-2-carboxylic acid ethyl ester, 1-Benzyl-5-trifluoromethanesulfonylamino-1H-indole-2-carboxylic acid or 1-Cyclohexylmethyl-5-trifluoromethanesulfonylamino-1H-indole-2-carboxylic acid.

As used herein, an "aldehyde" group refers to a carbonyl group, see below, where R7 is hydrogen.

As used herein, an "alkenyl" group refers to an alkyl group, as defined below, consisting of at least two carbon atoms and at least one carbon-carbon double bond.

As used herein, an "alkenylene" refers to an alkyl group as defined below, consisting of at least two carbon atoms and at least one carbon-carbon double bond as a linker (—R—, R is C2–C8).

As used herein, an "alkoxy" group refers to either an —O-alkyl and an —O-cycloalkyl group.

As used herein, an "alkyl" group refers to a saturated aliphatic hydrocarbon including straight chain and branched chain groups. Unless otherwise noted, the alkyl group has 1 to 20 carbon atoms (whenever a numerical range; "1–20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from alkoxy, aminoalkyl, aminoaryl, aryloxy, C-amido, C-carboxy, C-thioamido, carbonyl, cyano, cycloalkyl, guanidino, guanyl, halo, heteroalicyclic, heteroalicycloxy, heteroaryl, heteroaryloxy, hydroxy, N-amido, N-carbamyl, N-thiocarbamyl, nitro, O-carbamyl, O-carboxy, O-thiocarbamyl, phosphonyl, silyl, sulfinyl, sulfonamido, sulfonyl, thioalkoxy, thioaryloxy, thiocarbonyl, thioheteroalicycloxy, thioheteroaryloxy, thiohydroxy, trihaloalkyl, trihalomethane-sulfonamido, trihalomethanesulfonyl, ureido, and —NR8R9, wherein R8 and R9 are independently selected from the group consisting of hydrogen, alkyl, cycloalkyl, alkenyl, alkynyl, aryl, carbonyl, C-carboxy, sulfonyl, trihalomethanesulfonyl, trihalomethanecarbonyl, and, combined, a five- or six-member heteroalicyclic ring.

As used herein, an "alkylenedioxy" refers to an alkoxy group consisting of at least one carbon atom and two oxygen atoms as a linker (—O—R—O—, R is C1–C7).

As used herein, an "alkylene" refers to an alkyl group consisting of at least two carbon atoms as a linker (—R—, R is C2–C8).

As used herein, an "alkynyl" group refers to an alkyl group, consisting of at least two carbon atoms and at least one carbon-carbon triple bond.

As used herein, an "alkynylene" refers to an alkyl group consisting of at least two carbon atoms and at least at least one carbon—carbon triple bond as a linker (—R—, R is C2–C8).

As used herein, an "amino" group refers to an —NH2 group.

As used herein, an "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituted group(s) is preferably one or more selected from alkoxy, alkyl, alkyl morpholino, aminoaryl, aryloxy, C-amido, C-carboxy, C-thioamido, carbonyl, cyano, cycloalkyl, guanidino, guanyl, halo, heteroalicyclic, heteroalicycloxy, heteroaryl, heteroaryloxy, hydroxy, morpholino, N-amido, N-carbamyl, N-thiocarbamyl, nitro, O-carbamyl, O-carboxy, O-thiocarbamyl, phosphonyl, silyl, sulfinyl, sulfonamido, sulfonyl, thioalkoxy, thioaryloxy, thiocarbonyl, thioheteroalicycloxy, thioheteroaryloxy, thiohydroxy, trihalomethane-sulfonyl, trihalomethanesulfonamido, ureido, and —NR8R9, with R8 and R9 as defined above.

As used herein, an "aryloxy" group refers to both an —O-aryl and an —O-heteroaryl group.

As used herein, a "C-amido" group refers to a —C(=O) NR8R9, with R8 and R9 as defined herein.

As used herein, a "carbonyl" group refers to a —C(=O)—R7 group with R7 selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

As used herein, a "C-thioamido" group refers to a —C(=S)NR8R9 with R8 and R9 as defined herein.

As used herein, a "C-carboxy" group refers to a —C(=O) O—R7 group with R7 as defined herein.

As used herein, a "carboxylic acid" group refers to a C-carboxy group in which R7 is hydrogen.

As used herein, a "cyano" group refers to a —C≡N group.

As used herein, a "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkoxy, aminoaryl, aryloxy, C-amido, C-carboxy, C-thioamido, carbonyl, cyano, cycloalkyl, guanidino, guanyl, halo, heteroalicyclic, heteroalicycloxy, heteroaryl, heteroaryloxy, hydroxy, N-amido, N-carbamyl, N-thiocarbamyl, nitro, O-carbamyl, O-carboxy, O-thiocarbamyl, phosphonyl, silyl, sulfinyl, sulfonamido, sulfonyl, thioalkoxy, thioaryloxy, thiocarbonyl, thioheteroalicycloxy, thioheteroaryloxy, thiohydroxy, trihaloalkyl, trihalomethane-sulfonamido, trihalomethanesulfonyl, ureido, and —NR8R9 with R8 and R9 as defined above.

As used herein, an "ester" is a C-carboxy group, as defined herein, wherein R7 is any of the listed groups other than hydrogen.

As used herein, a "guanidino" group refers to a —R8NC (=N)NR9R10 with R8 and R9 as defined herein and R10 defined the same as R8 and R9.

As used herein, a "guanyl" group refers to a R8R9NC(=N)— group, with R8 and R9 as defined herein.

As used herein, a "halo" group refers to fluorine, chlorine, bromine or iodine.

As used herein, a "heteroalicyclic" group refers to a 5 or 6 membered monocyclic or fused ring group having in the ring(s) one or more atoms selected from the group consisting of nitrogen, oxygen and sulfur. The rings may also have one or more double bonds. However, the rings do not have a completely conjugated pi-electron system. The heteroalicyclic ring may be substituted or unsubstituted. When substituted, the substituted group(s) is preferably one or more selected from alkoxy, alkyl, aminoaryl, aryloxy, C-amido, C-carboxy, C-thioamido, carbonyl, cyano, cycloalkyl, guanidino, guanyl, halo, heteroalicyclic, heteroalicycloxy, heteroaryl, heteroaryloxy, hydroxy, N-amido, N-carbamyl, N-thiocarbamyl, nitro, O-carbamyl, O-carboxy, O-thiocarbamyl, phosphonyl, silyl, sulfinyl, sulfonamido, sulfonyl, thioalkoxy, thioaryloxy, thiocarbonyl, thioheteroalicycloxy, thioheteroaryloxy, thiohydroxy, trihalomethanesulfonamido, trihalomethanesulfonyl, ureido, and —NR8R9 with R8 and R9 as defined above As used herein, a "heteroalicycloxy" group refers to a heteroalicyclic—O— group with heteroalicyclic.

As used herein, a "heteroaryl" group refers to a 5 or 6 membered monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are carbazole, furan, imidazole, isoquinoline, oxazole, purine, pyrazole, pyridine, pyrimidine, pyrrole, quinoline, thiazole, thiophene. The heteroaryl group may be substituted or unsubstituted. When substituted, the substituted group(s) is preferably one or more selected from alkoxy, alkyl, aminoaryl, aryloxy, C-amido, C-carboxy, C-thioamido, carbonyl, cyano, cycloalkyl, guanidino, guanyl, halo, heteroalicyclic, heteroalicycloxy, heteroaryl, heteroaryloxy, hydroxy, N-amido, N-carbamyl, N-thiocarbamyl, nitro, O-carbamyl, O-carboxy, O-thiocarbamyl, phosphonyl, silyl, sulfinyl, sulfonamido, sulfonyl, thioalkoxy, thioaryloxy, thiocarbonyl, thioheteroalicycloxy, thioheteroaryloxy, thiohydroxy, trihalomethanesulfonamido, trihalomethanesulfonyl, ureido, and —NR8R9 with R8 and R9 as defined above.

As used herein, a "heteroaryloxy" group refers to a heteroaryl-O— group with heteroaryl.

As used herein, a "hydrazino" group refers to a —NR8NR9R10 group with R8, R9 and R10 as defined herein.

As used herein, a "hydroxy" group refers to an —OH group.

As used herein, a "keto" group refers to a —CC(=O)C— group wherein the carbon on either or both sides of the C=O may be part of an alkyl, cycloalkyl, aryl group or a carbon of a heteroaryl or heteroaliacyclic group.

As used herein, an "N-amido" group refers to a R8C(=O)NR9— group with R8 and R9 as defined herein.

As used herein, an "N-carbamyl" group refers to a R8OC(=O)NR9— group with R8 and R9 as defined herein.

As used herein, an "N-sulfonamido" group refers to a R8S(=O)2 NR9— group with R8 and R9 as defined herein.

As used herein, an "N-thiocarbamyl" group refers to a R8OC(=S)NR9— group with R8 and R9 as defined herein.

As used herein, an "O-carbamyl" group refers to a —OC(=O)NR8R9 group with R8 and R9 as defined herein.

As used herein, an "O-carboxy" group refers to a R8C(=O)O— group, with R8 as defined herein.

As used herein, an "O-thiocarbamyl" group refers to a —OC(=S)NR8R9 group with R8 and R9 as defined herein.

As used herein, a "phenylene" refers to an aryl group as defined herein, as a linker (—Ar—).

As used herein, a "phosphonyl" group refers to a P(=O)(OR8)(OR9) group with R8 and R9 as defined herein.

As used herein, the term "shortest path" refers to atoms in a direct linear linkage, which may be through a ring or a single atom linear chain. It refers to the minimum number of atoms required to connect the two aromatic rings. Atoms in the shortest path may have functional groups appended or branch points but such appendages or branches are not part of the calculated number of atoms in the shortest path. Examples of compounds with a 2–8 atom shortest path linkage include but are not limited to the compounds exemplified in the experimental section.

As used herein, an "S-sulfonamido" group refers to a —S(=O)2 NR8R9 group with R8 and R9 as defined herein.

As used herein, a "silyl" group refers to a —Si(R7)3, with R7 as defined herein.

As used herein, a "sulfinyl" group refers to a —S(=O)—R7 group, with R7 as defined herein and, in addition, as a bond only; i.e., —S(O)—.

As used herein, a "sulfonyl" group refers to a —S(=O)2-R7 group, with R7 as defined herein and, in addition as a bond only; i.e., —S(O)2-.

As used herein, a "thioalkoxy" group refers to both an S-alkyl and an —S-cycloalkyl group, as defined herein.

As used herein, a "thioaryloxy" group refers to both an —S-aryl and an —S-heteroaryl group, as defined herein.

As used herein, a "thiocarbonyl" group refers to a —C(=S)—R7 group, with R7 as defined herein.

As used herein, a "thioheteroalicycloxy" group refers to a heteroalicyclic-S— group with heteroalicyclic as defined herein.

As used herein, a "thioheteroaryloxy" group refers to a heteroaryl-S— group with heteroaryl as defined herein.

As used herein, a "thiohydroxy" group refers to an —SH group.

As used herein, a "trihalomethanecarbonyl" group refers to an X3CC(=O)— group with X as defined above.

As used herein, a "trihalomethanesulfonamido" group refers to a X3CS(=O)2NR8-group with X and R8 as defined herein.

As used herein, a "trihalomethanesulfonyl" group refers to an X3CS(=O)2-groups with X as defined above.

As used herein, a "trihalomethyl" group refers to a —CX3 group wherein X is a halo group as defined herein.

As used herein, a "ureido" group refers to a —NR8C(=O)NR9R10 group with R8, R9 and R10 as defined herein.

Any compound of the invention which modulates, or regulates, protein tyrosine enzyme activity in a signaling pathway may be used in the therapeutic methods of the invention. In a preferred embodiment, the activity of the compound is sufficiently specific for the particular protein tyrosine enzyme pathway so that the compound does not interfere with the function of other enzymatic activity, including other tyrosine enzyme activity, in the cell.

The compounds of the present invention may be readily synthesized using published methods in organic chemistry as found in such reference books as Larock "Comprehensive Organic Transformations" VCH Publishers, Inc.:New York, 1989 or March "Advanced Organic Chemistry", 3rd Ed., Wiley-Interscience:New York, 1985. Synthesis of a variety of trifluoromethysulfonyl and trifluoromethyl sulfamidyl compounds is exemplified in the examples section below.

Monofluoro sulfur compounds may be prepared using literature methods, e.g., Purrington et al., 1987, Tetrahedron Letters, 28:3901. Trifluoro sulfur compounds may be synthesized using methods such as disclosed in U.S. Pat. No.

5,480,568, the contents of which are hereby incorporated by reference in their entirety into the present application. See particularly columns 9 and 10.

Monofluoro thioethers may be oxidized to monofluoro sulfoxides using N-bromosuccinamide (NBS) as described by More et al., 1977, Synthesis, 791–792; or Lal., 1993, J. Org. Chem. 58:2791–2796. Monofluoro thioethers may be oxidized to monofluoro sulfoxides using m-chloroperbenzoic acid (MCPBA) as described by McCarthy et al., 1985, J. Amer. Chem. Soc. 107:735–737 or Wnuk et al., 1990, J. Org. Chem. 55:4757–4760. Difluoro thioethers may be oxidized to difluoro sulfoxides using chlorine in water, see Moore, 1979, J. Org. Chem. 44:1708–171 1. Trifluoro thioethers may be oxidized to trifluorosulfoxides using t-butyl hypochlorite in methanol as described by Haley et al., 1976, J. Chem. Soc. Perkin Trans. 1 525–532. Alternatively, aqueous hydrogen peroxide in acetic acid may be used, see Orda et al., 1965, J. Gen. Chem. USSR (Engl. Trans.) 35:1631–1637. The contents of all of which are hereby incorporated by reference in their entirety into the subject application.

Monofluoro thioethers may be oxidized to monofluoro sulfonyls using m-chloroperbenzoic acid (MCPBA) as described by Lal., 1993, J. Org. Chem. 58:2791–2796, McCarthy et al., 1985, J. Amer. Chem. Soc. 107:735–737, Gregory et al., 1990, J. Med. Chem. 33:2569–2578, Wnuk et al., 1990, J. Org. Chem. 55:4757–4760, McCarthy et al., 1990, Tetrahedron Lett. 31:5449–5452, Inbasekaran et al, 1985, J. Chem. Soc. Chem. Comm. 10:678–679, Uno et al., 1994, Bull. Chem. Soc. Jap. 67:1441–1448, Matthews et al., 1994, Org. Prep. Proced. Int. 26:605–608 or Robins et al., 1993, J. Org. Chem. 58:3800–3801. The oxidizing agent may be potassium persulfate, K2S208, as described in Rheude et al., 1985, Chem. Ber. 118:2208–2219. Difluoro thioethers may be oxidized to difluoro sulfonyls using hydrogen peroxide, see Moore, 1979, J. Org. Chem. 44:1708–1711, Hine et al., 1960, J. Amer Chem. Soc. 82:6178–6181 or Stahly, 1989, J. Fluorine Chem. 43:53–66. Trifluoro thioethers may be oxidized to trifluorosulfonyls using aqueous hydrogen peroxide in acetic acid, see Orda et al., 1965, J. Gen. Chem. USSR (Engl. Trans.) 35:1631–1637, Nodiff et al., 1960, J. Org. Chem. 25:60–65, Chem et al., 1993, J. Chem. Soc. Chem. Comm. 11:918–919. In addition, trifluoro thioethers may be oxidized to trifluoro sulfonyls using chromium trioxide, see DE 682971, U.S. Pat. No. 2,108,606, Beaumont et al., 1991, J. Fluorine Chem. 52:295–300 or Bernasconi et al., 1982, J. Amer. Chem. Soc. 104:7248–7257. The contents of all of which are hereby incorporated by reference in their entirety into the subject application.

The compounds and pharmaceutical compositions of the invention can be used, to inhibit a variety of important therapeutic targets whose cellular activity is regulated by phosphorylation or binding of phospho-derivatives including phosphotyrosine. The compounds and pharmaceutical compounds are particularly useful in mammals including humans, for treating, alleviating or preventing diseases including but not limited to diabetes mellitus; immune disorders in which cytokine signal transduction is deficient specifically anemia and immunodeficiency; rheumatoid arthritis; neurodegenerative diseases; cancer, particularly solid tumors, such as glioma, melanoma, Kaposi's sarcoma, hemangioma and ovarian, breast, lung, pancreatic, liver, prostate, colon and epidernoid cancer, in which the malignant cells proliferate and/or metastasize as a result of uncontrolled signal transduction mediated by growth factors; infectious diseases associated with PTPases; or osteoporosis.

Designing Phosphate Mimics Based on Crystal Structures and Molecular Modeling

Published crystallographic studies of a number of phosphatases have revealed a highly similar active-site structure. (Barford et al., 1994, Science 263:1397–1404; Jia, et al. Science 268 (1995) 1754–1758; Stuckey et al. Nature 370 (1994) 571–575: Schubert et al. Saper, Protein Science 4 (1995) 1904–1913; Fauman et al. J. Biol. Chem. 271 (1996) 18780–18788; Bilwes et cal. Nature 382 (1996) 555–559, Hoffmann et al. J. Biol. Chem. 272 (1997) 27505–27508; Hof et al. Cell 92 (1998) 441–450; Yuvaniyama et al Science 272 (1996) 1328–1331; Fauman et al. Cell 93 (1998) 617–625; Su et al. Nature 370 (1994) 575–578; Zhang et al. Biochemistry 33 (1994) 11097–11105; Zhang et al. J. Mol. Biol. 238 (1994) 281–283; Zhang et al. J. Biol. Chem. 273 (1998) 21714–21720; Puius et al. Proc. Natl. Acad. Sci. USA 94 (1997) 13420–13425; Burke et al. Biochemistry 35 (1996) 15989–15996.) The signature motif CXXXXXR in these tyrosine phosphatases forms a remarkably similar phosphate binding site in the three-dimensional structure despite, in some cases, little or no sequence homology in the catalytic domain. Clearly, the conserved signature motif, which recognizes the phosphoryl group in a similar way, dictates the common catalytic mechanism of PTPs. In addition, the crystal structure of PTPlB complexed with a high affinity substrate (DADEpYL-NH2) revealed significant ligand-protein interactions occurring outside the catalytic site. (Jia, et al. Science 268 (1995) 1754–1758.) These interactions between the peptide and the surface (Y-loop) in PTPs may be important to the substrate specificity as well as potency. Another crystallographic study of PTPlB complexed with a small molecule BPPM identified a second aryl phosphate-binding site in PTPlB. (Puius et al. Proc. Natl. Acad. Sci. USA 94 (1997) 13420–13425.) This is a low-affinity, noncatalytic binding site adjacent to the active site. These results suggest that potent and selective PTP inhibitors could be developed by including these additional surface interactions.

In one method a design strategy may focus on the development of PTP inhibitors which contain not only a phosphate mimic but also components for additional interactions outside the active site for higher affinity and specificity. Using the techniques of computational chemistry including de novo design, pharmacophore development, and database search, several candidate PTP inhibitors were chosen for screening. Among them a trifluoromethylsulfonyl compound was determined as the initial lead. Subsequently, analogs of it were synthesized and many of these analogs showed good potency as well as selectivity. The most critical component in these compounds is the trifluoromethylsulfonyl moiety and its derivative trifluoromethylsulfonamido that mimic the effects of the phosphate group in phosphotyrosine. These moieties were used as phosphate mimics. Molecular modeling studies indicated that these phosphate mimics could effectively replicate the important hydrogen bonding interactions of the parent phosphate with PTPs. The noncharged nature of our phosphate mimics were of particular interest since most of the membrane permeability problems associated with known PTP inhibitors are from a charged phosphate mimic.

A direct comparison of our three compounds shown in the table below indicated that a change of the R group from $CF_3SO_2NH-$ to $CH_3SO_2NH-$ resulted in a dramatic decrease in activity, and, furthermore, a change from $CF_3SO_2NH$ to $NH_2$ led to a complete loss of activity. These results provide a strong support to our hypothesis that the trifluoromethyl sulfonyl group is a phosphate mimic.

| | $IC_{50}$ ($\mu$M) | | | | | | |
|---|---|---|---|---|---|---|---|
| compound R = | 1B | SHP2 | Epsilon | MEG2 | Sigma | Beta | Mu |
| $CF_3SO_2NH$— | 10.6 | 3.4 | 16.9 | 39.4 | 44 | 12.1 | 4 |
| $CH_3SO_2NH$— | 51.9 | 33.6 | 51.4 | >100 | 22 | 62.6 | >100 |
| $NH_2$ | >100 | >100 | >100 | >100 | >100 | >100 | >100 |

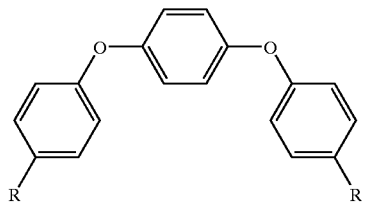

In addition to the phosphate mimic moiety, our analogs exemplified contain structural components expected to interact with either the surface Y-loop or the second pY binding site. These structural components were designed mainly based upon the known crystal structures. The molecular modeling studies used in the present invention have been performed using commercial software packages Sybyl (Tripos, Inc.) and Insight II (Molecular Simulations). The contents of each of these programs is hereby incorporated by reference into the subject application.

Pharmaceutical Compositions and Uses

A "pharmaceutical composition" refers to a mixture of one or more of the compounds described herein, or physiologically acceptable salts, solvates, or prodrugs thereof, with other chemical components, such as physiologically acceptable carriers and excipients. The purpose of a pharmaceutical composition is to facilitate administration of a compound to an organism.

As used herein, "pharmaceutically acceptable salt" refers to those salts which retain the biological effectiveness and properties of the compound and which are obtained by reaction with acids or bases. Examples as such include but are not limited to ethanesulfonic acid, hydrobromic acid, hydrochloric acid, methanesulfonic acid, nitric acid, p-toluenesulfonic acid, phosphoric acid, salicylic acid, sulfuric acid, and the like. Others are known in the pharmaceutical arts.

As used herein, a "physiologically acceptable carrier" refers to a carrier or diluent that does not cause significant irritation to an organism and does not abrogate the biological activity and properties of the administered compound.

A "prodrug" refers to an agent which is converted into the parent drug or active form in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention wherein it is administered as an ester (the "prodrug") to facilitate transmittal across a cell membrane where water solubility is not beneficial, but then it is metabolically hydrolyzed to the carboxylic acid once inside the cell where water solubility is beneficial. In addition, compounds of the present invention may be modified by the addition of one or more amino acids. Cleavage esters, such as phosphate esters, and amino acids are known in the art.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols. Excipients well known in the art can be found, inter alia, in "Remington's Pharmaceutical Sciences", Mack Publishing Co., Easton, Pa.

In addition to the above compounds and their pharmaceutically acceptable salts, the present invention is further directed, where applicable, to solvated as well as unsolvated forms of the compounds (e.g., hydrated forms) having the ability to regulate and/or modulate phosphatase activity.

The compounds described above may be prepared by any process known to be applicable to the preparation of chemically-related compounds. Suitable processes are illustrated by the representative examples provided, infra. Necessary starting materials may be obtained commercially or prepared by standard procedures of organic chemistry.

The formulations of the present invention normally will consist of at least one compound of formula I, II or III mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material, which serves as a vehicle, excipient or medium for the active therapeutic substance.

Some examples of the diluents or carriers which may be employed in the pharmaceutical compositions of the present invention are lactose, dextrose, sucrose, sorbitol, mannitol, propylene glycol, liquid paraffin, white soft paraffin, kaolin, microcrystalline cellulose, calcium silicate, silica polyvinylpyrrolidone, cetostearyl alcohol, starch, gum acacia, calcium phosphate, cocoa butter, oil of theobroma, arachis oil, alginates, tragacanth, gelatin, syrup B.P., methyl cellulose, polyoxyethylene sorbitan monolaurate, ethyl lactate and propylhydroxybenzoate, sorbitan trioleate, sorbitan sesquioleate and oleyl alcohol.

Routes Of Administration

As used herein, "administer" or "administration" refers to the delivery of a compound, salt, solvate or prodrug of the present invention or of a pharmaceutical composition containing a compound, salt, solvate or prodrug of this invention to an organism for the purpose of prevention or treatment of a disorder associated a phosphate binding protein including an abnormal enzyme related cellular signal transduction.

As used herein, a "disorder associated with an abnormal enzyme related cellular signal transduction" refers to a condition characterized by inappropriate, i.e., under or, more commonly, over, catalytic activity on the part of an enzyme. Inappropriate catalytic activity can arise as the result of either: (1) enzyme expression in cells which normally do not express such enzymes; (2) increased enzyme expression leading to unwanted cell proliferation, differentiation and/or growth; or, (3) decreased enzyme expression leading to unwanted reductions in cell proliferation, differentiation and/or growth. Over-activity of enzymes includes amplification of the gene encoding a particular enzyme or production of a level of enzyme activity which can correlate with a cell proliferation, differentiation and/or growth disorder (that is, as the level of the enzyme increases, the severity of one or more of the symptoms of the cellular disorder increases). Underactivity is, of course, the converse, wherein the severity of one or more symptoms of a cellular disorder increase as the level of the enzyme decreases.

As used herein, the terms "inhibit", "inhibiting" and "inhibition" of the activity of a phosphate binding protein refer to a method for reducing the activity either in an in vitro assay or in vivo system.

As used herein, the terms "modulate", "modulating" and "modulation" of the activity of a phosphate binding protein refer to a method for altering the activity either in an in vitro assay or in vivo system. The activity may be reduced or increased depending on the particular system.

As used herein, the terms "prevent", "preventing" and "prevention" refer to a method for barring an organism from in the first place acquiring a disorder associated with phosphate binding protein activity including kinase or phosphatase activity which may be related to cellular signal transduction.

As used herein, the terms "regulate", "regulating" and "regulation" of activity of a phosphate binding protein refer to a method for controlling the phosphate binding activity either in an in vitro assay or in vivo system. The term includes upregulation and downregulation.

As used herein, the terms "treat", "treating" and "treatment" refer to a method of alleviating or abrogating a disease and/or its attendant symptoms to provide a therapeutic benefit including those associated with a phosphate binding protein including an abnormal enzyme related cellular signal transduction disorder. With regard particularly to cancer, these terms simply mean that the life expectancy of an individual affected with a cancer will be increased or that one or more of the symptoms of the disease will be reduced.

The term "organism" refers to any living entity comprised of at least one cell. A living organism can be as simple as, for example, a single eukaryotic cell or as complex as a mammal, including a human being.

(Suitable routes of administration include, without limitation, oral, rectal, intransal, transmucosal, or intestinal administration; parentheral including but not limited to, intramuscular, subcutaneous, intramedullary, intrathecal, direct intraventricular, intravenous, intraperitoneal, or intraocular injections; transdermal, topical and vaginal application, and the like. Dosage forms include but are not limited to tablets, troches, dispersions, suspensions, lyophilized powders or solids suitable for reconstitution, suppositories, solutions, capsules, creams, patches, lotions, minipumps and the like.

Alternately, one may administer the compound in a local rather than systemic manner, for example, via injection (e.g., bolus injection) of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Composition/Formulation

The pharmaceutical compositions of the present invention may be manufactured by processes well known in the art, for example and without limitation by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants arc generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can, for instance, be prepared by adding a compound of this invention to a solid excipient, optionally grinding the resulting mixture and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner. For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds of this invention may be formulated for parenteral administration by injection, e.g., by bolus injection or continuous intravenous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives such as, for example, a sparingly soluble salt.

A pharmaceutical carrier for the hydrophobic compounds may be a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:0.5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied, for example, other low toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Numerous sustained release products are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

In addition to the common dosage forms set out above, the compounds of the present invention may also be administered by controlled release means and/or delivery devices including Alzet__osmotic pumps which are available from Alza Corporation. Suitable delivery devices are described in U.S. Pat. Nos. 3,845,770; 3,916,899; 3,536,809; 3,598,123; 3,944,064 and 4,008,719, the disclosures of which are incorporated in their entirety by reference herein.

Many of the phosphatase modulating compounds of the invention may be provided as salts with pharmaceutically compatible counterions. As previously discussed, pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Dosage

Pharmaceutical compositions suitable for use in the present invention include compositions wherein the active ingredients are contained in an amount effective to achieve its intended purpose. The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor; (2) inhibiting (that is, slowing to some extent, preferably stopping) tumor metastasis; (3) inhibiting to some extent (that is slowing to some extent, preferably stopping) tumor growth; and/or, (4) relieving to some extent (or preferably eliminating) one or more symptoms associated with the cancer. Determination of the therapeutically effective amount of a compound of this invention is well within the capability of those skilled in the art, especially in light of the detailed disclosure provided herein.

The therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the enzyme activity). Such information can be used to more accurately determine useful doses in humans or in other subjects.

Thus, a therapeutically effective dose refers to that amount of the compound that results in amelioration of symptoms in or a prolonged survival of a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The ratio of toxic does to therapeutic effective, e.g., LD50/ED50, is the therapeutic index. Compounds which exhibit high therapeutic indices are preferred. The data obtained from cell culture assays and animal studies can be used in formulating a range of dosages for use in humans. A dosage preferably lies within a range of circulating concentrations that include the ED50 and exhibits little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1, p.1), hereby incorporated by reference.

Dosage amount and interval may be adjusted individually to provide plasma levels of the active moiety which are sufficient to maintain the enzyme modulating effects, known as the minimal effective concentration (MEC). The MEC will vary for each compound but can be estimated from in vitro data; for example, without limitation, the concentration necessary to achieve a 50–90% inhibition of the tyrosine enzyme using the assays described herein. Dosages necessary to achieve the MEC will depend on individual characteristics and route of administration. HPLC assays or bioassays can be used to determine plasma concentrations.

Dosage intervals can also be determined using the MEC value. Compounds should be administered using a regimen which maintains plasma levels above the MEC for 10–90%, preferably between 30–90% and most preferably between 50–90% of the time.

Usual patient dosages for systemic administration of the therapeutics range from 1 to 2000 mg/day, commonly from 1 to 250 mg/day, and typically from 10 to 150 mg/day. Stated in terms of patient body weight, usual dosages range from 0.02 to 25 mg/kg/day, commonly from 0.02 to 3 mg/kg/day, typically from 0.2 to 1.5 mg/kg/day. Stated in terms of patient body surface areas, usual dosages range from 0.5 to 1200 mg/m$^2$/day, commonly from 0.5 to 150 mg/m$^2$/day, typically from 5 to 100 mg/m2/day. Usual average plasma levels should be maintained within 50 to 5000 µg/ml, commonly 50 to 1000 µg/ml, and typically 100 to 500 µg/ml.

In cases of local administration or selective uptake, the effective local concentration of the drug may not be related to plasma concentration.

The amount of a particular composition administered will, of course, be dependent on the subject being treated, on the subject's weight, the severity of the affliction, the manner of administration and the judgment of the prescribing physician.

Desirable blood levels may be maintained by a continuous infusion of the compound; plasma level can be monitored by HPLC. It should be noted that the attending physician would know how and when to terminate, interrupt or adjust therapy to lower dosage due to toxicity, or bone marrow, liver or kidney dysfunctions. Conversely, the attending physician would also know to adjust treatment to higher levels if the clinical response is not adequate and toxicity is not a problem.

The size of a prophylactic or therapeutic dose of a compound in the acute or chronic management of disease will vary with the severity of the condition to be treated and the route of administration. Again, it should be noted that the clinician or physician would know when to interrupt and/or adjust the treatment dose due to toxicity or bone marrow, liver or kidney dysfunctions. The dose, and perhaps the dosage frequency, will also vary according to the age, body weight, and response of the individual patient. In general, as discussed above, the total daily dose ranges for the compounds of the invention for the majority of the disorders described herein, is from about 0.02 to about 25 mg/kg patient. Preferably, a daily dose range should be between about 0.02 to about 3 mg/kg, while most preferably a daily dose range should be between about 0.2 to about 1.5 mg/kg per day. It is further recommended that infants, children, and patients over 65 years, and those with impaired renal, or hepatic function, initially receive low doses and that they be titrated based on individual clinical response(s) and blood level(s). It may be necessary to use dosages outside the above ranges in some cases; situations requiring such a decision will be apparent to those of ordinary skill in the art.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of the labeling approved by the U.S. Food and Drug Administration ("FDA") for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

Uses of the Compounds

In one embodiment, any compound of the invention which inhibits, modulates, or regulates, a phosphate binding protein may be used in the therapeutic methods of the invention. This includes enzymes in a signaling pathway. In a preferred embodiment, the activity of the compound is sufficiently specific for the particular enzyme pathway so that the compound does not interfere with the function of other enzymatic activity in the cell.

As discussed above, the invention encompasses the use of certain small-molecules as, inter alia, phosphate mimics. In one embodiment, these compounds are neither highly ionic, charged nor peptide-like in nature. They have a molecular weight of less than 2000 daltons and preferably contain a trifluoromethylsulfonyl or trifluoromethylsulfonamido moiety or an equivalent fluoro sulfonyl or fluoro sulfoxide. Thus, more specifically, this invention provides a method for inhibiting, regulating or modulating the activity of a phosphate binding protein in a cell which comprises administering to the cell an effective amount of a compound with a molecular weight less than 2000 daltons, or a pharmaceutically acceptable salt or solvate thereof. The compound contains at least one functional group selected from the group consisting of $C(R^{11})F_aSO_bZ—$, and $R^{12}SO_bC(R^{11})F_m—$; wherein a is 1, 2 or 3 and b is 1 or 2 and m is 1 or 2; Z is C or N; wherein $R^{11}$ may be present or absent and if present is independently H, halo, C1–C4 alkyl, $C_2$–$C_4$ alkenyl or C1–C4 haloalkyl, which may be substituted or unsubstituted; wherein $R^{12}$ is C1–C3 haloalkyl, C1–C3 alkyl which may be substituted or unsubstituted, or N which may be substituted or unsubstituted.

In this embodiment, the compound regulates, inhibits or modulates the activity of the phosphate binding protein.

In one embodiment of the method above the compound has the formula $C(R^{11})F_aSO_bZR^{13}$ or $R^{12}SO_bC(R^{11})F_mR^{13}$. $ZR^{13}$ or $R^{13}$ may be an amide, an amine, an ester, an ether, a monocyclic heterocycle, a polycyclic heterocycle, an acyclic hydrocarbon, a monocyclic aliphatic hydrocarbon, a polycyclic aliphatic hydrocarbon, a monocyclic aromatic hydrocarbon, a polycyclic aromatic hydrocarbon, a macrocycle, a nucleoside, a nucleotide, an oligoamide, an oligoamine, an oligoester, an oligoether, an oligonucleotide, an oligosaccharide, an oligourea, an oligourethane, a peptide, a peptide oligomer, a saccharide, a steroid, a urea, a urethane, which may be substituted or unsubstituted.

In a preferred embodiment, $ZR^{13}$ or $R^{13}$ is a monocyclic heterocycle, a polycyclic heterocycle, a monocyclic aromatic hydrocarbon, a polycyclic aromatic hydrocarbon which may be substituted or unsubstituted. Alternatively, Z is methylene which may be substituted or unsubstituted. The molecular weight of the compound maybe less than 1000 daltons, preferably less than 650 daltons.

In the method above, the phosphate binding protein may be a phosphohistidine phosphoserine, phosphothreonine or phosphotyrosine binding protein. It may also be an enzyme. The enzyme may be a metalloproteinase or an enzyme that forms a covalent phosphocysteine intermediate. The enzyme may be a phosphatase or a kinase such as a histidine kinase, a serine kinase, a threonine kinase or a tyrosine kinase. It may also be associated with protein tyrosine phosphatase signal transduction.

In one embodiment of the method, the phosphate binding protein is a dual-specificity phosphatase, histidine/lysine phosphatase, low-molecular weight phosphatase, a phosphotyrosine binding (PTB) domain, a pleckstrin homology domain, a Ser/Thr phosphatase, a Src homology 2 (SH2) domain, a protein tyrosine phosphatase, or a tyrosine-specific phosphatase. The phosphatase may be Alpha phosphatase, Beta phosphatase, cdc25 phosphatase, cdi phosphatase, CD45 phosphatase, DEP1 phosphatase, Epsilon phosphatase, LAR phosphatase, MAP kinase phosphatase, MEG2 phosphatase, Mu phosphatase, 1B phosphatase, PEST phosphatase, PP2 β (calcineurin) phosphatase, SHP1 phosphatase, SHP2 phosphatase, Sigma phosphatase, T-cell phosphatase, VH1-like phosphatase, VHR phosphatase, Yersinia phosphatase, or Zeta phosphatase.

Preferably, the activity of the phosphate binding protein is determined by an in vitro (either biochemical or cellular) assay. In addition, preferably the cell is a mammalian cell, more preferably a human cell.

Methods Of Treatment

The invention includes a method for treating a protein tyrosine phosphatase signal transduction associated disorder in a mammal which comprises a administering to the mammal therapeutically effective amount of a compound having the formula:

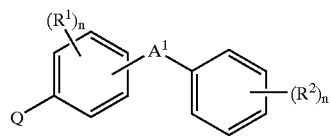

(I)

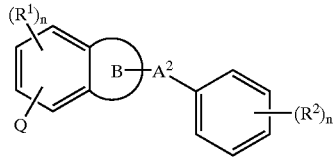

(II)

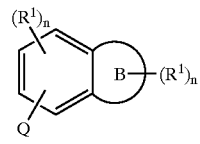

(III)

or a pharmaceutically acceptable salt or solvate thereof, wherein:

Q is $CF_3SO_2$, $CF_3SO_2NR^3$, $CF_3SO_2R^4$ or $CF_3SO_2N(R^3)R^4$, wherein $R^3$ is H, alkoxy, acyl or $C_1$–$C_3$ alkyl, each of which may be substituted or unsubstituted, and $R^4$ is methylene which may be substituted or unsubstituted;

each R1 is independently C1–C3 alkyl, C1–C3 haloalkyl (for example, but not limited to, CF3, CC13), CN, (C=O)OR, (C=O)R5, H, halo, O(C=O)R, OR, OH, NHR, NH(C=O)OR, NH(C=O)R5, NO2, NHSO2R5, SO2R5, R4SO2CF3 or tetrazole, wherein R5 is CF3, C1–C3 alkyl, NHR and wherein R is H, C1–C3 alkyl, aryl or heteroaryl, which may be substituted or unsubstituted;

each R2 is independently C1–C3 alkyl, C1–C3 haloalkyl (for example, but not limited to, CF3, CC13), CN, (C=O)OR, (C=O)R5, H, halo, O(C=O)R, OR, OH, NHR, NH(C=O)OR, NH(C=O)R5, NO2, NHSO2R5, SO2R5, tetrazole, or X1-R6-X2 wherein X1 may be present or absent and if present is O, N, (C=O), (C=O)NH, NH(C=O), SO2NH, NHSO2; R6 is C1–3 alkylene which may be substituted or unsubstituted; X2 is CF3, (C=O)OR, (C=O)R5, H, NH(C=O)R5, NH(C=O)OR, NHSO2R5, NRR3, O(C=O)R, OR, SO2R5, tetrazole;

each n is independently from 0 to 3;

Ring B is an aryl, carbocyclic, heteroaryl, heterocyclic or phenyl ring which may be substituted or unsubstituted;

A1 is a linkage in which the shortest path is 2–8 atoms in length wherein the atoms in the linkage are carbon which may be substituted or unsubstituted or the carbon replaced with a single nitrogen, oxygen or sulfur, or combination of nitrogen, oxygen and sulfur; the linkage may be or may contain an aryl, carbocyclic, heteroaryl, heterocyclic or a phenyl ring, which may be directly in the linkage or appended to the linkage; the linkage may be acylalkyl, alkenylene, alkoxy, alkoxyalkyl, alkoxyamino (—O—R—N—), alkoxyarylalkoxy (—O—R—Ar—R—O—), alkoxyarylalkyl (—O—R—Ar—R—), alkoxyarylamino (—O—R—Ar—N—), alkoxyaryloxyalkyl (—O—R—Ar—O—R—), alkylamino, alkylaminoalkyl, alkylaminoarylaminoalkyl (—R—N—Ar—N—R—), alkylaryl, alkylarylalkyl, alkylarylamino (—R—Ar—N—), alkylaryloxy (—R—Ar—O—), alkylene, alkylenediamine, alkylenedioxy, alkyloxy (—R—O—), alkyloxyaryl, alkyloxyarylalkyloxy (—R—O—Ar—R—O—), alkyloxyaryloxyalkyl (—R—O—Ar—O—R—), alkylsulfonylamino, alkylthio, alkylthioalkyl, alkynylene, N-sulfonamido (—N—SO2-R—), N-amido (—N—(C=O)—R—), aminoalkyl (—N—

R—), aminoalkylamino, aminoalkylarylalkyl (—N—R—Ar—R—), aminoalkylarylalkylamino (—N—R—Ar—R—N—), aminoalkylaryloxy (—N—R—Ar—O—), aminoalkyloxy (—N—R—O—), aminoaryl (—N—Ar—), aminoarylalkyl (—N—Ar—R—), aminoarylcarbonyl (—N—Ar—(C=O)—), aminoaryloxy (—N—Ar—O—), aminoaryloxyalkyl (—N—Ar—O—R—), aminoarylsulfonyl (—N—Ar—SO2-), aryl, arylamino, aryldioxy (—O—Ar—O—), aryldiamine (—N—Ar—N—), aryloxy, aryloxyalkyl (—O—Ar—R—), aryloxyamino (—O—Ar—N—), aryloxyaminoalkyl (—O—Ar—N—R—), aryloxycarbonyl (—O—Ar—(C=O)—), aryloxysulfonyl (—O—Ar—SO2-), benzimidazole, benzo[b]furan, benzo[b]thiophene, C-amido (—(C=O)—N—R—), carbonylarylamino (—(C=O)—Ar—N—), carbonylarylcarbonyl (—(C=O)—Ar—(C=O)—), carbonylaryloxy (—(C=O)—Ar—O—), chromene, cycloalkylene, disulfide, furan, haloalkyl, imidazole, imidazolidine, imidazoline, indole, isothiazole, isoxazole, morpholine, oxadiazole, oxazole, oxirane, parathiazine, phenothiazine, piperazine, piperidine, purine, pyran, pyrazine, pyrazole, pyrazolidine, pyrimidine, pyridine, pyrrole, pyrrolidine, quinoline, sulfonamido (—SO2-N—R), sulfonylalkyl, sulfonylarylamino (—SO2-Ar—N—), sulfonylaryloxy (—SO2-Ar—O—), sulfonylarylsulfonyl (—SO2-Ar—SO2-), thiadiazole, thiazole, thiophene, triazine, triazole, unsubstituted azeridine, ureido (—N—(C=O)—N—R—), which may be substituted or unsubstituted;

$A^2$ is a linkage in which the shortest path is 0–6 atoms in length wherein the atoms in the linkage are carbon which may be substituted or unsubstituted or the carbon replaced with a single nitrogen, oxygen or sulfur, or combination of nitrogen, oxygen and sulfur; the linkage may be or may contain an aryl, carbocyclic, heteroaryl, heterocyclic or a phenyl ring, which may be directly in the linkage or appended to the linkage; the linkage may be single atom C, O, S or N which may be substituted or unsubstituted; the linkage may be acylalkyl, alkenylene, alkoxy, alkoxyalkyl, alkoxyamino, alkoxyarylalkoxy, alkoxyarylalkyl, alkoxyarylamino, alkoxyaryloxyalkyl, alkylamino, alkylaminoalkyl, alkylaminoarylaminoalkyl, alkylaryl, alkylarylalkyl, alkylarylamino, alkylaryloxy, alkylene, alkylenediamine, alkylenedioxy, alkyloxy, alkyloxyaryl, alkyloxyarylalkyloxy, alkyloxyaryloxyalkyl, alkylsulfonylamino, alkylthio, alkylthioalkyl, alkynylene, N-sulfonamido, N-amido, aminoalkyl, aminoalkylamino, aminoalkylarylalkyl, aminoalkylarylalkylamino, aminoalkylaryloxy, aminoalkyloxy, aminoaryl, aminoarylalkyl, aminoarylcarbonyl, aminoaryloxy, aminoaryloxyalkyl, aminoarylsulfonyl, aryl, arylamino, ortho or para aryldioxy, substituted meta-aryldioxy, aryldiamine, aryloxy, aryloxyalkyl, aryloxyamino, aryloxyaminoalkyl, aryloxycarbonyl, aryloxysulfonyl, benzimidazole, benzo[b]furan, benzo[b]thiophene, C-amido, carbonylarylamino, carbonylarylcarbonyl, carbonylaryloxy, chromene, cycloalkylene, furan, haloalkyl, imidazole, imidazolidine, imidazoline, indole, isothiazole, isoxazole, morpholine, oxadiazole, oxazole, oxirane, parathiazine, phenothiazine, piperazine, piperidine, purine, pyran, pyrazine, pyrazole, pyrazolidine, pyrimidine, pyridine, pyrrole, pyrrolidine, quinoline, sulfonamido, sulfonylalkyl, sulfonylarylamino, sulfonylaryloxy, sulfonylarylsulfonyl, thiadiazole, thiazole, thiophene, triazine, triazole, unsubstituted azeridine, ureido, which may be substituted or unsubstituted.

In one embodiment, the compound is: Bis(4-Trifluoromethylsulfonylbenzyl)ether, 4-Trifluoromethylsulfonylbenzyl 4-trifluoromethylsulfonylphenyl ether, N,N-Bis(4-trifluoromethylsulfonylbenzyl)benzamide, 1,2-Bis(4-trifluoromethylsullfonylphenyl)ethane, N-(4-Trifluoromethylsulfonylbenzyl)-4-trifluoromethylsulfonylbenzamide, N-(4-Trifluoromethylsulfonylbenzyl)benzamide, Bis(4-Trifluoromethylsulfonylphenyl) disulfide, Bis-(2-Nitro-4-trifluoromethylsulfonylphenyl)disulfide, 3,5-Bis-(4-trifluoromethanesulfonyl-phenoxy)-benzoic acid methyl ester, [3,5-Bis-(2-nitro-4-trifluoromethanesulfonyl-phenoxy)-phenyl]-acetic acid methyl ester, 3,5-Bis-(2-nitro-4-trifluoromethanesulfonyl-phenoxy)-benzoic acid methyl ester, 1,3-Bis-(2-nitro-4-trifluoromethanesulfonyl-phenoxy)-cyclopentane, 4-Methyl-2,6-bis-(2-nitro-4-trifluoromethanesulfonyl-phenoxy)-benzoic acid methyl ester, 4-[2-(2-Nitro-4-trifluoromethanesulfonyl-phenoxy)-ethoxy]-benzoic acid methyl ester, 4-[3-(2-Nitro-4-trifluoromethanesulfonyl-phenoxy)-phenoxy]-benzoic acid, 1-(3,5-Bis-trifluoromethyl-phenyl)-5-(2-nitro-4-trifluoromethanesulfonyl-phenoxy)-1H-pyrazole-3-carboxylic acid methyl ester, {4-[4-(2-Nitro-4-trifluoromethanesulfonyl-phenoxy)-benzenesulfonyl]-phenoxy}-acetic acid ethyl ester, 4-[3-(4-Trifluoromethanesulfonyl-phenoxy)-phenoxy]-benzoic acid, {4-[4-(4-Trifluoromethanesulfonyl-phenoxy)-benzenesulfonyl]-phenoxy}-acetic acid ethyl ester, N-(3-Trifluoromethanesulfonyl-phenyl)-2-{2-[(3-trifluoromethanesulfonyl-phenylcarbamoyl)-methyl]-phenyl}-acetamide, N-(3-Trifluoromethanesulfonyl-phenyl)-2-{3-[(3-trifluoromethanesulfonyl-phenylcarbamoyl)-methyl]-phenyl}-acctamide, N-(3-Trifluoromethanesulfonyl-phenyl)-2-{4-[(3-trifluoromethanesulfonyl-phenylcarbamoyl)-methyl]-phenyl}-acetamide, 3,6-Bis-(morpholin-4-ylmethyl)-2,5-bis-(2-nitro-4-trifluoromethanesulfonyl-phenoxy)-benzene, [2,3-Bis-(2-nitro-4-trifluoromethanesulfonyl-phenoxy)-propyl]-dimethyl-amine, N-(2-Ethylamino-5-trifluoromethanesulfonyl-phenyl)-2-(4-methanesulfonyl-phenyl)-acetamide, 2-Hydroxy-5-(2-nitro-4-trifluoromethanesulfonyl-phenoxy)-terephthalic acid diethyl ester, {2-[(3-Trifluoromethanesulfonyl-phenylcarbamoyl)-methyl]-phenyl}-acetic acid, {3-[(3-Trifluoromethanesulfonyl-phenylcarbamoyl)-methyl]-phenyl}-acetic acid, {4-[(3-Trifluoromethanesulfonyl-phenylcarbamoyl)-methyl]-phenyl}-acetic acid, 3,5-Bis-(2-nitro-4-trifluoromethanesulfonyl-phenoxy)-benzamide, 3,5-Bis-(4-trifluoromethanesulfonyl-phenoxy)-benzoic acid, N-(4-Trifluoromethanesulfonyl-phenyl)-2-2-[(4-trifluoromethanesulfonyl-phenylcarbamoyl)-methyl]-phenyl}-acetamide, N-(4-Trifluoromethanesulfonyl-phenyl)-2-{3-[(4-trifluoromethanesulfonyl-phenylcarbamoyl)-methyl]-phenyl}-acetamide, N-(4-Trifluoromethanesulfonyl-phenyl)-2-{4-[(4-trifluoromethanesulfonyl-phenylcarbamoyl)-methyl]-phenyl}-acetamide, 4-(1-Ethyl-5-trifluoromethanesulfonyl-1H-benzoimidazol-2-yl)-benzoic acid methyl ester, 4-(1-Ethyl-5-trifluoromethanesulfonyl-1H-benzoimidazol-2-yl)-benzoic acid, 4-(1-Ethyl-5-trifluoromethanesulfonyl-1H-benzoimidazol-2-yl)-N-pyridin-4-yl-benzamide, 4-(1-Ethyl-5-trifluoromethanesulfonyl-1H-benzoimidazol-2-yl)-N-(4- methoxy-phenyl)-benzamide, 3-[4-(1-Ethyl-5-trifluoromethanesulfonyl-1H-benzoimidazol-2-yl)-benzoylamino]-benzoic acid ethyl ester, 4-(1-Ethyl-5-trifluoromethanesulfonyl-1H-benzoimidazol-2-yl)-N-(2-pyrrolidin-1-yl-ethyl)-benzamide, N-Ethyl-4-(1-ethyl-5-trifluoromethanesulfonyl-1H-benzoimidazol-2-yl)-benzamide, 1-Ethyl-5-trifluoromethanesulfonyl-1H-benzoimidazole-2-carboxylic acid, [2-(Benzoyl-butyl-amino)-2-(4-trifluoromethanesulfonyl-phenyl)-acetylamino]-acetic acid methyl ester, N-Benzyl-N-[butylcarbamoyl-(4-trifluoromethanesulfonyl-phenyl)-methyl]-benzamide, N-[Butylcarbamoyl-(4-trifluoromethanesulfonyl-phenyl)-methyl]-N-(2-hydroxy-ethyl)-benzamide, [2-(Acetyl-cyclopropyl-amino)-2-(4-trifluoromethanesulfonyl-phenyl)-acetylamino]-acetic acid ethyl ester, [2-(Acetyl-methyl-amino)-2-(4-trifluoromethanesulfonyl-phenyl)-acetylamino]-acetic acid ethyl ester, [2-(Benzoyl-cyclohexyl-amino)-2-(4-trifluoromethanesulfonyl-phenyl)-acetylamino]-acetic acid ethyl ester, N-Cyclohexyl-N-[(2,6-dimethyl-phenylcarbamoyl)-(4-trifluoromethanesulfonyl-phenyl)-methyl]-benzamide, [2-(Acetyl-propyl-amino)-2-(4-trifluoromethanesulfonyl-phenyl)-acetylamino]-acetic acid ethyl ester, [2-(Acetyl-cyclohexyl-amino)-2-(4-trifluoromethanesulfonyl-phenyl)-acetylamino]-acetic acid ethyl ester, {4-[4-(2-Nitro-4-trifluoromethanesulfonyl-phenoxy)-benzenesulfonyl]-phenoxy}-acetic acid, 4-[2-(2-Nitro-4-trifluoromethanesulfonyl-phenoxy)-ethoxy]-benzoic acid, 2,5-Bis-(2-nitro-4-trifluoromethanesulfonyl-phenoxy)-terephthalic acid diethyl ester, 1-[2,3-Bis-(2-nitro-4-trifluoromethanesulfonyl-phenoxy)-propyl]-piperidine, 4-[2,3-Bis-(2-nitro-4-trifluoromethanesulfonyl-phenoxy)-propyl]-morpholine, [2,3-Bis-(2-nitro-4-trifluoromethanesulfonyl-phenoxy)-propyl]-(2-nitro-phenyl)-amine, 1-(2-Nitro-phenylamino)-3-(2-nitro-4-trifluoromethanesulfonyl-phenoxy)-propan-2-ol, [2,3-Bis-(2-nitro-4-trifluoromethanesulfonyl-phenoxy)-propyl]-(4-nitro-phenyl)-amine, 1-(4-Nitro-phenylamino)-3-(2-nitro-4-trifluoromethanesulfonyl-phenoxy)-propan-2-ol, 4-[2-Hydroxy-3-(2-nitro-4-trifluoromethanesulfonyl-phenoxy)-propylamino]-benzenesulfonamide, 4-[2,3-Bis-(2-nitro-4-trifluoromethanesulfonyl-phenoxy)-propylamino]-benzenesulfonamide, Bis-{[4-(2-nitro-4-trifluoromethanesulfonyl)-phenoxy]-phenyl}sulfone, 2-[4-(Difluoro-methanesulfonyl)-phenyl]-5-naphthalen-2-yl-oxazole, [2-Nitro-4-(1,1,2,2-tetrafluoro-ethanesulfonyl)-phenyl]-p-tolyl-amine 1,2-Bis(4-trifluoromethylsulfonamidophenyl)ethane, 1,2-Bis(2-methyl-4-trifluoromethylsulfonamidophenyl)ethane, 1,3-Bis(4-trifluoromethylsulfonamidophenoxy)-2,2-dimethylpropane, 1,3-Bis(4-trifluoromethylsulfonamidophenoxy)propane, 1,4-Bis(4-trifluoromethylsulfonamidophenoxy)butane, 1,4-Bis(4-trifluoromethylsulfonamidophenoxy)benzene, 1-(4-Aminophenoxy)-4-trifluoromethylsulfonamidophenoxy benzene, Bis(4-trifluoromethylsulfonamidophenyl) ether, 1,3-Bis(4-trifluoromethylsulfonamidophenoxy)benzene, 2,5-Bis(4-trifluoromethylsulfonamidophenyl)-(1,3,4) oxadiazole, Bis(4-trifluoromethylsulfonamidophenyl)-1,4-diisopropylbenzene, 5-Trifluoromethanesulfonyl-1H-indole-2-carboxylic acid, 1-Methyl-5-trifluoromethanesulfonylamino-]1H-indole-2-carboxylic acid, (2-Methyl-5-trifluoromethanesulfonylamino-indol-1-yl)-acetic acid, 1-Methyl-5-trifluoromethanesulfonylamino-1H-indole-2-carboxylic acid phenylamide, 5-Trifluoromethanesulfonylamino-1H-indole-2-carboxylic acid phenylamide, 3-[(1-Methyl-5-trifluoromethanesulfonylamino-1H-indole-2-carbonyl)-amino]-benzoic acid, 3-[(5-Trifluoromethanesulfonylamino-1H-indole-2-carbonyl)-amino]-benzoic acid, 4-[(5-Trifluoromethanesulfonylamino-1H-indole-2-carbonyl)-amino]-benzoic acid, 4-[2-(2-Methyl-5-trifluoromethanesulfonylamino-indol-1-yl)-acetylamino]-benzoic acid, 3-[2-(2-Methyl-5-trifluoromethanesulfonylamino-indol-1-yl)-acetylamino]-benzoic acid, 4-{[2-(2-Methyl-5-trifluoromethanesulfonylamino-indol-1-yl)-acetylamino]-methyl}-benzoic acid, (2-Methyl-5-trifluoromethanesulfonylamino-indol-1-yl)-acetic acid tert-butyl ester, 1-Methyl-5-trifluoromethanesulfonylamino-1H-indole-2-carboxylic acid ethyl ester, 6-Trifluoromethanesulfonylamino-naphthalene-2-carboxylic acid, N,N-Bis[(6-carboxyl-naphthalen-2-yl) methyl] trifluoromethanesulfonamide, 6-[(Methyl-trifluoromethanesulfonyl-amino)-methyl]-naphthalene-2-carboxylic acid, 3-({6-[(Methyl-trifluoromethanesulfonyl-amino)-methyl]-naphthalene-2-carbonyl}-amino)-benzoic acid, 1-tert-Butoxycarbonylmethyl-5-trifluoromethanesulfonylamino-1H-indole-2-carboxylic acid ethyl ester, 1-Carboxymethyl-5-trifluoromethanesulfonylamino-1H-indole-2-carboxylic acid ethyl ester, 1-tert-Butoxycarbonylmethyl-5-trifluoromethanesulfonylamino-1H-indole-2-carboxylic acid, 1-Carboxymethyl-5-trifluoromethanesulfonylamino-1H-indole-2-carboxylic acid, 1-Carboxymethyl-5-(N,N-ditrifluoromethanesulfonyl)amino-1H-indole-2-carboxylic acid ethyl ester, 1-tert-Butoxycarbonylmethyl-5-(N,N-ditrifluoromethanesulfonyl)amino-1H-indole-2-carboxylic acid ethyl ester, 1-Carboxymethyl-5-(N,N-ditrifluoromethanesulfonyl)amino-1H-indole-2-carboxylic acid, 1-Cyclohexylmethyl-5-trifluoromethanesulfonylamino-1H-indole-2-carboxylic acid ethyl ester, 1-Benzyl-5-trifluoromethanesulfonylamino-1H-indole-2-carboxylic acid or 1-Cyclohexylmethyl-5-trifluoromethanesulfonylamino-1H-indole-2-carboxylic acid.

In addition, the invention is directed to a method for treating a disease in a mammal associated with a phosphate binding protein which comprises administering to a mammal in need thereof a therapeutically effective amount of a compound with a molecular weight less than 2000 daltons, or a pharmaceutically acceptable salt or solvate thereof, wherein the compound contains at least one functional group selected from the group consisting of $C(R^{11})F_aSO_bZ$—, and $R^{12}SO_bC(R^{11})F_m$—. In this embodiment, a is 1, 2 or 3 and b is 1 or 2 and m is 1 or 2; Z is C or N; $R^{11}$ may be present or absent and if present is independently H, halo, C1–C4 alkyl, $C_2$–$C_4$ alkenyl or C1–C4 haloalkyl, which may be substituted or unsubstituted; $R^{12}$ is C1–C3 haloalkyl, C1–C3 alkyl which may be substituted or unsubstituted, or N which may be substituted or unsubstituted; and a pharmaceutically acceptable carrier or excipient. Here, the compound treats the disease associated with the phosphate binding protein in the mammal.

Specifically, the phosphate binding protein is associated with cancer, a solid tumor, glioma, melanoma, Kaposi's sarcoma, hemangioma, ovarian cancer, breast cancer, lung cancer, pancreatic cancer, liver cancer, prostate cancer, colon cancer, or epidermoid cancer. In addition, the phosphate binding protein is associated with diabetics, neurological degenerative diseases, osteoporosis or a lymphatic function. Preferably, the phosphate binding protein is associated with lymphatic function is CD45. In addition, preferably the mammal is a human.

The phosphate mimic compounds disclosed herein may be used to treat and/or prevent cancer. Additional specific embodiments of the general method of treatment utilizing fluoro sulfonyl compounds may be found in the uses section above.

A compound of this invention can be administered to a veterinary or a human patient as such or in pharmaceutical compositions in which a therapeutically effective dose is mixed with suitable carriers or excipient(s) at doses to treat or ameliorate a variety of disorders, including solid cell tumor growth, including Kaposi's sarcoma, glioblastoma, and melanoma and ovarian, lung, mammary, prostate, pancreatic, colon and epidermoid carcinoma, diabetes, diabetic retinopathy, hemangioma and rheumatoid arthritis. A therapeutically effective dose further refers to that amount of the compound sufficient to result in amelioration of symptoms of uncontrolled vasculogenesis and angiogenesis. Techniques for formulation and administration of the compounds such as those of this invention may be found in "Remington's Pharmaceutical Sciences," Mack Publishing Co., Easton, Pa., latest edition.

The compounds and pharmaceutical compositions of the invention can be used for treating, preventing or controlling diabetes mellitus (including NIDDM, diabetes type I and II). The pathogenesis of diabetes generally involves insufficient or a total lack of insulin signal transduction. The paucity or absence of the insulin signal may be caused by a variety of factors such as a lack of insulin, loss of binding affinity, defective receptor or under expression of receptor. Insulin receptor activity can be modulated by inhibiting tyrosine phosphatases in the signaling using the compounds of the invention. Unlike currently available treatment modalities that are based on the insulin receptor, the insulin signal may be restored or stimulated in cells through the inhibition of dephosphorylating activity, even in the absence of insulin. The example of diabetes mellitus illustrates the principles of therapeutic applications of the compounds of this invention which may be applied to other disorders that implicate signal transduction by tyrosine enzymes, in particular, phosphotyrosine phosphatases.

The compounds and pharmaceutical compositions of the invention may be used to treat immune disorders in which cytokine signal transduction is deficient. Cytokines play a crucial role in hemopoiesis as well as coordinating immune and inflammatory responses. The compounds may be used to replace or enhance the activity of a cytokine in signaling the differentiation and proliferation of hemopoietic cells, as well as B and T cells in response to antigenic stimulation, and thus be useful for treating or preventing anemia and immunodeficiency.

The compounds may also be used as an antiinflammatory agent in treating or preventing disorders such as rheumatoid arthritis.

The compounds may also be therapeutically useful in treating or preventing neurodegenerative diseases by stimulating the growth and differentiation of neuronal cells which is regulated by neurotrophin-mediated signal transduction.

The compounds of this invention are useful for treating, alleviating or preventing neurologic degenerative diseases. A wide variety of PTPs arc expressed in the nervous system and there are more studies showing that RTPs play a role in growth cone guidance, neuronal survival, cell fate determination and connectivity (Chien, 1996, Neuron, 16(6): 1065–1068).

In addition the invention is directed to a method for treating, alleviating or preventing cancer in a human which comprises administering to a human in need thereof pharmaceutically effective amount of pharmaceutical composition comprising a compound of Formula (I), (II) or (III) as defined above. Specifically, the compounds and pharmaceutical compositions of the invention are useful for a variety of different cancers, particularly solid tumors, such as glioma, melanoma, Kaposi's sarcoma, hemangioma and ovarian, breast, lung, pancreatic, liver, prostate, colon and epidermoid cancer, in which the malignant cells proliferate and/or metastasize as a result of uncontrolled signal transduction mediated by growth factors. For example, over expression of a PTK, such as HER2 has been shown to correlate with the aberrant growth characteristics of tumor cells. Vasculogenesis and/or angiogenesis that facilitates tumor growth may also be inhibited by the compounds of this invention. The compounds may modulate signal transduction in these tumor cells so that normal growth characteristics are restored. The compounds may also be useful in treating psoriasis which is caused by excessive epidermal growth factor mediated signal transduction.

The compounds of this invention are useful for treating, alleviating or preventing Von Hippel Lindau Syndrome. (Maher et al., 1997, Medicine, 76(6):381–391).

The compounds of this invention are useful for immunomodulation. The overexpression of some protein-tyrosine phosphatases may result in the expression of a transformed phenotype. The human gene encoding the hematopocitic specific cytoplasmic protein tyrosine phosphatase, HePTP, was shown to be amplified and overexpressed in some myeloid malignancies and might contribute to abnormal myeloid cell growth (Zanke et al., 1994, Leukemia 8:236). Also CD45 has being shown to be required for T and B lymphocyte activation via their antigen receptors (Chan et al, 1994, Annu. Rev. Immunol. 12:555–592). Inhibition of CD45 could lead to immunosuppression.

The compounds of this invention are useful for treating, alleviating or preventing infectious diseases associated with PTPases. Thus, PTPase modulators may represent novel targets for antibiotic development. For instance Yersinia encodes a PTPase essential for its virulence. The genus Yersinia comprises three species of bacteria that are causative agents in human diseases ranging from gastrointestinal syndromes to the Bubonic Plague (Bolin and Wolf-Watz, 1988, Mol. Microbiol. 2(2):237)

The compounds of this invention may be useful for treating, alleviating or preventing osteoporosis. Bone remodeling requires regulated tyrosine phosphorylation mediated by specific protein tyrosine kinases and tyrosine phosphatases. Inhibition of PTPs would interfere with osteoclast resorption, resulting in reduced bone turnover and a net gain in bone mineral density (Rodan and Fleish, 1996, J. Clin. Invest. 97:2692–2696).

EXAMPLES

Compound Synthesis

FIG. 1 shows preferred chemical structures which are within the scope of this invention. The compounds shown are in no way to be construed as limiting the scope of this invention. These compounds and related compounds may be readily prepared using commercially available starting materials and standard synthetic methods. Moreover, compounds falling with the scope of the claimed invention that have not been exemplified may be readily tested using the methods described below to determine that they have the desired activity with a phosphate binding protein.

Abbreviations used in the Examples are as follows:

| | |
|---|---|
| g = | grams |
| mg = | milligrams |
| M = | molar |
| mL = | milliliters |
| N = | normal |
| mmol = | millimoles |
| equiv. = | equivalents |
| rt = | room temperature |
| hr = | hours |
| min = | minutes |
| TLC = | thin layer chromatography |
| MeOH = | methanol |
| EtOH = | ethanol |
| EtOAc = | ethyl acetate |
| DMF = | N,N-dimethylformamide |
| THF = | tetrahydrofuran |
| TEA = | triethylamine |
| Hex = | hexane |
| HCl = | hydrochloric acid |
| KOH = | potassium hydroxide |
| DMAP = | 4-dimethylaminopyridine |
| NaHCO3 = | sodium bicarbonate |
| DCM = | dichloromethane |
| POCl3 = | phosphorus oxychloride |
| AcOH = | acetic acid |
| MCPBA = | 3-chloroperbenzoic acid |
| TFA = | trifluoroacetic acid |
| NaH = | sodium hydride |
| NMR = | nuclear magnetic resonance spectroscopy |
| DMSO-d6 = | dimethyl-d6 sulfoxide |
| MS = | mass spectrometry |
| EI = | electron ionization |
| m/z = | mass to charge ratio |
| HPLC = | high pressure liquid chromatography |

In general the compounds of this invention may prepared in a variety of methods using commercially available starting materials using standard methods of synthesis. One skilled in the art would readily recognize following procedures are merely exemplary of methods to prepare the compounds of this invention.

Trifluoromethyl Sulfonyl Compounds

Example 1

Bis (4-trifluoromethylsulfonylbenzyl) ether (1). Sodium hydride (65 mg 60% dispersion oil, 1.58 mmol) was added to a solution of 4-(trifluoromethylthio)benzyl alcohol (300 mg, 1.44 mmol) in THF (10 mL) at rt. After stirring for 10 min, to the mixture was added 4-(trifluoromethylthio)benzyl bromide (410 mg, 1.51 mmol), stirring was continued overnight. The reaction was quenched with saturated ammonium chloride solution, extracted with EtOAc, washed with water and dried to give 0.5 g (85%) of bis(4-trifluoromethylthiobenzyl) ether as a yellow oil. 1HNMR (360 MHz, DMSO-d6) δ 7.70 (d, J=8.1 Hz, 4H), 7.53 (d, J=8.1 Hz, 4H), 4.65 (s, 4H, CH2OCH2). MS-EI m/z 398 [M+].

A mixture of bis (4-trifluoromethylthiobenzyl) ether (200 mg, 0.5 mmol) and MCPBA (600 mg, excess) in DCM (10 mL) was stirred at rt overnight. The reaction was quenched with saturated sodium bicarbonate solution, dried, concentrated and purified to give 230 mg (100%) 4-trifluoromethylsulfonylbenyl ether as a light yellow solid. 1HNMR (300 MHz, DMSO-d6) δ 8.13 (d, J=8.4 Hz, 4H), 7.84 (d, J=8.4 Hz, 4H), 4.84 (s, 4H, CH2OCH2). MS m/z 462 [M+].

Example 2

4-Trifluoromethylsulfonylbenzyl 4-trifluoromethylsulfonylphenyl ether (2). 4-(Trifluoromethylthio)benzyl alcohol (300 mg, 1.44 mmol) was coupled with 4-(trifluoromethylsulfonyl)chlorobenzene (370 mg, 1.51 mmol) using sodium hydride (65 mg, 60% dispersion in oil, 1.58 mmol) to give 400 mg of 4-trifluoromethylthiobenzyl 4-trifluoromethylsulfonylphenyl ether as a white solid. 1HNMR (360 MHz, DMSO-d6) δ 8.06 (d, J=8.4 Hz, 2H), 7.77 (d, J=8.4 Hz, 2H), 7.63 (d, J=8.4 Hz, 2H), 7.43 (d, J=8.4 Hz, 2H), 5.39 (s, 2H, OCH2).

4-trifluoromethylthiobenzyl 4-trifluoromethylsulfonylphenyl ether (66 gm, 0.16 mmol) was oxidized using 3-chloroperbenzoic acid (100 mg) to give 4-trifluoromethylsulfonylbenzyl 4-trifluoromethylsulfonylphenyl ether as a white solid. 1HNMR (360 MHz, DMSO-d6) δ 8.20 (d, J=8.6 Hz, 2H), 8.09 (d, J=8.6 Hz, 2H), 7.93 (d, J=8.6 Hz, 2H), 7.45 (d, J=8.6 Hz, 2H), 5.55 (s, 2H, OCH2). MS-EI m/z 448 [M+].

Example 3

N,N-Bis(4-trifluoromethylsulfonylbenzyl)benzamide (3). N-(4-trifluoromethylthiobenzyl)benzamide (100 mg, 0.32 mmol) was coupled with 4-(trifluoromethylthio) benzyl bromide (91 mg, 0.34 mmol) using sodium hydride (9.2 mg, 0.38 mmol) to give 130 mg (80%) of N,N-bis(4-trifluoromethylthiobenzyl)benzamide as a yellow oil. 1HNMR (360 MHz, DMSO-d6) δ 7.65 (m, 4H), 7.31–7.47 (m, 9H), 4.57–4.66 (m, 4H). MS-EI m/z 501 [M+].

N,N-bis-(4-trifluoromethylthiobenzyl)benzamide (100 mg, 0.2 mmol) was oxidized using 3-chloroperbenzoic acid (363 mg) to give 110 mg (100%) of N,N-bis(4-trifluoromethylsulfonylbenzyl)benzamide as a white solid. 1HNMR (360 MHz, DMSO-d6) δ8.04 (m, 4H), 7.87–7.89 (m, 2H), 7.67,7.69, 7.40–7.55 (7H), 4.77–4.81 (m, 4H). 565 [M+].

Example 4

1,2-Bis(4-trifluoromethylsulfonylphenyl)ethane (4). A mixture of 4-(trifluoromethylthio)bromobenzene (0.47 g, 1.82 mmol), bis (tri-N-butylstannyl)acetylene (0.5 g, 0.83 mmol) and tetrakis(triphenylphosphine)palladium(0) (0.05 g, 0.04 mmol) in THF (10 mL) under nitrogen was heated to reflux overnight. After the usual work-up, it was purified by column chromatography to give 0.24 g (80%) of 1,2-bis(4-trifluoromethylthiophenyl)acetylene as a white fluffy solid. 1HNMR (360 MHz, DMSO-d6) δ7.72–7.79 (m, 8H). MS-EI m/z 378 [M+].

1,2-bis(4-trifluoromethylthiophenyl)acetylene (200 mg, 0.53 mmol) was hydrogenated over 10% palladium on carbon (20 mg) in hexane (30 mL) at rt for 2 hours. The reaction was filtered and the filtrate was concentrated to give 0.21 g (100%) of 1,2-bis(4-trifluoromethylthiophenyl) ethane. 1HNMR (360 MHz, DMSO-d6) δ 7.61 (d, J=8.3 Hz, 4H), 7.40 (d, J=8.3 Hz, 4H), 2.97 (s, 4H, CH2CH2). MS-EI m/z 382 [M+].

A mixture of 1,2-bis(4-trifluoromethylthiophenyl)ethane (65 mg, 0.17 mmol) and 3-chloroperbenzoic acid (205 mg, excess) in DCM(10 mL) was stirred at rt overnight. The reaction was washed with saturated sodium bicarbonate solution, dried and concentrated to give 70 mg (95%) of 1,2-bis(4-trifluoromethylsulfonylphenyl)ethane. 1HNMR (360 MHz, DMSO-d6) δ 8.03 (d, J=8.3 Hz, 4H), 7.71 (d, J=8.3 Hz, 4H), 3.15 (s, 4H, CH2CH2). MS m/z 446 [M+].

Example 5

N-(4-Trifluoromethylsulfonylbenzyl)-4-trifluoromethylsulfonylbenzamide (5). A mixture of 4-(trifluoromethylthio)benzoic acid (300 mg, 1.35 mmol), 4-(trifluoromethylthio)benzylamine (308 mg, 1.49 mmol), benzotriazol-1-yl-oxytris-(dimethylamino)-phosphonium hexafluorophosphate (1.8 g, 4.05 mmol) and DMAP (198 mg, 1.62 mmol) in DMF (15 mL) was stirred at rt overnight. The reaction was diluted with ether, washed with water, dried and concentrated to give 520 mg (94%) of N-(4-trifluoromethylthiobenzyl)-4-trifluoromethylthiobenzamide as a white solid. 1HNMR (360 MHz, DMSO-d6) δ 9.27 (m, 1H, NH), 8.01 (d, J=8.0 Hz, 2H), 7.82 (d, J=8.0 Hz, 2H), 7.67 (d, J=8.0 Hz, 2H), 7.47 (d, J=8.0 Hz, 2H), 4.54 (d, J=5.8 Hz, 2H, NCH2). MS-EI m/z 411 [M+].

N-(4-trifloromethylthiolbenzyl)-4-trifloromethylthiobenzamide (300 mg, 0.73 mmol) was oxidized using 3-chloroperbenzoic acid (879 mg, excess) to give 310 mg (90%) of N-(4-trifluoromethylsulfonylbenzyl)-4-trifluoromethylsulfonylbenzamide. 1HNMR (360 MHz, DMSO-d6) δ 9.61 (m, 1H, NH), 8.28 (s, 4H), 8.10 (d, J=8.5 Hz, 2H), 7.79 (d, J=8.5 Hz, 2H), 4.69 (d, J=6.1 Hz, 2H, NCH2).

Example 6

N-(4-Trifluoromethylsulfonylbenzyl)benzamide (6). A mixture of 4-(trifluromethylthio)benzylamine (250 mg, 1.21 mmol), benzoyl chloride (178 mg, 1.27 mmol) and sodium bicarbonate (508 mg, 6.05 mmol) in DCM (15 mL) was stirred at rt until the reaction completed. The reaction was diluted with ethyl acetate, washed with brine and dried to give 372 mg (99%) of N-(4-trifluoromethylthiobenzyl) benzamide as a white solid. 1HNMR (360 MHz, DMSO-d6) δ 9.07 (m, 1H, NH), 7.88–7.90 (m, 2H), 7.66–7.68 (d, J=8.7 Hz, 2H), 7.45–7.56 (m, 5H), 4.53 (d, J=6.1 Hz, NCH2, 2H). MS-EI m/z 311 [M+].

N-(4-trifluoromethylthiobenzyl) benzamide (100 mg, 0.32 mmol) was oxidized using 3-chloroperbenzoic acid (391 mg, excess)) to give 110 mg (100%) of N-(4-trifluoromethylsulfonylbenzyl)benzamide as a white solid. 1HNMR (360 MHz, DMSO-d6) δ 9.18 (m, 1H, NH), 8.09 (d, J=8.7 Hz, 2H), 7.76 (d, J=8.7 Hz, 2H), 7.45–7.57 (m, 5H), 4,65 (d, J=6.1 Hz, NCH2, 2H). MS-EI m/z 343 [M+].

Example 7

Bis (4-trifluoromethylsulfonylphenyl) disulfide (7). Bis (4-trifluoromethylsulfonylphenyl) disulfide was purchased from Aldrich Chemicals (Milwaukee, Wis., USA) and used as is.

Example 8

Bis-(2-nitro-4-trifluoromethylsulfonylphenyl) disulfide (8). Bis-(2-nitro-4-trifluoromethylsulfonylphenyl) disulfide was purchased from ASINEX (Moscow, Russia) and used as is.

Example 9

3,5-Bis-(4-trifluoromethanesulfonyl-phenoxy)-benzoic acid methyl ester (9). A mixture of methyl 3,5-dihydroxybenzoate (100 mg, 0.595 mmol), 4-(trifluoromethylsulfonyl)chlorobenzene (291 mg, 2 equiv.) and potassium carbonate (330 mg, 4 equiv.) in DMF was heated to 100° C. overnight. The reaction was poured into water, extracted with EtOAc, washed the organic layer with water, brine, dried and concentrate. The residue was column chromatographed (1:2 EtOAc: Hex) to give 3,5-bis-(4-trifluoromethanesulfonyl-phenoxy)-benzoic acid methyl ester. 1HNMR (360 MHz, DMSO-d6) δ 8.12 (d, J=7.86 Hz, 4H), 7.67 (d, J=2.17 Hz, 2H), 7.61 (t, J=2.17 Hz, 1H), 7.42 (d, J=7.86 Hz, 4H), 3.85 (s, 3H, OCH3).

Example 10

[3,5-Bis-(2-nitro-4-trifluoromethanesulfonyl-phenoxy)-phenyl]-acetic acid methyl ester (10). To a solution of methyl 3,5-dihydroxyphenylacetate (50 mg, 0.274 mmol) in THF at rt was added NaH (24 mg, 60% dispersion in mineral oil), followed by 2-nitro-4-(trifluoromethylsulfonyl) chlorobenzene (159 mg, 2 equiv.). The mixture was stirred at rt for 5 hr. The reaction was acidified with 2N HCl, extracted into EtOAc, washed with water, brine, dried and concentrated. The residue was column chromatographed (EtOAc: Hex) to give [3,5-bis-(2-nitro-4-trifluoromethanesulfonyl-phenoxy)-phenyl]-acetic acid methyl ester. 1HNMR (360 MHz, DMSO-d6) δ 8.77 (d, J=2.3 Hz, 2H), 8.33 (dd, J=2.3 & 8.9 Hz, 2H), 7.46 (d, J=8.9 Hz, 2H), 7.40 (t, J=2.4 Hz, 1H), 7.30 (d, J=2.4 Hz, 2H), 3.89 (s, 2H, CH2), 3.63 (s, 3H, OCH3). MS-EI m/z 688 [M+].

Example 11

3,5-Bis-(2-nitro-4-trifluoromethanesulfonyl-phenoxy)-benzoic acid methyl ester (11). Using procedure as in example 10, a reaction of methyl 3,5-dihydroxybenzoate (50 mg, 0.297 mmol), NaH (26 mg, 2.2 equiv.) and 2-nitro-4-(trifluoromethylsulfonyl)chlorobenzene (172 mg, 0.595 mmol) afforded 3,5-bis-(2-nitro-4-trifluoromethanesulfonyl-phenoxy)-benzoic acid methyl ester.

1HNMR (360 MHz, DMSO-d6) δ 8.77 (d, J=2.4 Hz, 2H), 8.32 (dd, J=2.4 & 9.0 Hz, 2H), 7.87 (d, J=2.2 Hz, 2H), 7.82 (t, J=2.2 Hz, 1H), 7.54 (d, J=9.0 Hz, 2H), 3.87 (s, 3H, OCH3).

Example 12

1,3-Bis-(2-nitro-4-trifluoromethanesulfonyl-phenoxy)-cyclopentane (12). Using procedure as in example 10, a reaction of 1,3-cyclopetanediol (60 mg, 0.49 mmol), NaH (51.6 mg, 2.2 equiv.) and 2-nitro-4-(trifluoromethylsulfonyl) chlorobenzene (340 mg, 2 equiv.) afforded 1,3-bis-(2-nitro-4-trifluoromethanesulfonyl-phenoxy)-cyclopentane. 1HNMR (360 MHz, DMSO-d6) mixture of isomers.

Example 13

4-Methyl-2,6-bis-(2-nitro-4-trifluoromethanesulfonyl-phenoxy)-benzoic acid methyl ester (13). Using procedure as in Example 10, a reaction of methyl 2,6-dihydroxy-4-methylbenzoate (50 mg, 0.274 mmol), NaH (24 mg, 2.2 equiv.) and 2-nitro-4-(trifluoromethylsulfonyl) chlorobenzene (159 mg, 2 equiv.) afforded 4-methyl-2,6-bis-(2-nitro-4-trifluoromethanesulfonyl-phenoxy)-benzoic acid methyl ester. 1HNMR (360 MHz, DMSO-d6) δ 8.80 (d, J=2.2 Hz, 2H), 8.32 (dd, J=2.2 & 9.0 Hz, 2H), 7.48 (d, J=2.7 Hz, 2H), 7.44 (s, 2H), 3.50 (s, 3H, OCH3), 1.23 (s, 3H, CH3). MS-APCI (negative mode) m/z 686.6 [M+−2].

Example 14

4-[12-(2-Nitro-4-trifluoromethanesulfonyl-phenoxy)-ethoxy]-benzoic acid methyl ester (14). Using procedure as in Example 10, a reaction of methyl 4-(2-hydroxyethoxy) benzoic acid methyl ester (100 mg, 0.51 mmol), NaH (22 mg, 1.1 equiv.) and 2-nitro-4-(trifluoromethylsulfonyl) chlorobenzene (148 mg, 1 equiv.) afforded 4-[2-(2-nitro-4-trifluoromethanesulfonyl-phenoxy)-ethoxy]-benzoic acid methyl ester. 1HNMR (300 MHz, DMSO-d6) δ 8.64 (d, J=2.5 Hz, 1H), 8.39 (dd, J=2.5 & 8.9 Hz, 1H), 7.89 (d, J=8.8 Hz, 2H), 7.83 (d, J=8.9 Hz, 1H), 7.06 (d, J=8.8 Hz, 2H), 4.76 (m, 2H), 4.46 (m, 2H), 3.80 (s, 3H, OCH3). MS-EI m/z 449 [M+].

Example 15

4-[3-(2-Nitro-4-trifluoromethanesulfonyl-phenoxy)-phenoxy]-benzoic acid (15). Using procedure as in example 10, a reaction of 4-(3-hydroxyphenoxy)benzoic acid (100 mg, 0.4334 mmol), NaH (38 mg, 2.2 equiv.) and 2-nitro-4-(trifluoromethylsulfonyl)chlorobenzene (126 mg, 1 equiv.) afforded 4-[3-(2-nitro-4-trifluoromethanesulfonyl-phenoxy)-phenoxy]-benzoic acid. 1HNMR (360 MHz, DMSO-d6) δ 12.8 (br s, 1H, COOH), 8.75 (d, J=2.7 Hz, 1H), 8.30 (dd, J=2.7 & 9.0 Hz, 1H), 7.95 (m, 2H), 7.6 (m, 1H), 7.37 (d, J=9.0 Hz, 1H), 7.17–7.21 (m, 2H), 7.12 (m, 3H). MS-EI m/z 483 [M+].

Example 16

1-(3,5-Bis-trifluoromethyl-phenyl)-5-(2-nitro-4-trifluoromethanesulfonyl-phenoxy)-1H-pyrazole-3-carboxylic acid methyl ester (16). Using procedure as in example 10, a reaction of methyl 1-[3,5-di(trifluoromethyl)phenyl]-5-hydroxy-1H-pyrazole-3-carboxylate (100 mg, 0.282 mmol), NaH (12 mg, 1.1 equiv.) and 2-nitro-4-(trifluoromethylsulfonyl)chlorobenzene (82 mg, 1 equiv.) afforded 1-(3,5-bis-trifluoromethyl-phenyl)-5-(2-nitro-4-trifluoromethanesulfonyl-phenoxy)-1H-pyrazole-3-carboxylic acidmethyl ester. 1HNMR (300 MHz, DMSO-d6) δ 8.76 (d, J=2.1 Hz, 1H), 8.58 (dd, J=2.1 & 8.2 Hz, 1H), 8.42 (s, 2H), 8.30 (s, 1H), 8.13 (d, J=8.2 Hz, 1H), 6.76 (m, 1H), 3.7 (s, 3H, OCH3). MS-EI m/z 607 [M+].

Example 17

{4-[4-(2-Nitro-4-trifluoromethanesulfonyl-phenoxy)-benzenesulfonyl]-phenoxy}-acetic acid ethyl ester (17). Using procedure as in example 10, a reaction of ethyl [4-(4-hydroxyphenylsulfonyl)phenoxy]acetate (100 mg, 0.297 mmol), NaH (13 mg, 1.1 equiv.) and 2-nitro-4-(trifluoromethylsulfonyl)chlorobenzene (86 mg, 1 equiv.) afforded {4-[4-(2-nitro-4-trifluoromethanesulfonyl-phenoxy)-benzenesulfonyl]-phenoxy}-acetic acid ethyl ester. 1HNMR (300 MHz, DMSO-d6) δ 8.79 (d, J=2.3 Hz, 1H), 8.29 (dd, J=2.3 & 9.0 Hz, 1H), 8.07 (d, J=8.9 Hz, 2H), 7.92 (d, J=8.9 Hz, 2H), 7.52 (d, J=8.9 Hz, 2H), 7.47 (d, J=9.0 Hz, 1H), 7.14 (d, J=8.9 Hz, 2H), 4.91 (s, 2H, CH2), 4.15 (q, J=7.2 Hz, 2H, OCH2CH3), 1.19 (t, J=7.2 Hz, 3H, OCH2CH3). MS-EI m/z 589 [M+].

Example 18

4-[3-(4-Trifluoromethanesulfonyl-phenoxy)-phenoxy]-benzoic acid (18). A mixture of 4-(3-hydroxyphenoxy)benzoic acid (100 mg, 0.434 mmol), 4-(trifluoromethylsulfonyl)chlorobenzene (106 mg, 1 equiv.) and potassium carbonate (240 mg, 4 equiv.) in DMF was heated to 100° C. overnight. The reaction was poured into water, extracted with EtOAc, washed the organic layer with water, brine, dried and concentrated. The residue was column chromatographed to give 4-[3-(4-trifluoromethanesulfonyl-phenoxy)-phenoxy]-benzoic acid. 1HNMR (300 MHz, DMSO-d6) δ 8.09 (d, J=8.97 Hz, 2H), 7.95 (d, J=8.94 Hz, 2H), 7.56 (t, J=8.54 Hz, 1H), 7.33 (d, J=8.94 Hz, 2H), 7.10 (d, J=8.97 Hz, 2H), 7.04–7.11 (m, 3H). MS-EI m/z 438 [M+].

Example 19

{4-[(4-Trifluoromethanesulfonyl-phenoxy)-benzenesulfonyl]-phenoxy}-acetic acid ethyl ester (19). A mixture of ethyl [4-(4-hydroxyphenylsulfonyl)phenoxy]acetate (100 mg, 0.3 mmol), 4-(trifluoromethylsulfonyl)chlorobenzene (73 mg, 1 equiv.) and potassium carbonate (164 mg, 4 equiv.) in DMF was heated to 100° C. overnight. The reaction was poured into water, extracted with EtOAc, washed with organic layer with water, brine, dried and concentrated. The residue was column chromatographed to give {4-[4-(4-trifluoromethanesulfonyl-phenoxy)-benzenesulfonyl]-phenoxy}-acetic acid ethyl ester. 1HNMR (300 MHz, DMSO-d6) δ 8.11 (d, J=8.92 Hz, 2H), 8.03 (d, J=8.77 Hz, 2H), 7.90 (d, J=8.98 Hz, 2H), 7.39–7.43 (m, 4H), 7.14 (d, J=8.77 Hz, 2H), 4.90 (s, 2H, CH2), 4.15 (q, J=7.02 Hz, 2H, OCH2CH3), 1.19 (t, J=7.02 Hz, 3H, OCH2CH3). MS-EI m/z 544 [M+].

Example 20

N-(3-Trifluoromethanesulfonyl-phenyl)-2-{2-[(3-trifluoromethanesulfonyl-phenylcarbamoyl)-methyl]-phenyl}-acetamide (20). Oxalyl chloride (0.57 mL) was added to a solution of 1,2-phenylenediacetic acid (100 mg, 0.515 mmol) in dichloromethane, followed by 5 drops of DMF. The mixture was stirred at room temperature for 1.5 hours and cooled to 0° C. To the cooled mixture was added 4-dimethylaminopyridine (DMAP 144 mg, 1.18 mmol) and 3-aminophenyl trifluoromethyl sulfone (232 mg, 1.03 mmol). The mixture was allowed to warm to room temperature and extracted with ethyl acetate. The organic layer was washed with water, brine, dried and purified to give 200 mg (64%) of the title compound. 1H NMR (360 MHz, DMSO-d6) δ 10.73 (s, 2H, NH), 8.51 (s, 2H, 2×CH), 8.07 (m, 2H, 2×CH), 7.78 (m, 4H), 7.31 (m, 2H, 2×CH), 7.24 (m, 2H, 2×CH), 3.86 (s, 4H, 2×CH2). MS 609 [M++1].

Example 21

N-(3-Trifluoromethanesulfonyl-phenyl)-2-{3-[(3-trifluoromethanesulfonyl-phenylcarbamoyl)-methyl]-phenyl}-acetamide (21). Same procedure as Example 20 except 1,3-phenylenediacetic acid was used. 1H NMR (360 MHz, DMSO-d6) δ 10.74 (s, 2H, NH), 8.51 (s, 2H, 2×CH), 8.07 (m, 2H, 2×CH), 7.77 (m, 4H), 7.30 (m, 2H, 2×CH), 7.24 (m, 2H, 2×CH), 3.69 (s, 4H, 2×CH2). MS 609 [M++1].

Example 22

N-(3-Trifluoromethanesulfonyl-phenyl)-2-{4-[(3-trifluoromethanesulfonyl-phenylcarbamoyl)-methyl]-phenyl}-acetamide (22). Same procedure as example 20 except 1,4-phenylenediacetic acid was used. 1H NMR (360 MHz, DMSO-d6) δ 10.72 (s, 2H, NH), 8.49 (s, 2H, 2×CH), 8.07 (m, 2H, 2×CH), 7.77 (m, 4H), 7.30 (m, 4H), 3.6 (s, 4H 2×CH2). MS 609 [M++1].

Example 23

3,6-Bis-(morpholin-4-ylmethyl)-2,5-bis-(2-nitro-4-trifluoromethanesulfonyl-phenoxy)-benzene (23). To a solution of 2,5-bis-(morpholinomethyl)-hydroquinone (100 mg, 0.324 mmol) in THF was added sodium hydride (26 mg of 60% dispersion in mineral oil) followed by 2-nitro-4-(trifluoromethylsulfonyl)chlorobenzene (188 mg, 0.648 mmol). The mixture was stirred at room temperature for overnight. The reaction was extracted with ethyl acetate, the organic layer was washed with water and brine, dried, concentrated and purified to give the title compound. 1H NMR (300 MHz, DMSO-d6) δ 8.81 (d, J=2.2 Hz, 2H), 8.23 (m, 2H), 7.60 (s, 2H), 7.27 (m, 2H), 3.4 (m, 4H, 2×CH2), 3.06 (m, 8H, 4×CH2), 2.18 (m, 8H, 4×CH2). MS 815 [M++1].

Example 24

[2,3-Bis-(2-nitro-4-trifluoromethanesulfonyl-phenoxy)-propyl]-dimethyl-amine (24). Same procedure as Example 23 except 3-(dimethylamino)-1,2-propanediol was used. 1H NMR (300 MHz, DMSO-d6) δ 8.59 (m, 2H), 8.32 (m, 2H), 7.96 (d, J=9.4 Hz, 1H), 7.77 (d, J=9.4 Hz, 1H), 5.74 (s, 1H), 5.47 (m, 1H), 4.77 (m, 1H), 4.61(m, 1H), 2.70 (d, J=5.3 Hz, 2H), 2.22 (s, 6H, 2×CH3). MS 626 [M++1].

Example 25

N-(2-Ethylamino-5-trifluoromethanesulfonyl-phenyl)-2-(4-methanesulfonyl-phenyl)-acetamide (25). To a solution of 4-methylsulfonylphenylacetic acid (100 mg, 0.467 mmol) in acetonitrile was added 1-hydroxybenzotriazole (76 mg, 0.56 mmol), 1-ethyl-3-(3-dimethylaminopropyl) carboiimide hydrochloride (108 mg, 0.56 mmol), triethylamine (0.143 mL, 1.03 mmol) and N1-ethyl-4-[(trifluoromethyl)sulfonyl]benzene-1,2-diamine (125 mg, 0.467 mmol). The mixture was stirred at room temperature for overnight. The reaction was extracted with ethyl acetate, washed with water and brine, dried, concentrated and recrystallized from ethyl acetate to give the title compound. 1H NMR (300 MHz, DMSO-d6) δ9.54 (br s, 1H, NH), 7.88 (d, J=8.3 Hz, 2H), 7.75 (d, J=2.1 Hz, 1H), 7.64 (dd, 1H), 7.61 (d, J=8.3 Hz, 2H), 6.90 (d, J=9.0 Hz, 1H), 6.70 (t, J=5.2 Hz, 1H, NH), 3.86 (s, 2H, CH2), 3.31 (s, 3H, CH3), 3.29 (m, 2H, NCH2CH3), 1.20 (t, J=7.1 Hz, 3H, NCH2CH3). MS 465 [M++1].

Example 26

2-Hydroxy-5-(2-nitro-4-trifluoromethanesulfonyl-phenoxy)-terephthalic acid diethyl ester (26). To a solution of diethyl 2,5-dihydroxyterephthalate (100 mg, 0.393 mmol) in THF was added sodium hydride (32 mg of 60% dispersion in mineral oil) followed by 2-nitro-4-(trifluoromethylsulfonyl)chlorobenzene (228 mg, 0.787 mmol). The mixture was stirred at room temperature for overnight. The reaction was extracted with ethyl acetate, the organic layer was washed with water and brine, dried, concentrated and purified to give the title compound. 1H NMR (300 MHz, DMSO-d6) δ 10.77 (br s, 1H, OH), 8.78 (d, J=2.3 Hz, 1H), 8.22 (dd, J=2.3 & 9.0 Hz, 1H), 7.82(s, 1H), 7.56 (s, 1H), 7.19 (d, J=9.0 Hz, 1H), 4.32 (q, J=7.2 Hz, 2H, OCH2CH3), 4.09 (q, J=7.2 Hz, 2H, OCH2CH3), 1.3 (t, J=7.2 Hz, 3H, OCH2CH3), 0.92 (t, J=7.2 Hz, 3H, OCH2CH3).

Example 27

{2-[(3-Trifluoromethanesulfonyl-phenylcarbamoyl)-methyl)-phenyl}-acetic acid (27). Oxalyl chloride (0.285 mL) was added to a solution of 1,2-phenylenediacetic acid (100 mg, 0.515 mmol) in dichloromethane, followed by 5 drops of DMF. The mixture was stirred at room temperature for 1.5 hours and cooled to 0° C. To the cooled mixture was added DMAP (63 mg, 0.62 mmol) and 3-aminophenyl trifluoromethyl sulfone (116 mg, 0.515 mmol). The mixture was allowed to warm to room temperature and extracted with ethyl acetate. The organic layer was washed with water, brine, dried and purified to give the title compound. 1H NMR (300 MHz, DMSO-d6) δ 11.31 (br s, 1H), 8.51 (s, 1H), 8.04 (m, 1H), 7.75 (d, J=5.1 Hz, 2H), 7.28 (m, 1H), 7.19 (m, 3H), 3.75 (s, 2H, CH2), 3.62 (s, 2H, CH2). MS 401.9 [M++1].

Example 28

{3-[(3-Trifluoromethanesulfonyl-phenylcarbamoyl)-methyl]-phenyl}-acetic acid (28). Same procedure as example 27 except 1,3-phenylenediacetic acid was used. 1H NMR (300 MHz, DMSO-d6) δ 10.78 (br s, 1H), 8.51 (br s, 1H), 8.16 (m, 1H), 7.78 (d, J=5.2 Hz, 2H), 7.20 (m, 4H), 3.67 (s, 2H, CH2), 3.50 (s, 2H, CH2).

Example 29

{4-[(3-Trifluoromethanesulfonyl-phenylcarbamoyl)-methyl]-phenyl}-acetic acid (29). Same procedure as example 27 except 1,4-phenylenediacetic acid was used. 1H NMR (300 MHz, DMSO-d6) δ 10.76 (br s, 1H), 8.50 (br s, 1H), 8.07 (m, 1H), 7.78 (d, J=5.1 Hz, 2H), 7.26 (d, J=8.4 Hz, 2H), 7.20 (d, J=8.4 Hz, 2H), 3.66 (s, 2H, CH2), 3.51 Hz,

Example 30

3,5-Bis-(2-nitro-4-trifluoromethanesulfonyl-phenoxy)-benzamide (30). To a solution of diethyl 3,5-dihydroxybenzamide (100 mg, 0.6553 mmol) in THF was added sodium hydride (60 mg of 60% dispersion in mineral oil) followed by 2-nitro-4-(trifluoromethylsulfonyl) chlorobenzene (378 mg, 1.306 mmol). The mixture was stirred at room temperature for overnight. The reaction was extracted with ethyl acetate, the organic layer was washed with water and brine, dried, concentrated and purified to give the title compound. 1H NMR (300 MHz, DMSO-d6) δ 11.32 (br s, 1H, NH), 10.58 (br s, 1H, NH), 8.78 (d, J=2.2 Hz, 1H), 8.57 (br s, 1H), 8.47 (br d, 1H), 8.33 (dd, J=2.2 & 8.8 Hz, 1H), 8.25 (d, J=8.8 Hz, 1H), 7.40 (d, J=9.3 Hz, 1H), 7.35 (m, 2H), 7.01 (br s, 1H).

Example 31

3,5-Bis-(4-trifluoromethanesulfonyl-phenoxy)-benzoic acid (31). A mixture of methyl 3,5-dihydroxybenzoate (100 mg, 0.595 mmol), 4-(trifluoromethylsulfonyl)chlorobenzene (291 mg, 1.189 mmol) and potassium carbonate (330 mg, 2.379 mmol) was heated in DMF to give 3,5-bis-(4-trifluoromethanesulfonyl-phenoxy)-benzoic acid methyl ester. It was then hydrolysed with potassium hydroxide (25 mg) in THF (10 mL) and water (10 mL) to give the title compound. 1H NMR (300 MHz, DMSO-d6) δ 8.11 (d, J=9.2 Hz, 4H), 7.57 (d, J=2.11 Hz, 2H), 7.39 (d, J=9.2 Hz, 4H), 7.39 (m, 1H).

Example 32

N-(4-Trifluoromethanesulfonyl-phenyl)-2-{2-[(4-trifluoromethanesulfonyl-phenylcarbamoyl)-methyl]-phenyl}-acetamide (32). Same procedure as example 20 except 4-aminophenyl trifluoromethyl sulfone was used. 1H NMR (300 MHz, DMSO-d6) δ 10.90 (s, 2H, 2×NH), 8.03 (d, J=9.2 Hz, 4H), 8.0 (d, J=9.2 Hz, 4H), 7.31 (m, 2H), 7.25 (m, 2H), 3.87 (s, 4H, 2×CH2). MS 609 [M++1].

Example 33

N-(4-Trifluoromethanesulfonyl-phenyl)-2-{3-[(4-trifluoromethanesulfonyl-phenylcarbamoyl)-methyl]-phenyl}-acetamide (33). Same procedure as example 20 except 4-aminophenyl trifluoromethyl sulfone and 1,3-phenylenediacetic acid were used. 1H NMR (300 MHz, DMSO-d6) δ 10.91 (s, 2H, 2×NH), 8.05 (d, J=9.1 Hz, 4H), 7.99 (d, J=9.1 Hz, 4H), 7.21–7.29 (m, 4H), 3.73 (s, 4H, 2×CH2). MS 609 [M++1].

Example 34

N-(4-Trifluoromethanesulfonyl-phenyl)-2-{4-[(4-trifluoromethanesulfonyl-phenylcarbamoyl)-methyl]- phenyl}-acetamide (34). Same procedure as Example 20 except 4-aminophenyl trifluoromethyl sulfone and 1,4-phenylenediacetic acid were used. 1H NMR (300 MHz, DMSO-d6) δ 10.90 (s, 2H, 2×NH), 8.04 (d, J=8.9 Hz, 4H), 7.99 (d, J=8.9 Hz, 4H), 7.84 (d, J=8.9 Hz, 2H), 7.23 (d, J=8.9 Hz, 2H), 3.71 (s, 4H, 2×CH2). MS 609 [M++1].

Example 35

4-(1-Ethyl-5-trifluoromethanesulfonyl-1H-benzoimidazol-2-yl)-benzoic acid methyl ester (35). $N^1$-Ethyl-4-trifluoromethanesulfonyl-benzene-1,2-diamine (134 mg, 0.50 mmol) and methyl 4-formylbenzoate (82 mg, 1.1 equiv) were dissolved in 0.8 mL dry pentanol and heated to reflux for 18 h. The reaction mixture was then evaporated to one-third volume by blowing with a stream of nitrogen while heating. Upon cooling, the solids were collected and washed with ether to yield 155 mg upon drying. The solids may be recrystallized from EtOAc/ether to yield pure ester 35: $^1$HNMR (400 MHz, $d_6$-DMSO) δ 8.48 (d, J=1.65 Hz, 1H), 8.19 (m, 3H), 8.01 (m, 3H), 4.45 (q, J=7.24 Hz, 2H), 3.92 (s, 3H), 1.36 (t, J=7.22 Hz, 3H); LCMS-APCI in/z 413 [M+1]$^+$.

Example 36

4-(1-Ethyl-5-trifluoromethanesulfonyl-1H-benzoimidazol-2-yl)-benzoic acid (36). 4-(1-Ethyl-5-trifluoromethanesulfonyl-1H-benzoimidazol-2-yl)-benzoic acid methyl ester (152 mg, 0.368 mmol) was dissolved in warm ethanol (7 mL) and 1 M sodium hydroxide (1.0 mL) was added. The reaction mixture was heated to near reflux and stirred for 3 h. The reaction mixture was then partially evaporated by blowing with a stream of nitrogen and transferred to a vial containing EtOAc and 1 M aqueous hydrochloric acid. The organic phase was separated, washed with saturated brine, dried ($Na_2SO_4$) and evaporated to yield the acid 36: $^1$HNMR (400 MHz, $d_6$-DMSO) δ 8.47 (d, J=1.55 Hz, 1H), 8.18 (d, J=8.66 Hz, 1H), 8.15 (d, J=8.81 Hz, 2H), 8.01 (dd, J=7.17, 1.17 Hz, 1H), 7.95 (d, J=8.25 Hz, 2H), 4.45 (q, J=7.11 Hz, 2H), 1.37 (t, J=7.09 Hz, 3H); LCMS-APCI m/z 397 [M−1]$^-$.

Example 37

4-(1-Ethyl-5-trifluoromethanesulfonyl-1H-benzoimidazol-2-yl)-N-pyridin-4-yl-benzamide (37)-General Procedure for Amide Coupling to Compounds 37–40. 4-(1-Ethyl-5-trifluoromethanesulfonyl-1H-benzoimidazol-2-yl)-benzoic acid (20 mg, 0.0503 mmol) was suspended in acetonitrile (1 mL) with DMF (5 μL) and stirred at room temperature. To the reaction mixture was added dropwise 2 M oxalyl chloride solution in methylene chloride (50 μL, 2.0 equiv). The reaction mixture was then slowly heated over 2 h to 60° C., cooled to room temperature, TEA (28 μL, 4.0 equiv) was added dropwise followed by added 4-aminopyridine (7 mg, 1.5 equiv). The reaction mixture was then slowly heated to 60° C. and stirred for 4 h, then cooled to room temperature and transferred to a funnel containing chloroform-isopropanol (4/1) and 1 M aqueous $KH_2PO_4$. The organic phase was separated, washed with 1 M aqueous $KH_2PO_4$, half saturated aqueous $NaHCO_3$, saturated brine, dried ($Na_2SO_4$) and evaporated to yield the crude amide 37. This amide could be further purified by passage through silica gel (DCM/hexane/EtOAc): $^1$HNMR (400 MHz, $d_6$-DMSO) δ 10.82 (s, 1H), 8.51 (dm, J=4.75 Hz, 2H), 8.49 (d, J=2.03 Hz, 1H), 8.20 (m, 3H), 8.03 (m, 3H), 7.82 (dm, J=4.53 Hz, 2H), 4.47 (q, J=7.32 Hz, 2H), 1.37 (t, J=7.22 Hz, 3H); LCMS-APCI m/z 475 [M+1]$^+$.

Example 38

4-(1-Ethyl-5-trifluoromethanesulfonyl-1H-benzoimidazol-2-yl)-N-(4-methoxy-phenyl)-benzamide (38): Same procedure as example 37 except 4-methoxyaniline was used. LCMS-APCI m/z 504 [M+1]$^+$.

Example 39

3-[4-(1-Ethyl-5-trifluoromethanesulfonyl-1H-benzoimidazol-2-yl)-benzoylamino]-benzoic acid ethyl ester (39): Same procedure as example 37 except ethyl 3-amino-benzoic acid ethyl ester was used. LCMS-APCI m/z 546 [M+1]$^+$.

Example 40

4-(1-Ethyl-5-trifluoromethanesulfonyl-1H-benzoimidazol-2-yl)-N-(2-pyrrolidin-1-yl-ethyl)-benzamide (40): Same procedure as example 37 except 2-pyrrolidin-1-yl-ethylamine was used. LCMS-APCI m/z 495 [M+1]$^+$.

Example 41

N-Ethyl-4-(1-ethyl-5-trifluoromethanesulfonyl-1H-benzoimidazol-2-yl)-benzamide (41). 4-(1-Ethyl-5-trifluoromethanesulfonyl-1H-benzoimidazol-2-yl)-benzoic acid methyl ester (20 mg, 0.0484 mmol) was dissolved in 2 M ammonia in methanol (4 mL) and stirred in a capped vial. The reaction mixture was heated to ~60° C. and stirred for 60 h. The reaction mixture was then evaporated to yield the amide 41: $^1$HNMR (400 MHz, d6-DMSO) δ 8.68 (t, J=5.46, 1H), 8.46 (d, J=1.67 Hz, 1H), 8.18 (d, J=8.49 Hz, 1H), 8.06 (d, J=8.42 Hz, 2H), 8.01 (dd, J=8.72, 1.72 Hz, 1H), 7.93 (d, J=8.70 Hz, 2H), 4.45 (q, J=7.21 Hz, 2H), 2.5 (obsc., 2H) 1.35 (t, J=7.09 Hz, 3H), 1.16 (t, J=7.09 Hz, 3H); LCMS-APCI m/z 426 [M+1]$^+$.

Example 42

1-Ethyl-5-trifluoromethanesulfonyl-1H-benzoimidazole-2-carboxylic acid (42). $N^1$-Ethyl-4-trifluoromethanesulfonyl-benzene-1,2-diamine (134 mg, 0.50 mmol) and 2-oxo-malonic acid diethyl ester (91 μL, 1.2 equiv) were dissolved in 0.7 mL dry pentanol and heated to reflux for 24 h. The reaction mixture was then evaporated by blowing with a stream of nitrogen while heating, the oil was then placed under full vacuum for at least 20 h whereupon a low melting solid began to form. 1-Ethyl-5-trifluoromethanesulfonyl-1H-benzoimidazole-2-carboxylic acid pentyl ester $^1$HNMR (400 MHz, $d_6$-DMSO) δ 8.52 (d, J=2.0 Hz, 1H), 8.30 (dd, J=9.2, 2.0 Hz, 1H), 8.07 (d, J=9.2 Hz, 1H), 4.37 (t, J=6.6 H 4.31 (q, J=7.2 Hz, 2H), 1.71 (m, 2H), 1.37 (m, 4H), 1.27 (t, J=7.4 Hz, 3H), 0.89 (T, J=7.0 Hz, 3H); LCMS-APCI m/z 393 [M+1]$^+$. This pentyl ester was used directly (85 mg, 0.217 mmol) and dissolved in warm ethanol (3 mL) with the addition of 1 M sodium hydroxide (1 mL). The reaction mixture was warmed to 40° C. and stirred for 2 h. The reaction mixture was then partially evaporated by blowing with a stream of nitrogen and transferred to a vial containing chloroform and water. The two phases were shaken together, the organic phase was removed, and the process repeated once with additional chloroform. To the aqueous phase was added ethyl acetate, the mixture was acidified with 3 M aqueous hydrochloric acid to pH 2.5, and the organic phase was separated, washed with saturated brine, dried ($Na_2SO_4$) and evaporated to yield the acid 42: $^1$HNMR (400 MHz, $d_6$-DMSO) 8 14.3 (br s, 1H), 8.51 (d, J=2.35 Hz, 1H), 8.30 (dd, J=9.06, 2.28 Hz, 1H), 8.07 (d, J=9.09 Hz, 1H), 4.31 (q, J=7.14 Hz, 2H), 1.28 (t, J=7.10 Hz, 3H); LCMS-APCI m/z [M−1]$^-$ 321.

Examples 43–51

Procedure 1: 4-(Trifluoromethylthio)benzaldehyde was dissolved in methanol. The amine was added followed by the addition of acetic acid. It was stirred for five minutes before the isocyanide was added. It was stirred at rt for 48 h. The solvent was evaporated and the residue was purified by silica gel chromatography. Pure Ugi product was dissolved in acetic acid, hydrogen peroxide (30%) was added. It was heated to 75° C. and stirred for 24 h at this temperature. EtOAc and sat. $NaHCO_3$ were added, the layers were separated. The aq. layer was extracted with EtOAc (1×), and the organic layers were washed with brine and dried over $Na_2S_2O_4$. The solvent was removed and the residue was purified by silica gel chromatography.

Procedure 2: 4-(Trifluoromethylthio)benzaldehyde and benzoic acid were dissolved in methanol. The amine was added. It was stirred for five minutes before the isocyanide was added. It was stirred at rt for 48 h. The solvent was evaporated and the residue was purified by silica gel chromatography. Oxidation as in procedure 1.

Procedure 3: 4-(Trifluoromethylthio)benzaldehyde was dissolved in methanol. The amine was added followed by the addition acetic acid. It was stirred for five minutes before the isocyanide was added. It was stirred at rt for 48 h, the solvent was removed. The crude reaction mixture was dissolved in acetic acid, hydrogen peroxide (30%) was added. It was heated to 75° C. and stirred for 24 h at this temperature. EtOAc and sat. $NaHCO_3$ were added and the layers were separated. The aq. Layer was extracted with EtOAc (1×), the organic layers were washed with brine and dried over $Na_2S_2O_4$. Silica gel purification of the individual compounds is described in detail below.

Procedure 4: Ugi reaction as in procedure 2, oxidation on crude reaction mixture (see procedure 3).

Example 43

[2-(Benzoyl-butyl-amino)-2-(4-trifluoromethanesulfonyl-phenyl)-acetylamino]-acetic acid methyl ester (43). Procedure 2 was applied. 4-(Trifluoromethylthio)benzaldehyde (113 mg, 0.55 mmol), benzoic acid (70 mg, 0.58 mmol), methanol (0.7 ml), butylamine (57 µl, 0.58 mmol), methyl isocyanoacetate (50 µl, 0.55 mmol). The residue was purified by flash column chromatography on silica gel (EtOAc/Hex 1/1) to yield pure Ugi product (44%). Oxidation to the sulfone: Ugi product (115 mg, 0.24 mmol), acetic acid (0.43 ml), hydrogen peroxide (0.32 ml). The residue was purified by flash column chromatography on silica gel (EtOAc/Hex: 1/1) to give the title compound as a white solid (55%). $^1$H NMR (400 MHz, $CDCl_3$) δ 8.06 (d, J=8.3 Hz, 2H), 7.83 (d, J=8.2 Hz, 2H), 7.42–7.50 (m, 5H), 5.73 (s, 1H), 4.14 (t, J=5.4 Hz, 2H), 3.80 (s, 3H), 3.30–3.46 (m, 2H), 1.45–1.55 (m, 1H), 1.26–1.28 (m, 1H), 1.02–1.05 (m, 2H), 0.68 (t, J=7.3 Hz, 3H).

Example 44

N-Benzyl-N-[butylcarbamoyl-(4-trifluoromethanesulfonyl-phenyl)-methyl]-benzamide (44). Procedure 2 was applied. 4-(Trifluoromethylthio) benzaldehyde (85 mg, 0.41 mmol), benzoic acid (55 mg, 0.45 mmol), methanol (0.5 ml), benzylamine (49 µl, 0.45 mmol), butylisocyanide (45 µl, 0.41 mmol). The residue was purified by flash column chromatography on silica gel (EtOAc/Hex 1/1) to yield pure Ugi product (86%). Oxidation to the sulfone: Ugi product (110 mg, 0.22 mmol), acetic acid (0.40 ml), hydrogen peroxide (0.30 ml). The residue was purified by flash column chromatography on silica gel (EtOAc/Hex 1/1) to give the title compound as a white solid (82%). $^1$H NMR (400 MHz, $CDCl_3$) δ 7.90 (d, J=8.4 Hz, 2H), 7.65–7.70 (m, 2H), 7.53 (dd, J=7.1, 1.6 Hz, 2H), 7.41–7.47 (m, 3H), 7.17–7.22 (m, 3H), 7.02–7.05 (m, 2H), 6.23 (br s, 1H), 5.59 (s, 1H), 4.79 (d, J=16.3 Hz, 1H), 4.65 (d, J=16.0 Hz, 1H), 3.23–3.30 (m, 2H), 1.44–1.51 (m, 2H), 1.25–1.37 (m, 2H), 0.91 (t, J=3.7 Hz, 3H). LCMS –cAPCI m/z 531 (M–H).

Example 45

N-[Butylcarbamoyl-(4-trifluoromethanesulfonyl-phenyl)-methyl]-N-(2-hydroxy-ethyl)-benzamide (45). Procedure 2 was applied. 4-(Trifluoromethylthio)benzaldehyde (90 mg, 0.41 mmol), benzoic acid (56 mg, 0.46 mmol), methanol (0.8 ml), ethanolamine (28 µl, 0.46 mmol), butylisocyanide (45 µl, 0.41 mmol). The residue was purified by flash column chromatography on silica gel (EtOAc/Hex 1/1) to yield pure Ugi product (79%). Oxidation to the sulfone: Ugi product (110 mg, 0.22 mmol), acetic acid (0.40 ml), hydrogen peroxide (0.30 ml). The residue was purified by flash column chromatography on silica gel (EtOAc/Hex 1/1) to give the title compound as a white solid (23%). LCMS –cAPCI m/z 485 (M–H).

Example 46

[2-(Acetyl-cyclopropyl-amino)-2-(4-trifluoromethanesulfonyl-phenyl)-acetylamino]-acetic acid ethyl ester (46). Procedure 3 was applied. 4-(Trifluoromethylthio)benzaldehyde (103 mg, 0.46 mmol), methanol (0.7 ml), cyclopropylamine (32 µl, 0.46 mmol), acetic acid (27 µl, 0.47 mmol), ethyl isocyanoacetate (50 µl, 0.46 mmol). Oxidation of the crude reaction mixture. Acetic acid (0.90 ml), hydrogen peroxide (0.66 ml). Aqueous workup as described above. The residue was filtered through silica gel and purified by chromatotron (silica gel plate, EtOAc/Hex 2/1) to yield the title compound as a white solid/glass (43%). $^1$H NMR (400 MHz, $d_6$-DMSO) δ 8.46 (t, J=5.7 Hz, 1H), 8.10 (d, J=8.7 Hz, 2H), 7.77 (d, J=8.1 Hz, 2H), 6.02 (s, 1H), 4.13 (q, J=7.3 Hz, 2H), 3.89 (t, J=5.4 Hz, 2H), 2.22 (s, 3H), 1.21 (t, J=7.1 Hz, 3H), 1.03–1.09 (m, 1H), 0.70–0.76 (m, 2H), 0.38–0.49 (m, 1H). LCMS –cAPCI m/z 449 (M–H).

Example 47

[2-(Acetyl-methyl-amino)-2-(4-trifluoromethanesulfonyl-phenyl)-acetylamino]-acetic acid ethyl ester (47). Procedure 1 was applied. 4-(Trifluoromethylthio)benzaldehyde (95 mg, 0.43 mmol), methanol (0.8 ml), methylamine (2 M in THF, 0.21 ml, 0.42 mmol), acetic acid (24 µl, 0.42 mmol), ethyl isocyanoacetate (46 µl, 0.42 mmol), The residue was purified by flash column chromatography on silica gel (EtOAc/Hex:4/1; EtOAc/MeOH 98/2) to yield pure Ugi product (42%). Oxidation to the sulfone: Ugi product (65 mg, 0.17 mmol), acetic acid (0.30 ml), hydrogen peroxide (0.22 ml). The residue was purified by flash column chromatography on silica gel (EtOAc/Hex 6/1; EtOAc/MeOH 98/2) to give the title compound as a white solid/glass (47%). $^1$H NMR (400 MHz, $d_6$-DMSO, 4/1 mixture of rotamers, major rotamer) δ 8.80 (t, J=5.8 Hz, 1H), 8.14 (d, J=8.1 Hz, 2H), 7.72 (d, J=8.5 Hz, 2H), 6.43 (s, 1H), 4.12 (q, J=7.2 Hz, 2H), 3.90 (t, J=5.6 Hz, 2H), 2.84 (s, 3H), 2.11 (s, 3H), 1.19 (t, J=7.3 Hz, 3H). LCMS –cAPCI m/z 423 (M–H).

Example 48

[2-(Benzoyl-cyclohexyl-amino)-2-(4-trifluoromethanesulfonyl-phenyl)-acetylamino]-acetic acid ethyl ester (48). Procedure 4 was applied. 4-(Trifluoromethylthio)benzaldehyde (90 mg, 0.41 mmol), benzoic acid (52 mg, 0.43 mmol), cyclohexylamine (49 μl, 0.43 mmol), ethyl isocyanoacetate (45 μl, 0.41 mmol). Oxidation of the crude reaction mixture. Acetic acid (0.80 ml), hydrogen peroxide (0.59 ml). Aqueous workup as described above. The residue was filtered through silica gel and purified by chromatotron (silica gel plate, EtOAc/Hex) to yield the title compound as a white solid (33%). LCMS –cAPCI m/z 553 (M–H).

Example 49

N-Cyclohexyl-N-[(2,6-dimethyl-phenylcarbamoyl)-(4-trifluoromethanesulfonyl-phenyl)-methyl]-benzamide (49). Procedure 4 was applied. 4-(Trifluoromethylthio) benzaldehyde (92 mg, 0.41 mmol), benzoic acid (53 mg, 0.43 mmol), cyclohexylamine (49 μl, 0.43 mmol), 2,6-dimethylphenylisocyanide (54 mg, 0.41 mmol). Oxidation of the crude reaction mixture. Acetic acid (0.80 ml), hydrogen peroxide (0.59 ml). Aqueous workup as described above. The residue was filtered through silica gel and purified by chromatotron (silica gel plate, EtOAc/Hex) to yield the title compound as a white solid (32%). $^1$H NMR (400 MHz, $d_6$-DMSO) δ 8.65 (br s, 1H), 8.14 (d, J=8.8 Hz, 2H), 7.98 (d, J=8.8 Hz, 2H), 7.55–7.59 (m, 2H), 7.49–7.53 (m, 3H), 7.05–7.08 (m, 3H), 5.67 (s, 1H), 3.53–3.63 (m, 1H), 2.20 (s, 6H), 1.86–1.96 (m, 2H), 1.73–1.78 (m, 1H), 1.55–1.63 (m, 1H), 1.39–1.49 (m, 2H), 1.00–1.08 (m, 2H), 0.82–0.90 (m, 2H). LCMS –cAPCI m/z 571 (M–H).

Example 50

[2-(Acetyl-propyl-amino)-2-(4-trifluoromethanesulfonyl-phenyl)-acetylamino]-acetic acid ethyl ester (50). Procedure 3 was applied. 4-(Trifluoromethylthio)benzaldehyde (106 mg, 0.51 mmol), methanol (0.8 ml), propylamine (42 μl, 0.51 mmol), acetic acid (29 μl, 0.51 mmol), ethyl isocyanoacetate (56 μl, 0.51 mmol). Oxidation of the crude reaction mixture. Acetic acid (0.92 ml), hydrogen peroxide (0.68 ml). Aqueous workup as described above. The residue was filtered through silica gel and purified by chromatotron (silica gel plate, EtOAc/Hex 2/1, EtOAc/Hex 4/1) to yield the title compound as a white solid (39%). $^1$H NMR (400 MHz, $d_6$-DMSO, 3/1 mixture of rotamers, major rotamer) δ 8.65 (t, J=5.8 Hz, 1H), 8.14 (d, J=8.3 Hz, 2H), 7.75 (d, J=8.6 Hz, 2H), 6.19 (s, 1H), 4.11 (q, J=7.0 Hz, 2H), 3.88 (dd, J=11.9, 5.7 Hz, 2H), 3.20–3.32 (m, 2H), 2.12 (s, 3H), 1.34–1.44 (m, 1H), 1.20 (t, J=7.2 Hz, 3H), 0.80–0.90 (m, 1H), 0.61 (t, J=7.3 Hz, 3H). LCMS –cAPCI m/z 451 (M–H).

Example 51

[2-(Acetyl-cyclohexyl-amino)-2-(4-trifluoromethanesulfonyl-phenyl)-acetylamino]-acetic acid ethyl ester (51). Procedure 3 was applied. 4-(Trifluoromethylthio)benzaldehyde (101 mg, 0.49 mmol), methanol (0.8 ml), hexylamine (56 μl, 0.49 mmol), acetic acid (28 μl, 0.49 mmol), ethyl isocyanoacetate (54 μl, 0.49 mmol). Oxidation of the crude reaction mixture. Acetic acid (0.88 ml), hydrogen peroxide (0.65 ml). Aqueous workup as described above. The residue was filtered through silica gel and purified by chromatotron (silica gel plate, EtOAc/Hex 3/2) to yield the title compound as a white solid (22%). $^1$H NMR (400 MHz, $d_6$-DMSO, 3/1 mixture of rotamers, major rotamer) δ 8.03 (d, J=8.6 Hz, 2H), 7.75 (d, J=8.4 Hz, 2H), 7.66 (t, J=4.9 Hz, 1H), 5.27 (s, 1H), 4.10 (q, J=7.3 Hz, 2H), 3.85 (d, J=5.6 Hz, 1H), 3.80 (d, J=5.5 Hz, 1H), 2.15 (s, 3H), 1.96–2.02 (m, 1H), 1.63–1.80 (m, 4H), 1.52–1.62 (m, 2H), 1.27–1.43 (m, 3H), 1.21 (t, J=7.0 Hz, 3H). LCMS –cAPCI m/z 491 (M–H).

Example 52

{4-[4-(2-Nitro-4-trifluoromethanesulfonyl-phenoxy)-benzenesulfonyl]-phenoxy}-acetic acid (52). A mixture of {4-[4-(2-nitro-4-trifluoromethanesulfonyl-phenoxy)-benzenesulfonyl]-phenoxy}-acetic acid ethyl ester [Example 17, 61 mg, 0.1 mmol] in isopropanol (3.1 mL) and tetrahydrofuran (0.6 mL) was heated to reflux to dissolve all the solids. The mixture was cooled to 35° C. followed by addition of 1M NaOH solution (0.21 mL). It was then stirred at 35° C. for 2 hours. The reaction was concentrated, acidified with 1M HCl and extracted with ethyl acetate. The organic extracts were dried and concentrated to give the title compound. $^1$H NMR (300 MHz, DMSO-d6) δ 12.2 (br s, 1H, COOH), 10.57 (s, 1H), 8.36 (d, J=2.6 Hz, 1H), 7.79 (m, 1H), 7.78 (d, J=9.0 Hz, 2H), 7.72 (d, J=8.8 Hz, 2H), 7.06 (d, J=9.0 Hz, 2H), 7.01 (d, J=9.3 Hz, 1H), 6.89 (d, J=8.8 Hz, 2H), 4.77 (s, 2H).

Example 53

4-[2-(2-Nitro-4-trifluoromethanesulfonyl-phenoxy)-ethoxyl-benzoic acid (53). 4-[2-(2-Nitro-4-trifluoromethanesulfonyl-phenoxy)-ethoxy]-benzoic acid methyl ester (Example 14, 45 mg, 0.1 mmol] dissolved in tetrahydrofuran (0.5 mL) and ethanol (1 mL), was heated to reflux while 1M HCl (1 mL) was added. After heating for 18 hours, 6M HCl (0.2 mL) was added to the reaction and heating was continued for 6 more hours. The reaction was concentrated and the residue was column chromatographed to give the title compound. $^1$H NMR (360 MHz, DMSO-d6) δ 8.63 (d, J=2.4 Hz, 1H), 8.37 (dd, J=2.4 & 8.8 Hz, 1H), 7.85 (t, 3H), 7.01 (d, 2H), 4.76 (m, 2H), 4.44 (m, 2H).

Example 54

2,5-Bis-(2-nitro-4-trifluoromethanesulfonyl-phenoxy)-terephthalic acid diethyl ester (54). A mixture of diethyl 2,5-dihydroxyterephthalate (127 mg, 0.5 mmol) and sodium hydride (60%, 20 mg) in tetrahydrofuran (1.5 mL) was stirred at room temperature for 30 minutes followed by the addition of 1-chloro-2-nitro-4-trifluoromethanesulfonyl-benzene (75 mg, 0.26 mmol). After 45 mintues, more 1-chloro-2-nitro-4-trifluoromethanesulfonyl-benzene (63 mg, 0.22 mmol) was added. Tetrahydrofuran (1 mL) was added after each addition of 1-chloro-2-nitro-4-trifluoromethanesulfonyl-benzene. After 18 hours at room temperature, more 1-chloro-2-nitro-4-trifluoromethanesulfonyl-benzene (75 mg) was added and the temperature was increased to 60° C. for 2 hours. The reaction was diluted with chloroform/isopropanol, washed with brine and purified on silica gel to give the title compound. $^1$H NMR (360 MHz, DMSO-d6) δ 8.82 (d, J=2.2 Hz, 2H), 8.27 (dd, 2H), 8.18 (s, 2H), 7.48 (d, J=9 Hz, 2H), 4.15 (q, J=6.8 Hz, 4H), 0.98 (t, J=6.8 Hz, 6H).

Example 55

1-[2,3-Bis-(2-nitro-4-trifluoromethanesulfonyl-phenoxy)-propyl]-piperidine (55). Using the same procedure as for example 54, a mixture of 3-piperidino-1,2-propanediol (40 mg, 0.25 mmol), sodium hydride (60%, 30 mg) and 1-chloro-2-nitro-4-trifluoromethanesulfonyl-benzene (174 mg, 0.6 mmol) in acetonitrile (1 mL+0.6 mL) was heated to reflux for 18 hours, worked-up and purified on silica gel to give the title compound. MS +ve APCI 666 [M+1].

Example 56

4-[2,3-Bis-(2-nitro4-trifluoromethanesulfonyl-phenoxy)-propyl]-morpholine (56). Using the same procedure as for Example 54, a mixture of 3-morpholin-4-yl-propane-1,2-diol (40 mg, 0.25 mmol), sodium hydride (60%, 30 mg) and 1-chloro-2-nitro-4-trifluoromethanesulfonyl-benzene (174 mg, 0.6 mmol) in acetonitrile (1 mL) was heated to reflux, worked-up and purified on silica gel to give the title compound. $^1$H NMR (360 MHz, DMSO-d6) δ 8.59 (d, J=2.3 Hz, 2H), 8.35 (dd, J=2.3 & 9.2 Hz, 1H), 8.30 (dd, J=2.3 & 9.2 Hz, 1H), 7.97 (d, J=9.2 Hz, 1H), 7.79 (d, J=9.2 Hz, 1H), 5.49 (m, 1H), 4.79 (m, 1H), 4.66 (m, 1H), 3.41 (m, 4H), 2.74 (d, J=6.1 Hz, 2H), 2.4–2.5 (m, 4H). MS+ve APCI 668 [M+1].

Example 57

2,3-Bis-(2-nitro-4-trifluoromethanesulfonyl-phenoxy)-propyl]-(2-nitro-phenyl)-amine (57). A mixture of 3-(2-nitroanilino)-1,2-propanediol (71 mg, 0.33 mmol), 1-chloro-2-nitro-4-trifluoromethanesulfonyl-benzene (135 mg, 0.47 mmol) and potassium carbonate (190 mg, 1.33 mmol) in acetonitrile (2 mL) was heated to reflux for 2 days. The reaction was diluted with chloroform/isopropanol mixture, washed with brine, dried, concentrated and column chromatographed to give the title compound (di-arylated) and 1-(2-nitro-phenylamino)-3-(2-nitro-4-trifluoromethanesulfonyl-phenoxy)-propan-2-ol (mono-arylated) example 58. MS +ve ESI 719 [M+1].

Example 58

1-(2-Nitro-phenylamino)-3-(2-nitro-4-trifluoromethanesulfonyl-phenoxy)-propan-2-ol (58). See procedure for Example 57. $^1$H NMR (360 MHz, DMSO-d6) δ 8.82 (d, 1H), 8.34 (dd, J=2.5 & 9 Hz, 1H), 8.23 (t, 1H), 8.06 (dd, J=1.6 & 8.8 Hz, 1H), 7.78 (d, J=9 Hz, 1H), 7.52 (t, 1H), 7.07 (d, J=9 Hz, 1H), 6.69 (t, 1H), 5.64 (d, J=4.7 Hz, 1H), 4.41 (d, 2H), 4.15 (m, 1H), 3.59 (m, 1H), 3.44 (m, 1H). MS +ve APCI 466 [M+1].

Example 59

[2,3-Bis-(2-nitro-4-trifluoromethanesulfonyl-phenoxy)-propyl]-(4-nitro-phenyl)-amine (59). A mixture of 3-(4-nitroanilino)-1,2-propanediol (71 mg, 0.33 mmol), 1-chloro-2-nitro-4-trifluoromethanesulfonyl-benzene (135 mg, 0.47 mmol) and potassium carbonate (190 mg, 1.33 mmol) in acetonitrile (2 mL) was heated to reflux for 2 days. The reaction was diluted with chloroform/isopropanol mixture, washed with brine, dried, concentrated and column chromatographed to give the title compound (di-arylated) and 1-(4-nitro-phenylamino)-3-(2-nitro-4-trifluoromethanesulfonyl-phenoxy)-propan-2-ol (mono-arylated). $^1$H NMR (360 MHz, DMSO-d6) δ 8.63 (d, 1H), 8.37 (dd, 1H), 8.30 (d, J=8.8 Hz, 2H), 7.83 (d, 1H), 7.66 (d, J=8.8 Hz, 2H), 7.50 (dd, 1H), 7.42 (d, 1H), 7.31 (d, 1H), 4.91 (m, 1H), 4.76 (m, 2H), 4.15 (dd, 1H), 3.91 (dd, 1H).

Example 60

1-(4-Nitro-phenylamino)-3-(2-nitro-4-trifluoromethanesulfonyl-phenoxy)-propan-2-ol (60). See procedure for Example 59. $^1$H NMR (360 MHz, DMSO-d6) δ 8.30 (d, J=9.0 Hz, 2H), 7.63 (d, J=9 Hz, 2H), 7.46 (dd, J=2.2 & 8.8 Hz, 1H), 7.41 (d, J=2.2 Hz, 1H), 7.30 (d, J=8.8 Hz, 1H), 5.06 (t, 1H), 4.37 (m, 1H), 3.97 (dd, 1H), 3.80 (dd, 1H), 3.65 (m, 2H).

Example 61

4-[2-Hydroxy-3-(2-nitro-4-trifluoromethanesulfonyl-phenoxy)-propylamino]-benzenesulfonamide (61). A mixture of N4-(2,3-dihydroxypropyl)sulfanilamide (82 mg, 0.33 mmol), 1-chloro-2-nitro-4-trifluoromethanesulfonyl-benzene (135 mg, 0.47 mmol) and potassium carbonate (190 mg, 1.33 mmol) in acetonitrile (2 mL) was heated to reflux for 2 days. The reaction was diluted with chloroform/isopropanol mixture, washed with brine, dried, concentrated and column chromatographed to give the title compound (mono-arylated) and 4-[2,3-bis-(2-nitro-4-trifluoromethanesulfonyl-phenoxy)-propylamino]-benzenesulfonamide (di-arylated) example 62. $^1$H NMR (300 MHz, DMSO-d6) δ 8.63 (d, 1H), 8.35 (dd, 1H), 7.75 (d, 1H), 7.63 (d, 2H), 6.68 (d, 2H), 4.35 (d, 2H), 3.98 (t, 1H), 3.2 (m, 2H). MS –ve APCI 498 [M–1].

Example 62

4-[2,3-Bis-(2-nitro-4-trifluoromethanesulfonyl-phenoxy)-propylamino]-benzenesulfonamide (62). See procedure for Example 61. MS –ve ESI 751 [M–1].

Example 63

Bis-{[4-(2-nitro-4-trifluoromethanesulfonyl)-phenoxy]-phenyl}sulfone (63). Bis-{[4-(2-nitro-4-trifluoromethanesulfonyl)-phenoxy]-phenyl}sulfone was purchased from AsInEx (Moscow, Russia) and used as is.

Example 64

2-[4-(Difluoro-methanesulfonyl)-phenyl]-5-naphthalen-2-yl-oxazole (64). 2-[4-(Difluoro-methanesulfonyl)-phenyl]-5-naphthalen-2-yl-oxazole was purchased from InterBioScreen (Moscow, Russia) and used as is.

Example 65

[2-Nitro-4-(1,1,2,2-tetrafluoro-ethanesulfonyl)-phenyl]-p-tolyl-amine (65). [2-Nitro-4-(1,1,2,2-tetrafluoro-ethanesulfonyl)-phenyl]-p-tolyl-amine was purchased from SPECS (Netherlands) and used as is.

Trifluoromethyl Sulfonamido Compounds

Example 66

1,2-Bis(4-trifluoromethylsulfonamidophenyl)ethane (66). To a solution of 4,4'-ethylenedianliline (0.5 g, 2.36 mmol) in DCM at 0° C. was added trifluoromethanesulfonyl chloride (0.55 mL) and DMAP (720 mg, 5.9 mmol). After stirring at rt overnight, the reaction was extracted with EtOAc, washed with brine, dried and concentrated to give 1,2-bis(4-trifluoromethylsulfonamidophenyl)ethane. 1HNMR (300 MHz, DMSO-d6) δ 11.74 (s, br, 2H, 2×NH), 7.22 (d, J=8.5 Hz, 4H), 7.13 (d, J=8.5 Hz, 4H), 2.84 (s, 4H, 2×CH2). MS-EI m/z 476 [M+].

Example 67

1,2-Bis(2-methyl-4-trifluoromethylsulfonamidophenyl)ethane (67). A mixture of 4,4'-diamino-2,2'dimethylbibenzyl (0.5 g, 2.08 mmol), triflic anhydride (0.77 mL) and sodium bicarbonate (0.7 g, 8.32 mmol) in DCM was stirred at rt overnight to give 1,2-bis(2-methyl-4-trifluoromethylsulfonamidophenyl)ethane. 1HNMR (300 MHz, DMSO-d6) δ 11.61 (s, br, 2H, 2×NH), 7.14 (d, J=7.5 Hz, 2H), 6.99 (m, 4H), 2.75 (s, 4H, 2×CH2), 2.21 (s, 6H, 2×CH3). MS-EI m/z 504 [M+].

Example 68

1,3-Bis(4-trifluoromethylsulfonamidophenoxy)-2,2-dimethylpropane (68). A mixture of neopentyl glycol bis(4- aminophenyl) ether (0.5 g, 1.75 mmol), triflic anhydride (0.65 mL) and sodium bicarbonate (0.59 g, 7 mmol) in DCM was stirred at rt overnight to give 1,3-bis(4-trifluoromethylsulfonamidophenoxy)-2,2-dimethylpropane. 1HNMR (300 MHz, DMSO-d6) δ 11.55 (s, br, 2H, 2×NH), 7.13 (d, J=9.15 Hz, 4H), 6.96 (d, J=9.15 Hz, 4H), 3.82 (s, 4H, 2×CH2), 1.07 (s, 6H, 2×CH3). MS-EI m/z 550 [M+].

Example 69

1,3-Bis(4-trifluoromethylsulfonamidophenoxy)propane (69). A mixture of 4-[3-(4-aminophenoxy)propoxy]aniline (0.5 g, 1.94 mmol), triflic anhydride (0.72 mL) and sodium bicarbonate (0.65 g, 7.76 mmol) in DCM was stirred at rt overnight to give 1,3-bis(4-trifluoromethylsulfonamidophenoxy)propane. 1HNMR (360 MHz, DMSO-d6) δ 11.53 (s, br, 2H, 2×NH), 7.16 (m, 4H), 6.97 (m, 4H), 4.11 (t, J=6.3 Hz, 4H, CH2CH2CH2), 2.14 (m, 2H, CH2CH2CH2). MS-EI m/z 522 [M+].

Example 70

1,4-Bis(4-trifluoromethylsulfonamidophenoxy)butane (70). A mixture of 4-[4-(4-aminophenoxy)butoxy]aniline (0.5 g, 1.84 mmol), triflic anhydride (0.68 mL) and sodium bicarbonate (0.62 g, 7.36 mmol) in DCM was stirred at rt overnight to give 1,4-bis(4-trifluoromethylsulfonamidophenoxy)butane. 1HNMR (360 MHz, DMSO-d6) δ 11.54 (s, br, 2H, 2×NH), 7.15 (d, J=9.2 Hz, 4H), 6.95 (d, J=9.2 Hz, 4H), 4.02 (m, 4H, 2×CH2), 1.84 (m, 4H, 2×CH2). MS-EI m/z 536 [M+].

Example 71

1,4-Bis(4-trifluoromethylsulfonamidophenoxy)benzene (71). A mixture of 1,4-bis(4-aminophenoxy)benzene (0.5 g, 1.71 mmol), triflic anhydride (0.63 mL) and sodium bicarbonate (575 mg, 6.84 mmol) in DCM was stirred at rt to give 1,4-bis(4-trifluoromethylsulfonamidophenoxy)benzene. 1HNMR (300 MHz, DMSO-d6) δ 11.7 (s, br, 2H, 2×NH), 7.24 (m, 4H), 7.08 (s, 4H), 7.03 (m, 4H). MS-EI m/z 556 [M+].

Example 72

1-(4-Aminophenoxy)-4-trifluoromethylsulfonamidophenoxy benzene (72). A mixture of 1,4-bis(4-aminophenoxy)benzene (1 g, 3.4 mmol), triflic anhydride (0.52 mL, 3.07 mmol) and sodium bicarbonate (1.14 g, 13.6 mmol) in DCM was stirred at rt overnight. The reaction was then extracted with EtOAc, washed with brine, dried and concentrated to give 1-(4-aminophenoxy)-4-trifluoromethylsulfonamidophenoxy benzene. 1HNMR (300 MHz, DMSO-d6) δ 7.55 (br s, 2H, NH2), 7.18 (m, 2H), 6.99 (m, 2H), 6.94 (m, 2H), 6.90 (m, 2H), 6.80 (m, 2H), 6.66 (m, 2H). MS-EI m/z 424 [M+].

Example 73

Bis(4-trifluoromethylsulfonamidophenyl) ether (73). A mixture of 4,4'-diaminodiphenyl ether (0.5 g, 2.5 mmol), triflic anhydride (0.84 mL, 5 mmol) and sodium bicarbonate (0.84 g, 10 mmol) in DCM was stirred at rt overnight. The reaction was extracted with EtOAc, washed with brine, dried and concentrated to give bis(4-trifluoromethylsulfonamidophenyl) ether. 1HNMR (300 MHz, DMSO-d6) δ 11.7 (br s, 2H, 2×NH), 7.26 (m, 4H), 7.06 (m, 4H). MS-EI m/z 464 [M+].

Example 74

1,3-Bis(4-trifluoromethylsulfonamidophenoxy)benzene (74). A mixture of 1,3-bis(4-aminophenoxy)benzene (0.5 g, 1.7 mmol), triflic anhydride (0.575 mL, 3.42 mmol) and sodium bicarbonate (0.57 g, 6.84 mmol) in DCM was stirred at rt overnight. The reaction was then extracted with EtOAc, washed with brine, dried and concentrated to give 1,3-bis (4-trifluoromethylsulfonamidophenoxy)benzene. 1HNMR (360 MHz, DMSO-d6) δ 11.71 (br s, 2H, 2×NH), 7.38 (t, J=8.2 Hz, 1H), 7.26 (m, 4H), 7.08 (m, 4H), 6.77 (dd, J=2.2 & 8.2 Hz, 2H), 6.64 (t, J=2.2 Hz, 1H). MS-EI m/z 556 [M+].

Example 75

2,5-Bis(4-trifluoromethylsulfonamidophenyl)-(1,3,4) oxadiazole (75). A mixture of 2,5-bis(4-aminophenyl)-(1,3,4)oxadiazole (0.25 g, 0.99 mmol), triflic anhydride (0.333 mL, 1.98 mmol) and 4-dimethylaminopyridine (0.484 g, 3.96 mmol) in DCM was stirred at rt overnight. The reaction was then extracted with EtOAc, washed with brine, dried and concentrated to give 2,5-bis(4-trifluoromethylsulfonamidophenyl)-(1,3,4)oxadiazole. 1HNMR (300 MHz, DMSO-d6) δ 8.28 (m, 2H), 7.98 (m, 2H), 7.79 (m, 2H), 6.70 (m, 2H). MS-EI m/z 516 [M+].

Example 76

Bis(4-trifluoromethylsulfonamidophenyl)-1,4-diisopropylbenzene (76). A mixture of α,α'-bis(4-aminophenyl)-1,4-diisopropylbenzene (1 g, 2.9 mmol), triflic anhydride (0.976 mL, 5.8 mmol) and sodium bicarbonate (0.975 g, 11.61 mmol) in DCM was stirred at rt overnight. The reaction was then extracted with EtOAc, washed with brine, dried and concentrated to bis(4-trifluoromethylsulfonamidophenyl)-1,4-diisopropylbenzene. 1HNMR (300 MHz, DMSO-d6) δ 7.18 (m, 4H), 7.07 (m, 8H), 1.57 (s, 12H, 4×CH3). MS-EI m/z 608 [M+].

Example 77

5-Trifluoromethanesulfonylamino-1H-indole-2-carboxylic acid (77). The Ethyl 5-Nitroindole-2-carboxylic acid ethyl ester (5 g, 21 mmol)) was mixed with 600 mg of $Pd(OH)_2$ (Pearlman's catalyst) in 200 ml of MeOH. To the mixture was applied a Hydrogen balloon with stirring. After 16 hrs, The reaction mixture was filtered through a pellet of celite. The filtrate was concentrated to give 5-aminoindole-2-carboxylate (4.1 g) as a dark gray solid. $^1$H-NMR (400 MHz, DMSO-d6) δ 11.39 (s, 1H, NH-1), 7.15 (d×d, J=0.8, 9.4 Hz, 1H, H-7), 6.83 (dd, J=0.9, 2 Hz, 1H, H-4), 6.70 (s, 1H, H-3), 6.68 (dd, J=2, 9 Hz, 1H, H-6), 4.68 (s, 1H, NH$_2$-1), 4.29 (q, J=7 Hz, 2H, CH$_2$CH$_3$), 1.31 (t, J=7 Hz, 3H, CH$_2$CH$_3$), MS m/z 205 [M+H].

The above product (2 g, 9.8 mmol) was added with 60 ml of $CH_2Cl_2$ and triethyl amine (2.7 ml, 19.6 mmol). The reaction mixture was brought to −78 degree (dry ice-acetone) under $N_2$. After $(CF_3SO_2)_2O$ (2.0 ml, 11.8 mmol) was added into it slowly via a syringe, the reaction mixture was stirred at −78 degree for 30 min and slowly brought to room temperature. The reaction was treated with 300 ml of $CH_2Cl_2$ and washed with Sat. $Na_2SO_4$ (100 ml×3), $H_2O$ (100 ml×50, and brine. TLC (20% EA/Hexane) showed two components, the desired product with smaller Rf (0.4) and 5-(N,N-ditrifluoromethansulfonyl)amino-1H-indole-2-carboxylic ethyl ester (Rf 0.5). After the methylene dichloride solution was concentrated, the residue was purified by recrystalization with ethyl Acetate-$CH_2Cl_2$-Hexane or column chromatography (20% ErOAc in Hexane). The purified product (5-Trifluoromethanesulfonylamino-1H-indole-2-carboxylic acid ethyl ester) was obtained as a brown solid (2.7 g). $^1$H-NMR (400 MHz, DMSO-d6) δ 11.47 (s, 1H, SNH-5), 8.96 (br, 1H, NH-1), 7.15 & 7.18 9 (s+d, 2H, H-7 & H-4 or H-3), 6.93 & 6.91 (s+dd, 2H, H-6 & H-4 or H-3), 4.30 (q, J=7 Hz, 2H, CH$_2$CH$_3$), 1.32 (t, 3H, CH$_2$CH$_3$), MS m/z 335 [M–H].

The above product (1.5 g, 4.7 mmol) was dissolved in 40 ml of MeOH. To it was added 20 ml of 1N NaOH. The mixture was stirred at room temperature for 2 hrs. After the volume of reaction solution was reduced to less than a half via a rotor-evaporator, the reaction pH was adjusted to pH4–5 with 6N HCl while kept the reaction flask in an ice-water bath. The solid was filtered out and dried under vacuum. The product (5-Trifluoromethanesulfonylamino-1H-indole-2-carboxylic acid) was a light orange solid, 1.1 g. $^1$H-NMR (400 MHz, DMSO-d6) δ 13.08 (s, 1H, COOH), 11.95 (s, 1H, NH-1), 11.62 (s, 1H, SNH-5), 7.56 (d, J=2.0 Hz, 1H, H-4), 7.46 (d, J=8.7 Hz, 1H, H-7), 7.13 (m, 2H, H-3 &H-6), MS m/z 307[M–H].

Example 78

1-Methyl-5-trifluoromethanesulfonylamino-1H-indole-2-carboxylic acid (78). Ethyl 5-Nitroindole-2-carboxylic acid ethyl ester (5.4 g, 22 mmol) in 16 ml of DMF was added with Cs$_2$CO$_3$ (21 g, 66 mmol) and MeI (1.7 ml, 28 mmol). After the reaction mixture was stirred under N$_2$ at room temperature for a day or until TLC (20% Ethyl Acetate in Hexane) showed starting materials disappeared completely, the reaction flask was transferred to an ice-water bath and to it was added 120 ml of water. The brown solid appeared and was filtered out, washed by water and dried under high vacuum. The product (N-methyl-5-nitroindole-2 carboxylic acid ethyl ester) was a yellow solid (4.6 g). $^1$H-NMR (400 MHz, DMSO-d6) δ 8.72 (d, J=2.3 Hz, 1H, H-4), 8.16 (dd, J=2.4, 9.3 Hz, 1H, H-6), 7.80 (d, J=9.2 Hz, H-7), 7.52 (s, 1H, H-3), 4.35 (q, J=7 Hz, 2H, —CH$_2$CH$_3$, 4.08 (s, 3H, N—CH$_3$), 1.35 (t, J=7 Hz, 3H, —CH$_2$CH$_3$).

The above product (3 g, 12 mmol)) was treated with 160 ml of MeOH. The mixture was added with 300 mg of Pd(OH)$_2$ (Pearlman's catalyst) and applied a Hydrogen balloon with stirring. After 16 hrs, The reaction mixture was filtered through a pellet of celite. Methanol was evaporated and collected residue was the product (2.4 g) as a brown solid. $^1$H-NMR (400 MHz, DMSO-d6) δ 7.26 (d, J=8.9 Hz, 1H, H-7), 6,95 (s, 1H, H-3), 6.77 (dd, J=1.7 Hz, 8.9 Hz, 1H, H-6), 6.71(s, J=2.1 Hz, 1H, H-4), 4.74 (br, 2H, NH$_2$-5), 4.28 (q, J=7 Hz, 2H, CH$_2$CH$_3$), 3.92 (s, 3H, CH$_3$), 1.31(t, J=7 Hz, 3H, CH$_2$CH$_3$) MS m/z 219 [M+H].

The N-methyl-5-aminoindole2-carboxylic acid ethyl ester (2.4 g, 11 mmol) was added with 100 ml of CH$_2$Cl$_2$ and triethyl amine (2.3 ml, 16.5 mmol). The reaction mixture was brought to –78 degree (dry ice-acetone) under N$_2$. After (CF$_3$SO$_2$)$_2$O (2.0 ml, 12 mmol) was added into it slowly via a syringe, the reaction mixture was stirred at –78 degree for 30 min and slowly brought to room temperature. The reaction was treated with 300 ml of CH$_2$Cl$_2$ and washed with Sat. Na$_2$SO$_4$ (100 ml×3), H$_2$O (100 ml×50, and brine. TLC (20% EA/Hexane) showed two components, the desired product with smaller Rf value and the corresponding 5-(N,N-ditrifluoromethanesulfonyl)aminoindole. After the solvent was evaporated, the residue was purified either via recrystalization with CH$_2$Cl$_2$/Hexane or Flash Column (20% EA/Hexane). The purified product (1-Methyl-5-trifluoromethansulfonylamino-1H-indole-2-carboxylic acid ethyl ester) was obtained as a light orange solid (1.6 g). $^1$H-NMR (400 MHz, DMSO-d6) δ 11.69 (s, 1H, SNH-5), 7.64 (d, J=8.6 Hz, 1H, H-7), 7.60 (d, J=2.2 Hz, 1H, H-4), 7.31 (s, 1H, H-3), 7.23 (dd, J=2.2, 8.6 Hz, 1H, H-6), 4.33 (q, J=7 Hz, 2H, CH$_2$CH$_3$), 4.02 (s, 3H, NCH$_3$), 1.33 (t, 3H, CH$_2$CH$_3$), MS m/z 349 [M–H].

The above product (1.6 g, 4.6 mmol) was dissolved in 40 ml of MeOH. To it was added 25 ml of 1N NaOH. The mixture was stirred at room temperature for 2 hrs. The reaction solution was concentrated down to less than half of its original volume via a rotor-evaporator. The reaction pH was adjusted to pH4–5 with 6N HCl while the reaction flack was kept in an ice-water bath. The solid was filtered out and dried under vacuum. The product (1-Methyl-5-trifluoromethansulfonylamino-1H-indole-2-carboxylic acid) was a pink solid, 1.2 g. $^1$H-NMR (400 MHz, DMSO-d6) δ 13.04 (s, 1H, COOH), 11.66 (s, 1H, SNH-5), 7.52 (d, J=9.4 Hz, 1H, H-7), 7.58 (d, J=1.9 Hz, 1H, H-4), 7.26 (s, 1H, H-3), 7.21 (dd, J=1.9, 9.4 Hz, 1H, H-6), 4.02 (s, 3H, CH3-1), MS m/z 321 [M–1].

Example 79

(2-Methyl-5-trifluoromethanesulfonylamino-indol-1-yl)-acetic acid (79). To a solution of (5 g, 21.4 mmol) 2-Methyl-5-nitroindole in 16 ml of DMF was added Cs$_2$CO$_3$ (17 g, 54 mmol) and followed by t-Butyl Bromoacetate (3.48 ml, 23.5 mmol). After the reaction mixture was stirred under N$_2$ at room temperature for 24 hrs, to it was added 200 ml of water while the reaction flask was kept in an ice-water bath. The brown solid appeared and was filtered out, washed by water and dried under high vacuum. The product was a yellow solid (8.6 g). $^1$H-NMR (400 MHz, DMSO-d6) δ 8.44 (d, J=2.0 Hz, 1H, H-4), 7.96 (dd, J=2, 9 Hz, 1H, H-6), 7.58 (d, J=9 Hz, 1H, H-7), 6.55(s, 1H, H-3), 5.09 (s, 2H, NCH$_2$CO), 2.36 (s, 3H, NCCH$_3$), 1.41 (s, 9H, —C(CH$_3$)$_3$). MS m/z 291[M+H].

The above product (8.6 g, 29.6 mmol)) was treated with 280 ml of MeOH. The mixture was added with 800 mg of Pd(OH)$_2$ (Pearlman's catalyst) and applied a Hydrogen balloon with stirring. After 16 hrs, the reaction mixture was filtered through a pellet of celite. Methanol was evaporated and collected residue was the product (2-methyl-5-aminoindole-1-yl)-acetic acid t-butyl ester as a brown solid (8 g), which was used without further purification for the next step. $^1$H-NMR (400 MHz, DMSO-d6) δ 6.97 (d, J=8.5 Hz, 1H, H-7), 6.58 (d, J=2.1 Hz, 1H, H-4), 6.41(dd, J=2.1, 8.5 Hz, 1H, H-6), 5.94 (s, 1H, H-3), 4.75 (s, 2H, NCH$_2$CO), 4.43 (br, 2H, NH$_2$-5), 2.23 (s, 3H, CH$_3$-2), 1.41 (s, 3H, C(CH$_3$)$_3$), MS m/z 261 [M+H].

The 5-amino-indole (8 g, 32.5 mmol) from above reaction was added with 80 ml of CH$_2$Cl$_2$ and triethyl amine (7.2 ml, 52 mmol). The reaction mixture was brought to –78 degree (dry ice-acetone) under N$_2$. After (CF$_3$SO$_2$)$_2$O (6.0 ml, 35.8 mmol) was added into it slowly via a syringe, the reaction mixture was stirred at –78 degree for 30 min and slowly brought to room temperature. The reaction was treated with 300 ml of CH$_2$Cl$_2$ and washed with Sat. Na$_2$SO$_4$ (100 ml×3) and H$_2$O (100 ml×50, then brine. TLC (20% EA/Hexane) showed two components, the desired product with smaller Rf value and the corresponding 5-(N,N-ditrifluoromethanesulfonyl)aminoindole. After the solvent was evaporated, the residue was purified either via recrystallization with CH$_2$Cl$_2$/Hexane or flash column (20% EtOAc). The purified product was obtained as a light gray solid (4.78 g). $^1$H-NMR (400 MHz, DMSO-d6) δ 11.46 (s, 1H, SNH-5), 7.36 (d, J=9 Hz, 1H, H-7) 7.32 (d, J=2 Hz, 1H, H-4 ), 6.93 (dd, J=2, 9 Hz, 1H, H-6), 6.29 (s, 1H, H-3), 4.95 (s, 2H, NCH$_2$CO), 2.31 (s, 3H, CH$_3$), 1.42 (s, 9H, C(CH$_3$)$_3$), MS m/z 393 [M+H].

The above product (4 g, 4.6 mmol) was dissolved in 80 ml of CH$_2$Cl$_2$. To it was added 20 ml of TFA. The mixture was stirred at room temperature for 24 hrs. The solvents were evaporated using a rotor-evaporator. The residue was purified by recrystalization from CH$_2$Cl$_2$-Hexane. The collected product was a pink solid, 2.55 g. $^1$H-NMR (400 MHz, DMSO-d6) δ 12.64 (br, 1H, COOH), 11.47 (s, 1H, NH-5), 7.37 (d, J=8.8 Hz, 1H, H-7 ), 7.32 (d, J=2.3 Hz, 1H, H-4), 6.93 (dd, J=2.3, 8.6 Hz, 1H, H-6), 6.28 (s, 1H, H-3), 4.96 (s, 2H, NCH$_2$CO), 2.33 (s, 3H, CH$_3$), 1.91 (s, 9H, C(CH$_3$)$_3$). MS m/z 335 [M−H].

Example 80

1-Methyl-5-trifluoromethanesulfonylamino-1H-indole-2-carboxylic acid phenylamide (80). To 1-Methyl-5-Trifluoromethansulfonylamino-1H-Indole-2-Carboxylic Acid (0.21 g, 0.65 mmol) in 8 ml of DMF was added HOBt (96 mg, 0.71 mmol), EDC (145 mg, 0.78 mmol), TEA (131 mg, 1.3 mmol), and aniline (0.65 ml, 72 mmol). The reaction mixture was stirred at room temperature for a day. The reaction was diluted with 200 ml of methylene dichloride and washed with water and brine, then concentrated. The residue was purified by flash column with 50% EtOAc/Hexane to give 0.13 g of 1-Methyl-5-trifluoromethansulfonylamino-1H-indole-2-carboxylic acid phenylamide as a beige solid. $^1$H-NMR (400 MHz, DMSO-d6) δ 11.61 (s, 1H, SNH), 10.37 (s, 1H, NHCO), 7.78 (d, J=8 Hz, 2H, ArH-o), 7.63 (d, J=9 Hz, 1H, H-7), 7,61 (d, J=2 Hz, 1H, H-4), 7.37 (t, J=8 Hz, 2H, ArH-m), 7.32 (s, 1H, H-3), 7.20 (dd, J=2, 9 Hz, 1H, H-6), 7.12 (t. J=7.4 Hz, 1H. ArH-p).MS m/z 396 (M−H).

Example 81

5-Trifluoromethanesulfonylamino-1H-indole-2-carboxylic acid phenylamide (81). Same procedure as Example 80 except 5-Trifluoromethansulfonylamino-1H-Indole-2-Carboxylic Acid was used. $^1$H-NMR (400 MHz, DMSO-d6) δ 11.94 (s, 1H, SNH), 11.60 (s, 1H, NH-1), 10.27 (s, 1H, NHCO), 7.80 (dd, J=0.9, 8 Hz, 1H, ArH-o), 7.59 (d, J=1.6 Hz, 1H, H-4), 7.49 (d, J=8.5 Hz, 1H, H-7), 7.44 (s, 1H, H-3), 7.38 (t, J=8 Hz, 2H, ArH-m), 7.20 (dd, J=1.5, 8 Hz, 1H, H-6), 7.11 (t, J=8 Hz, 1H, ArH-p). MS m/z 382 (M−H).

Example 82

3-[(1-Methyl-5-trifluoromethanesulfonylamino-1H-indole-2-carbonyl)-amino]-benzoic acid (82). To 1-Methyl-5-Trifluoromethansulfonylamino-1H-Indole-2-Carboxylic Acid (0.51 g, 1.6 mmol) in 8 ml of DMF was added HOBt (240 mg, 1.8 mmol), EDC (370 mg, 1.9 mmol), TEA (0.445, 3.2 mmol), and 3-aminobenzoic acid ethyl ester (265 mg, 1.6 mmol). The reaction mixture was stirred at room temperature for a day. The reaction was diluted with 200 ml of methylene dichloride and washed with water and brine, then concentrated. The residue was treated with 40 ml of MeOH and 20 ml of 1H NaOH. The reaction mixture was stirred at room temperature for 4 hr and then concentrated via a rotor-evaporator to remove the methanol. The aqueous solution was adjusted pH to 4 with 6N HCl. The solid was filtered, washed with water, and purified by either recrystalization with CH$_2$Cl$_2$/Hexane or flash column using 30% EtOAc/Hexane with 1% AcOH to give 0.19 g of 3-[1-Methyl-5-trifluoromethansulfonylamino-1H-indole-2-carbonyl)-amino]-benzoic acid as a beige solid. $^1$H-NMR (400 MHz, DMSO-d6) δ 12.75 (s, 1H, COOH), 11.68 (s, 1H, SNH), 10.65 (s, 1H, NHCO), 7.93 (m, 4H, ArH), 7.64 (m, 2H, H-7 & H-4), 7.38 (s, 1H, H-3), 7.20 (dd, J=1.6, 9 Hz, H-6), 4.01 (s, 3H, CH$_3$), MS, m/z 440 (M−H).

Example 83

3-[(5-Trifluoromethanesulfonylamino-1H-indole-2-carbonyl)-amino]-benzoic acid (83). Same procedure as Example 82 except 5-Trifluoromethansulfonylamino-1H-Indole-2-Carboxylic Acid was used. $^1$H-NMR 400 MHz, DMSO-d6) δ 13.01 (s, 1H, COOH), 11.96 (s, 1H, NHCO), 11.58 (s, 1H, SNH), 10.46 (s, 1H, NH-1), 8.41 (t, J=2 Hz, 1H, ArH), 8.10 (d, J=8 Hz, 1H, ArH), 7.69 (d, J=8 Hz, 1H, ArH), 7.60 (d, J=2 Hz, 1H-4), 7.5 (m, 3H, ArH, H-7, & H-3), 7.13 (dd, J=2, 8.6 Hz, 1H, H-6), MS m/z 426 (M−H).

Example 84

4-[(5-Trifluoromethanesulfonylamino-1H-indole-2-carbonyl)-amino]-benzoic acid (84). Same procedure as Example 82 except 5-Trifluoromethansulfonylamino-1H-Indole-2-Carboxylic Acid and 4-aminobenzoic methyl ester was used. 1H-NMR (400 MHz, DMSO-d6) δ 12.74 (s, 1H, COOH), 11.99 (d, J=1.2 Hz, 1H, NHCO), 11.61 (s, 1H, SNH), 10.54 (s, 1H, NH-1), 7.95 (m, 4H, ArH), 7.61 (d, J=2.1 Hz, 1H H-4), 7.50 (m, 2H, H-7 & H-3), 7.14 (dd, J=2, 9 Hz, 1H, H-6), MS m/z 426 (M−H).

Example 85

4-[2-(2-Methyl-5-trifluoromethanesulfonylamino-indol-1-yl)-acetylamino]-benzoic acid (85). Same procedure as Example 82 except (2-Methyl-5-trifluoromethanesulfonylamino-indol-1-yl)-acetic acid and 4-aminobenzoic methyl ester was used. $^1$H-NMR (400 MHz, DMSO-d6) δ 12.72 (s, 1H, COOH), 11.45 (s, 1H, SNH), 10,73 (s, 1H, NHCO), 7.90 (d, J=7 Hz, 2H, ArH), 7.70 (d, 2H, ArH), 7.38 (d, J=9 Hz, 1H, H-7), 7.32 (d, J=2 Hz, 1H, H-4), 6.94 (dd, J=2, 8 Hz, 1H, H-6), 6.28 (s, 1H, H-3), 5.04 (s, 2H, CH2), 2.38 (s, 3H, CH3), MS m/z 454 (M−H).

Example 86

3-[2-(2-Methyl-5-trifluoromethanesulfonylamino-indol-1-yl)-acetylamino]-benzoic acid (86). Same procedure as Example 82 except (2-Methyl-5-trifluoromethanesulfonylamino-indol-1-yl)-acetic acid and 3-aminobenzoic ethyl ester was used. $^1$H-NMR (400 MHz, DMSO-d6) δ 12.93 (s, 1H, COOH), 11.44 (s, 1H, SNH), 10.62 (s, 1H, NHCO), 8.23 (t, J=2 Hz, 1H, ArH), 7.82 (dq, J=1, 8 Hz, 1H, ArH), 7.65 (dt, J=1, 8 Hz, 1H, ArH), 7.45 (t, J=8 Hz, 1H, ArH), 7.39 (d, J=8.6 Hz, 1H, H-7), 7.33 (d, J=2.3 Hz, 1H, H-4), 6.94 (dd, J=2.3, 8.6 Hz, 1H, H-6), 6.30 (s, 1H, H-3), 5.02 (s, 2H, CH2), 2.39 (s, 3H, CH3), MS m/z 454 (M−H).

Example 87

4-{[2-(2-Methyl-5-trifluoromethanesulfonylamino-indol-1-yl)-acetylamino]-methyl}-benzoic acid (87). Same procedure as Example 82 except (2-Methyl-5-trifluoromethanesulfonylamino-indol-1-yl)-acetic acid and methyl-4-(aminomethyl)benzoate hydrochloride was used. $^1$H-NMR (400 MHz, DMSO-d6) δ 12. 84 (s, 1H, COOH), 11.45 (s, 1H, SNH), 8.75 (t, J=6.4 Hz, 1H, NHCO), 7.89 (d, J=8.6 Hz, 2H, ArH), 7.3 (m, 4H, ArH, H-7, & H-4), 6.93 9dd, J=2, 8.5 Hz, 1H, H-6), 6.27 (s, 1H, H-3), 4.86 (s, 2H, CH$_2$N-2), 4.37 (d, J=6.6 Hz, 2H, NCH$_2$Ar), 2.35 (s, 3H, CH$_3$), MS m/z 468 (M−H).

Example 88

(2-Methyl-5-trifluoromethanesulfonylamino-indol-1-yl)-acetic acid tert-butyl ester (88). To a solution of (5 g, 21.4 mmol) 2-Methyl-5-nitroindole in 16 ml of DMF was added Cs$_2$CO$_3$ (17 g, 54 mmol) and followed by t-Butyl bromoacetate (3.48 ml, 23.5 mmol). After the reaction mixture was stirred under N$_2$ at room temperature for 24 hrs, to it was added 200 ml of water while the reaction flask was kept in an ice-water bath. The brown solid appeared and was filtered out, washed by water and dried under high vacuum. The product was a yellow solid (8.6 g). $^1$H-NMR (400 MHz, DMSO-d6) δ 8.44 (d, J=2.0 Hz, 1H, H-4), 7.96 (dd, J=2, 9 Hz, 1H, H-6), 7.58 (d, J=9 Hz, 1H, H-7), 6.55(s, 1H, H-3), 5.09 (s, 2H, NCH$_2$CO), 2.36 (s, 3H, NCCH$_3$), 1.41 (s, 9H, —C(CH$_3$)$_3$). MS m/z 291[M+H].

The above product (8.6 g, 29.6 mmol)) was treated with 280 ml of MeOH. The mixture was added with 800 mg of Pd(OH)$_2$ (Pearlman's catalyst) and applied a Hydrogen balloon with stirring. After 16 hrs, the reaction mixture was filtered through a pellet of celite. Methanol was evaporated and collected residue was the product (2-methyl-5-aminoindole-1-yl)-acetic acid t-butyl ester as a brown solid (8 g), which was used without further purification for the next step. $^1$H-NMR (400 MHz, DMSO-d6) δ 6.97 (d, J=8.5 Hz, 1H, H-7), 6.58 (d, J=2.1 Hz, 1H, H-4), 6.41(dd, J=2.1, 8.5 Hz, 1H, H-6), 5.94 (s, 1H, H-3), 4.75 (s, 2H, NCH$_2$CO), 4.43 (br, 2H, NH$_2$-5), 2.23 (s, 3H, CH$_3$-2), 1.41 (s, 3H, C(CH$_3$)$_3$), MS m/z 261[M+H].

The 5-amino-indole (8 g, 32.5 mmol) from above reaction was added with 80 ml of CH$_2$Cl$_2$ and triethyl amine (7.2 ml, 52 mmol). The reaction mixture was brought to –78 degree (dry ice-acetone) under N$_2$. After (CF$_3$SO$_2$)$_2$O (6.0 ml, 35.8 mmol) was added into it slowly via a syringe, the reaction mixture was stirred at –78 degree for 30 min and slowly brought to room temperature. The reaction was treated with 300 ml of CH$_2$Cl$_2$ and washed with Sat. Na$_2$SO$_4$ (100 ml×3) and H$_2$O (100 ml×50, then brine. TLC (20% EA/Hexane) showed two components, the desired product with smaller Rf value and the corresponding 5-(N,N-ditrifluoromethanesulfonyl)aminoindole. After the solvent was evaporated, the residue was purified either via recrystallization with CH$_2$Cl$_2$/Hexane or flash column (20% EtOAc). The purified product was obtained as a light gray solid (4.78 g). $^1$H-NMR (400 MHz, DMSO-d6) δ11.46 (s, 1H, SNH-5), 7.36 (d, J=9 Hz, 1H, H-7) 7.32 (d, J=2 Hz, 1H, H-4), 6.93 (dd, J=2, 9 Hz, 1H, H-6), 6.29 (s, 1H, H-3), 4.95 (s, 2H, NCH$_2$CO), 2.31 (s, 3H, CH$_3$), 1.42 (s, 9H, C(CH$_3$)$_3$), MS m/z 393 [M+H].

Example 89

1-Methyl-5-trifluoromethanesulfonylamino-1H-indole-2-carboxylic acid ethyl ester (89). Ethyl 5-Nitroindole-2-carboxylic acid ethyl ester (5.4 g, 22 mmol) in 16 ml of DMF was added with Cs$_2$CO$_3$ (21 g, 66 mmol) and MeI (1.7 ml, 28 mmol). After the reaction mixture was stirred under N$_2$ at room temperature for a day or until TLC (20% Ethyl Acetate in Hexane) showed starting materials disappeared completely, the reaction flask was transferred to an ice-water bath and to it was added 120 ml of water. The brown solid appeared and was filtered out, washed by water and dried under high vacuum. The product (N-methyl-5-nitroindole-2 carboxylic acid ethyl ester) was a yellow solid (4.6 g). $^1$H-NMR (400 MHz, DMSO-d6) δ 8.72 (d, J=2.3 Hz, 1H, H-4), 8.16 (dd, J=2.4, 9.3 Hz, 1H, H-6), 7.80 (d, J=9.2 Hz, H-7), 7.52 (s, 1H, H-3), 4.35 (q, J=7 Hz, 2H, —CH$_2$CH$_3$), 4.08 (s, 3H, N—CH$_3$), 1.35 (t, J=7 Hz, 3H, —CH$_2$CH$_3$).

The above product (3 g, 12 mmol)) was treated with 160 ml of MeOH. The mixture was added with 300 mg of Pd(OH)$_2$ (Pearlman's catalyst) and applied a Hydrogen balloon with stirring. After 16 hrs, The reaction mixture was filtered through a pellet of celite. Methanol was evaporated and collected residue was the product (2.4 g) as a brown solid. $^1$H-NMR (400 MHz, DMSO-d6) δ 7.26 (d, J=8.9 Hz, 1H, H-7), 6.95 (s, 1H, H-3), 6.77 (dd, J=1.7 Hz, 8.9 Hz, 1H, H-6), 6.71(s, J=2.1 Hz, 1H, H-4), 4.74 (br, 2H, NH$_2$-5), 4.28 (q, J=7 Hz, 2H, CH$_2$CH$_3$), 3.92 (s, 3H, CH$_3$), 1.31(t, J=7 Hz, 3H, CH$_2$CH$_3$) MS m/z 219 [M+H].

The N-Methyl-5-aminoindole2-carboxylic acid ethyl ester (2.4 g, 11 mmol) was added with 100 ml of CH$_2$Cl$_2$ and triethyl amine (2.3 ml, 16.5 mmol). The reaction mixture was brought to –78 degree (dry ice-acetone) under N$_2$. After (CF$_3$SO$_2$)$_2$O (2.0 ml, 12 mmol) was added into it slowly via a syringe, the reaction mixture was stirred at –78 degree for 30 min and slowly brought to room temperature. The reaction was treated with 300 ml of CH$_2$Cl$_2$ and washed with Sat. Na$_2$SO$_4$ (100 ml×3), H$_2$O (100 ml×50, and brine. TLC (20% EA/Hexane) showed two components, the desired product with smaller Rf (0.4) value and the corresponding 5-(N, N-ditrifluoromethanesulfonyl)aminoindole (Rf 0.6). After the solvent was evaporated, the residue was purified either via recrystalization with CH$_2$Cl$_2$/Hexane or Flash Column (20% EA/Hexane). The purified product (1-Methyl-5-trifluoromethansulfonylamino-1H-indole-2-carboxylic acid ethyl ester) was obtained as a light orange solid (1.6 g). $^1$H-NMR (400 MHz, DMSO-d6) δ 11.69 (s, 1H, SNH-5), 7.64 (d, J=8.6 Hz, 1H, H-7), 7.60 (d, J=2.2 Hz, 1H, H-4), 7.31 (s, 1H, H-3), 7.23 (dd, J=2.2, 8.6 Hz, 1H, H-6), 4.33 (q, J=7 Hz, 2H, CH$_2$CH$_3$), 4.02 (s, 3H, NCH$_3$), 1.33 (t, 3H, CH$_2$CH$_3$), MS m/z 349 [M–H].

Example 90

6-Trifluoromethanesulfonylamino-naphthalene-2-carboxylic acid (90). A suspension of 2,6-Naphthalendicarboxylic acid (10.8 g, 50 mmol) in anhydrous DMF (400 ml) with 1,8-diazabicyclo[5,4,0]undec-7-ene (DBU, 7.5 ml, 50 mmol) was heated to near boiling, then kept stirring at 60° C. To it was added benzyl bromide solution (6 ml, 50 mmol, in 200 ml of DMF) dropwise. After 3 hours the solution was concentrated and 0.5 N HCl/brine (400 ml) was added, extracted with EtOAc and the combined organic extracts were washed with H$_2$O, and taken to dryness to yield a white solid. The solid was dissolved in EtOAc, and NEt$_3$ was added with slight warming to effect total dissolution of all solid. This solution was filtered through silica gel. Initial elution with EtOAc provided 2,6-naphathalenedicarboxylic acid dibenzyl ester. Subsequent elution with EtOAc/Acetic acid (99/1) brought desired product. Evaporation of solvent and suspension of the resulting solid in petroleum ether, following by collection and drying of solid gave pure product 2,6-Naphthalenedicarboxylic acid monobenzyl ester (5 g, 33%). $^1$H NMR (360 MHz, DMSO-d6) δ13 (br. 1H, —COOH), 8.725 (s, 1H, Ar—H), 8.664 (s, 1H, Ar—H), 8.251(d, J=8.2 Hz, 2H, Ar—H), 8.087–8.044 (m, 2H, Ar—H), 7.539 (d, J=7.0 Hz, 2H, Ar—H), 7.450–7.350 (m, 3H, Ar—H), 5.439 (s, 2H, —COOCH$_2$—), MS m/e 305 [M$^+$-1].

A suspension of 2,6-Naphthalenedicarboxylic acid monobenzyl ester (1.53 g, 5 mmol) in t-BuOH (100 ml) was treated sequentially with diphenylphosphoryl azide (DPPA, 1.3 ml, 6 mmol) and Et$_3$N (0.84 ml, 6 mmol), and the mixture was stirred at reflux for 6 hours. The mixture was cooled and concentrated in vacuo. The residue was crystallized from methylene chloride. The solid was collected by vacuum filtration, and dried to get a white solid. LCMS report showed the major product was desired compound which was put into 50% TFA/DCM for 1 hour. Evaporated the solvent. The residue was chromatographed on silica gel. Used 20–40% EtOAc/Hexanes to elute compound (6-Amino-naphthalene-2-carboxylic acid benzyl ester). $^1$H NMR (360 MHz, DMSO-d6) δ 8.391 (s, 1H, Ar—H), 7.840–7.785 (m, 2H, Ar—H), 7.608 (d, J=8.3 Hz, 1H, Ar—H), 7.495 (d, J=6.9 Hz, 2H, Ar—H), 7.434–7.329 (m, 3H, Ar—H), 7.058–7.029 (m, 1H, Ar—H), 6.936–6.932 (m, 1 H, Ar—H), 6.2 (br. 2H, —NH$_2$), 5.361 (s, 2H, COOCH$_2$—), MS m/e 278 [M+H]$^+$.

To a solution of 6-Amino-naphthalcne-2-carboxylic acid benzyl ester (850 mg, 3 mmol) and triethylamine (0.5 ml, 3.6 mmol) in dichloromethane (60 ml) cooled in a dry ice bath, was added trifluoromethanesulfonic anhydride (0.6 ml, 3.6 mmol). Let the mixture warm to room temperature and stir for two more hours. Added more dichloromethane, washed with brine. The organic layer was concentrated to get 800 mg of 6-Trifluoromethanesulfonylamino-naphthalene-2-carboxylic acid benzyl ester. $^1$H NMR (360 MHz, DMSO-d6) δ 8.640 (s, 1H, Ar—H), 8.169–8.193 (m, 1H, Ar—H), 8.014–8.023 (m, 1H, Ar—H), 7.830 (d, J=1.8 Hz, 1H, Ar—H), 7.367–7.532 (m, 6H, Ar—H), 5.416 (s, 2H, —COOCH2-), MS m/e 408 [M$^+$-1].

To the crude 6-Trifluoromethanesulfonylamino-naphthalene-2-carboxylic acid benzyl ester (800 mg, ~1.9 mmol) in THF (40 ml) was added 0.2N LiOH (40 ml). The mixture was refluxed for 6 hours. Evaporated the THF. The aqueous layer was washed with methylene chloride, then, acidified with 6N HCl. The resulting solid was collected by vacuum filtration, washed with H$_2$O, dried and purified through flush column to get 6-Trifluoromethanesulfonylamino-naphthalcne-2-carboxylic acid (silica gel, 10% MeOH/DCM elute the compound). $^1$H NMR (DMSO-d6) δ 12.7 (br. 2H, —COOH, CF3SO2NH—), 8.527 (s, 1H, Ar—H), 8.067 (d, J=8.8 Hz, 1H, Ar—H), 7.946–7.898 (m, 2H, Ar—H), 7.734 (s, 1H, Ar—H), 7.450–7.423 (dd, J=1.9&7.0 Hz, 1H, Ar—H). MS m/e 318[M$^+$-1].

Example 91

N,N-Bis[(6-carboxyl-naphthalen-2-yl)methyl]trifluoromethanesulfonamide (91). To a suspension of 2,6-Naphthalenedicarboxylic acid monobenzyl ester (2.9 g, 9.5 mmol) in anhydrous THF (50 ml) under N$_2$ at 0° C., was added 1.0M BH$_3$.THF (14.3 ml, 14.3 mmol). The mixture was stirred at room temperature for overnight, then partitioned between brine (200 ml) and EtOAc (3×75), dried over Na$_2$SO$_4$, and taken to dryness to yield a white solid (6-Hydroxymethyl-2-naphthalenecarboxylic acid benzyl ester, 2.6 g). $^1$H NMR (360 MHz, DMSO-d6): δ 8.635 (s, 1H, Ar—H), 8.110 (d, J=8.6 Hz, 1H, Ar—H), 8.004 (m, 2H, Ar—H), 7.919 (s, 1H, Ar—H), 7.574–7.366 (m, 6H, Ar—H), 5.425–5.393 (m, 2H, —COOCH$_2$—), 4.71–4.696(d, J=5.2 Hz, 2H, HO—CH$_2$—), MS m/e 291 [M$^+$-1].

Dissolved 1.2 g (4 mmol) of 6-Hydroxymethyl-2-naphthalenecarboxylic acid benzyl ester in 100 ml of CH$_2$Cl$_2$, slowly added 5.2 g of MnO$_2$ (60 mmol) and stirred at room temperature for 2 hours, then filtered through Ceilite. The Celite was washed with CH$_2$Cl$_2$ and combined organics taken to dryness. The oily residue was solidified with EtOAc/Hexanes (1:1) and collected by vacuum filtration, washed with small amount of methanol, dried to get 1.2 g of 6-Formyl-2-naphthalenecarboxylic acid benzyl ester. $^1$H NMR (400 MHz, DMSO-d6): δ 10.192 (s, 1H, —CHO), 8.754 (s, 1H, Ar—H), 8.667 (s, 1H, Ar—H), 8.327(t, J=9.4, 2H, Ar—H), 8.142(dd, J=1.6&7.0 Hz, 1H, Ar—H), 7.987–7.962 (dd, J=1.6&7.0 Hz, 1H, Ar—H), 7.544–7.526 (m, 2H, Ar—H), 7454–7.375 (m, 3H, Ar—H), 5.442 (s, 2H, —COOCH$_2$—), MS m/e 289[M$^+$-1].

To a mixture of 6-Formyl-2-naphthalenecarboxylic acid benzyl ester (1.2 g, 4 mmol) and ammonia (10 ml, 2.0M solution in ethyl alcohol, 20 mmol) in THF (15 ml) was added sodium cyanoborohydride (1.25 g, 20 mmol.). The mixture was stirred at room temperature for 20 min., a small amount of AcOH was added to maintain a neutral pH. The mixture was stirred for 5 hours, filtered, and the white solid was washed with DCM. The combined reaction solution and the DCM wash were concentrated. The residue was treated with DCM, washed with sodium bicarbonate and brine, dried and taken to dryness to get 785 mg of product as a white solid. $^1$H NMR (360 MHz, DMSO-d6) δ 8.632 (s, 2H, Ar—H), 8.130–8.089 (m, 2H, ArH), 8.027–7.953 (m, 6H, Ar—H), 7.672–7.644(m, 2H, Ar—H), 7.529–7.510 (m, 4H, Ar—H), 7.447–7.347 (m, 6H, Ar—H), 5.417 (s, 4H, 2×—COOCH$_2$—), 4.137–4.099 (m, 1H, >NH—), MS m/e 566 [M+H]$^+$.

To a solution of above product (780 mg, 1.4 mmol) and triethylamine (293 ul, 1.5 eq.) in dichloromethane (50 ml) cooled in a dry ice bath, was added trifluoromethanesulfonic anhydride (259 ul, 11. eq.). Let the mixture warm to room temperature, then stirred for two more hours. Added more dichloromethane, washed with brine. The organic layer was concentrated to get product MS m/e 695.4 [M+H]$^+$. To it (~1.4 mmol) in THF (35 ml) was added 0.2N LiOH (35 ml). The mixture was stirred at 60° C. for 3 hours. Evaporated the THF. The aqueous layer was washed with methylene chloride, then, acidified with 6N HCl. The resulting solid was collected by vacuum filtration, washed with H$_2$O, dried to get N,N-Bis[(6-carboxyl-naphthalen-2-yl)methyl] trifluoromethanesulfonamide_as a white solid. $^1$H NMR (400 MHz, DMSO-d6) δ 13 (br. 2H, 2×—COOH), 8.456 (s, 2H, Ar—H), 7.978(d, J=8.5 Hz, 2H, Ar—H), 7.909 (dd, J=1.6&7.0 Hz, 2H, Ar—H), 7.815 (d, J=8.4 Hz, 2H, Ar—H), 7.740 (s, 2H, ArH), 7.434(dd, J=1.3&7.3 Hz, 2H, Ar—H), 4.857 (s, 4H, —CH$_2$NCH$_2$—), MS m/e 516 [M-1]$^+$.

Example 92

6-[(Methyl-trifluoromethanesulfonyl-amino)-methyl]-naphthalene-2-carboxylic acid (92). NaBH$_3$CN (1.57 g, 25 mmol) was added to a solution of 6-Formyl-2-naphthalenecarboxylic acid benzyl ester (1.5 g, 5 mmol) and methylamine (2.2 ml, 40% wt. % solution in water, 25 mmol) in THF (20 ml). The mixture was stirred at room temperature for 20 min, a small amount of AcOH was added to maintain a neutral pH. The mixture was stirred for 1 hours, decanted the solution, and the white solid was washed with DCM. The combined reaction solution and the DCM wash were concentrated. The residue was treated with DCM, washed with sodium bicarbonate and brine, dried and taken to dryness to get 1.3 g of product as a colorless oil, which was chromatographed on silica gel eluting with 5% MeOH/DCM to get 580 mg pure product as a oil. $^1$H NMR (360 MHz, DMSO-d6): δ 8.632 (s, 1H, Ar—H), 8.105(d, J=8.5 Hz, 1H, Ar—H), 7.991 (s, 2H, Ar—H), 7.907(s, 1H, Ar—H), 7.612 (dd, J=1.8&6.6 Hz, 1H, Ar—H), 7.553–7.512 (m, 2H, Ar—H), 7.452–7.367 (m, 3H, Ar—H), 5.417 (s, 2H, —COOCH$_2$—), 3.858 (s, 2H, —NHCH$_2$—), 2.316 (s, 3H, —NHCH$_3$). MS m/e 306 [M+H]$^+$.

To a solution of above product (574 mg, 1.9 mmol) and triethylamine (393 ul, 1.5 eq) in dichloromethane (50 ml) cooled in a dry ice bath, was added trifluoromethanesulfonic anhydride (348 ul, 1.1 eq.). After the mixture warmed to room temperature, allowed it stir for two more hours. Added more dichloromethane, washed with brine. The organic layer was concentrated to give product. $^1$H NMR (400 MHz, DMSO-d6): δ 8.92–8.690 (d, J=0.4 Hz, 1H, Ar—H), 8.246 (d, J=8.5 Hz, 1H, Ar—H), 8.108–8.039 (m, 2H, Ar—H), 7.990 (s, 1H, Ar—H), 7.587–7.521 (m, 3H, Ar—H), 7.456–7.376 (m, 3H, Ar—H), 5.429 (s, 2H—COOCH$_2$—), 4.8 (s, 2H, >NCH$_2$—), 2.983 (s, 3H, —CH$_3$).

To the crude above product (~1.9 mmol) in THF (40 ml) was added 0.2N LiOH (40 ml). The mixture was stirred at 60° C. for 3 hours. Evaporated the THF. The aqueous layer was washed with methylene chloride, then, acidified with 6N HCl. The resulting solid was collected by vacuum filtration, washed with H$_2$O, dried to get 500 mg of 6-[(Methyl-trifluoromethanesulfonyl-amino-)-methyl]-naphthalene-2-carboxylic acid as a white solid. $^1$H NMR (400 MHz, DMSO-d6) δ 13 (br. 1H, —COOH), 8.624(s, 1H, Ar—H), 8.20 (d, J=8.5 Hz, 1H, Ar—H), 8.067–7.976 (m, 3H, Ar—H), 7.575(dd, J=1.8&6.7 Hz, 1H, Ar—H), 4.771 (s, 2H, —CH$_2$—), 2.981 (s, 3H, —CH$_3$). MS m/e 346 [M+H]$^+$.

Example 93

3-({6-[(Methyl-trifluoromethanesulfonyl-amino)-methyl]-naphthalene-2-carbonyl}-amino)-benzoic acid (93). PyBOP (604 mg, 1.16 mmol) was added to the mixture of 6-[(Methyl-trifluoromethanesulfonyl-amino-)-methyl]-naphthalene-2-carboxylic acid (200 mg, 0.58 mmol), ethyl-3-amino-benzoate (86 ul, 0.58 mmol) in DCM (5 ml), followed by addition of DMAP (106 mg, 0.87 mmol). Allowed the mixture stirred at room temperature for overnight. Added more DCM, washed with 1N HCl, NaHCO$_3$ (sat.), and brine. Evaporated the solvent to give a white solid which was dissolved in 10 ml of methanol, added NaOH (5 eq, 116 mg) in H$_2$O (10 ml), stirred at room temperature for overnight. Added more H$_2$O and NaOH, then washed with DCM. Separated the DCM, the aqueous layer was acidified with 6N HCl, the resulting white solid was collected by vacuum filtration, washed with H$_2$O, vacuum dry to get 100 mg of 3-({6-[(Methyl-trifluoromethanesulfonyl-amino)-methyl]-naphthalene-2-carbonyl}-amino)-benzoic acid.

$^1$H NMR (400 MHz, DMSO-d6) δ 13.007(s. 1H, —COOH), 10.633(s, 1H, —NH—), 8.648 (s, 1H, Ar—H), 8.472 (s, 1H, Ar—H), 8.180–8 (d, J=8 Hz, 1H, Ar—H), 8.122–8.074 (m, 3H, ArH), 7.994 (s, 1H, Ar—H), 7.714 (d, J=8 Hz, 1H, ArH), 7.603 (d, J=8 Hz, 1H, Ar—H), 7.53 (t, J=8 Hz, 1H, Ar—H), 4.787 (s, 2H, —CH$_2$—), 2.995 (s, 3H, —CH$_3$), MS m/e 467 [M+H]$^+$.

Example 94

1-tert-Butoxycarbonylmethyl-5-trifluoromethanesulfonylamino-1H-indole-2-carboxylic acid ethyl ester (94). Same procedure as Example 78 except t-Butyl bromoacetate was used. $^1$H-NMR (400 MHz, DMSO-d6) δ 11.68 (s, 1H, SNH), 7.68 (d, J=8.8 Hz, 1H, H-7) 7.62 (d, J=2.0 Hz, 1H, H4), 7.37 (s, 1H, H-3), 7.21 (dd, J=2,9 Hz, 1H, H-6), 5.26 (s, 2H, NCH$_2$CO), 4.30 (q, J=7 Hz, 2H, CH$_2$CH$_3$), 1.40 (s, 9H, C(CH$_3$)$_3$), 1.32 (t, J=7 Hz, 3H, CH$_2$CH$_3$). MS m/z 449 (M–H).

Example 95

1-Carboxymethyl-5-trifluoromethanesulfonylamino-1H-indole-2-carboxylic acid ethyl ester (95). Same procedure as Example 79 except was Ethyl 5-nitroindole-2-carboxylic acid ethyl ester used. $^1$H-NMR (400 MHz, DMSO-d6) δ 12.90 (s, 1H, COOH), 11.72 (s, 1H, SNH), 7.70 (d, J=9 Hz, 1H, H-7), 7.62 (d, J=2 Hz, 1H, H-4), 7.37 (s, 1H, H-3), 7.22 (dd, J=2, 9 Hz, 1H, H-6), 5.30 (s, 2H, NCH$_2$CO), 4.31 (q, J=7 Hz, 2H, CH$_2$CH$_3$), 1.95 (t, J=7 Hz, 3H, CH$_2$CH$_3$), MS m/z 393 (M–1).

Example 96

1-tert-Butoxycarbonylmethyl-5-trifluoromethanesulfonylamino-1H-indole-2-carboxylic acid (96). Same procedure as Example 78 except t-Butyl bromoacetate was used.
$^1$H-NMR (400 MHz, DMSO-d6) δ 13.11 (s, 1H, COOH), 11.67 (s, 1H, SNH), 7.66 (d, J=9 Hz, 1H, H-7), 7.60 (d, J=2 Hz, 1H, H-4), 7.31 (s, 1H, H-3), 7.19 (dd, J=2, 9 Hz, 1H, H-6), 5.25 (s, 2H, NCH$_2$CO), 1.40 [s, 9H, C(CH$_3$)$_3$], MS, m/z 421 (M–H).

Example 97

1-Carboxymethyl-5-trifluoromethanesulfonylamino-1H-indole-2-carboxylic acid (97). The above product (0.13 g, 0.3 mmol) was dissolved in 20 ml of CH$_2$Cl$_2$. To it were added 4 ml of TFA. The mixture was stirred at room temperature for 24 hrs and was concentrated using a rotor-evaporator. The residue was purified by recrystalization from CH$_2$Cl$_2$-Hexane. The collected product was a white solid 0.1 g. $^1$H-NMR (400 MHz, DMSO-d6) δ 13.05 (s, 2H, 2COOH), 11.70 (s, 1H, NSH), 7.67 (d, J=9 Hz, 1H, H-7), 7.61 (d, J=2 Hz, H-4), 7.32 (s, 1H, H-3), 7.19 (dd, J=2,9 Hz, 1H, H-6), 5.30 (s, 2H, NCH$_2$O), MS m/z 365 (M–H).

Example 98

1-Carboxymethyl-5-(N,N-ditrifluoromethanesulfonyl) amino-1H-in dole-2-carboxylic acid ethyl ester (98). Same procedure as Example 78 except t-Butyl bromoacetate was used. $^1$H-NMR (400 MHz, DMSO-d6) δ 13.01 (s, 1H, COOH), 8.13 (d, J=2 Hz, 1H, H-4), 7.90 (d, J=9 Hz, 1H, H-7), 7.52 (dd, J=2, (Hz, 1H, H-6), 7.50 (s, 1H, H-3), 5.37 (s, 2H, NCH$_2$CO), 4.33 (q, J=7 Hz, 2H, CH$_2$CH$_3$), 1.33 (t, J=7 Hz, 3H, CH$_2$CH$_3$), MS m/z 525 (M–1).

Example 99

1-tert-Butoxycarbonylmethyl-5-(N,N-ditrifluoromethanesulfonyl)amino-1H-indole-2-carboxylic acid ethyl ester (99). Same procedure as Example 78 except t-Butyl bromoacetate was used. $^1$H-NMR (400 MHz, DMSO-d6) δ 8.13 (d, J=2 Hz, 1H, H-4), 7.89 (d, J=9 Hz, 1H, H7), 7.52 (dd, J=2, 9 Hz, 1H, H-6), 7.49 (s, 1H, H-3), 5.33 (s, 2, NCH$_2$CO$_2$), 4.32 (q, 2H, CH$_{2CH3}$), 1.40 (s. 9H, C(CH$_3$)$_3$), 1.30 (t, J=7 Hz, CH$_2$CH$_3$). MS m/z 581 (M–1).

Example 100

1-Carboxymethyl-5-(N,N-ditrifluoromethanesulfonyl) amino-1H-indole-2-carboxylic acid (100). Same procedure as Example 97 except t-Butyl bromoacetate was used. $^1$H-NMR (400 MHz, DMSO-d6) δ 12.80 (br, 2H, COOH), 7.45 (d, J=9 Hz, 1H, H-7), 7.38 (s, 1H, H-3 or H-4), 7.17 (s, 1H, H-3 or H-4), 7.07 (d, J=9 Hz, 1H, H-6), 5.24 (s, NCH$_2$CO), MS, m/z 498.

Example 101

1-Cyclohexylmethyl-5-trifluoromethanesulfonylamino-1H-indole-2-carboxylic acid ethyl ester (101). Same procedure as Example 78 except Bromomethylcyclohexane was used. $^1$H-NMR (400 MHz, DMSO-d6) δ 11.6 (br, 1H, SNH), 7.67 (d, J=9 Hz, 1H, H-7), 7.58 (d, J=2 Hz, 1H, H-4), 7.33 (s, 1H, H-3), 7.19 (dd, J=2, 9 Hz, 1H, H-6), 4.41 (d, J=Hz, 2H, NCCH$_2$CH(, 4.32 (q, J=7 Hz, 2H, CH$_2$CH$_3$), 1.32 (t, J=7

Hz, 3H, CH$_2$CH$_3$), 1.6, 1.5, 1.3, & 1.0 (m, 11H, CH(CH$_2$)$_5$), Ms, m/z 431 (M–H).

Example 102

1-Benzyl-5-trifluoromethanesulfonylamino-1H-indole-2-carboxylic acid (102). Same procedure as Example 78 except Benzyl bromide was used. $^1$H-NMR (400 MHz, DMSO-d6) δ 13.10 (br, 1H, COOH), 11.70 (s, 1H, SNH), 7.62 (d, J=1.4 Hz, 1H. H-4), 7.59 (s, J=9.2 Hz, 1H, H-7), 7.38 (s, 1H, H-3), 7.24 (m, 3H, ArH), 7.17 (dd, J=1.4, 9.4 Hz, 1H, H-6), 7.03 (d, J=7 Hz, 2H, ArH), 5.87 (s, 2H, NCH$_2$ArH), MS, m/z 397 (M–H).

Example 103

1-Cyclohexylmethyl-5-trifluoromethanesulfonylamino-1H-indole-2-carboxylic acid (103). Same procedure as Example 78 except Bromomethylcyclohexane was used.

$^1$H-NMR (400 MHz, DMSO-d6) δ 13.0 (br, 1H, COOH), 11.68 (s, 1H, SNH), 7.63 (d, J=9 Hz, 1H, H-7), 7.56 (d, J=1.6 Hz, 1H, H-4), 7.26 (s, 1H, H-3), 7.16 (dd, J=1.6, 9 Hz, 1H, H-6), 4.43 (d, J=7 Hz, 2H, NCH$_2$CH), 1.7, 1.6, 1.4, & 1.0 (m, 10H, CH(CH$_2$)$_5$), MS m/z 403 (M-1).

Compound Evaluation

It will be appreciated that, in any given series of compounds, a spectrum of biological activity will be observed. In one preferred embodiment, the present invention relates to trifluoromethyl sulfonyl and trifluoromethyl sulfonamido compounds demonstrating the ability to modulate phosphate binding proteins including enzymes related to cellular signal transduction, such as, protein tyrosine phosphatases. The assays described below are employed to select those compounds demonstrating the optimal degree of the desired activity.

As used herein, the phrase "optimal degree of desired activity" refers to the highest therapeutic index, defined above, against a phosphate binding protein including enzymes which mediates cellular signal transduction and which is related to a particular disorder so as to provide an animal or a human patient, suffering from such disorder with a therapeutically effective amount of a compound of this invention at the lowest possible dosage.

Assays For Determining Inhibitory Activity

Various procedures known in the art may be used for identifying, evaluating or assaying the inhibition of activity of phosphate binding proteins, including protein tyrosine phosphatases, by the compounds of the invention. For example but without limitation, with regard to phosphatases such assays involve exposing target cells in culture to the compounds and a) biochemically analyzing cell lysates to assess the level and/or identity of tyrosine phosphorylated proteins; or (b) scoring phenotypic or functional changes in treated cells as compared to control cells that were not exposed to the test substance.

Where mimics of the natural ligand for a signal transducing receptor are to be identified or evaluated, the cells are exposed to the compound of the invention and compared to positive controls which are exposed only to the natural ligand, and to negative controls which were not exposed to either the compound or the natural ligand. For receptors that are known to be phosphorylated at a basal level in the absence of the natural ligand, such as the insulin receptor, the assay may be carried out in the absence of the ligand. Where inhibitors or enhancers of ligand induced signal transduction are to be identified or evaluated, the cells are exposed to the compound of the invention in the presence of the natural ligand and compared to controls which are not exposed to the compound of the invention.

The assays described below may be used as a primary screen to evaluate the ability of the compounds of this invention to inhibit phosphatase activity of the compounds of the invention. The assays may also be used to assess the relative potency of a compound by testing a range of concentrations, in a range from 100 μM to 1 pM, for example, and computing the concentration at which the amount of phosphorylation or signal transduction is reduced or increased by 50% (IC$_{50}$) compared to controls.

Biochemical Assays

In one embodiment target cells having a substrate molecule that is phosphorylated or dephosphorylated on a tyrosine residue during signal transduction are exposed to the compounds of the invention and radiolabelled phosphate, and thereafter, lysed to release cellular contents, including the substrate of interest. The substrate may be analyzed by separating the protein components of the cell lysate using a sodium dodecyl sulphate-polyacrylamide gel electrophoresis (SDS-PAGE) technique, in either one or two dimensions, and detecting the presence of phosphorylated proteins by exposing to X-ray film. In a similar technique, but without radioactive labeling, the protein components separated by SDS-PAGE are transferred to a nitrocellulose membrane, the presence of ptyr is detected using an antiphosphotyrosine (anti-pTyr) antibody. Alternatively, it is preferred that the substrate of interest be first isolated by incubating the cell lysate with a substrate-specific anchoring antibody bound to a solid support, and thereafter, washing away non-bound cellular components, and assessing the presence or absence of pTyr on the solid support by an anti-pTyr antibody. This preferred method can readily be performed in a microtiter plate format by an automated robotic system, allowing for testing of large numbers of samples within a reasonably short time frame.

The anti-pTyr antibody can be detected by labeling it with a radioactive substance which facilitates its detection by autoradiography. Alternatively, the anti-pTyr antibody can be conjugated with an enzyme, such as horseradish peroxidase, and detected by subsequent addition of an appropriate substrate for the enzyme, the choice of which would be clear to one skilled in the art. A further alternative involves detecting the anti-pTyr antibody by reacting with a second antibody which recognizes the anti-pTyr antibody, this second antibody being labelled with either a radioactive substance or an enzyme as previously described. Any other methods for the detection of an antibody known in the art may be used.

The above methods may also be used in a cell-free system wherein cell lysate containing the signal-transducing substrate molecule and phosphatase is mixed with a compound of the invention and a kinase. The substrate is phosphorylated by initiating the kinase reaction by the addition of adenosine triphosphate (ATP). To assess the activity of the compound, the reaction mixture may be analyzed by the SDS-PAGE technique or it may be added to a substrate-specific anchoring antibody bound to a solid support, and a detection procedure as described above is performed on the separated or captured substrate to assess the presence or absence of pTyr. The results are compared to those obtained with reaction mixtures to which the compound is not added. The cell-free system does not require the natural ligand or knowledge of its identity. For example, Posner et al (U.S. Pat. No. 5,155,031) describes the use of insulin receptor as a substrate and rat adipocytes as target cells to demonstrate the ability of pervanadate to inhibit PTP activity. Burke et al., 1994, Biochem. Biophys. Res. Comm., 204:129–134) describes the use of autophosphorylated insulin receptor and recombinant PTPIB in assessing the inhibitory activity of a phosphotyrosyl mimetic.

In addition to measuring phosphorylation or dephosphorylation of substrate proteins, activation or modulation of second messenger production, changes in cellular ion levels, association, dissociation or translocation of signaling molecules, gene induction or transcription or translation of specific genes may also be monitored. These biochemical assays may be performed using conventional techniques developed for these purposes.

Biological Assays

The ability of the compounds of this invention to modulate the activity of PTPs, which control signal transduction, may also be measured by scoring for morphological or functional changes associated with ligand binding. Any qualitative or quantitative techniques known in the art may be applied for observing and measuring cellular processes which come under the control of phosphatases in a signaling pathway. Such cellular processes may include, but are not limited to, anabolic and catabolic processes, cell proliferation, cell differentiation, cell adhesion, cell migration and cell death.

The techniques that have been used for investigating the various biological effects of vanadate as a phosphatase inhibitor may be adapted for use with the compounds of the invention. For example, vanadate has been shown to activate an insulin-sensitive facilitated transport system for glucose and glucose analogs in rat adipocytes (Dubyak et al., 1980, J. Biol. Chem., 256:5306–5312). The activity of the compounds of the invention may be assessed by measuring the increase in the rate of transport of glucose analog such as 2-deoxy-3H-glucose in rat adipocytes that have been exposed to the compounds. Vanadate also mimics the effect of insulin on glucose oxidation in rat adipocytes (Shechter et al., 1980, Nature, 284:556–558). The compounds of this invention may be tested for stimulation of glucose oxidation by measuring the conversion of 14C-glucose to 14CO2. Moreover, the effect of sodium orthovanadate on erythropoietin-mediated cell proliferation has been measured by cell cycle analysis based on DNA content as estimated by incorporation of tritiated thymidine during DNA synthesis (Spivak et al., 1992, Exp. Hematol., 20:500–504). Likewise, the activity of the compounds of this invention toward phosphatases that play a role in cell proliferation may be assessed by cell cycle analysis.

The activity of the compounds of this invention can also be assessed in animals using experimental models of disorders caused by or related to dysfunctional signal transduction. For example, the activity of a compound of this invention may be tested for its effect on insulin receptor signal transduction in non-obese diabetic mice (Lund et al., 1990, Nature, 345:727–729), B B Wistar rats and streptozotocin-induced diabetic rats (Solomon et al., 1989, Am. J. Med. Sci., 297:372–376). The activity of the compounds may also be assessed in animal carcinogenesis experiments since phosphatases can play an important role in dysfunctional signal transduction leading to cellular transformation. For example, okadaic acid, a phosphatase inhibitor, has been shown to promote tumor formation on mouse skin (Suganuma et al., 1988, Proc. Natl. Acad. Sci., 85:1768–1771).

The data obtained from these cell culture assays and animal studies can be used in formulating a range of dosages for use in humans. The dosage of the compounds of the invention should lie within a range of circulating concentrations with little or no toxicity. The dosage may vary within this range depending on the dosage form employed and the route of administration.

Phosphotyrosine Enzyme Linked Immunosorbent Assay

This assay may be used to test the ability of the compounds of the invention to inhibit dephosphorylation of phosphotyrosine (ptyr) residues on insulin receptor (IR). Those skilled in the art will recognize that other substrate molecules, such as platelet derived growth factor receptor, may be used in the assay by using a different target cell and anchoring antibody. By using different substrate molecules in the assay, the activities of the compounds of this invention toward different protein tyrosine enzymes may be assessed. In the case of IR, an endogenous kinase activity is active at low level even in the absence of insulin binding. Thus, no insulin is needed to stimulate phosphorylation of IR. That is, after exposure to a compound, cell lysates can be prepared and added to microtiter plates coated with anti-insulin receptor antibody. The level of phosphorylation of the captured insulin receptor is detected using an anti-pTyr antibody and an enzyme-linked secondary antibody.

Assay Methods in Determination of Compound-PTP $IC_{50}$

The following in vitro assay procedure is preferred to determine the level of activity and effect of the different compounds of the present invention on one or more of the PTPs. Similar assays can be designed along the same lines for any PTP using techniques well known in the art.

The catalytic assays described herein are performed in a 96-well format. The general procedure begins with the determination of PTP optimal pH using a three-component buffer system that minimizes ionic strength variations across a wide range of buffer pH. Next, the Michaelis-Menten constant, or Km, is determined for each specific substrate-PTP system. This Km value is subsequently used as the substrate reaction concentration for compound screening. Finally, the test PTP is exposed to varying concentrations of compound for fifteen minutes and allowed to react with substrate for ten minutes. The results are plotted as percent inhibition versus compound concentration and the $IC_{50}$ interpolated from the plot.

The following materials and reagents were used:

1. Assay Buffer was used as solvent for all assay solutions unless otherwise indicated.

| Component | Concentration |
|---|---|
| Acetate (Fisher Scientific A38-500) | 100 mM |
| Bis-tris (Sigma B-7535) | 50 mM |
| Tris (Fisher Scientific BP152-5) | 50 mM |
| Glycerol (Fisher Scientific BP229-1) | 10% (v/v) |

*1 mM DTT is add immediately prior to use.

2. 96 Well Easy Wash Plate (Costar 3369)
3. p-Nitrophenyl Phosphate (pNPP) (Boehringer Mannheim 738–379)
4. Fluorescein Diphosphate (FDP) (Molecular Probes F-2999)
5. 0.22 μm Stericup Filtration System 500 ml (Millipore SCGPU05RE)
6. 10N NaOH (Fisher Scientific SS255-1)

7. 10N HCl (Fisher Scientific A144–500)
8. Compounds were dissolved in DMSO (Sigma D-5879) at 5 or 10 mM concentrations and stored at −20° C. in small aliquots.

Methods

All assays were performed using pNPP or FDP as substrate. The optimum pH was determined for each PTP used.

PTP Assay

PTPase activity was assayed at 25° C. in a 100-µl reaction mixture containing an appropriate concentration of pNPP or FDP as substrate. The reaction was initiated by addition of the PTP and quenched after 10 min by addition of 50 µl of IN NaOH. The non-enzymatic hydrolysis of the substrate was corrected by measuring the control without the addition of the enzyme. The amount of p-nitrophenol produced was determined from the absorbance at 410 nm. To determine the kinetic parameter, Km, the initial velocities were measured at various substrate concentrations and the data were fitted to the Michaelis equation where velocity=(Vmax*[S])/(Km+[S]), and [S]=substrate reaction concentration.

Inhibition studies

The effect of the compounds on PTP was evaluated at 25° C. using pNPP or FDP as substrate. PTP was pre-incubated for fifteen minutes with various concentrations of compound. Substrate was then added at a fixed concentration (usually equal to the Km previously calculated). After 10 minutes, NaOH was added to stop the reaction. The hydrolysis of pNPP was followed at 410 nm on the Biotek Powerwave 200 microplate scanning spectrophotometer. The percent inhibition was calculated as follows: Percent Inhibition=[(control signal−compound signal)/control signal] ×100%. The $IC_{50}$ was then determined by interpolation of a percent inhibition versus compound concentration plot.

Plasmids designed for bacterial GST-PTP fusion protein expression were derived by insertion of PCR-generated human PTP fragments into pGEX vectors (Pharmacia Biotech). Several of these constructs were then used to subclone phosphatases into pFastBac-1for expression in Sf-9 insect cells. Oligonucleotides used for the initial amplification of PTP genes are shown below. The cDNAs were prepared using the Gilbo BRL superscript preamplification system on RNAs purchased from Clontech.

PTP SHP2

SHP-2 cDNA was used as described earlier (Vogel W., et al.,1993, Science, 259:1611-4). The catalytic domain was amplified using the following oligonucleotides 5'oligo: 5'-TCTGTTGGATCCGAGACACTACAAC-3' (SEQ ID NO: 2) 3'oligo: 5'-CCGACATCTAGATCAGTCACGATGAATTCTGCG-3' (SEQ ID NO: 3) and subsequently subcloned into BamH1-Xba-1 sites. It was then ligated into pfas Bac-G2T BamH1-Xba-1 sites.

PTP 1B

The PTP1b cDNA was amplified from human placenta single strand cDNA (Clontech RNA) using the following oligonucleotides: 5'oligo: 5'-CCGACAGGATCCGAGATGGAAAAGGAGTTCGAGCAGATCGAC (SEQ ID NO: 4) 3'oligo: 5'-CCGACATCTAGACTATGTGTTGCTGTTGAACAGGAACCTG (SEQ ID NO: 5) It was subsequently ligated into pFasBac G2TBamH1Xba-1 sites.

PTP EPSILON

The PTPepsilon cDNA was amplified from human placenta single-strand cDNA (Clontech RNA) using the following oligonucleotides: 5'oligo: 5'-GCTGGATCC AGCACCAGCGACAAGAAGATG-3' (SEQ ID NO: 6) 3'oligo: 5'-GTAGTACTCGAGTAAGGCTTGG-3' (SEQ ID NO: 7) After cloning this PCR product into the Bam HI/Xho I sites of pGEX 6P-1, this phosphatase was subcloned using the same restriction sites in pFastBac-G2T.

PTP MEG2

The PTP MEG2 cDNA was amplified from human placenta single strand cDNA (Clontech RNA) using the following oligonucleotides: 5'oligo: 5'-GATGAATTC GATGAGATCATCCTGTTCTC-3' (SEQ ID NO: 8) 3'oligo: 5'-GTACTCGAGTTACTGACTCTCCACGGC-3' (SEQ ID NO: 9) and subsequently ligated into pGex 6P-1 Eco RI/Xho I sites.

PTP ZETA

The PTP Zeta cDNA was amplified from human placenta single strand cDNA (Clontech RNA) using the following oligonucleotides 5'oligo: 5'-AAAGAATTCCAG ACTGCACACTTTTACTTAG-3' (SEQ ID NO: 10) 3'oligo: 5'-TGGCTCTCAGACTGGAATTGTTTCTCTAGC-3' (SEQ ID NO: 11) and subsequently ligated into pGEX 6P-1 Eco RI/Xho I sites.

PTP SIGMA

The PTP Sigma cDNA was amplified from human brain single strand cDNA (Clontech RNA) using the following oligonucleotides: 5'oligo: 5'-TCAGAATTCCGCACC AAATGCCTCCTG-3' (SEQ ID NO: 12) 3'oligo: 5'-GGCCTCGAGGCTGCGTGCGGGCACTTC-3' (SEQ ID NO: 13) and subsequently ligated into pGex 6P-1 Eco RI/Xho I sites.

PTP PEST

The PTP PEST CDNA was amplified from an HeLa cDNA library (Clonetech RNA) using the following oligonucleotides: 5'oligo: 5'-GCGGAATTCATGGAG CAAGTGGAGATCCTG-3' (SEQ ID NO: 14) 3'oligo: 5'-TTCCTCGAGGCAACTGCGGGTCCTTGG-3' (SEQ ID NO: 15) It was subsequently ligated into the Eco RI/Xho I sites of pGEX 6P-1.

PTP ALPHA

RTPα intracellular domain construct was obtained, Schlessinger et al., U.S. Pat. No. 5,888,794, the contents of which are hereby incorporated in their entirety into the present application. The RTPα fragment was cloned into pGEX 3× using the following procedure. The portion from EclX I/Xma III/Eag I (N-terminus blunted by Klenow) to Eco RV was cloned into the Sma I site. The EclX I site is approximately 15 residues downstream of the transmembrane domain.

PTP BETA

The PTP Beta cDNA used has been described earlier (Levy et al., 1993, J. Biol. Chem, 268:10573–10581). The catalytic domain was amplified using the following oligonucleotides: 5'oligo: 5'-GAGAATCCCCCTCTG CCCGTCTGAGCATTC-3' (SEQ ID NO: 16) 3'oligo: 5'-TAGCTCGAGTCTCAATGCCTTGAATAGACTGG-3' (SEQ ID NO: 17) and subsequently cloned into the Eco RI/Xho I sites of pGEX 6P-1.

PTP MU

The PTP Mu cDNA was amplified from a human lung cDNA library (Clontech) using the following oligonucleotides; 5'oligo: 5'-AAAGAATTCACACTG AGCACATCGGTGCC-3' (SEQ ID NO: 18) 3'oligo: 5'-TTCCTCGAGAATCTGGCTTGAGTTTGTCTGTG-3' (SEQ ID NO: 19) It was subsequently ligated into the Eco RI/Xho I sites of pGEX 6P-1.

PTP DEP1

The full length DEP1 cDNA was isolated from a human mammary cDNA library (Clontech). The construction of GST-fusion proteins encompassing the entire cytoplasmic domain was done by PCR using the following oligos;

5'oligo: 5'-TCCGAATTCTGAGGCCTACT-3' (SEQ ID NO: 20) 3'oligo: 5'-CCTGGATCCATGGGCGATGT-3' (SEQ ID NO: 21) It was subsequently ligated into the Eco RI/Bam H1 sites of pGEX 2T.

The GST fusion protein constructs in pGEX were transformed into BL-21 bacteria for high level GST fusion protein expression. Overnight cultures were diluted 1:10 in fresh LB amp (100 μg/ml) media and after shaking for 1 h, isopropyl β-D-thiogalactopyranoside (IPTG, 100 μM final concentration) was added. After another 4 h shaking at 37° C., the cells were lyse in PBS, 1% Triton X-100, 1 mg/ml lysozyme, 10 mg/ml aprotinin/leupeptin by sonication and the supernatants were incubated with glutathione-agarose beads (Pharmacia Biotech) overnight at 40° C. After three washes in TBS with 1% Triton X-100, the GST fusion proteins were eluted with 5 mM reduced glutathione for 10 min at room temperature.

For GST-PTP expression in Sf-9 insect cells, the Spodoptera frugiperda cell line Sf-9 was propagated in supplement Grace's insect medium with 5% fetal bovine serum, 50 IU/ml penicillin (Gibco). 1×106 cells/ml were infected with recombinant baculovirus with a multiplicity of infection of 5 or higher. The cells were then incubated at 27° C. for 3 days, collected, then lysed on ice in Triton Lysis buffer (20 mM Tris-HCl, pH 7.5, 150 mM NaCl, 5 mM EDTA, 10% glycerol, 2 mM phenymethylsulfonyl fluoride, 5 μg/ml leupeptin, 2.5 μg/ml aproyinin) for 60 min. After centrifugation, the supernatant was purified on glutathione-agarose beads (Pharmacia Biotech) as described above.

Table 1 shows PTP $IC_{50}$ values determined for Examples 1–31 and 66–76 using pNPP or FDP as substrate.

TABLE 1

Biological Data PTP $IC_{50}$ (μM).

| Ex. # | SHP2 | 1B | Epilson | MEG2 | Zeta | Sigma | PEST | Alpha | Beta | Mu | DEP1 |
|---|---|---|---|---|---|---|---|---|---|---|---|
| 1 | 2 | >100 | 24.3 | 55 | >100 | >100 | >100 | >100 | 5.9 | >100 | 24.2 |
| 2 | 42.6 | 55.7 | 8.1 | 62.1 | >100 | 30.5 | 25.6 | >100 | 3.5 | >100 | 16.5 |
| 3 | 74.5 | 44.9 | 28.1 | 85.9 | >100 | 42.6 | >100 | >100 | 17.2 | >100 | 40.9 |
| 4 | >100 | >100 | 16.6 | 45.9 | >100 | 81.1 | >100 | >100 | 6.8 | >100 | 26.1 |
| 5 | >100 | >100 | 38.6 | >100 | >100 | >100 | >100 | >100 | 44.8 | >100 | >100 |
| 6 | >100 | >100 | >100 | >100 | >100 | >100 | >100 | >100 | >100 | >100 | >100 |
| 7 | 18.8/28 | 67.5/>100 | 24.4/27.2 | 46.1/81.2 | >100 | 41.2/59 | 22 | >100 | 22.6/18 | >100/>100 | 41 |
| 8 | 37 | 46.8 | 53.7 | >100 | | 27.7 | | | 26.5 | >100 | |
| 9 | >100 | >100 | >100 | >100 | | 49.9 | | | 45.6 | >100 | |
| 10 | >100 | >100 | 60.8 | >100 | | 33.8 | | | 20.5 | >100 | |
| 11 | >100 | >100 | 38.7 | >100 | | 24.1 | | | 11.2 | >100 | |
| 12 | 79.8 | >100 | >100 | >100 | | 91.7 | | | 17.9 | >100 | |
| 13 | >100 | >100 | 80.4 | >100 | | 84.5 | | | 15.1 | 76 | |
| 14 | >100 | >100 | >100 | >100 | | 6.75 | | | 13.4 | >100 | |
| 15 | 10.7 | 15.7 | 10 | 21.1 | | 11.7 | | | 10.3 | 15.5 | |
| 16 | >100 | >100 | 64.7 | 79.5 | | 29.4 | | | 9.6 | >100 | |
| 17 | >100 | >100 | >100 | 88.5 | | >100 | | | 26 | >100 | |
| 18 | 18.4 | 16.4 | 0.77 | 44 | | 22.1 | | 40.4 | 13.5 | 21.6 | |
| 19 | >100 | 42.5 | 31.4 | 52.2 | | 93.3 | | >100 | 1.9 | 69.5 | |
| 20 | 54.3 | 43.3 | 7.5 | >100 | | 22.9 | | >100 | 8.7 | 37.9 | |
| 21 | 56.8 | 35.3 | 57.8 | 49.4 | | 21.1 | | >100 | 3.1 | 47.7 | |
| 22 | 16.3 | 25.7 | 8.3 | 27.5 | | 7.8 | | >100 | 1.4 | 17.4 | |
| 23 | 27.6 | 11.6 | 2.2 | >100 | | 8.5 | | >100 | 1.1 | 18.3 | |
| 24 | >100 | >100 | >100 | >100 | | 53.5 | | >100 | 5.1 | >100 | |
| 25 | >100 | 16.4 | 41.4 | 52.6 | | >71 | | >100 | 0.35 | 48.8 | |
| 26 | >100 | >100 | 6.2 | 90.8 | | 69 | | >100 | 2.9 | 65 | |
| 27 | >100 | >100 | 3.8 | >100 | | >100 | | >100 | 61.4 | >100 | |
| 28 | 17.9 | 27.6 | 3.1 | 33.3 | | 45.1 | | 36.2 | 3.2 | >100 | |
| 29 | 37 | 35.4 | 26.1 | 68.3 | | 60.6 | | 19.3 | 6.4 | >100 | |
| 30 | 52.8 | >100 | 4.3 | 64.3 | | 26.5 | | >100 | 3.4 | 28.4 | |
| 31 | 5.7 | 6.2 | 1.8 | 9.6 | | 7.7 | 6 | | 4.5 | 8.7 | |
| 66 | 36.6 | 60.4 | >100 | >100 | >100 | >100 | 13.3 | >100 | 39.9 | 70.9 | >100 |
| 67 | 17 | 35 | 50.8 | 85.7 | >100 | 41.4 | 10.5 | 53.6 | 55.9 | 41.3 | 85.6 |
| 68 | 6.2 | 44.6 | 37 | 34.4 | >100 | 11.6 | 9.33 | 27 | 15.2 | 42 | 25 |
| 69 | 20.3 | 78.9 | 40.7 | >100 | >100 | 41.7 | 7.86 | 31 | >100 | 37 | >100 |
| 70 | 17.1 | 85 | 48.4 | 70.7 | >100 | 38.1 | 6.75 | 46 | 7 | 65.3 | 24.5 |
| 71 | 3.4 | 10.6 | 16.9 | 39.4 | 64.3 | 44 | 0.98 | 11.9 | 12.1 | 4 | 49 |
| 72 | 17 | 28.2 | 48.3 | >100 | | 41.1 | | | 22.7 | >100 | |
| 73 | >100 | >100 | 23.1 | >100 | | >100 | | | >100 | 76.1 | |
| 74 | 2.8 | 7.7 | 1.8 | 58.7 | | 7.6 | | | 26.6 | 3.9 | |
| 75 | 8.0 | 8.4 | 11.5 | 12.8 | | 13.2 | | | 2.9 | 32.4 | |
| 76 | 1.8 | 2.5 | 8.4 | 12.9 | | 20 | | | 6.4 | 6.7 | |

Assay Methods in Determination of Compound-PTP $IC_{50}$: Fluorescent Substrate

The following in vitro assay procedure is preferred to determine the level of activity and effect of the different compounds of the present invention on one or more of the PTPs. Similar assays can be designed along the same lines for any PTP using techniques well known in the art.

The catalytic assays described herein are performed in a 96-well format. The general procedure begins with the determination of PTP optimal pH using a three-component buffer system that minimizes ionic strength variations across a wide range of buffer pH. Next, the Michaelis-Menten constant, or Km, is determined for the substrate 6,8-difluoro-4-methylumbelliferyl phosphate (DiFMUP). This Km value is subsequently used as the substrate reaction concentration for compound screening. Finally, the test PTP is exposed to varying concentrations of compound for fifteen minutes and allowed to react with substrate for ten minutes. The results are plotted as percent inhibition versus compound concentration and the $IC_{50}$ interpolated from the plot.

The following materials and reagents were used:
1. Assay Buffer was used as solvent for all assay solutions unless otherwise indicated.

| Component | Concentration |
|---|---|
| Acetate (Fisher Scientific A38-500) | 100 mM |
| Bis-tris (Sigma B-7535) | 50 mM |
| Tris (Fisher Scientific BP152-5) | 50 mM |
| Glycerol (Fisher Scientific BP229-1) | 10% (v/v) |

*1 mM DTT is add immediately prior to use.

2. 96-well plate (black, untreated Costar 3694)
3. 6,8-difluoro-4-methylumbelliferyl phosphate (DiFMUP) (Molecular Probes D-6567).
4. 10N NaOH (Fisher Scientific SS255-1)
5. 10N HCl (Fisher Scientific A144-500)
6. Hydrogen peroxide ($H_2O_2$) (30% solution, Sigma)
7. Compounds were dissolved in DMSO (Sigma D-5879) at 5 or 10 mM concentrations and stored at −20° C. in small aliquots.

Methods

All assays were performed using DiFMUP as substrate. The optimum pH and substrate $K_m$ was determined for each PTP used.

PTP Assay

PTPase activity was assayed at 25° C. in a 100-$\mu l$ reaction mixture containing an appropriate concentration of DiFMUP as substrate. The reaction was initiated by addition of the purified PTP and quenched after 10 min by addition of 1% $H_2O_2$/100 mM NaCl. The non-enzymatic hydrolysis of the substrate was corrected by measuring the control without the addition of the enzyme. The amount of DiFMU produced was determined from the increase in the fluorescence (360 nm excitation/460 nm emission) over that of background in the absence of PTPase. To determine the kinetic parameter, Km, the initial velocities were measured at various substrate concentrations and the data were fitted to the Michaelis equation where velocity=(Vmax*[S])/(Km+[S]), and [S]= substrate reaction concentration.

Inhibition Studies

The effect of the compounds on PTP was evaluated at 25° C. using DiFMUP as substrate. PTP was pre-incubated for fifteen minutes with various concentrations of compound. Substrate was then added at a fixed concentration (usually equal to the Km previously calculated). After 10 minutes, the reaction was quenched. The hydrolysis of DiFMUP was followed as described above. The percent inhibition was calculated as follows: Percent Inhibition=[(control signal−compound signal)/control signal]×100%. The $IC_{50}$ was then determined by interpolation of a percent inhibition versus compound concentration plot.

Plasmids designed for bacterial GST-PTP fusion protein expression were derived by insertion of PCR-generated human PTP fragments into pGEX vectors (Pharmacia Biotech). Several of these constructs were then used to subclone phosphatases into pFastBac-1 for expression in Sf-9 insect cells. Oligonucleotides used for the initial amplification of PTP genes are as described above. The cDNAs were prepared using the Gilbo BRL superscript preamplification system on RNAs purchased from Clontech.

Table 2 shows PTP $IC_{50}$ values determined for Examples 32–65 and 77–103 using DiFMUP as substrate.

TABLE 2

Biological Data PTP $IC_{50}$ ($\mu M$).

| Ex. # | SHP2 | 1B | Epilson | MEG2 | Zeta | Sigma | PEST | Alpha | Beta | Mu | DEP1 |
|---|---|---|---|---|---|---|---|---|---|---|---|
| 32 | | 14.6 | | 7.8 | | | | 17.4 | | | |
| 33 | | 2.3 | | 2.3 | | | | 20.4 | | | |
| 34 | | 2.3 | | 3.9 | | | | 9.1 | | | |
| 35 | | 31.6 | | | | | | 32.5 | | | |
| 36 | | 58 | | >20 | | | | 61.2 | | | |
| 37 | | 19.0 | | >20 | | | | 20.5 | | | |
| 38 | | 1.1 | | 1.1 | | | | 5.1 | | | |
| 39 | | 1.2 | | 3.7 | | | | 1.5 | | | |
| 40 | | >100 | | >20 | | | | >100 | | | |
| 41 | | 19.0 | | >20 | | | | 13.5 | | | |
| 42 | | >100 | | >20 | | | | 98.0 | | | |
| 43 | | 74.6 | | >20 | | | | 53.9 | | | |
| 44 | | 22.7 | | 15.8 | | | | 19.0 | | | |
| 45 | | >100 | | >100 | | | | >100 | | | |
| 46 | | >100 | | >100 | | | | >100 | | | |
| 47 | | >100 | | | | | | | | | |
| 48 | | 37.7 | | 22.7 | | | | 20.0 | | | |
| 49 | | 10.6 | | 8.3 | | | | 9.3 | | | |
| 50 | | >100 | | >100 | | | | >100 | | | |
| 51 | | >100 | | >100 | | | | >100 | | | |
| 52 | | 8.0 | | >20 | | | | 64.5 | | | |
| 53 | | 1.5 | | 1.5 | | | | 22.2 | | | |
| 54 | | 0.7 | | >20 | | | | | | | |
| 55 | | 3.3 | | | | | | 2.4 | | | |
| 56 | | 2.9 | | 4.8 | | | | | | | |
| 57 | | | | >20 | | | | 0.6 | | | |
| 58 | | 4.4 | | 9.4 | | | | 29.1 | | | |
| 59 | | 0.2 | | 0.9 | | | | 38.1 | | | |
| 60 | | 4.8 | | 16.2 | | | | 50.9 | | | |
| 61 | | 1.7 | | | | | | 7.4 | | | |

TABLE 2-continued

Biological Data PTP IC$_{50}$ ($\mu$M).

| Ex. # | SHP2 | 1B | Epilson | MEG2 | Zeta | Sigma | PEST | Alpha | Beta | Mu | DEP1 |
|---|---|---|---|---|---|---|---|---|---|---|---|
| 62 | | 2.3 | | | | | | 5.7 | | | |
| 63 | | 0.4 | | 0.7 | | | | 2.4 | | | |
| 64 | | 5.9 | | 5.4 | | | | | | | |
| 65 | | 13.1 | | 11.5 | | | | | | | |
| 77 | | >100 | | >100 | | | | >20 | | | |
| 78 | | >100 | | >100 | | | | >100 | | | |
| 79 | | >100 | | >100 | | | | >20 | | | |
| 80 | | 58.1 | | >20 | | | | 26.9 | | | |
| 81 | | 6.2 | | 14.6 | | | | 4.4 | | | |
| 82 | | 87.7 | | >20 | | | | 7.7 | | | |
| 83 | | 58.5 | | >20 | | | | 8.4 | | | |
| 84 | | 62.0 | | >20 | | | | 16.1 | | | |
| 85 | | 20 | | 17.4 | | | | >20 | | | |
| 86 | | >100 | | >20 | | | | >20 | | | |
| 87 | | 97 | | >20 | | | | >20 | | | |
| 88 | | 31.4 | | >20 | | | | 8.2 | | | |
| 89 | | 69 | | >20 | | | | >20 | | | |
| 90 | | 64 | | >20 | | | | 35.9 | | | |
| 91 | | 25.9 | | >20 | | | | >20 | | | |
| 92 | | 48 | | >20 | | | | 5.1 | | | |
| 93 | | 15.8 | | 15.9 | | | | 7.4 | | | |
| 94 | | 1.5 | | 12.0 | | | | 4.2 | | | |
| 95 | | >20 | | >100 | | | | >100 | | | |
| 96 | | 9.1 | | 34.7 | | | | 31.2 | | | |
| 97 | | 6.1 | | 44.2 | | | | 62.9 | | | |
| 98 | | >20 | | >100 | | | | 41.6 | | | |
| 99 | | 7.0 | | 4.8 | | | | 27.5 | | | |
| 100 | | >20 | | >100 | | | | >100 | | | |
| 101 | | 3.4 | | 6.6 | | | | 1.4 | | | |
| 102 | | 4.0 | | 43.1 | | | | 12.2 | | | |
| 103 | | 17.9 | | >100 | | | | 34.7 | | | |

Auto- and Transphosphorylation Kinase Assays

In vitro cdk2/cyclin A Kinase Assay

The following kinase assay sets forth the procedures used to analyze protein serine/theonine kinase activity of a cell cycle dependent kinase (cdk2) and cyclin A complex, cdk2/cyclin A in a Scintillation Proximity Assay (SPA).

Materials and Reagents

Reactions are performed in Wallac 96-well polyethylene terephthalate (flexi) plates (Wallac, #1450–401). The detectable label is Amersham Redivue [$\gamma^{33}$P] ATP (Amersham, #AH 9968), and the beads are Amersham streptavidin coated polyvinyltoluene (SPA) beads (Amersham, #NIF 1077) which are purchased from the commercial suppliers as indicated.

The SPA beads should be reconstituted in phosphate buffered saline (PBS) without magnesium or calcium, at 50 mg/ml, and stored at 4° C. prior to use.

Tris buffer, at 1 M, pH 7.4 is prepared by mixing approximately 70 ml dH$_2$O is added to a 250 ml beaker to which 12.11 grams of Tris is added. When the solid Tris has dissolved, the pH is adjusted to 7.4 with HCl. The buffer is then transferred to a 100 ml graduated cylinder and the volume brought to 100 ml with dH$_2$O.

Magnesium chloride (MgCl2) is prepared in a 1 M stock solution by mixing 20.33 grams of commercially available reagent grade MgCl2 with 100 ml of dH$_2$O. Once dissolved completely, the 1 M MgCl2 solution is stored in small aliquots at −20° C.

A stock solution of 1 M Dithiothreitol (DTT) is prepared as follows. 15.42 grams of DTT is added to 100 ml dH$_2$O, dissolved and stored in small aliquots at −20° C. This reagent can be stored in small aliquots to be taken out just prior to use.

PBS is purchased from a commercial supplier (Gibco BRL, #14190–144), or prepared without magnesium or calcium. The individual reagents are available from commercial suppliers such as Gibco BRL, and are prepared as follows:

| Reagent | Molecular Weight | 10x Stock Concentration | Amt. per Liter | 1x Reaction Concentration |
|---|---|---|---|---|
| KCl | 74.56 | 27 mM | 2.013 g | 2.7 mM |
| KH2PO4 | 174.18 | 11 mM | 1.916 g | 1.1 mM |
| NaCl | 58.44 | 1.38 M | 80.65 g | 138 mM |
| Na2HPO4 | 141.96 | 81 mM | 11.50 g | 8.1 mM |

1 liter of 10×PBS is prepared by: 1) adding approximately 900 ml dH$_2$O to a graduated cylinder; 2) adding the reagents listed in the above table to the dH$_2$O; 3) when all reagents have dissolved, the solution is adjusted to pH 7.2 with HCl and the volume is brought to 1 liter with dH$_2$O. PBS can be left at room temperature, but 4° C. is preferred.

10 ml of kinase buffer is sufficient for approximately 4.5 assay plates. Kinase buffer is prepared as follows:

| Reagent | Stock solution | Amount per 10 ml | Working Concentration |
|---|---|---|---|
| dH$_2$O | 55.5 M | 9.1 ml | |
| Tris pH 7.4 | 1 M | 0.5 ml | 50 mM |
| MgCl2 | 1 M | 0.2 ml | 20 mM |
| NP4O | 10% | 0.2 ml | 0.2% |
| *DTT (add fresh) | 1 M | 0.02 ml | 2 mM |

Non-radioactive adenosine-5'-triphosphate (ATP) from Equine muscle (Sigma, #A-5394), is preferably stored as a 10 mM stock solution at −20° C. To make 10 mM Stock solution, add 5 ml of dH$_2$O to 27.5 mg ATP and vortex. Any milligram amount of ATP can be used provided it is kept in the same ATP to dH$_2$O ratio. This reagent can be stored in small aliquots to be taken out just prior to use.

Ethylenediamine-tetraacetic acid (EDTA) is prepared by adding approximately 70 ml dH$_2$O to a 250 ml beaker. Then, 14.12 grams of EDTA is added to the beaker. Next, the solution pH is adjusted by adding 10 N NaOH drop-wise to the beaker, EDTA will dissolve at approximately pH 7.0. When the EDTA dissolves, the pH will fall, thus, NaOH need be added until the pH stabilizes at pH 8.0. The volume is then brought to 100 ml with dH$_2$O.

Stop solution is prepared with the following reagents in the concentrations in following table:

| Reagent | Stock solution | Amount per 10 ml | Working Concentration |
|---|---|---|---|
| PBS | | 9.25 ml | |
| ATP | 10 mM | 0.05 ml | 50 μM |
| EDTA | 0.5 M | 0.1 ml | 5 mM |
| Triton X-100 | 10% | 0.1 ml | 0.1% |
| SPA beads | 50 mg/ml | 0.5 ml | 0.5 mg/well (200 μl) |

Procedure

Solutions of phosphate mimics or inhibitors are prepared at 4× the desired final concentration in 20% DMSO and 10 μl is added to each well. For positive and negative controls, 10 μl 20% DMSO is added to a well without the phosphate mimic or inhibitor. The peptide substrate (deb-tide) is diluted 1:250 with dH$_2$O to make 0.02 mg/ml. Make at least 600 μl per plate. The stock solution is diluted from a 10 mM stock 1:100 in water to make 0.1 mM. The following mixture is prepared for each plate:

1) 24 μL 0.1 mM ATP
2) 24 μCi γ$^{33}$P ATP
3) dH$_2$O to 600 μL.

The diluted peptide and ATP solutions are mixed 1:1 (600 μL+600 μL per plate), and 10 μL of the mix is added per well. The final concentrations are 0.5 μM cold ATP, 0.1 μg/well of peptide substrate, and 0.2 μCi/well of radiolabeled ATP.

5 μL of cdk2/cyclin A is diluted into 2.1 ml 2×kinase buffer for each plate. 20 μL cdk2/cyclin A mixed with the kinase buffer is then added to each well. For negative controls, 20 μL 2×kinase buffer without cdk2/cyclin A is added.

The reaction mixture is briefly shaken on a plate shaker and then incubated 60 min. Finally, 200 μL stop solution per well is added and let stand at least 10 min. The plate is then spun approximately 2300 rpm for 10–15 min. The plate is then counted on a Trilux reader under standard conditions.

2. In vitro FGF3-R Kinase Activity

The following kinase assay provides a consistent method for measuring the in vitro kinase activity of the FGF3-R in an Enzyme-linked immunosorbent assay (ELISA).

Materials and Reagents

The following supplies are obtained from commercial sources: Costar 96-well ELISA plates (Corning, #3369), Poly(Glu,Tyr) is available from commercial suppliers, such as, Sigma, (Catalog, #PO275), which is stored at below 0° C., and PBS (Gibco BRL, #450–1300EB).

| Reagent | Molecular Weight | 10x Stock Concentration | Amt. per L | 1x Working Concentration |
|---|---|---|---|---|
| KCL | 74.56 | 27 mM | 2.013 g | 2.7 mM |
| KH2PO4 | 174.18 | 1 mM | 1.916 g | 1.1 mM |
| MgCl2.6H2O | 203.31 | 5 mM | 1.017 g | 0.5 mM |
| NaCl | 58.44 | 1.38 M | 80.65 g | 138 mM |
| Na2HPO4 | 141.96 | 81 mM | 11.50 g | 8.1 mM |

To make 1 liter of 10× stock solution of PBS: 1) add approximately 900 ml dH$_2$O to a graduated cylinder; 2) add all reagents except the MgCl2; 3) when all reagents have dissolved, adjust the pH to 7.2 with HCl; 4) Add MgCl2; and 5) bring volume to 1 liter dH$_2$O 50 mM Hepes Buffer Solution is prepared in 1 liter of 1× working solution as follows: 1) To a 1 liter graduated cylinder add approximately 450 ml dH$_2$O; 2) Add 5.95 g Hepes; 3) When reagent has dissolved, pH to 7.5 with HCl; and 4) Bring volume to 500 ml dH$_2$O. Alternatively one can use Hepes made commercially, for example by GIBCO BRL which is a 1 M stock solution and is prepared by adding 475 ml of dH$_2$O to 25 ml 1 M Hepes and stirring.

TBB Blocking Buffer:

| Reagent | M.W. | 10x Working Concentration | Amount per Liter |
|---|---|---|---|
| BSA | NA | 10% | 100 g |
| Tris-pH 7.5 | 121.14 | 100 mM | 100 ml of 1 M stock solution |
| NaCl | 58.44 | 1 M | 200 ml of 5 M stock solution |
| Tween-20 | NA | 1% | 10 ml |

Use a 1× solution to block:

1) Use 1.5 mls of 10× TBB to 13.5 mls of dH$_2$O per plate.

2) Block each well with 150 μl. (15 ml per plate)

GST-FGF3-R (purified), aliquot and store at −80° C. Prepared by expression of a

GST, FGF3-R chimera in baculovirus SF9 cells. (Keegan et al., 1999, PNAS 88:1095–1099.)

Kinase Dilution Buffer is prepared as follows:

50 μl of 1 M Hepes (GIBCO, BRL)

20 μl 5% BSA/PBS

10 μl 100 mM Na-orthovanadate

50 μl 5 M NaCl

Use 5 ml per plate.

Adenosine-5'-triphosphate (from Equine muscle) 10 mM ATP (Sigma, #A-5394). To make 10 mM Stock solution:

1) Add 500 μl of dH$_2$O to 2.75 mg ATP
2) Vortex

Any mg amount of ATP can be used provided it is kept in the same ATP to dH$_2$O ratio. This reagent should be made up immediately prior to use and kept on ice.

Prepare 1 M MnCl2 by adding 19.79 g MnCl2 per 100 ml, filter sterilizing and storing in aliquots at either 4° C. or −20° C.

ATP/MnCl2 phosphorylation mix is as follows:

| Reagent | Stock solution | Amount per 10 ml | Working Concentration |
|---|---|---|---|
| ATP | 10 mM | 20 µl | 20 M |
| MnCl2 | 1 M | 400 µl | 40 mM |
| dH$_2$O | | 9.56 ml | |

10 ml of phosphorylation mix is enough for approximately 6 assay plates. Make fresh and keep on ice immediately before use. Though the preferred ATP is fresh from powder stock, any remaining stock solution of ATP may be frozen at −20° C. in small aliquots to be used at a later time.

The reactions are performed in NUNC 96-well V bottom polypropylene plates (Applied Scientific, #AS-72092).

Prepare 0.5 M EDTA stock solution as follows:

| Reagent | M.W. | Stock solution | Amount per 100 ml | Working Solution |
|---|---|---|---|---|
| ethylenediamine-tetraacetic acid | 292.25 | 500 mM | 14.61 g | 500 mM |

To make stock solution:
1) Add approximately 70 ml dH$_2$O to a 250 ml beaker
2) Add EDTA
3) With pH probe in beaker, add 10N NaOH dropwise EDTA will not dissolve until pH is around 7.0 As EDTA dissolves the pH will fall, add more NaOH
4) When all EDTA is dissolved, adjust the pH to 8.0
5) Transfer to 100 ml graduated cylinder, bring volume to 100 ml with dH$_2$O.

0.05% TBSTween
Per 1 liter of TBS add 500 µl of Tween.
Rabbit polyclonal anti-phosphotyrosine serum, stored at −80° C. in 1 ml aliquots. Goat anti-rabbit immunoglobulin-G (IgG) peroxidase conjugate (Biosource, #ALI0404).

A stock solution of the horse radish peroxidase (HRP) developing reagent, 2,2'-azino-bis(3-ethylbenzthiazoline-6-sulfonic acid) (ABTS) (Sigma, #A-1888), is prepared as follows:

| Reagent | M.W. | Working Concentration | Amount per L |
|---|---|---|---|
| Citric Acid | 192.12 | 100 mM | 19.21 g |
| Na2HPO4 | 141.96 | 250 mM | 35.49 g |
| ABTS | NA | 0.5 mg/ml | 500 mg |

To make 1 liter of working solution:
1) To a 1 liter graduated cylinder add approximately 900 ml dH$_2$O
2) Add Citric Acid and Na2HPO4
3) pH to 4.0 with phosphoric acid
4) ABTS
5) Cover with foil and let dissolve for about ½ hr
6) Filter the solution.
Keep solution in dark at 4° C. until ready to use
Hydrogen peroxide 30% solution (Fisher, #H325). Store in the dark at 4C until ready to use.

ABTS/H$_2$O$_2$, Formulation: 15 mls ABTS solution with 2 µl H$_y$O$_y$. Prepare 5 minutes before use and leave at room temperature Procedure Coat Costar 96 well ELISA plates with 2 µg per well Poly(Glu,Tyr) in a volume of 100 µl PBS overnight, at 4° C. or 2 hours. Wash coated plates once with PBS. Add 150 µl of TBB Blocking Buffer to each well. Incubate for 60 min at room temperature, with shaking. Wash plate 2× with PBS, then once with 50 mM Hepes. Pat plates on a paper towel to remove excess liquid and bubbles.

Add 25 µl of drugs (in 4% DMSO in water) or DMSO controls (4% in water) to plate. If starting with a 10 mM stock of compound in 100% DMSO then make a 25 fold dilution into water for the starting concentration in the drug dilution plate of 0.4 mM in 4% DMSO. Do serial dilutions down the drug plate in 4% DMSO/water. Final compound concentration (highest) in the assay plate will be 0.1 mM in 1% DMSO.

Dilute purified GST-FGF3-R in Kinase Dilution Buffer (1 ng kinase/50 1 KDB/well). When the GST stock concentration is 20 ng, the final dilution is 1 l of GST to 1 ml of KDB. Add 50 µl of diluted kinase to each well.

Start kinase reaction with the addition of 25 µl/well of ATP/Mn++ (Make fresh) at a starting concentration of 20 µM for a final of 5 µM. Negative controls get Mn alone . . . . no ATP. The reaction time is 5 minutes.

The reaction mix for 10 mls is:
0.4 ml 1 M MnCl
20 µl 10 mM ATP
9.56 ml water

This is a fast kinase reaction and must be stopped with 25 µl of 0.5 M EDTA in a manner similar to the addition of ATP. Wash plate 4× with freshly prepared TBS-Tween (0.05% tween20). Make up Antibody Dilution Buffer per 50 mls:

| 0.5% BSA | 5 mls of 5% BSA |
|---|---|
| 0.025% milk | 250 1 ml 5% milk |
| 0.1 mM Sodium Vanadate | 50 1 of 100 mM Vanadate |

Bring to volume with 0.05% TBS-Tween. Add 100 µl per well of anti-pnosphotyrosine (1:10000 dilution in ADB). Incubate 45 min at room temperature, with shaking. Wash as described above.

Add 100 µl per well of Biosource Goat anti-rabbit IgG peroxidase conjugate (1:6000 dilution in ADB). Incubate 45 min at room temperature, with shaking. Wash as described in above, with a final rinse of PBS to reduce bubbles and get rid of excess Tween.

Add 100 µl of ABTS/H$_2$O$_2$ solution to each well. Incubate 10 to 20 minutes while shaking. Remove any bubbles. Read assay on Dynatech MR7000 ELISA reader. Test Filter: 410 nM, Reference Filter: 630 nM.

3. Auto-Phosphorylation by Kit Kinase

The following kinase assay sets forth a procedure for measuring phosphate deposition on the kinase, Kit.

Seed CHO/GyrB-Kit cells into 6-well plates. One confluent 15 cm dish will be sufficient to seed 4 6-well plates. Seed 11 wells for each compound to be tested: 9 samples and 2 controls. Incubate overnight. Swap media with serum free media, (DMEM+0.1% BSA) and incubate overnight.

Preincubate cells with the test compound diluted in 1 ml of serum free media for 2 hours. (100 M top concentration with 1:5 dilutions for $IC_{50}$ determination). Control wells receive only serum free media.

Add 100 l of 10× coumermycin (10 M) diluted in serum free medium to sample and positive control wells for 30 min. Aspirate media from cells and lyse in 300 l of RIPA with protease inhibitors and vanadate. Agitate for 1–3 min for cell disruption. Add 300 l of HNTG (Hepes, NaCl, Triton-X100, and Glycerol) with protease inhibitors and vanadate. Transfer lysate to a microcentrifuge tube. Vortex and centrifuge at maximum RPM for 5 min.

Add the cleared lysate (about 500 l) to another tube with anti-DNR antibody and protein L. Agitate at 4° C. for 1 hr. Centrifuge and wash at least 3× with HNTG. Solubilize pellet with 20–25 l of 2× reducing SDS sample buffer. Boil for 5 min and fractionate by SDS-PAGE on an 8% gel.

Transfer fractionated proteins to nitrocellulose and block overnight in Pierce Super Block with 10% normal goat serum at 4° C. Probe with anti-phosphotyrosine antibodies, then strip and reprobe with anti-Kit antibodies.

4. Transphosphorylation Activity by GST-Flk1

The following kinase assay sets forth a consistent method for measuring transphosphorylation activity of glutathione-s-transferase fused in frame to Flk-1 (GST-Flk1) on poly (Glu,Tyr) in a high throughput screening assay.

Materials and Reagents

Reactions are performed in Corning 96-well ELISA plates (Corning, #25805-96), poly (Glu,Tyr) 4:1, lyophilized (Sigma #P0275). Prepare 1 mg/ml poly (Glu,Tyr) in sterile PBS and store in 1 ml aliquots at −20° C. Coat 2 µg/well of poly (Glu,Tyr) (pEY) in 100 l PBS at room temperature for 2 hours or +40C. overnight. Cover plates well to prevent evaporation.

PBS Buffer, PBS-Tw Buffer

| Reagent | M.W. | 1x Working Concentration | Amount per L |
|---|---|---|---|
| KH2PO4 (monobasic) | 136.09 | 1.4 mM | 0.2 g |
| Na2HPO4 (dibasic) | 141.96 | 8.1 mM | 1.15 g |
| KCl | 74.56 | 2.7 mM | 0.2 g |
| NaCl | 58.44 | 138 mM | 8.0 g |
| Tween-20 | | 0.1% | 1 ml |

To make 1 liter of a 1× working solution:

1) To a 1 liter graduated cylinder add approximately 900 ml $dH_2O$
2) Add all reagents except Tween-20.
3) When all reagents have dissolved, pH to 7.2 with HCL
4) Add Tween-20, and stir until dissolved.
5) Bring volume to 1 liter with $dH_2O$ A 10×stock solution can be made by multiplying the amounts by 10 (but keeping the final volume of 1 liter). This stock is then diluted 10 fold with $dH_2O$ and the pH is adjusted to 7.2.

Alternatively one can use PBS from supply in glass cabinets and add 0.1% Tween-20:

1) To 1 liter of PBS add 1.0 ml Tween-20.
2) Stir until dissolved.

Stock solutions of TBB—Blocking Buffer, are prepared as follows:

| Reagent | M.W. | 1x Working Concentration | Amount per L |
|---|---|---|---|
| Tris | 121.14 | 10 mM | 1.21 g |
| NaCl | 58.44 | 150 mM | 8.77 g |
| Tween-20 | NA | 0.1% | 1 ml |
| BSA | NA | 1% | 10 g |

Procedure for making a 1× working solution of TBB:

1) To a 1 liter graduated beaker add approximately 900 ml $dH_2O$
2) Add all reagents except the BSA
3) When all reagents have dissolved, pH to 7.2 with HCl
4) Add BSA, stir until dissolved.
5) Bring volume to 1 liter with $dH_2O$
6) Filter the solution to remove any particulate matter, and store at +40C.

A 10× stock solution can be made by multiplying the amounts by 10 (but keeping the final volume of 1 liter). This stock is then diluted 10 fold with $dH_2O$. Filter the solution to remove any particulate matter, and store at +40C.

Prepared stock and working solutions of each of the following: 1% BSA in PBS and 50 mM Hepes pH 7.5, $dH_2O$+4% DMSO, 10 mM ATP, 1 M MnCl2, 40 mM MnCl2, 100 ml of kinase buffer mix is enough for approximately 40 assay plates.

GST-Flk1cd purified from sf9 recombinant baculovirus transformation; stored at −80° C.; 100 µl aliquots (use 5 ng (0.005 µg)/well in kinase dilution buffer, KDB) Millauer et al., 1993, Cell 72:835–846; Matthews et al., 1991, PNAS 88:9026–9030.

Kinase Dilution Buffer (KDB):

| Reagent | Stock solution | Amount per 100 ml | Working Concentration |
|---|---|---|---|
| $dH_2O$ | 55.5 M | 88.56 ml | |
| Hepes pH 7.5 | 1 M | 10 ml | 100 mM |
| NaCl | 5 M | 1 ml | 50 mM |
| NaVO4 | 100 mM | 40 µl | 40 µM |
| BSA (in $dH_2O$) | 5% | 0.4 ml | 0.020% |

100 ml of kinase buffer mix is enough for approximately 40 assay plates. NUNC 96-well V bottom polypropylene plates (Applied Scientific, #AS-72092).

Ethylenediamine-tetraacetic acid (EDTA). To make stock solution:

1) Add approximately 70 ml $dH_2O$ to a 250 ml beaker
2) Add EDTA
3) With pH probe in beaker, add 10N NaOH dropwise EDTA will not dissolve until pH is around 7.0. As EDTA dissolves the pH will fall, add more NaOH
4) When all EDTA is dissolved, adjust the pH to 8.0
5) Transfer to 100 ml graduated cylinder, bring volume to 100 ml with $dH_2O$.

The 1° and 2° Antibodies are utilized in the following Dilution Buffer

| Reagent | Stock solution | Amount per 100 ml | Working Concentration |
|---|---|---|---|
| PBSTw (0.1%) | | 89.5 ml | |
| Milk in PBS | 5% | 0.5 ml | 0.025% |
| Sodium Vanadate | 10 mM | 1 ml | 100 μM |
| BSA in PBS | 5% | 10 ml | 0.5% |

Anti-phosphotyrosine rabbit polyclonal antisera (Babco, Berkeley, Calif.). Goat anti-rabbit HRP conjugate (Biosource; #A110404).

2,2'-azino-bis(3-ethylbenzthiazoline-6-sulfonic acid) (Sigma, #A-888) (ABTS) solution which is the developer for HRP is prepared as follows:

| Reagent | M.W. | Working Concentration | Amount per L |
|---|---|---|---|
| Citric Acid | 192.12 | 100 mM | 19.21 g |
| Na2HPO4 | 141.96 | 250 mM | 35.49 g |
| ABTS | NA | 0.5 mg/ml | 500 mg |

To make 1 liter of working solution:

1) To a 1 liter graduated cylinder add approximately 900 ml $dH_2O$
2) Add Citric Acid and Na2HPO4
3) pH to 4.0 with phosphoric acid
4) add ABTS
5) Cover with foil and let dissolve for about ½ hr
6) Filter the solution Keep solution in dark at 4° C. until ready to use.

Hydrogen peroxide 30% solution (Fisher, #H325); Store in the dark at 4° C. until ready to use.

An ABTS/H2O2 solution is prepared as follows: Take ABTS out of cold storage (described above), about 60 minutes prior to use and warm to room temperature. Or warm quickly by placing tube in 37° C. water bath, and add the 3 μl H2O2 to the 15 mls ABTS solution immediately prior to use.

Prepared a stock solution of 0.2 M HCl by adding 1.7 ml Concentrated HCl (12N) to 98.3 ml $dH_2O$, and store at room temperature.

Procedure

Coat Corning 96 well ELISA plates with 2 μg of poly (Glu,Tyr) peptide in sterile PBS, as described above. Remove unbound liquid from wells by inverting plate. Wash 1× with TBSTw. Pat the plate on a paper towel to remove excess liquid. Add 100 l of 1% BSA in PBS to each well. Incubate for 1 hr. at room temperature, with shaking.

Repeat coating step again. Soak wells with 50 mM Hepes pH 7.5 150 μl/well. Dilute drugs/extracts at 4× the desired final assay concentration in $dH_2O$+4% DMSO (unless specified otherwise) in 96-well polypropylene plates. Always add the larger volume of water to the smaller volume of compound to ensure rapid mixing.

Add 25 μl diluted drugs/extracts to ELISA plate. To control wells (wells which do not receive any drug) add 25 μl of $dH_2O$+4% DMSO.

Dilute GST-Flk1 0.005 μg (5 ng)/well in KDB. For 50 ml KDB add 100 μl of 0.050 mg/ml GST-Flk1 enzyme. This is enough for 10 assay plates. Add 50 μl of diluted enzyme to each well. Add 25 μl 0.5 M EDTA to negative control wells.

Add 25 μl of 40 mM MnCl2 with 4×ATP (2 AM) directly to all wells. 100 μl final volume in well with 0.5 μM ATP final concentration in well. Incubate for 15 minutes while shaking at room temperature. After 15 minutes stop reaction with addition of 25 μl of 500 mM EDTA pH 8.0 for 50 mM final in well.

Wash 3× with TBSTw and pat plate on paper towel to remove excess liquid. Add 100 μl per well of anti-phosphotyrosine antisera (1:10,000 dilution in antibody dilution buffer). Incubate 90 min at room temperature, with shaking. Wash as described above.

Add 100 μl per well of goat anti-rabbit HRP conjugate (1:6,000 dilution in antibody dilution buffer). Incubate 90 min. at room temperature with shaking. Wash as described above.

Add 100 μl of room temp. ABTS/H2O2 solution to each well. Incubate 15 to 30 minutes while shaking. Remove any bubbles. If necessary stop reaction with the addition of 100 μl of 0.2M HCl per well. Read assay on Dynatech MR7000 ELISA reader. Test Filter: 410 nM and Reference Filter: 630 nM.

5. Transphosphorylation Activity by GST-lck

The following kinase assay sets forth a consistent method for measuring transphosphorylation activity of a fusion protein, GST-lck, on poly (lys-tyr) in a high throughput screening assay.

Materials and Reagents

The reactions are performed in Corning 96-well ELISA plates (Corning, #25805-96). The substrate for the phosphorylation assay is poly (lys-tyr) 4:1, hydrobromide; (Sigma, #P4659). Prepare 5 mg/ml poly (lys-tyr) stock solution in sterile PBS and store in 1 ml aliquots at −20° C.

Prepare poly (lys-tyr) (pKY) coated assay plates. Coat 2 μg/well of pKY in 100 μl PBS at room temperature for 2 hours or +40C overnight. Cover plates well to prevent evaporation.

PBS Buffer is prepared as described in the above kinase assays. A stock solution of PBS-Tween (PBS-Tw) Buffer is prepared as follows:

| Reagent | M.W. | 1× Working Concentration | Amount per L |
|---|---|---|---|
| KH2PO4 (monobasic) | 136.09 | 1.4 mM | 0.2 g |
| Na2HPO4 (dibasic) | 141.96 | 8.1 mM | 1.15 g |
| KCl | 74.56 | 2.7 mM | 0.2 g |
| NaCl | 58.44 | 138 mM | 8.0 g |
| Tween-20 | | 0.1% | 1 ml |

To make 1 liter of a 1× working solution:

1) To a 1 liter graduated cylinder add approximately 900 ml $dH_2O$
2) Add all reagents except Tween-20.
3) When all reagents have dissolved, pH to 7.2 with HCl
4) Add Tween-20, and stir until dissolved.
5) Bring volume to 1 liter with $dH_2O$ A 10× stock solution can be made by multiplying the amounts by 10 (but keeping the final volume of 1 liter). This stock is then diluted 10 fold with $dH_2O$ and readjust the pH to 7.2.

A stock solution of TBB, the blocking buffer is prepared as follows:

| Reagent | M.W. | 1x Working Concentration | Amount per L |
|---|---|---|---|
| Tris | 121.14 | 10 mM | 1.21 g |
| NaCl | 58.44 | 150 mM | 8.77 g |
| Tween-20 | NA | 0.1% | 1 ml |
| BSA | NA | 1% | 10 g |

Procedure for making a 1x working solution of TBB:
1) To a 1 liter graduated beaker add approximately 900 ml $dH_2O$
2) Add all reagents except the BSA
3) When all reagents have dissolved, pH to 7.2 with HCL
4) Add BSA, stir until dissolved.
5) Bring volume to 1 liter with $dH_2O$
6) Filter the solution to remove any particulate matter, and store at +40C. A 10x stock solution can be made by multiplying the amounts by 10 (but keeping the final volume of 1 liter). This stock is then diluted 10 fold with $dH_2O$. Filter the solution to remove any particulate matter, and store at +40C.

A one liter stock solution of 1% BSA in PBS is prepared. Filter the solution to remove any particulate matter, and store at +40C.

A stock solution of 50 mM Hepes pH 7.5 is prepared as described in the kinase assays above.

GST-lck purified from sf9 recombinant baculovirus transformation. (Wright et al., 1994, Mol.Cell. Biol. 14:2429–2437.)

$dH_2O$+4% DMSO, and a 5 ml stock solution of 10 mM ATP (Sigma, #A-5394) is prepared as follows:
1) Add 5 ml of $dH_2O$ to 27.5 mg ATP
2) Vortex Any mg amount of ATP can be used provided it is kept in the same ATP to $dH_2O$ ratio. This reagent can be stored at −20 in small aliquots to be taken out just prior to use and kept on ice.

A 1 M $MnCl_2$ stock solution is prepared as described in kinase assays above, and 100 ml of a 40 mM $MnCl_2$ working solution is also prepared as described above.

Kinase Dilution Buffer (KDB) is prepared as follows:

| Reagent | Stock solution | Amount per 100 ml | Working Solution |
|---|---|---|---|
| $dH_2O$ | 55.5 M | 88.56 ml | |
| Hepes pH 7.5 | 1 M | 10 ml | 100 mM |
| NaCl | 5 M | 1 ml | 50 mM |
| $NaVO_4$ | 100 mM | 40 µl | 40 µM |
| BSA (in PBS) | 5% | 0.4 ml | 0.020% |

NUNC 96-well V bottom polypropylene plates (Applied Scientific, #AS-72092). EDTA is prepared as follows:
1) Add approximately 70 ml $dH_2O$ to a 250 ml beaker
2) Add EDTA
3) With pH probe in beaker, add 10N NaOH dropwise EDTA will not dissolve until pH is around 7.0. As EDTA dissolves the pH will fall, add more NaOH
4) When all EDTA is dissolved, adjust the pH to 8.0
5) Transfer to 100 ml graduated cylinder, bring volume to 100 ml with $dH_2O$.

A stock solution of the 1o and 2o Antibody Dilution Buffer is prepared as follows:

| Reagent | Stock solution | Amount per 100 ml | Working Concentration |
|---|---|---|---|
| PBSTw (0.1%) | | 89.5 ml | |
| Milk in PBS | 5% | 0.5 ml | 0.025% |
| BSA in PBS | 5% | 10 ml | 0.5% |

The antibodies utilized in this kinase assay are: anti-phosphotyrosine rabbit polyclonal antisera (Babco, Berkeley, Calif.) and goat anti-rabbit HRP conjugate (Biosource, #A110404).

2,2'-azino-bis(3-ethylbenzthiazoline-6-sulfonic acid) (ABTS) (Sigma, #A-1888) Solution is prepared as described above.

| Reagent | M.W. | Working Concentration | Amount per L |
|---|---|---|---|
| Citric Acid | 192.12 | 100 mM | 19.21 g |
| Na2HPO4 | 141.96 | 250 mM | 35.49 g |
| ABTS | NA | 0.5 mg/ml | 500 mg |

To make 1 liter of working solution:
1) To a 1 liter graduated cylinder add approximately 900 ml $dH_2O$
2) Add Citric Acid and Na2HPO4
3) pH to 4.0 with phosphoric acid
4) add ABTS
5) Cover with foil and let dissolve for about ½ hr
6) Filter the solution Keep solution in dark at 4° C. until ready to use
Hydrogen peroxide 30% solution (Fisher, #H325); Store in the dark at 4° C. until ready to use. A stock solution of $ABTS/H2O2$ is prepared. The formulation is 15 mls ABTS solution, and 3 µl $H2O2$. Take out ABTS about 60 minutes prior to use and warm to room temperature. Or warm quickly by placing tube in 37° C. water bath. Add 3 µl $H2O2$ prior to use.

A stock solution of 0.2 M HCl is prepared as described in kinase assays above and stored at room temperature.

Procedure

Coat Corning 96 well ELISA plates with 2 µg of polyKY peptide in sterile PBS, as described in step 3 of Materials and Reagents. Remove unbound liquid from wells by inverting plate. Wash 1xPBSTw. Pat the plate on a paper towel to remove excess liquid. Add 150 l of 1% BSA in PBS to each well. Incubate for 1 hr. at room temperature, with shaking. Repeat the coating step.

Soak wells with 50 mM Hepes pH7.5 150 µl/well. Dilute GST-lck in KDB. BATCH 1 #1044p22 [0.200 mg/ml] 0.020 g (20 ng)/well. For 100 ml KDB add 200 µl of 0.200 mg/ml GST-lck enzyme. This is enough for 20 assay plates. Add 50 µl of diluted enzyme to each well. Dilute phosphate mimic to be tested at 4x the desired final assay concentration in $dH_2O$+4% DMSO (unless specified otherwise) in 96-well polypropylene plates. Add 25 l diluted drugs/extracts to ELISA plate. To control wells (wells which do not receive any drug) add 25 µl of $dH_2O$+4% DMSO.

To initiate the phosphorylation reaction, add 25 l of 40 mM $MnCl_2$ with 4xATP (8 µM) directly to all wells except negative control wells which do not receive ATP, i.e., A 100 µl final volume per well with 2.0 µM ATP final concentration per well. Incubate for 30 minutes while shaking at room temperature.

After 30 minutes stop reaction with addition of 10 l of 500 mM EDTA pH 8.0 for 50 mM final in well. Wash 3× with PBSTw and pat plate on paper towel to remove excess liquid.

Add 100 µl per well of anti-phosphotyrosine antisera (1:10,000 dilution in antibody dilution buffer). Incubate 60 min at room temperature, with shaking. Wash as described above.

Add 100 µl per well of goat anti-rabbit HRP conjugate (1:10,000 dilution in antibody dilution buffer). Incubate 60 min. at room temperature with shaking. Wash as described above.

Add 100 µl of room temp. ABTS/H2O2 solution to each well. Incubate 15 to 30 minutes while shaking. Remove any bubbles. If necessary stop reaction with the addition of 100 µl of 0.2M HCl per well.

Read assay on Dynatech MR7000 ELISA reader. Test Filter: 410 nM, Reference Filter: 630 nM.

6. Transphosphorylation Activity by GST-Tie2-kd

The following kinase assay sets forth a consistent method for measuring transphosphorylation activity of GST-Tie2-kd on poly (Glu,Tyr) in a high throughput screening assay.

Materials and Reagents

Reactions are performed in Corning 96-well ELISA plates (Corning, #25805-96) and the substrate for the phosphorylation reaction is Poly (Glu,Tyr) 4:1, lyophilizate (Sigma #P0275). Prepare 10 mg/ml poly (Glu,Tyr) in sterile PBS and store in 1 ml aliquots at −800C. Preparation of poly (Glu,Tyr) (pEY) coated assay plates. Coat 2 µg/well of poly (Glu,Tyr) (pEY) in 100 µl PBS at room temperature for 2 hours or+4° C. overnight. Cover plates well to prevent evaporation.

TBB (blocking buffer), PBS and PBS-Tw Buffer is prepared as described in the kinase assays above.

A stock of 1% BSA in PBS is prepared. Filter the solution to remove any particulate matter, and store at +40C. A stock solution of 50 mM Hepes pH 7.5 is prepared as described in kinase assays above.

GST-Tie2-kd is purified from sf9 recombinant baculovirus transformation. (Sato et al., 1993, PNAS 90:9355–9358).

A stock solution of 250 ml of dH$_2$O+4% DMSO and 5 ml of 10 mM ATP (Sigma, #A-5394) are prepared. ATP can be stored at −20 in small aliquots to be taken out just prior to use and kept on ice.

A 100 ml stock solution of 1 M MnCl2 and a 100 ml stock solution of 40 mM MnCl2 are prepared as described in the kinase assays above.

A Kinase Dilution Buffer (KDB) stock solution is prepared as follows:

| Reagent | Stock solution | Amount per 100 ml | Working Concentration |
| --- | --- | --- | --- |
| dH$_2$O | 55.5 M | 88.56 ml | |
| Hepes pH 7.5 | 1 M | 10 ml | 100 mM |
| NaCl | 5 M | 1 ml | 50 mM |
| NaVO4 | 100 mM | 40 µl | 40 µM |
| BSA (in PBS) | 5% | 0.4 ml | 0.020% |
| DTT (add fresh) | 1 M | 50 µl | 0.5 mM |

100 ml of kinase buffer mix is enough for approximately 40 assay plates.

The reactions are performed in NUNC 96-well V bottom polypropylene plates (Applied Scientific, #AS-72092).

A stock solution of 100 ml EDTA is prepared as described in the kinase assays above.

The 1o and 2o antibodies are diluted prior to use in an Antibody Dilution Buffer which is prepared as follows:

| Reagent | Stock solution | Amount per 100 ml | Working Concentration |
| --- | --- | --- | --- |
| PBSTw | | 89.5 ml | |
| Milk in PBS | 5% | 0.5 ml | 0.025% |
| BSA in PBS | 5% | 10 ml | 0.5% |

The two antisera used are: Anti-phosphotyrosine rabbit polyclonal antisera (Babco, Berkeley, Calif.) and goat anti-rabbit HRP conjugate (Biosource, #A110404).

ABTS Solution (Sigma, A-1888) is prepared as described in the kinase assays above. Hydrogen peroxide 30% solution (Fisher, #H325) is prepared and stored in the dark at 4° C. until ready to use ABTS/H2O2 is prepared using the following formulation: 15 mls ABTS solution (described above) and 3 µl H2O2. Take out ABTS about 60 minutes prior to use and warm to room temperature. Or warm quickly by placing liquid into a 37° C. water bath. Add 3 µl H2O2 prior to use.

A stock solution of 0.2 M HCl is prepared as described above and stored at room temperature Procedure Coat Corning 96 well ELISA plates with 2 µl of polyEY peptide in sterile PBS, as described in step 3 of Materials and Reagents. Remove unbound liquid from wells by inverting plate. Wash 1×PBSTw. Pat the plate on a paper towel to remove excess liquid. Add 150 µl of 1% BSA in PBS to each well. Incubate for 1 hr. at room temperature, with shaking. Repeat the coating step.

Soak wells with 50 mM Hepes pH 7.5, 150 µl/well. Dilute drugs/extracts at 4× the desired final assay concentration in dH$_2$O+4% DMSO (unless specified otherwise) in 96-well polypropylene plates. Dilute GST-Tie2 in KDB with fresh DTT. BATCH 1 #917p86 [0.200 mg/ml]–0.020 µl(20 ng)/well. For 100 ml KDB add 200 µl of 0.200 mg/ml GST-Tie2 enzyme. This is enough for 20 assay plate. Add 50 µl of diluted enzyme to each well.

Add 25 l diluted drugs/extracts to ELISA plate. To control wells (wells which do not receive any drug) add 25 µl of dH$_2$O+4% DMSO. Add 25 µl of 40 mM MnCl2 with 4×ATP (10 µM) directly to all wells except negative control wells which do not receive ATP. 100 µl final volume in well with 2.5 µM ATP final concentration in well.

Incubate for 20 minutes while shaking at room temperature. After 20 minutes stop reaction with addition of 10 µl of 500 mM EDTA pH 8.0 for 50 mM final in well. Wash 3× with PBSTw and pat plate on paper towel to remove excess liquid.

Add 100 µl per well of anti-phosphotyrosine antisera (1:10,000 dilution in antibody dilution buffer). Incubate 90 min at room temperature, with shaking. Wash as described above.

Add 100 µl per well of goat anti-rabbit HRP conjugate (1:10,000 dilution in antibody dilution buffer). Incubate 90 min. at room temperature with shaking. Wash as described above.

Add 100 µl of room temp. ABTS/H2O2 solution to each well. Incubate 25 to 45 minutes while shaking. Remove any bubbles. If necessary stop reaction with the addition of 100 µl of 0.2M HCl per well. Read assay on Dynatech MR7000 ELISA reader. Test Filter: 410 nM, Reference Filter: 630 nM

7. Phosphorylation Regulation of Src Family Kinases by Csk

The following procedure provides an assay to test for regulation of Src family kinases by the regulatory kinase, Csk.

Materials and Reagents

The coating buffer is PBS+Sodium azide at 0.2 mg/ml, 5% w/v BSA in PBS. The wash buffer is PBS+0.05% v/v Tween 20 (PBS-TWEEN), 500 mM HEPES pH 7.4, ATP (40 $\mu$M)+MgCl2 (80 mM) in distilled water. MgCl2 (80 mM) is dissolved in distilled water (for no ATP blanks). The compounds for test are dissolved at 10 mM in DMSO. The assay Buffer is 100 mM HEPES, pH 7.4, containing 2 mM DTT, 0.2 mM sodium orthovanadate, 0.2 mgs/ml BSA.

Recombinant Csk kinase is purified from insect cells or yeast. Preferably, Csk affinity purified from SF9 cells is utilized in the present assay. Brauninger et al., 1993, Oncogene 8:1365–1369. Anti-phosphotyrosine antibodies are prepared to specifically recognize phospho-tyrosine residues (Babco, Berkeley, Calif.).

HRP-linked goat anti-rabbit Immunoglobulin (Ig) is obtained from Biosource International, (Catalogue #6430). The HRP substrate is ABTS or Pierce Peroxidase substrate. All assays are performed in Corning ELISA plates.

Procedure

Coat plates overnight at 4° C. with 100 $\mu$l of 20 $\mu$g/ml poly(Glu,Tyr) (Sigma #P0275) and add 0.01% sodium azide for longer term storage. Block with 5% BSA at 150 $\mu$l/well for one hour at RT. Wash plates once with PBS-TWEEN, and leave to soak with 50 mM HEPES pH 7.4.

Plate test compounds (10 mM in DMSO) 2 $\mu$l/well in a Costar plate ready for dilution with dH$_2$O and plating to reaction plates. Dilute Csk kinase 1:5,000 in Reaction Buffer for example, for 5 plates prepare 25 mls as follows: 2.5 mls 1 M HEPES pH7.4 (stored sterile at 4° C.), 21.85 ml distilled water, 0.1 ml 5% BSA, 0.5 ml 10 mM Sodium, Orthovanadate (stored sterile at 4° C.), 50 $\mu$l 1.0 M DTT (stored frozen at –20° C.), 5 $\mu$l Csk Kinase (stored frozen at –80° C.).

Add 48 $\mu$l of distilled water to the 2 $\mu$l of each compound in the dilution plate then add 25 $\mu$l/well of this to the reaction plate. This will ultimately give a final concentration of 100 $\mu$M in the reaction if the original is 10 mM in DMSO.

Add: i) 50 $\mu$l of enzyme in reaction buffer/well.

ii) 25 $\mu$l ATP-MgCl2/well to plates, MgCl2 only to no ATP blanks

Incubate at RT for 15 minutes, on plate shaker at RT. Terminate reaction by addition of 25 $\mu$l of 0.5 mM EDTA. This step can be automated for up to 4 plates using the Zymark Rapid-Plate 96 by preparing a costar 96-well plate containing 125 $\mu$l ATP and controls/well in the required pattern, and a similar EDTA plate to stop the reaction. Wash ×4 with PBS-TWEEN.

Add 100 $\mu$l anti-phosphotyrosine (anti-pTyr)(1:10,000 of anti-pTyr serum; or 1:3,000 of 10% glycerol diluted PA-affinity purified antibody) in PBS-TWEEN+0.5% BSA+ 0.025% Non-fat milk powder+100 $\mu$M Orthovanadate and incubate at RT for one hour, continuously shaken. Wash plates 4× with PBS-TWEEN.

Add 100 $\mu$l HRP-linked 1 g (1:5,000) in PBS-TWEEN+ 0.5% BSA+0.025% Non-fat milk powder+100 $\mu$M Orthovanadate and incubate at RT for one hour, continuously shaken. Wash plates 4× with PBS-TWEEN and once in PBS. Develop plate using ABTS or other peroxidase substrate.

8. Src Kinase Transphosphorylation Activity

The following kinase assay sets forth a method to screen for modulators of the tyrosine kinase Src.

Materials and Reagents

Coating buffer–PBS+ Sodium azide at 0.2 mg/ml, 1% w/v BSA in PBS, Wash buffer–PBS+0.05% v/v Tween 20 (PBS-TWEEN) and 500 mM HEPES pH 7.4.

ATP (40 $\mu$M)+MgCl2 (80 mM) in distilled water and MgCl2 (80 mM) in distilled water for no ATP blanks. Compounds for test are dissolved at 10 mM in DMSO. The Assay Buffer is 100 mM HEPES pH 7.4 containing 2 mM DTT, 0.2 mM sodium orthovanadate, 0.2 mg/ml BSA Partially purified recombinant human Src supplied by UBI (14-117). Anti-phosphotyrosine (rabbit polyclonal anti-PY) (Babco, Berkeley, Calif.).

The following reagents are commercially available: HRP-linked goat anti-rabbit Ig (Biosource International #6430), HRP substrate ABTS or Pierce Peroxidase substrate, and Corning ELISA plates Procedure Coat plates overnight at 40° C. with 100 $\mu$l of 20 $\mu$l/ml poly(Glu,Tyr) (Sigma #P0275) (containing 0.01% sodium azide for longer term storage), and block with 1% BSA at 100 $\mu$l/well for one hour at ambient temperature. Plate test compounds (10 mM in DMSO) 2 $\mu$l/well in a Costar plate ready for dilution with dH$_2$O and plating to reaction plates.

Dilute Src kinase 1:10,000 in Reaction Buffer, for example, for 5 plates prepare 25 mls as follows:

2.5 mls 1 M HEPES pH7.4 (stored sterile at 4° C.)

21.85 ml distilled water 0.1 ml 5% BSA 0.5 ml 10 mM Sodium Orthovanadate (stored sterile at 4° C.)

50 $\mu$l 1.0 M DTT (stored frozen at –20° C.)

2.5 $\mu$l Src Kinase (stored frozen at –80° C.)

Add 48 $\mu$l of distilled water to the 2 l of each compound in the dilution plate then add 25 $\mu$l/well of this to the reaction plate. This will ultimately give a final concentration of 100 $\mu$M in the reaction if the original is 10 mM in DMSO.

Add i) 50 $\mu$l of enzyme in reaction buffer/well.

ii) 25 $\mu$l ATP-MgCl2/well to plates, MgCl2 only to no ATP blanks

Incubate at RT for 15 minutes, on plate shaker at RT. Terminate reaction by addition of 25 $\mu$l of 0.5 M EDTA. This step can be automated for up to 4 plates using the Zymark Rapid-Plate 96 by preparing a costar 96-well plate containing 125 $\mu$l ATP and controls/well in the required pattern, and a similar EDTA plate to stop the reaction.

Wash 4× with PBS-TWEEN. Add 100 $\mu$l anti-phosphotyrosine (1:10,000 of anti-pTyr serum; or 1:3,000 of 10% glycerol diluted PA-affinity purified antibody) in PBS-TWEEN+0.5% BSA+0.025% Non-fat milk powder+100 $\mu$M Orthovanadate and incubate at RT for one hour, continuously shaken. Wash plates 4× with PBS-TWEEN.

Add 100 $\mu$l HRP-linked Ig (1:5,000) in PBS-TWEEN+ 0.5% BSA+0.025% Non-fat milk powder+100 $\mu$M Orthovanadate and incubate at RT for one hour, continuously shaken. Wash plates ×4 with PBS-TWEEN and once in PBS. Develop plate using ABTS or other peroxidase substrate.

9. Kit Receptor Transphosphorylation Activity

The following kinase assay sets forth a consistent method for measuring modulation of the kinase activity of the Kit receptor using an enzyme linked immunosorbent assay (ELISA).

Materials and Reagents

A stock solution of HNTG is prepared as follows:

| Reagent | M.W. | 5x Stock Concentration | Amount per L | 1x Working Concentration |
|---|---|---|---|---|
| HEPES | 238.3 | 100 mM | 23.83 g | 20 mM |
| NaCl | 58.44 | 750 mM | 43.83 g | 150 mM |
| Glycerol | NA | 50% | 500 ml | 10% |
| Triton X-100 | NA | 2.5% | 25 ml | 0.5% |

To make a liter of 5x stock solution:
a) dissolve HEPES and NaCl in about 350 ml dH$_2$O.
b) pH to 7.2 with HCl or NaOH (depends on the HEPES that is used)
c) Add glycerol and Triton X-100
d) Add dH$_2$O to volume To make a liter of 1x working solution:
a) Add 200 ml 5x stock HNTG solution to 800 ml dH$_2$O
b) check and adjust pH to 7.2 if necessary (this is an optional step)

The 5x and 1xHNTG must be stored at 4° C. or else it will become milky in appearance.

Dulbecco's Phosphate-Buffered Saline (PBS) (Gibco, #450-1300EB) is prepared as described above.

| Reagent | Molecular Weight | 10x Stock Concentration | Amt. per L | 1x Working Concentration |
|---|---|---|---|---|
| KCl | 74.56 | 27 mM | 2.013 g | 2.7 mM |
| KH2PO4 | 174.18 | 11 mM | 1.916 g | 1.1 mM |
| MgCl2.6H2O (anhydrous) | 203.31 | 5 mM | 1.017 g | 0.5 mM |
| NaCl | 58.44 | 1.38 M | 80.65 g | 138 mM |
| Na2HPO4 | 141.96 | 81 mM | 11.50 g | 8.1 mM |

To make 1 liter of 10x stock solution:
1) To a 1 liter graduated cylinder add approximately 900 ml dH$_2$O
2) Add all reagents except the MgCl2
3) When all reagents have dissolved, pH to 7.2 with HCl
4) Add MgCl2
5) Bring volume to 1 liter with dH$_2$O One does not necessarily have to make this buffer up. There are two sources of stock PBS:
1) Sterile GIBCO PBS (1x) in 500 ml bottles found in the media refrigerator (This is the buffer of choice)
2) Sterile 10x and 1xPBS found in the glass cabinets. If this PBS is used the pH must be adjusted to 7.2 with HCl It is advisable to check the pH after diluting the 10x stock. PBS can be left at room temperature, but 4° C. is the preferred storage temp.

Blocking Buffer is prepared as follows:

| Reagent | M.W. | 10x Stock Concentration | Amount per L | 1x Working Concentration |
|---|---|---|---|---|
| BSA | NA | 10% | 100 g | 1% |
| TRIS-pH 7.5 | 121.14 | 100 mM | 12.1 g | 10 mM |
| NaCl | 58.44 | 1 M | 58.44 g | 100 mM |
| Triton X-100 | NA | 1% | 10 ml | 0.1% |

Kinase Buffer is prepared as follows:

| Reagent | M.W. | 10x Stock Concentration | Amount per L | 1x Working Concentration |
|---|---|---|---|---|
| HEPES | 238.3 | 250 mM | 59.6 g | 25 mM |
| NaCl | 58.44 | 1 M | 58.4 g | 100 mM |
| MgCl2 | 203.32 | 100 mM | 20.3 g | 10 mM |
| MnCl2 | 197.9 | 60 mM | 1.9 g | 6 mM |

A stock solution of 25 ml of 100 mM phenylmethylsulfonyl fluoride (PMSF) (Sigma, #P-7626) is prepared by mixing 435.5 mg PMSF with 100% ethanol and vortexing.

ATP (Bacterial source) (Sigma, A-7699) is prepared as described above and stored in aliquots at −20° C.

UB40 anti-phosphotyrosine mAb HRP conjugated sheep anti-Mouse IgG-HRP (Amersham, #NA 931). ABTS (5Prime-3Prime, 7-579844) is prepared as described above.

Stocks of 1 M TRIS-HCL and 1 M TRIS (Fisher, #BP 152-5) are prepared by adding 600 ml MilliQue H2O, adjusting the pH to 7.5 (or 7.2) using HCl, and bringing the volume to one Liter with MilliQue H2O. A 5 M stock solution of NaCl is prepared and stored at ambient temperature (Fisher, #S271-10). Triton X-100 is obtained (Fisher, BP151-100).

A 0.1 M stock solution of Na3VO4 (Fisher, #S454-50) is prepared by adding 80 ml distilled water, adjusting the pH to 10.0 with either HCl or NaOH, boiling in the microwave, cooling, checking the pH, and repeating pH and boil until pH is stable at pH 10, making 1 ml aliquots and store at −80° C.

A stock solution of 1 M MgCl2 (Fisher, #M33-500) is prepared in appropriate volume with MilliQue H2O, e.g., 40 ml. A stock solution of 1 M MnCl2 (Fisher, #M87-500) is prepared in appropriate volume with MilliQue H2O, e.g., 40 ml.

A stock solution of 1 M HEPES (Fisher, #BP310-500) is prepared by adding the 47.7 grams of HEPES to 200 ml MilliQue H2O, bringing the pH to 7.0 bring to volume with MilliQue H2O, and sterile filtering.

An Albumin, Bovine (BSA) (Sigma, #A-8551) stock solution is prepared as a 30% solution, i.e., 30 grams of BSA dissolved in 300 ml of distilled H20, followed by filter sterilization and store at 4° C.

TBST Buffer is comprised of the following chemicals:

| Reagent | M.W. | 1x Working Concentration | Amount per L |
|---|---|---|---|
| Tris | 121.14 | 50 mM | 6.057 g |
| NaCl | 58.44 | 150 mM | 8.766 g |
| Triton X-100 | NA | 0.1% | 1.0 ml |

To make 1 liter of 1x working solution:
To a 1 liter graduated cylinder add approximately 900 ml dH$_2$O
Add all reagents except the Triton X-100
When all reagents have dissolved, pH to 7.2 with HCl
Add Triton X-100
Bring volume to 1 liter with dH$_2$O
Alternatively, one can use TBS (see Below) to which Triton is added to 0.1%:
To 1 liter of TBS add 1.0 ml Triton X-100
Stir until dissolved
TBST can be left at room temperature, but 4° C. is the preferred storage temp.

Goat affinity purified antibody Rabbit IgG (whole molecule) from Cappel, #55641, and Anti-Kit (C-20) rabbit polyclonal IgG antibody (Santa Cruz, #sc-168) at a concentration of 100 g/ml vial are obtained and stored.

CHO cells stably expressing GyrB/Kit, are grown in standard CHO medium, supplemented with 1 mg/ml G418 for Kit see Yarden et al., 1987, EMBO J 6:3341–3351; for Gyr B see Funatsuki et al. 1997 J. Biol. Chem 272:13307–13308.

Procedure

All of the following steps are conducted at room temperature unless it is specifically indicated. All ELISA plate washing is by rinsing 4× with TBST. Kit Cell Lysis is performed 1 hour prior to the start of receptor capture. Firstly, the cells are washed when >95% confluent in a 15 cm dish, with PBS and the PBS is aspirated as much as possible. The cells are lysed with 3 ml of 1×HNTG containing 1 mM PMSF/15 cm dish. Scrape the cells from the plate and transfer to a 50 ml centrifuge tube.

Pool supernatants, and allow to sit, on ice, for one hour with occasional vortexing. Failure to do so with result in an increased background (approximately 3-fold higher). Balance tubes and centrifuge at 10,000×g for 10 min at 4° C. Remove an aliquot to determine the concentration of protein using standard methods.

ELISA Procedure

Coat Corning 96-well ELISA plates with 2 g per well Goat anti-rabbit antibody in PBS for a total well volume of 100 l . Store overnight at 4° C. Remove unbound Goat anti-rabbit antibody by inverting plate to remove liquid. Add 100 l of Blocking Buffer to each well. Shake at room temperature for 60 minutes. Wash 4× with TBST. Pat plate on a paper towel to remove excess liquid and bubbles Add 0.2 g per well of Rabbit anti -Kit antibody diluted in TBST for a total well volume of 100 l . Shake at room temperature for 60 min. Dilute lysate in HNTG (180 g lysate/100 l). Add 100 l of diluted lysate to each well. Shake at room temperature for 60 min. Wash 4× with TBST. Pat plate on a paper towel to remove excess liquid and bubbles Dilute compounds/extracts (or as stated otherwise) in 1× kinase buffer, with 5 M ATP in a polypropylene 96 well plate. Transfer 100 l of diluted drug to ELISA plate wells. Incubate at room temperature with shaking for 60 minutes.

Stop reaction with the addition of 10 l of 0.5 M EDTA. Plate is now stable for a reasonable period of time. Wash 4× with TBST. Pat plate on a paper towel to remove excess liquid and bubbles.

Add 100 l per well of UB40 (1:2000 dilution in TBST). Incubate 60 min at room temperature, with shaking. Wash 4× with TBST. Pat plate on a paper towel to remove excess liquid and bubbles.

Add 100 l per well of sheep anti-mouse IgG—HRP (1:5000 dilution in TBST).

Incubate 60 min at room temperature, with shaking. Wash 4× with TBST. Pat plate on a paper towel to remove excess liquid and bubbles.

Add 100 l per well of ABTS. Incubate with shaking for 15–30 min. Read assay on Dynatech MR7000 ELISA reader. Test Filter=410 nm, Reference Filter=630 nm.

Template for placement of controls:

10. Met Kinase Transphosphorylation Activity

The following assay provides a consistent method for measuring modulation of phosphotyrosine deposition on Poly (Glu,Tyr)(4:1) substrate by the Met kinase.

Materials and Reagents

The reactions are performed in Corning 96-well ELISA plates, (Corning, #25805-96). The kinase substrate is Poly (Glu,Tyr) (4: 1) (Sigma, #P 0275). All dilutions are in PBS (Gibco, #450-1300EB) which is prepared in a stock solution as described in kinase assays above.

50 mM HEPES: Dilute Gibco Tissue Culture Grade 1 M HEPES to a final concentration of 50 mM HEPES using MilliQue H2O.

Prepare Blocking Buffer 1% Bovine Serum Albumin (BSA) (Sigma, #A-7888) in 10× stock and 1× working concentration as described above. If filtered, Sodium Azide does not need to be added.

Purified GST fusion protein containing the Met kinase domain is stored at −80° C.

TBS-W Buffer

| Reagent | M.W. | 1× Working Concentration | Amount per L |
|---|---|---|---|
| Tris | 121.14 | 50 mM | 6.057 g |
| NaCl | 58.44 | 150 mM | 8.766 g |
| Tween-20 | | 0.05% | 0.5 ml |

To make 1 liter of a 1× working solution:

1) To a 1 liter graduated cylinder add approximately 900 ml $dH_2O$

2) Add all reagents

3) When all reagents have dissolved, pH to 7.6 with HCl

4) Bring volume to 1 liter $dH_2O$

5) Do not keep a 10% stock solution of Tween20. Add 100% Tween20 to the buffer.

MilliQue H2O+4% DMSO, and a solution of 10 mM ATP (Sigma, #A-5394) are used to make 10 mM Stock solution.

1) Add 5 ml of $dH_2O$ to 27.5 mg ATP

2) Vortex

This reagent can be stored at −20 in small aliquots to be taken out just prior to use and kept on ice.

A 1 M MnCl2 stock is prepared, 19.79 grams is dissolved in 100 ml of distilled water and sterile filtered.

2× Kinase Dilution Buffer

| Reagent | Stock solution | Amount per 100 ml | Working Concentration |
|---|---|---|---|
| $dH_2O$ | NA | 88.4 ml | |
| Hepes pH 7.5 | 1 M | 10 ml | 100 mM |
| BSA/PBS | 5% | 0.4 ml | 0.02% |
| Na -orthovanadate | 0.1 M | 0.2 ml | 0.2 mM |
| NaCl | 5 M | 1 ml | 50 mM |

4×ATP Reaction Mixture

| Reagent | Stock solution | Amount per 10 ml | Working Concentration |
|---|---|---|---|
| $dH_2O$ | NA | 9.56 ml | |
| MnCl2 | 1 M | 0.4 ml | 40 mM |
| ATP | 10 mM | 0.02 ml | 20 M |

4× Negative Controls Mixture

| Reagent | Stock solution | Amount per 10 ml | Working Concentration |
|---|---|---|---|
| dH$_2$O | NA | 9.60 ml | |
| MnCl2 | 1 M | 0.4 ml | 40 mM |

NUNC 96-well V bottom polypropylene plates (Applied Scientific, Catalog #AS-72092), and EDTA. The procedure to make stock solution of EDTA is as follows:

1) Add approximately 70 ml dH$_2$O to a 250 ml beaker
2) Add EDTA
3) With pH probe in beaker, add 10N NaOH dropwise EDTA will not dissolve until pH is around 7.0 As EDTA dissolves the pH will fall, add more NaOH
4) When all EDTA is dissolved, adjust the pH to 8.0
5) Transfer to 100 ml graduated cylinder, bring volume to 100 ml with dH$_2$O.

Antibody Dilution Buffer

| Reagent | Stock solution | Amount per 100 ml | Working Concentration |
|---|---|---|---|
| TBS-W | | 88.4 | NA |
| BSA/PBS | 5% | 10 ml | 0.5% |
| Milk/PBS | 5% | 0.5 ml | 0.025% |
| Na-orthovanadate | 0.1 M | 0.1 ml | 0.1 mM |

Rabbit Polyclonal Anti-Phosphotyrosine Antibody (Babco, Berkeley, Calif.) Goat Anti-Rabbit HRP Conjugated Antibody, (Biosource)

2,2'-azino-bis(3-ethylbenzthiazoline-6-sulfonic acid (ABTS) is obtained from a commercial supplier, i.e., Sigma, #A-1888.

| Reagent | M.W. | Working Concentration | Amount per L |
|---|---|---|---|
| Citric Acid | 192.12 | 100 mM | 19.21 g |
| Na2HPO4 | 141.96 | 250 mM | 35.49 g |
| ABTS | NA | 0.5 mg/ml | 500 mg |

To make 1 liter of working solution:
1) To a 1 liter graduated cylinder add approximately 900 ml dH$_2$O
2) Add Citric Acid and Na2HPO4
3) pH to 4.0 with phosphoric acid
4) ABTS
5) Cover with foil and let dissolve for about ½ hr
6) Filter the solution Keep solution in dark at 4° C. until ready to use Prepare a hydrogen peroxide 30% solution (Fisher, #H325) and store in the dark at 4° C. until ready to use.

ABTS (Two options)
a) Formulation: 15 mls ABTS solution (above) 2 1 H2O2
Prepare 5 minutes before use and leave at room temperature
b) ABTS from Moss, Inc. Product no. ABTS-1000

A stock solution of 0.2 M HCl is prepared as described above, and stored at room temperature.

Procedure

Coat ELISA plates with 2 g Poly((Glu,Tyr)) in 100 l PBS overnight at 4 degrees (PolyEY stock 1.0 mg/ml in PBS at −80). Block plate with 150 l of 1% BSA/PBS for 60 min. Wash plate twice with PBS, once with 50 mM Hepes buffer pH 7.4 (Using Titertek Washer MRD8). Plates can sit in HEPES buffer if other buffers need to be prepared. The Kinase Dilution Buffer, ATP mixture, negative control mixture, and TBS-W should all be prepared before proceeding.

Add 50 l of diluted kinase into all wells (Using Titertek Multidrop S20 Stacker). Purified kinase is diluted into "Kinase Dilution Buffer" to achieve a concentration of 10 ng/well. (Concentration of present purified kinase batch is 0.2 mg/ml)

Add 25 l drugs (in 4% DMSO) or DMSO controls (4% in water) to plate (Using Rapid Plate-96 Zymark). If starting with a 10 mM stock of compound in 100% DMSO, make a 25 fold dilution into water. The concentration of the drug dilution plate will be 400 M in 4% DMSO. If creating serial dilutions, dilute in 4% DMSO/water down the drug plate. Final compound concentration (highest) in the assay plate will be 100 M in 1% DMSO.

Incubate the kinase/compound mixture for 15 minutes. Add 25 l of 0.5 M EDTA to the negative control wells.

Reaction Step

Add 25 l ATP/MnCl2 mixture to the all wells. The reaction time is 5 minutes and is the most critical part of the assay. This is a fast kinase reaction and assay must be stopped with 25 l 500 mM EDTA in a manner similar to the addition of ATP. Fill and label this basin now, so it is easily available for kinase reaction termination. Wash plate 3× with TBS-W.

Detect substrate phosphorylation with rabbit polyclonal anti-pTyr diluted 11:10,000 in Antibody Dilution Buffer. Add 100 l per well and incubate at room temperature, with shaking, for one hour. Wash plate 3× with TBS-W.

Dilute Biosource HRP conjugated anti-rabbit antibody 1:6,000 in Antibody Dilution buffer. Add 100 l per well and incubate at room temperature, with shaking, for one hour. Wash plate 3× with TBS-W. Wash plate 1× with PBS. Residual Tween20 from the washing buffer can inhibit HRP and decrease the delta.

Add 100 l of ABTS/H2O2 solution to each well using the Proline Biohit Repeating Pipetor. If necessary, stop the development reaction with the addition of 100 l of 0.2M HCl per well. Read plate on Dynatech MR7000 ELISA reader. Test Filter: 410 nM, Reference Filter: 630 nM. Plate template for placement of controls as in Kinase assay 1.

11. GST-Flk1 Transphosphorylation Activity

The following kinase assay provides a consistent method for measuring transphosphorylation activity of GST-Flk1 on poly (Glu,Tyr) in a high throughput screening assay.

Materials and Reagents

The reactions are performed in Corning 96-well ELISA plates (Corning, #25805-96) and the substrate is Poly (Glu, Tyr) 4:1, lyophilized (Sigma, #P0275). Poly (Glu,Tyr) is prepared at a concentration of 1 mg/ml in sterile PBS and stored in 1 ml aliquots at −20° C. Preparation of poly (Glu,Tyr) (pEY) coated assay plates is as follows: Coat 2 g/well of poly (Glu,Tyr) (pEY) in 100 l PBS at room temperature for 2 hours or+4° C. overnight. Cover plates well to prevent evaporation and store at 4° C. for not more than 7 to 10 days for best results.

PBS Buffer, PBS-Tw Buffer

| Reagent | M.W. | 1x Working Concentration | Amount per L |
|---|---|---|---|
| KH2PO4(monobasic) | 136.09 | 1.4 mM | 0.2 g |
| Na2HPO4(dibasic) | 141.96 | 8.1 mM | 1.15 g |
| KCl | 74.56 | 2.7 mM | 0.2 g |
| NaCl | 58.44 | 138 mM | 8.0 g |
| Tween-20 | | 0.1% | 1 ml |

Tris Blocking Buffer (TBB):

| Reagent | M.W. | 1x Working Concentration | Amount per L |
|---|---|---|---|
| Tris | 121.14 | 10 mM | 1.21 g |
| NaCl | 58.44 | 150 mM | 8.77 g |
| Tween-20 | NA | 0.1% | 1 ml |
| BSA | NA | 1% | 10 g |

Procedure for making a 1x working solution of TBB:
1) To a 1 liter graduated beaker add approximately 900 ml dH$_2$O
2) Add all reagents except the BSA
3) When all reagents have dissolved, pH to 7.2 with HCl
4) Add BSA, stir until dissolved.
5) Bring volume to 1 liter with dH$_2$O
6) Filter the solution to remove any particulate matter, and store at +4° C.

A 10x stock solution can be made by multiplying the amounts by 10 (but keeping the final volume of 1 liter). This stock is then diluted 10 fold with dH$_2$O. Filter the solution to remove any particulate matter, and store at +4° C.

A 1% BSA stock solution is prepared in PBS, as described above, and stored at 4° C. In addition, a stock solution of 50 mM Hepes pH 7.5 is prepared as described above.

GST-Flk1cd purified from sf9 recombinant baculovirus transformation; −80°C.; 100 1 aliquots. (use 5 ng (0.005 g)/well in kinase dilution buffer, KDB) dH$_2$O+4% DMSO To make 10 mM Stock solution of ATP: 1) Add 5 ml of dH$_2$O to 27.5 mg ATP; and 2) Vortex. Any milligram amount of ATP can be used provided it is kept in the same ATP to dH$_2$O ratio. This reagent can be stored at −20° C. in small aliquots to be taken out just prior to use and kept on ice.

A stock solution of 1 M MnCl2, and working concentration of 40 MM MnCl2 are prepared as described above.

Kinase Dilution Buffer (KDB) is prepared as described above. 100 ml of kinase buffer mix is enough for approximately 40 assay plates.

The reactions are performed in NUNC 96-well V bottom polypropylene plates (Applied Scientific, #AS-72092). EDTA is prepared as described above.

The 1° and 2° antibodies are diluted in the Antibody Dilution Buffer which is prepared as follows:

| Reagent | Stock solution | Amount per 100 ml | Working Concentration |
|---|---|---|---|
| PBSTw | | 89.5 ml | |
| Milk in PBS | 5% | 0.5 ml | 0.025% |
| Sodium Vanadate | 10 mM | 1 ml | 100 M |
| BSA in PBS | 5% | 10 ml | 0.5% |

The antisera are as described above: anti-phosphotyrosine rabbit polyclonal antisera; Biochemistry lab, and goat anti-rabbit HRP conjugate (Biosource, #A110404).

The ABTS solution is prepared as described above, and kept in the dark at 4° C. until ready to use. Hydrogen peroxide 30% solution (Fisher, #H325) is prepared and is stored in the dark at 4° C. until ready to use ABTS/H2O2 is prepared by mixing 15 mls ABTS solution with 3 1 H2O2. The ABTS is warmed to room temperature about one hour prior to use. Or warm quickly by placing tube in 37° C. water bath. Add 3 1 H2O2 prior to use, and 0.2 M HCl which is stored at room temperature.

Procedure

Coat Corning 96 well ELISA plates with 2 g of polyEY peptide in sterile

PBS, as described above. Remove unbound liquid from wells by inverting plate. Wash 1×TBSTw. Pat the plate on a paper towel to remove excess liquid. Add 100 1 of 1% BSA in PBS to each well. Incubate for 1 hr. at room temperature, with shaking. Repeat coating step.

Soak wells with 50 mM Hepes pH7.5, using approximately 150 l/well. Dilute drugs/extracts at 4x the desired final assay concentration in dH$_2$O+4% DMSO (unless specified otherwise) in 96-well polypropylene plates. Always add the larger volume of water to the smaller volume of compound to ensure rapid mixing. Add 25 1 diluted drugs/extracts to ELISA plate. To control wells (wells which do not receive any drug) add 25 1 of dH$_2$O+4% DMSO.

Dilute GST-Flk1 0.005 g (5 ng)/well in KDB. For 50 ml KDB add 100 1 of 0.050 mg/ml GST-Flk1 enzyme. This is enough for 10 assay plate. (Check recommendations for each batch of GST-Flk) Add 50 1 of diluted enzyme to each well. Add 25 1 0.5 M EDTA to negative control wells.

Add 25 1 of 40 mM MnCl2 with 4×ATP (2 M) directly to all wells. Approximately 100 1 final volume in well with 0.5 M ATP final concentration. Incubate for 15 minutes while shaking at room temperature. After 15 minutes stop reaction with addition of 25 1 of 500 mM EDTA pH 8.0 for 50 mM final in well.

Wash 3x with TBSTw and pat plate on paper towel to remove excess liquid. Add 100 1 per well of anti-phosphotyrosine antisera (1:10,000 dilution in antibody dilution buffer). Incubate 90 min at room temperature, with shaking. Wash as described above.

Add 100 1 per well of goat anti-rabbit HRP conjugate (1:6,000 dilution in antibody dilution buffer). Incubate 90 min. at room temperature with shaking. Wash as described above.

Add 100 1 of room temp. ABTS/H2O2 solution to each well. Incubate 15 to 30 minutes while shaking. Remove any bubbles. If necessary stop reaction with the addition of 100 1 o f 0.2M HCl per well. Read assay on Dynatech MR7000 ELISA reader. Test Filter: 410 nM, Reference Filter: 630 nM.

12. GST-FGFR1 Transphosphorylation Activity

Coat ELISA plates with 1 g Poly(Glu, Tyr) 4:1 (Sigma P0275) in 100 1 PBS overnight at 4 degrees (Poly(Glu, Tyr) 4:1 stock 1.0 mg/ml in PBS at −20). Wash plate once with PBS. Block plate with 150 1 5% BSA/PBS for 60 minutes. Wash plate twice with PBS, once with 50 mM Hepes buffer pH 7.5.

Add 0.025 ml drugs (in 4% DMSO) or DMSO controls (4% in water) to plate. If starting with a 10 mM stock of compound in 100% DMSO then make a 25 fold dilution into water for the starting concentration in the drug dilution plate of 0.4 mM in 4% DMSO. Do serial dilutions down the drug plate in 4% DMSO/water. Final compound concentration (highest) in the assay plate will be 0.1 mM in 1% DMSO.

Add 0.05 ml of diluted kinase into all wells. Purified kinase is diluted into "kinase dilution buffer" (KDB):

For 25 ml: 2.5 ml 1 M Hepes (tissue culture stuff 0.1 ml 5% BSA/PBS 0.01 ml 500 mM Na-orthovanadate 0.25 ml 5 M NaCl For GST-FGFR1 use 5 ng of purified protein per well. Concentration of present batch of purified GST-FGFR1 (917p79 9/17/98) is at 85 g/ml. For one plate (120 wells for ease of pipetting) you will need 0.6 g (7.06 microliters) diluted into 6.0 ml of KDB.

Start kinase reaction with the addition of ATP/Mn++. ATP/MN is made at a "4×" concentration. For FGFR the 4× concentration is: 40 micromolar ATP/40 mM Mn in water. For 10 ml:

0.4 ml 1 M MnCl 40 microliters 10 mM ATP 9.56 ml water

For negative controls, add Mn alone, with no ATP. Reaction time is 10 minutes. This is a fast kinase reaction and assay must be stopped with 0.025 ml 500 mM EDTA in a manner similar to the addition of ATP. Wash plate 4× with TBSTween (0.05% tween20).

Detect with rabbit polyclonal anti-phosphotyrosine antisera at a dilution of 1:10,000 into Antibody Dilution Buffer: TBSTween containing 0.5% BSA (i.e., 10 fold dilution of BSA block solution)

0.025% nonfat dry milk (from 5% stock)

0.01 mM Na-orthovanadate 50 ml Antibody Dilution Buffer:

5 ml 5% BSA 0.25 ml 5% milk 0.01 ml 500 mM Vanadate brought up to final volume of 50 ml with TBSTween.

Use 0.1 ml per well. Incubate for 1 hour. Wash plate as above.

Dilute anti-rabbit HRP 1:6,000 in Antibody Dilution buffer. And incubate for 1 hour. Wash plate as above, follow with one wash of PBS to reduce bubbles and get rid of excess Tween-20.

Develop with addition of ABTS.

Kinase Activity and the Effect on Cellular Survivial and Proliferation

13. Modulation of Raf-1Function and Cell Viability

The following kinase assay provides a consistent calorimetric method for determining the number of viable cells in chemosensitivity assay in 96-well format which measures cell survival due to raf-1 kinase function.

Materials and Reagents

Cell lines used in this assay are:

32D cl.3: murine lymphoblastoid cell, IL-3 dependent (ATCC CRL 11346).

32D cl.3 J2/leuk: 32D cl.3 expressing raf and myc, IL-3 independent.

32D bcr/abl mix: 32D over expressing bcr/abl kinase, pooled, IL-3 independent.

All of the above cell lines are grown in incubator with 5% CO2 and 37° C. The cell growth media are (fetal bovine serum (FBS)):

| 32D cl.3: | RPMI + 10% FBS + 1 ng/ml IL-3 + 2 mM Glutamine |
| 32D cl.3 J2/leuk: | RPMI + 10% FBS + 2 mM Glutamine |
| 32D bcr/ab1 mix: | RPMI + 10% FBS + 2 mM Glutamine. |

IL-3: Interleukin-3, mouse (UBI Cat. #01-374)

PBS (Dulbecco's Phosphate Buffered Saline); Gibco Cat. #450-1300EB. MTT (3-[4,5-Dimethylthiazol-2-yl]-2,5-diphenyltetrazolium bromide; Thiazolyl blue); Sigma Cat. #

M-2128 working solution: 5 mg/ml PBS, store in dark at 4° C.

Solubilization Buffer SDS Electrophoresis Grade, (Fisher Cat. #BP166), N,N-Dimethyl-formamide (DMF), (Fisher Cat. #BP1160), Acetic Acid, Glacial, (Fisher Cat. #A38) working solution: Dissolve 200 g SDS in 250 ml warm H2O and 500 ml DMF, stir in low heat. When SDS is almost solubilized, add 25 ml 80% acetic acid and 25 ml 1N HCL to solution. Adjust volume to 1000 ml.

A working solution of the solubilization buffer is prepared as follows: Dissolve 200 g SDS in 250 ml warm H2O and 500 ml DMF, stir in low heat. When SDS is almost solubilized, add 25 ml 80% acetic acid and 25 ml 1N HCL to solution. Adjust volume to 1000 ml.

Procedure

All the following steps are conducted in room temperature unless it is specifically indicated.

The cells are grown in tissue culture dish (10 cm, Corning 25020-100) to about 1×106 cell/ml, subculture every 2–3 day at 1:10 (1:20 for 32D bcr/abl mix line). Count cells with Trypan blue. Resuspend sufficient cells with medium, centrifuge once at 1000 rpm, at room temperature for 3–5 minutes. Resuspend cells in fresh medium at a density of 4×105 cells/ml, and transfer cells to 96-well tissue culture plate (Corning, 25806-96) at 75 ml per well to reach about 3×104 cells/well. An identical number of cells of the three cell lines should be seeded on three separate plates. Each cell line should have its own positive and negative control (negative control well receive medium alone). 32D cl.3 seeding medium should contain 1.33 ng/ml IL-3.

Dilute drug stock (10 mM in DMSO) 1:25 in RPMI medium in first well, then do 1:2 dilution for 8-points in tissue culture plate. Transfer 25 ml/well of this solution to each of the three cell lines with same pattern. Control wells receive medium alone. Incubate the cells with drugs in 5% CO2 at 370C for 15 hrs.

Add 15 ml MTT to each well, incubate plate at 370C for 4 hours. After 4 hours, add 100 ml solubilization solution to each well. Cover the plate with aluminum foil, let plate sit on ELISA plate shaker and shake overnight at room temperature to completely solubilize formazan crystals.

Read absorbance at 570 nm wavelength with a reference wavelength of 630 nm using a Dynatech ELISA plate reader, Model MR 500.

14. Raf-1Kinase Function and Cell Viability

The following kinase assay provides a consistent colorimetric method for detemining the number of viable cells in chemosensitivity assay in 96-well format which measures cell survival due to raf-1kinase function.

Materials and Reagents

Cell lines used in this assay are:

32D cl.3: murine lymphoblastoid cell, IL-3 dependent (ATCC CRL 11346).

32D cl.3 J2/leuk: 32D cl.3 expressing raf and myc, IL-3 independent.

32D bcr/abl mix: 32D over expressing bcr/abl kinase, pooled, IL-3 independent.

All the above cell lines are grown in incubator with 5% CO2 and 370C. Their growth media are:

| | |
|---|---|
| 32D cl.3: | RPMI + 10% FBS + 1 ng/ml IL-3 + 2 mM Glutamine |
| 32D cl.3 J2/leuk: | RPMI + 10% FBS + 2 mM Glutamine |
| 32D bcr/ab1 mix: | RPMI + 10% FBS + 2 mM Glutamine |

IL-3: Interleukin-3, mouse (UBI Cat. #01-374) resuspend IL-3 in RPMI+10% FBS to make 1 g/ml stock. Store the aliquot in −800C. Once thawed, store in refrigerator.

Stock solutions are prepared with PBS (Gibco Cat. #450-1300EB) as described above. MTT (3-[4,5-Dimethylthiazol-2-yl]-2,5-diphenyltetrazolium bromide; Thiazolyl blue) (Sigma, #M-2128) working solution is prepared as follows: 5 mg/ml PBS, stored in the dark at 40° C.

Solubilization Buffer SDS Electrophoresis Grade, (Fisher Cat. #BP166), N,N-Dimethyl-formamide (DMF), (Fisher Cat. #BP1160), Acetic Acid, Glacial, (Fisher Cat. #A38) working solution: Dissolve 200 g SDS in 250 ml warm H2O and 500 ml DMF, stir in low heat. When SDS is almost solubilized, add 25 ml 80% acetic acid and 25 ml 1N HCL to solution. Adjust volume to 1000 ml.

Procedure

All the following steps are conducted in room temperature unless it is specifically indicated. The cells are grown in tissue culture dish (10 cm, Corning 25020-100) to about 1×106 cell/ml, subculture every 2–3 day at 1:10 (1:20 for 32D bcr/abl mix line). Count cells with trypan blue. Resuspend sufficient cells with medium, centrifuge once at 1000 rpm, at room temperature for 3–5 minutes. Resuspend cells in fresh medium at a density of 4×105 cells/ml, and transfer cells to 96-well tissue culture plate (Corning, 25806-96) at 75 1 per well to reach about 3×104 cells/well. An identical number of cells of the three cell lines should be seeded on three separate plates. Each cell line should have its own positive and negative control (negative control well receive medium alone). 32D cl.3 seeding medium should contain 1.33 ng/ml IL-3.

Assay Procedure

Dilute drug stock (10 mM in DMSO) 1:25 in RPMI medium in first well, then do 1:2 dilution for 8-points in tissue culture plate. Transfer 25 l/well of this solution to each of the three cell lines with same pattern. Control wells receive medium alone. Incubate the cells with phosphate mimics to be tested in 5% CO2 at 37° C. for 16–20 hrs.

MTT Procedure

Add 15 µl MTT to each well, incubate plate at 370C for 2–4 hours. After 4 hours, add 100 µl solubilization solution to each well. Cover the plate with aluminum foil, let plate sit on ELISA plate shaker and shake overnight at room temperature to completely solubilize formazan crystals.

Read absorbance at 570 nm wavelength with a reference wavelength of 630 nm using a Dynatech ELISA plate reader, Model MR 500.

Resazurin Procedure

10 µl Resazurin is added (0.3 mg/ml) to each well, incubate plate at 37° C. for 1–4 hours. Then read the plate in Fluorescence Reader at excitation filter 530/25 and Emission 590/35 with 50% Gain.

15. HGF/SF-Met Kinase Activity Induced Cell Invasiveness

The following kinase assay provides a consistent method for measuring Scatter factor/hepatocyte growth factor (HGF/SF) and Met signaling-induced invasiveness of tumor or engineered cells in vitro.

Materials and Reagents

Hepatocyte Growth Factor (HGF): recombinant human HGF, Cat. No. 249-HG, R&D Systems, Inc., USA. HGF is dissolved in PBS with 0.1% BSA at a stock concentration of 50 mg/ml. Matrigel Basement Membrane Matrix, Cat. No. 40234, Becton Dickinson Labware. Store the Matrigel in −20° C.

Procedure

The cell lines of the assay are A549 (ATCC CRL 185) and B16-F1 (ATCC CRL 6323). Thaw Matrigel in ice tray (keep at 4° C.). Trypsinize the cells, count cells, make a cell suspension of 2×104 cell/ml, and set the cell suspension in ice to keep at 4° C. Mix the cell suspension gently with a equal volumes of Matrigel, and plate the mixture at 100 l per well in 96-well plate while being very careful to avoid bubble. Place the plate in incubator for 10–20 min to induce gel formation.

Add 100 µl of HGF-contained culture medium on top of each Matrigel cell plug(regular culture medium for negative control). The effective HGF concentration to induce cell invasiveness is 10–50 ng/ml. We use 40 ng/ml her e(final 20 ng/ml after balance with 100 µl Matrigel plug). To test compound, dilute compound with HGF-contained culture medium to 2×, and add on to Matrigel cell plug.

16. Met Signaling Induced Tumor Cell Invasiveness

The following kinase assay provides a consistent method for measuring HGF/SF-Met signaling-induced invasiveness of some tumor or engineered cells in vitro.

Materials and Reagents

DIFCO BACTO-Agar, Cat. #0140-01, STERILIN sterile individual microplate lids, (Nunc, #642000), sterile flat bottomed microtitre plates (not tissue culture treated), (Nunc, #12-565-210). The culture medium is RPMI+10% FCS+L-Glu. There are two waterbaths, one at at 37° C. and another at between 42 & 44° C. Gilson pipettes/multichannel pipettes (or like) for dosing. A 2 l fixed volume pipette is useful to plate agarose microdroplets and appropriate sterile tips. Compounds for test are dissolved in 10 mM DMSO. Invert T.C. microscope fitted with an eyepiece graticule and calibrated with a stage graticule to allow accurate measurement of cell migration from origin to periphery of agarose microdroplet.

Procedure

Weigh 1 g Agarose to glass universal and add 50 mis PBS/A to give 2% stock agarose soln. Loosely fit lid and autoclave (with tips if required). Then keep agar stock in 4° C. fridge). Before use, microwave the stock at 50% power for 1–2 min to liquilize the agar stock and keep the agar at 42° C.

Trypsinize NCI H441 cells, (ATCC HTB 174) count for total cells (heamocytometer or coulter) and centrifuge to pellet. For each ml of plating solution (for agarose microdroplets) require:

1.6×107 cells (as a pellet)
RPMI+10%FCS+L-Glu (at 37° C.) to 0.85 mls
0.15 mls of 2% Agar stock solution (at 42–44° C.)

Resuspend cell pellet with required volume of medium at 37° C., transfer to a 7 ml sterile bijoux container add required agarose solution (gives 0.3% agarose conc. in microdroplets).

Quickly but carefully place 2 µl cell/agarose microdroplets approx. centrally in each well of the 48-well microtitre plates. Place lid on completed plate(s) and place on ice (or in fridge) for a few minutes to assist gelling of the agarose.

Very slowly pipette 90 μl of cooled medium (at 4° C.) into the wells of each microplate. A manual multichannel pipette is fine for this but our electronic pipettes are too vigorous even at the slowest setting and disturb the microdroplets.

Make growth medium with 400 ng/ml HGF and transfer (again slowly) 10 μl spikes to the test plates to make final 40 ng/ml of HGF. For negative control add 10 μl regular growth medium.

Transfer plates to 37° C. incubator for migration to occur. NCI H441 cells require approximately 40 Hrs before measurement.

Measure distance of migration front from edge of agar droplet for 4 perpendicular axes per droplet and score means

17. Ligand Induced Cellular Proliferation in FDCP Cells

To provide a consistent method for measuring Ligand-induced cell proliferation in FDCP, FDCP/R1, FDCP/R3 cells, see Spooncer et al. 1986, Diffentiation 31:111–118.

Materials and Reagents

FGF1: 10 μl/ml (Acidic FGF, human; Boehringer-Mannheim; Cat. No.439 600), store aliquot in −80° C. freezer. Once thawed, store in Refrigerator.

Heparin: 50 mg/ml (Sigma Chemical Co.; Cat. No. H-3149), store in refrigerator.

IL-3: Interleukin-3, mouse (Upstate Biotechnology Inc.; Cat. No. 01-374) Resuspend in RPMI 1640+10% FBS to make 1 μg/ml stock and store in −80° C. in aliquot. Once thawed, store in Refrigerator.

Cell lines used in this assay are:

FDCP: murine lymphoblastoid cell, IL-3 dependent.

FDCP/R1: FDCP overexpressing FGFr1, IL-3- or FGF-dependent.

FDCPIR3: FDCP overexpressing FGFr3, IL-3 or FGF-dependent.

All of the above cell lines are grown in an incubator with 5% $CO_2$ at 37° C. Their growth media are:

| | |
|---|---|
| FDCP: | RPMI 1640 + 10% FBS + 0.1 ng/ml IL-3 |
| FDCP/R1: | RPMI 1640 + 10% FBS + 10 ng/ml FGF1 + 5 μg/ml Heparin |
| FDCP/R3: | RPMI 1640 + 10% FBS + 10 ng/ml FGF1 + 5 μg/ml Heparin |

Iscove's-modified MEM can be substituted for RPMI 1640 if desired.

Procedure

All the following steps are conducted at room temperature unless otherwise indicated.

Cell seeding is as follows. The cells are grown in tissue culture dishes (10 cm, Corning 25020-100) to a density of about $1 \times 10^6$ cells/ml, subcultured every 2–3 days at 1:10–1:20 dilutions. Count cells with the Coulter Counter. Take out sufficient cells and resuspend cells with 10 to 20 ml PBS, centrifuge once at 1000 rpm, at room temperature for 3–5 minutes. Remove PBS, and add back 10–20 ml PBS to wash one more time and remove PBS.

Resuspend cell pellet in RPMI+10% FBS to make cell suspension of $2.4 \times 10^5$ cells/ml, and transfer cells to 96-well tissue culture plates (Corning, 25806-96) at 50 μl per well to reach about $1.2 \times 10^4$ cells/well. An identical number of cells of the three cell lines should be seeded on three separate plates.

Make 2.5× of ligand medium (containing FGF1 for R1 and R3, or IL-3 for FDCP), add 50 μl/well into the cells. Each plate should have its own positive and negative control (negative control wells receive medium alone without ligand).

Dilute drug stock (25 mM in DMSO) 1:100 in RPMI medium in the first well of a drug dilution plate, then do 1:3 dilutions for 7-points. Transfer 25 μl/well of this solution to each of the three cell lines with same pattern. Control wells receive medium alone. Incubate the cells with drugs in 5% $CO_2$ at 37° C. for about 64 hrs.

Add 10 μl Resazurin (0.3 mg/ml) to each well, incubate plate at 37° C. for 1–4 hours. Then read the plate in the fluorescence plate reader with an excitation filter of 530/25 nm and an emission filter of 590/35 nm at 50% gain.

18. EGF Induced DNA Synthesis

The kinase assay sets forth a consistent method for measuring EGF-induced DNA synthesis in 3T3/EGFRc7 cells that over-express EGF receptors.

Materials and Reagents

EGF: mouse EGF, 201 (Toyobo, Co., Ltd. Japan), BrdU Labeling Reagent: 10 mM, in PBS (pH7.4), (Boehringer Mannheim, Germany, Cat. No. 1 647 229). FixDenat: fixation solution (Boehringer Mannheim, Germany, Cat. No. 1 647 229).

Anti-BrdU-POD: mouse monoclonal antibody conjugated with peroxidase, (Boehringer Mannheim, Germany, Cat. No. 1 647 229).

TMB Substrate Solution: tetramethylbenzidine (TMB) (Boehringer Mannheim, Germany, Cat. No. 1 647 229). PBS Washing Solution: 1×PBS, pH 7.4, made in house.

Albumin, Bovine (BSA): fraction V powder (Sigma Chemical Co., USA, A-8551).

Procedure

The cell line used in the following procedure is derived from a NIH 3T3 engineered cell line: 3T3/EGFRc7. (Reedmann et al. 1992 Mol. Cell 12:491–498.)

Cells are seeded at 8000 cells/well in 10% CS, 2 mM Gln in DMEM, in a 96 well plate. Cells are incubated overnight at 37° C. in 5% $CO_2$. After 24 hours, the cells are washed with PBS, and then are serum starved in serum free medium (0° C.S DMEM with 0.1% BSA) for 24 hours.

On day 3, ligand (EGF=2 nM, prepared in DMEM with 0.1% BSA) and test compounds are added to the cells simultaneously. The negative control wells receive serum free DMEM with 0.1% BSA only; the positive control cells receive the ligand (EGF) but no test compound. Test compounds are prepared in serum free DMEM with ligand in a 96 well plate, and serially diluted for 7 test concentrations.

After 18 hours of ligand activation, diluted BrdU labeling reagent (1:100 in DMEM, 0.1% BSA) is added and the cells are incubated with BrdU (final concentration=10 M) for 1.5 hours.

After incubation with labeling reagent, the medium is removed by decanting and tapping the inverted plate on a paper towel. FixDenat solution is added (50 μl/well) and the plates are incubated at room temperature for 45 minutes on a plate shaker.

The FixDenat solution is thoroughly removed by decanting and tapping the inverted plate on a paper towel. Milk is added (5% dehydrated milk in PBS, 200 μl/well) as a blocking solution and the plate is incubated for 30 minutes at room temperature on a plate shaker.

The blocking solution is removed by decanting and the wells are washed once with PBS. Anti-BrdU-POD solution (1:200 dilution in PBS, 1% BSA) is added (50 μl/well) and the plate is incubated for 90 minutes at room temperature on a plate shaker.

The antibody conjugate is thoroughly removed by decanting and rinsing the wells 5 times with PBS, and the plate is dried by inverting and tapping on a paper towel.

TMB substrate solution is added (100 μl/well) and incubated for 20 minutes at room temperature on a plate shaker until color development is sufficient for photometric detection.

The absorbance of the samples are measured at 410 nm (in "dual wavelength" mode with a filter reading at 490 nm, as a reference wavelength) on a Dynatech ELISA plate reader.

19. PDGF Induced DNA Synthesis

The following kinase assay provides a consistent method for measuring PDGF-induced DNA synthesis in 3T3/EGFRc7 cells that overexpress endogenous PDGF receptors.

Materials and Reagents

PDGF: human PDGF B/B; 1276-956, Boehringer Mannheim, Germany. BrdU Labeling Reagent: 10 mM, in PBS (pH 7.4), Cat. No. 1 647 229, Boehringer Mannheim, Germany. FixDenat: fixation solution (ready to use), Cat. No. 1 647 229, Boehringer Mannheim, Germany. Anti-BrdU-POD: mouse monoclonal antibody conjugated with peroxidase, Cat. No. 1 647 229, Boehringer Mannheim, Germany. TMB Substrate Solution: tetramethylbenzidine (TMB), ready to use, Cat. No. 1 647 229, Boehringer Mannheim, Germany. PBS Washing Solution: 1×PBS, pH 7.4, made in house. Albumin, Bovine (BSA): fraction V powder; A-8551, Sigma Chemical Co., USA.

Procedure

The cell line used in the following procedure is derived from a NIH 3T3 engineered cell line: 3T3/EGFRc7. See above.

Cells are seeded at 8000 cells/well in DMEM, 10% CS, 2 mM Gln in a 96 well plate. Cells are incubated overnight at 37° C. in 5% CO2. After 24 hours, the cells are washed with PBS, and then are serum starved in serum free medium (0° C.S DMEM with 0.1% BSA) for 24 hours.

On day 3, ligand (PDGF=3.8 nM, prepared in DMEM with 0.1% BSA) and test compounds are added to the cells simultaneously. The negative control wells receive serum free DMEM with 0.1% BSA only; the positive control cells receive the ligand (PDGF) but no test compound. Test compounds are prepared in serum free DMEM with ligand in a 96 well plate, and serially diluted for 7 test concentrations.

After 18 hours of ligand activation, diluted BrdU labeling reagent (1:100 in DMEM, 0.1% BSA) is added and the cells are incubated with BrdU (final concentration=10 μM) for 1.5 hours.

After incubation with labeling reagent, the medium is removed by decanting and tapping the inverted plate on a paper towel. FixDenat solution is added (50 μl/well) and the plates are incubated at room temperature for 45 minutes on a plate shaker.

The FixDenat solution is thoroughly removed by decanting and tapping the inverted plate on a paper towel. Milk is added (5% dehydrated milk in PBS, 200 μl/well) as a blocking solution and the plate is incubated for 30 minutes at room temperature on a plate shaker.

The blocking solution is removed by decanting and the wells are washed once with PBS. Anti-BrdU-POD solution (1:200 dilution in PBS, 1% BSA) is added (50 1/well) and the plate is incubated for 90 minutes at room temperature on a plate shaker.

The antibody conjugate is thoroughly removed by decanting and rinsing the wells 5 times with PBS, and the plate is dried by inverting and tapping on a paper towel.

TMB substrate solution is added (100 μl/well) and incubated for 20 minutes at room temperature on a plate shaker until color development is sufficient for photometric detection.

The absorbance of the samples are measured at 410 nm (in "dual wavelength" mode with a filter reading at 490 nm, as a reference wavelength) on a Dynatech ELISA plate reader.

20. FGF Induced DNA Synthesis

The following kinase assay provides a consistent method for measuring FGF-induced DNA synthesis in 3T3c7/IEGFr cells that overexpress endogenous FGF receptors.

Materials and Reagents

FGF: human FGF2/bFGF; 13256-029, Gibco BRL, Gaithersburg, MD. BrdU Labeling Reagent: 10 mM, in PBS (pH7.4), Cat. No. 1 647 229, Boehringer Mannheim, Germany. FixDenat: fixation solution (ready to use), Cat. No. 1 647 229, Boehringer Mannheim, Germany. Anti-BrdU-POD: mouse monoclonal antibody conjugated with peroxidase, Cat. No. 1 647 229, Boehringer Mannheim, Germany. TMB Substrate Solution: tetramethylbenzidine (TMB), ready to use, Cat. No. 1 647 229, Boehringer Mannheim, Germany. PBS Washing Solution: 1×PBS, pH 7.4. Albumin, Bovine (BSA): fraction V powder; A-8551, Sigma Chemical Co., USA.

Procedure

The cell line used in the following procedure is derived from a NIH 3T3 engineered cell line: 3T3c7/EGFr.

Cells are seeded at 8000 cells/well in DMEM, 10% CS, 2 mM Gln in a 96 well plate. Cells are incubated overnight at 37° C. in 5% CO2. After 24 hours, the cells are washed with PBS, and then are serum starved in serum free medium (0° C.S DMEM with 0.1% BSA) for 24 hours.

On day 3, ligand (FGF2=1.5 nM, prepared in DMEM with 0.1% BSA) and test compounds are added to the cells simultaneously. The negative control wells receive serum free DMEM with 0.1% BSA only; the positive control cells receive the ligand (FGF2) but no test compound. Test compounds are prepared in serum free DMEM with ligand in a 96 well plate, and serially diluted for 7 test concentrations.

After 18 hours of ligand activation, diluted BrdU labeling reagent (1:100 in DMEM, 0.1% BSA) is added and the cells are incubated with BrdU (final concentration=10 M) for 1.5 hours.

After incubation with labeling reagent, the medium is removed by decanting and tapping the inverted plate on a paper towel. FixDenat solution is added (50 μl/well) and the plates are incubated at room temperature for 45 minutes on a plate shaker.

The FixDenat solution is thoroughly removed by decanting and tapping the inverted plate on a paper towel. Milk is added (5% dehydrated milk in PBS, 200 μl/well) as a blocking solution and the plate is incubated for 30 minutes at room temperature on a plate shaker.

The blocking solution is removed by decanting and the wells are washed once with PBS. Anti-BrdU-POD solution (1:200 dilution in PBS, 1% BSA) is added (50 μl/well) and the plate is incubated for 90 minutes at room temperature on a plate shaker.

The antibody conjugate is thoroughly removed by decanting and rinsing the wells 5 times with PBS, and the plate is dried by inverting and tapping on a paper towel. TMB substrate solution is added (100 μl/well) and incubated for 20 minutes at room temperature on a plate shaker until color development is sufficient for photometric detection.

The absorbance of the samples are measured at 410 nm (in "dual wavelength" mode with a filter reading at 490 nm, as a reference wavelength) on a Dynatech ELISA plate reader.

21. EGF and Her-2 Induced DNA Synthesis

The following kinase assay provides a consistent method for measuring EGF-induced, Her2-driven DNA synthesis in 3T3/EGFr/Her2/EGFr cells that express chimeric EGFr receptors with a Her2 kinase domain.

Materials and Reagents

EGF: mouse EGF, 201; Toyobo,Co., Ltd. Japan. BrdU Labeling Reagent: 10 mM, in PBS (pH7.4), Cat. No. 1 647 229, Boehringer Mannheim, Germany. FixDenat: fixation solution (ready to use), Cat. No. 1 647 229, Boehringer Mannheim, Germany. Anti-BrdU-POD: mouse monoclonal antibody conjugated with peroxidase, Cat. No. 1 647 229, Boehringer Mannheim, Germany. TMB Substrate Solution: tetramethylbenzidine (TMB), ready to use, Cat. No. 1 647 229, Boehringer Mannheim, Germany. PBS Washing Solution: 1×PBS, pH 7.4. Albumin, Bovine (BSA): fraction V powder; A-8551, Sigma Chemical Co., USA.

Procedure

The cell line used in the following procedure is derived from a NIH 3T3 engineered cell line: 3T3/EGFr/Her2/EGFr (EGFr with a Her2 kinase domain). (Hudziak et al. 1987 PNAS 84:7159–7163)

Cells are seeded at 8000 cells/well in DMEM, 10% CS, 2 mM Gln in a 96 well plate. Cells are incubated overnight at 37° C. in 5% CO2. After 24 hours, the cells are washed with PBS, and then are serum starved in serum free medium (0° C.S DMEM with 0.1% BSA) for 24 hours.

On day 3, ligand (EGF=2 nM, prepared in DMEM with 0.1% BSA) and test compounds are added to the cells simultaneously. The negative control wells receive serum free DMEM with 0.1% BSA only; the positive control cells receive the ligand (EGF) but no test compound. Test compounds are prepared in serum free DMEM with ligand in a 96 well plate, and serially diluted for 7 test concentrations.

After 18 hours of ligand activation, diluted BrdU labeling reagent (1:100 in DMEM, 0.1% BSA) is added and the cells are incubated with BrdU (final concentration=10 M) for 1.5 hours.

After incubation with labeling reagent, the medium is removed by decanting and tapping the inverted plate on a paper towel. FixDenat solution is added (50 μl/well) and the plates are incubated at room temperature for 45 minutes on a plate shaker.

The FixDenat solution is thoroughly removed by decanting and tapping the inverted plate on a paper towel. Milk is added (5% dehydrated milk in PBS, 200 μl/well) as a blocking solution and the plate is incubated for 30 minutes at room temperature on a plate shaker.

The blocking solution is removed by decanting and the wells are washed once with PBS. Anti-BrdU-POD solution (1:200 dilution in PBS, 1% BSA) is added (50 μl/well) and the plate is incubated for 90 minutes at room temperature on a plate shaker.

The antibody conjugate is thoroughly removed by decanting and rinsing the wells 5 times with PBS, and the plate is dried by inverting and tapping on a paper towel. TMB substrate solution is added (100 l/well) and incubated for 20 minutes at room temperature on a plate shaker until color development is sufficient for photometric detection.

The absorbance of the samples are measured at 410 nm (in "dual wavelength" mode with a filter reading at 490 nm, as a reference wavelength) on a Dynatech ELISA plate reader.

22. EGF and Her4 Induced DNA Synthesis

The following kinase assay provides a consistent method for measuring EGF-induced, Her4-driven DNA synthesis in 3T3/EGFr/Her4/EGFr cells that express chimeric EGFr receptors with a Her4 kinase domain.

Materials and Reagents

EGF: mouse EGF, 201; Toyobo,Co., Ltd. Japan, BrdU Labeling Reagent: 10 mM, in PBS (pH7.4), Cat. No. 1 647 229, Boehringer Mannheim, Germany, FixDenat: fixation solution (ready to use), Cat. No. 1 647 229, Boehringer Mannheim, Germany, Anti-BrdU-POD: mouse monoclonal antibody conjugated with peroxidase, Cat. No. 1 647 229, Boehringer Mannheim, Germany, TMB Substrate Solution: tetramethylbenzidine (TMB), ready to use, Cat. No. 1 647 229, Boehringer Mannheim, Germany, PBS Washing Solution: 1×PBS, pH 7.4, Albumin, Bovine (BSA): fraction V powder; A-8551, Sigma Chemical Co., USA.

Procedure

The cell line used in the following procedure is derived from a NIH 3T3 engineered cell line: 3T3/EGFr/Her4/EGFr (EGFr with a Her4 kinase domain). For a similar cell line see Zhang et al., 1996, JBC 271:3884–3890.

Cells are seeded at 8000 cells/well in DMEM, 10% CS, 2 mM Gln in a 96 well plate. Cells are incubated overnight at 37° C. in 5% CO2. After 24 hours, the cells are washed with PBS, and then are serum starved in serum free medium (0° C.S DMEM with 0.1% BSA) for 24 hours.

On day 3, ligand (EGF=2 nM, prepared in DMEM with 0.1% BSA) and test compounds are added to the cells simultaneously. The negative control wells receive serum free DMEM with 0.1% BSA only; the positive control cells receive the ligand (EGF) but no test compound. Test compounds are prepared in serum free DMEM with ligand in a 96 well plate, and serially diluted for 7 test concentrations.

After 18 hours of ligand activation, diluted BrdU labeling reagent (1:100 in DMEM, 0.1% BSA) is added and the cells are incubated with BrdU (final concentration=10 M) for 1.5 hours.

After incubation with labeling reagent, the medium is removed by decanting and tapping the inverted plate on a paper towel. FixDenat solution is added (50 l/well) and the plates are incubated at room temperature for 45 minutes on a plate shaker.

The FixDenat solution is thoroughly removed by decanting and tapping the inverted plate on a paper towel. Milk is added (5% dehydrated milk in PBS, 200 l/well) as a blocking solution and the plate is incubated for 30 minutes at room temperature on a plate shaker.

The blocking solution is removed by decanting and the wells are washed once with PBS. Anti-BrdU-POD solution (1:200 dilution in PBS, 1% BSA) is added (50 l/well) and the plate is incubated for 90 minutes at room temperature on a plate shaker.

The antibody conjugate is thoroughly removed by decanting and rinsing the wells 5 times with PBS, and the plate is dried by inverting and tapping on a paper towel.

TMB substrate solution is added (100 l/well) and incubated for 20 minutes at room temperature on a plate shaker until color development is sufficient for photometric detection.

The absorbance of the samples are measured at 410 nm (in "dual wavelength" mode with a filter reading at 490 nm, as a reference wavelength) on a Dynatech ELISA plate reader.

23. IGF-1 Induced DNA Synthesis

The following kinase assay provides a consistent method for measuring Insulin like Growth Factor (IGF-1)-induced DNA synthesis in 3T3/IGF1r cells that over-express IGF1 receptors.

Materials and Reagents

IGF1 Ligand: human, recombinant; G511, Promega Corp, USA, BrdU Labeling Reagent: 10 mM, in PBS (pH7.4), Cat. No. 1 647 229, Boehringer Mannheim, Germany, FixDenat: fixation solution (ready to use), Cat. No. 1 647 229, Boehringer Mannheim, Germany, Anti-BrdU-POD: mouse monoclonal antibody conjugated with peroxidase, Cat. No. 1 647 229, Boehringer Mannheim, Germany, TMB Substrate Solution: tetramethylbenzidine (TMB), ready to use, Cat. No. 1 647 229, Boehringer Mannheim, Germany, PBS Washing Solution: 1×PBS, pH 7.4, Albumin, Bovine (BSA): fraction V powder; A-8551, Sigma Chemical Co., USA.

Procedure

The cell line used in the following procedure is derived from a NIH 3T3 engineered cell line: 3T3/IGF1r. (See Ullrich et al., 1986, EMBO J 5:2503–2512)

Cells are seeded at 8000 cells/well in DMEM, 10% CS, 2 mM Gln in a 96 well plate. Cells are incubated overnight at 37° C. in 5% CO2. After 24 hours, the cells are washed with PBS, and then are serum starved in serum free medium (0° C.S DMEM with 0.1% BSA) for 24 hours.

On day 3, ligand (IGF1, prepared in 250 ng/1 (33 mM), final conc.=25 ng/ml(3.3 nM)) and test compounds are added to the cells simultaneously. The negative control wells receive serum free DMEM with 0.1% BSA only; the positive control cells receive the ligand (IGF1) but no test compound. Test compounds are prepared in serum free DMEM with ligand in a 96 well plate, and serially diluted for 7 test concentrations.

After 16 hours of ligand activation, diluted BrdU labeling reagent (1:100 in DMEM, 0.1% BSA) is added and the cells are incubated with BrdU (final concentration=10 M) for 1.5 hours.

After incubation with labeling reagent, the medium is removed by decanting and tapping the inverted plate on a paper towel. FixDenat solution is added (50 1/well) and the plates are incubated at room temperature for 45 minutes on a plate shaker.

The FixDenat solution is thoroughly removed by decanting and tapping the inverted plate on a paper towel. Milk is added (5% dehydrated milk in PBS, 200 1/well) as a blocking solution and the plate is incubated for 30 minutes at room temperature on a plate shaker.

The blocking solution is removed by decanting and the wells are washed once with PBS. Anti-BrdU-POD solution (1:100 dilution in PBS, 1% BSA) is added (100 1/well) and the plate is incubated for 90 minutes at room temperature on a plate shaker.

The antibody conjugate is thoroughly removed by decanting and rinsing the wells 5 times with PBS, and the plate is dried by inverting and tapping on a paper towel.

TMB substrate solution is added (100 1/well) and incubated for 20 minutes at room temperature on a plate shaker until color development is sufficient for photometric detection.

The absorbance of the samples are measured at 410 nm (in "dual wavelength" mode with a filter reading at 490 nm, as a reference wavelength) on a Dynatech ELISA plate reader.

24. Insulin Induced DNA Synthesis

The following kinase assay provides a consistent method for measuring Insulin-induced DNA synthesis in H25 cells that over-express Insulin receptors. (See Lammers et al., 1989, EMBO J 8:1369–1375.)

Materials and Reagents

Insulin is obtained as a crystalline, bovine, Zinc (Gibco BRL, USA, #13007).

BrdU Labeling Reagent: 10 mM, in PBS (pH7.4), (Boehringer Mannheim, Germany, #1 647 229), FixDenat: fixation solution (ready to use), (Boehringer Mannheim, Germany, #1 647 229), Anti-BrdU-POD: mouse monoclonal antibody conjugated with peroxidase, (Boehringer Mannheim, Germany, #1 647 229), TMB Substrate Solution: tetramethylbenzidine (TMB), ready to use, (Boehringer Mannheim, Germany, #1 647 229), PBS Washing Solution: 1×PBS, pH 7.4, Albumin, Bovine (BSA): fraction V powder (Sigma Chemical Co., USA, #A-8551).

Procedure

The cell line used in the following procedure is derived from a NIH 3T3 engineered cell line: H25. Cells are seeded at 8000 cells/well in DMEM, 10% CS, 2mM Gln in a 96 well plate. Cells are incubated overnight at 37° C. in 5% CO2. After 24 hours, the cells are washed with PBS, and then are serum starved in serum free medium (0° C.S DMEM with 0.1% BSA) for 24 hours.

On day 3, ligand (Insulin=10 nM, prepared in DMEM with 0.1% BSA) and test compounds are added to the cells simultaneously. The negative control wells receive serum free DMEM with 0.1% BSA only; the positive control cells receive the ligand (Insulin) but no test compound. Test compounds are prepared in serum free DMEM with ligand in a 96 well plate, and serially diluted for 7 test concentrations.

After 16 hours of ligand activation, diluted BrdU labeling reagent (1:100 in DMEM, 0.1% BSA) is added and the cells are incubated with BrdU (final concentration=10 M) for 1.5 hours.

After incubation with labeling reagent, the medium is removed by decanting and tapping the inverted plate on a paper towel. FixDenat solution is added (50 1/well) and the plates are incubated at room temperature for 45 minutes on a plate shaker.

The FixDenat solution is thoroughly removed by decanting and tapping the inverted plate on a paper towel. Milk is added (5% dehydrated milk in PBS, 200 1/well) as a blocking solution and the plate is incubated for 30 minutes at room temperature on a plate shaker.

The blocking solution is removed by decanting and the wells are washed once with PBS. Anti-BrdU-POD solution (1:100 dilution in PBS, 1% BSA) is added (100 1/well) and the plate is incubated for 90 minutes at room temperature on a plate shaker.

The antibody conjugate is thoroughly removed by decanting and rinsing the wells 5 times with PBS, and the plate is dried by inverting and tapping on a paper towel.

TMB substrate solution is added (100 1/well) and incubated for 20 minutes at room temperature on a plate shaker until color development is sufficient for photometric detection.

The absorbance of the samples are measured at 410 nm (in "dual wavelength" mode with a filter reading at 490 nm, as a reference wavelength) on a Dynatech ELISA plate reader.

25. HGF Induced DNA Synthesis

The following kinase assay provides a consistent method for measuring HGF-induced DNA synthesis in BxPC-3 cells which express endogenous Met receptors.

Materials and Reagents

HGF: recombinant human HGF, Cat. No. 249-HG, R&D Systems, Inc., USA. HGF is dissolved in PBS with 0.1% BSA at a stock concentration of 50 mg/ml, BrdU Labeling Reagent: 10 mM, in PBS (pH7.4), Cat. No. 1 647 229, Boehringer Mannheim,Germany, FixDenat: fixation solution (ready to use), Cat. No. 1 647 229, Boehringer Mannheim, Germany, Anti-BrdU-POD: mouse monoclonal antibody conjugated with peroxidase, Cat. No. 1 647 229, Boehringer Mannheim, Germany, TMB Substrate Solution: tetramethylbenzidine (TMB), ready to use, Cat. No. T-8540, Sigma Chemical Co., USA, PBS Washing Solution: 1×PBS, pH 7.4, Albumin, Bovine (BSA): fraction V powder A-8551 (Sigma Chemical Co., USA).

Procedure

The cell line used in the following procedure is a BxPC-3 cells (ATCC CRL-1687).

Cells are seeded at 9000 cells/well in RPMI 10% FBS in a 96 well plate. Cells are incubated overnight at 37° C. in 5% CO2. After 24 hours, the cells are washed with PBS, and then are serum starved in 100 l serum-free medium (RPMI with 0.1% BSA) for 24 hours.

On day 3, 25 l containing ligand (prepared at 1 g/ml in RPMI with 0.1% BSA; final HGF conc.=200 ng/ml) and test compounds are added to the cells. The negative control wells receive 25 l serum-free RPMI with 0.1% BSA only; the positive control cells receive the ligand (HGF) but no test compound. Test compounds are prepared at 5 times their final concentration in serum-free RPMI with ligand in a 96 well plate, and serially diluted for 7 test concentrations. Typically, the highest final concentration of test compound is 100 M, and 1:3 dilutions are used (i.e. final test compound concentration range=0.137–100 M).

After 18 hours of ligand activation, 12.5 l of diluted BrdU labeling reagent (1:100 in RPMI, 0.1% BSA) is added to each well and the cells are incubated with BrdU (final concentration=10 M) for 1 hour.

After incubation with labeling reagent, the medium is removed by decanting and tapping the inverted plate on a paper towel. FixDenat solution is added (50 l/well) and the plates are incubated at room temperature for 45 minutes on a plate shaker.

The FixDenat solution is thoroughly removed by decanting and tapping the inverted plate on a paper towel. Milk is added (5% dehydrated milk in PBS, 200 l/well) as a blocking solution and the plate is incubated for 30 minutes at room temperature on a plate shaker.

The blocking solution is removed by decanting and the wells are washed once with PBS. Anti-BrdU-POD solution (1:100 dilution in PBS, 1% BSA) is added (100 l/well) and the plate is incubated for 90 minutes at room temperature on a plate shaker.

The antibody conjugate is thoroughly removed by decanting and rinsing the wells 5 times with PBS, and the plate is dried by inverting and tapping on a paper towel.

TMB substrate solution is added (100 l/well) and incubated for 20 minutes at room temperature on a plate shaker until color development is sufficient for photometric detection.

The absorbance of the samples are measured at 410 nm (in "dual wavelength" mode with a filter reading at 490 nm, as a reference wavelength) on a Dynatech ELISA plate reader.

26. LPA Induced DNA Synthesis

The following kinase assay provides a consistent method for measuring LPA-induced DNA synthesis in NIH/3T3 c7 cells.

Materials and Reagents

LPA Ligand: L—Lysophosphatidic Acid, Oleoyl; L-7260, Sigma Corp, USA, BrdU Labeling Reagent: 10 mM, in PBS (pH7.4), Cat. No. 1 647 229, Boehringer Mannheim, Germany, FixDenat: fixation solution (ready to use), Cat. No. 1 647 229, Boehringer Mannheim, Germany, Anti-BrdU-POD: mouse monoclonal antibody conjugated with peroxidase, Cat. No. 1 647 229, Boehringer Mannheim, Germany, TMB Substrate Solution: tetramethylbenzidine (TMB), ready to use, Cat. No. 1 647 229, Boehringer Mannheim, Germany, PBS Washing Solution: 1×PBS, pH 7.4, Albumin, Bovine (BSA): fraction V powder; A-8551, Sigma Chemical Co., USA.

Procedure

The cell line used in the following procedure is derived from a NIH 3T3 parental cell line: NIH/3T3 c7 Z3 a clone of 3T3 cells (CRL 1658).

Cells are seeded at 8000 cells/well in DMEM, 10% CS, 2 mM Gln in a 96 well plate. Cells are incubated overnight at 37° C. in 5% CO2. After 24 hours, the cells are washed with PBS, and then are serum starved in serum free medium (0° C.S DMEM with 0.1% BSA) for 24 hours.

On day 3, ligand (LPA, prepared at 12.5 mg/ml in H20, final LPA conc.=250 ng/ml) and test compounds are added to the cells simultaneously. The negative control wells receive serum free DMEM with 0.1% BSA only; the positive control cells receive the ligand (LPA) but no test compound. Test compounds are prepared in serum free DMEM with ligand in a 96 well plate, and serially diluted for 7 test concentrations.

After 18 hours of ligand activation, diluted BrdU labeling reagent (1:100 in DMEM, 0.1% BSA) is added and the cells are incubated with BrdU (final concentration=10 M) for 1 hour.

After incubation with labeling reagent, the medium is removed by decanting and tapping the inverted plate on a paper towel. FixDenat solution is added (50 l/well) and the plates are incubated at room temperature for 45 minutes on a plate shaker.

The FixDenat solution is thoroughly removed by decanting and tapping the inverted plate on a paper towel. Milk is added (5% dehydrated milk in PBS, 200 l/well) as a blocking solution and the plate is incubated for 30 minutes at room temperature on a plate shaker.

The blocking solution is removed by decanting and the wells are washed once with PBS. Anti-BrdU-POD solution (1:100 dilution in PBS, 1% BSA) is added (100 l/well) and the plate is incubated for 90 minutes at room temperature on a plate shaker.

The antibody conjugate is thoroughly removed by decanting and rinsing the wells 5 times with PBS, and the plate is dried by inverting and tapping on a paper towel.

TMB substrate solution is added (100 l/well) and incubated for 20 minutes at room temperature on a plate shaker until color development is sufficient for photometric detection.

The absorbance of the samples are measured at 410 nm (in "dual wavelength" mode with a filter reading at 490 nm, as a reference wavelength) on a Dynatech ELISA plate reader.

27. Modulation of Tumor Cell Colony Formation

The following kinase assay provides a consistent method for measuring colony forming ability of tumor cells in soft agar upon activation or inhibition of a kinase.

Materials and Reagents

Soft agar: SeaPlaque Agrose, prepared at 1.2% in H20, Autoclaved, refrigerated. Medium I: 2×DMEM+20% Fetal Bovine Serum+4 mM Glu, Medium II: 1×DMEM+10% Fetal Bovine Serum+2 mM Glu.

Procedure

Procedure for base plates: Have all media warmed to 37C and dishes organized for plating. Melt agarose in a microwave (about 1 min on a high setting). Be certain to loosen the bottle cap. Let the agarose cool to about 37C.

Mix 1.2% agarose 1:1 with Medium 1 to give 0.6% agarose in 1× medium. Dispense 0.5 ml/per well into 12-well plate to form a uniform base layer. Refrigerate base layers for 10 min to solidify. Keep the remaining 0.6% agarose solution at 37C for making the top layer.

Procedure for Soft Agar Assay:

All tissue culture and plating is conducted aseptically in laminar flow hood. Sterile dilutions are prepared of each compound using Medium II. The initial concentration is 20-fold greater than the final assay concentration. Harvest the A431 cell by trypsin, and dilute an appropriate volume to give 6000 cells/ml in Medium II.

The Assay Mix is prepared by combining the following into sterile test tubes: 1) 0.48 ml cell suspension (6000 cells/ml); 2) 0.12 ml initial test compound dilutions in medium II; and 3) 0.60 ml 0.6% agarose, and a total of 1.2 ml cell compound mixture is used to add to two plates in duplicate. Approximately 0.5 ml of the Assay Mix is plated onto the 0.5 ml base layers. Dishes are refrigerated for 10 minutes to solidify the agarose. Approximately 0.5 ml of growth media that is added over the solidified agar layer. Dishes are incubated for 7 to 14 days in a 100% humidified, 5% CO2 incubator, and colonies that are 60 microns and larger are scored positive. The colony size is determined by visual judgment of colonies and visually counting colonies in each well, or by using colony counter.

28. Flk-1 Phosphorylation Activity

The following kinase assay sets forth a method for testing the efficacy of Flk-1 modulators in vitro using a human umbilical vein endothelial cell line (HUVEC) that expresses the Flk-1receptor.

Procedure

DAY 1

Wash flasks 2× with 7–10 ml PBS/75 cm2 surface area and aspirate after each wash. HUVEC cells are trypsinized with 2–3 ml/75 cm2 surface area 0.05% trypsin in cell dissociation medium (Ca++- and Mg++-free HBSS) for about 5 minutes at 37° C.

Approximately 10 ml per 75 cm2 surface area, of EBM medium (Clonetics, San Diego)+0.5% heat inactivated FBS (henceforth referred to as "assay medium") and resuspend cells. Next, transfer the cells to a sterile centrifuge tube. An appropriate volume is taken for continued passaging of the HUVEC cells, and are placed in another centrifuge tube. Equal amounts of assay medium are added to each tube and centrifuged at 250×g for 5–10 minutes at room temperature.

The supernatants are aspirated and cells are washed prior to the assay 2× with about 30–40 ml PBS, each time centrifuging and aspirating the supernatants. Plate the cells to be passaged in normal growth medium (EBM+2% FBS+1 g/ml hydrocortisone+50 g/ml gentamycin+50 ng/ml amphiteracin+24 g/ml protein from bovine brain extract+10 ng/ml EGF)

Resuspend cells in assay medium (10 ml/150 cm2 surface area of original flask from step A.1.); take 0.5 ml of the cells and add to a Coulter Counter cup with 10 ml counting medium. Count cells on the Coulter Counter and add assay medium to the cells to yield 5×104 cells/ml.

Pipet cells into a sterile pipetting reservoir. Using a multi-channel pipettor, add 100 l cells/well to sterile flat-bottom 96 well plates. If 1 have a steady stream of drugs to be tested, then I add all the cells available and whatever number of plates this results in is the number of plates I use for the assay. If there is a distinct number of drugs to be tested, you can estimate 4 drugs/2 plates (1 each for vascular endothelial growth factor (VEGF) and acidic fibroblast growth factor (aFGF)) for wells with ligand +12 drugs/plate for non-ligand control wells (1 column per drug),+2 columns for ligand dose curves. For example, if 8 drugs are to be tested, this would require 4 ligand plates +2/3 of a plate for controls (8 columns)+2 columns for ligand dose curves. This would necessitate almost 5 plates, or almost 2.5×106 cells (5×103 cells/100 l/well×96 well/plate×approximately 6 plates). Incubate plates overnight (20–24 h) at 37° C.

DAY 2

Make up working stocks of compounds. The compounds are in stocks of 20 mM (in DMSO), though some are at other concentrations. At 20 mM, the compounds are diluted 1:100 in assay medium to arrive at 200 M , which is a 4× concentration (i.e., it comprises ¼ of the total volume of the well and ultimately will be 50 M). Do not dilute any compound <1:50 as this may give a concentration of DMSO that may be detrimental to the HUVEC cells. Because of this, compounds that are relatively insoluble and are therefore in stocks of <20 mM will not be able to be used at as high a dose as the 20 mM compounds. Thus, a 2 mM stock can only be used at doses at 10 M or less (2 mM at 1:50=40 M which becomes 10 M upon completion of additional of material to the wells).

For each compound, 90 l/well are needed for 7 wells (3 each for VEGF and aFGF; 1 for non-ligand media control); thus make up at least 630 $\mu$l/compound. At 1:100 dilution (20 mM to 200 $\mu$M), this requires 8 $\mu$l/compound. Add 8 $\mu$l/compound to 792 $\mu$l assay medium in 2 ml screw-cap microcentrifuge tubes and vortex.

Since the compounds are in 1:100 DMSO:assay medium, a diluent of the same DMSO:assay medium ration needs to be make for the compound titrations. This is done so as to keep the DMSO concentration constant when diluting the compound. 60 $\mu$l/well will be needed, or approximately 6 ml/plate. In the example in A.9. where the set-up for an assay for 8 compounds is described, approximately 5 plates of DMSO:assay medium diluent is needed. At 6 ml/plate, this would require approximately 30 ml total. It is best to aim for a little more, e.g. 34 ml. At 1:100, 340 $\mu$l DMSO would be added to 33.66 ml assay medium to get 34 ml.

Titrate the compounds as follows:
a. Use new 96-well round-bottom plates to do the compound titrations.
b. Add 90 $\mu$l/well of the compound in the wells of the top row of a plate (row A). 4 compounds can be assayed/plate (3 column×1 ligand (VEGF or aFGF)×4 drugs= the 12 columns of the plate. Also add 90 $\mu$l/well to the top well of a designated column in the non-ligand media control plate(s).
c. Add 60 $\mu$l/well of the DMSO:assay medium diluent to the rest of the rows of the plates (rows B-H), but only where compound had been added to row A.
d. Make 3-fold dilutions by pipetting 30 $\mu$l of the 90 $\mu$l/well in row A into row B, making 90 l/well of compound that is 3-fold more dilute than the 60 $\mu$l/well remaining in row A. Pipet 30 $\mu$l of the 90 $\mu$l/well in row B into row C, making 90 $\mu$l/well of compound that is 3-fold more dilute than the 60 $\mu$l/well remaining in row B, and so on until row G. When the 30 $\mu$l of the 90 $\mu$l/well in row F have been mixed with the 60 $\mu$l/well in row G, take 30 $\mu$l/well out and discard; i.e. don't add to row H. Leave row H without any drug as the no-drug control. At the end of this pipetting cascade, you are left with 60 $\mu$l/well of 3-fold titrated compound. In the example in B.1. where 20 mM compounds are diluted 1:100 to 200 $\mu$M, giving 50 $\mu$M final concentration, the dilutions yield compound concentrations as follows: 50, 16.7, 5.5, 1.8, 0.6, 0.2, 0.07, and 0 $\mu$M e. Transfer 50 μl/well of the 60 μl/well to the assay plate and incubate for 2–3 h at 37° C.

Add ligand (VEGF and aFGF) and media control as follows:

a. For each compound tested, 1.5 ml of VEGF and aFGF will be needed. This is because a separate volume of each ligand is needed per compound so that during pipetting of ligand, the previous compounds don't get mixed with subsequent compounds. 24 wells/compound will each get VEGF and a FGF. 50 μl/well of ligand will be needed, so 1.2 ml of VEGF and aFGF will be needed per drug. Since there will be some loss of volume due to surface tension in the pipetting reservoirs, 1.6 ml will be needed of each ligand. Thus in the example from A.9. where 8 compounds are tested, then 12.8 ml of each ligand is needed in total (1.6 ml/compound×8 compounds). For insurance, make a little more (14 ml).

b. For VEGF, the stock is 5 μg/ml, and the final concentration in the assay is 20 ng/ml. Since the volume of VEGF is ¼ that of the total assay (as with the compounds), a 4× concentration is needed (80 ng/ml). 5 μg/ml down to 20 ng/ml requires a 1:62.5 dilution, thus in the example in 5.a., a 1:62.5 dilution would require bringing 224 l VEGF up to 14 ml assay medium.

c. For aFGF, the stock is 10 μg/ml (as with VEGF), and the final concentration in the assay is 0.5 ng/ml. Since the volume of aFGF is ¼ that of the total assay (as with the compounds and VEGF), a 4× concentration is needed (2 ng/ml). 10 μg/ml down to 0.5 ng/ml requires a 1:5000 dilution. In the example in 5.a., just add 3 μl to 15 ml.

d. In the wells that had compound added earlier, add 50 μl of VEGF (or aFGF) to columns 1–12, except the media control wells in plate 5, which get 50 μl/well of assay medium. In addition, do not put ligand in wells H7-12; add assay medium instead. These wells will be the no drug/no ligand (negative ligand control) wells, and wells H1–6 will have no drug, but will have ligand (positive ligand control). These wells will be necessary in order for the Superb program to calculate the results.

e. Incubate plates overnight (20–24 h) at 37° C.

DAY 3

Add BrdU, (20 μl/well, 10 μM final concentration) and incubate overnight (20–24 h) at 37° C. BrdU is made up in serum free F12K medium or F12K medium with 0.5% FBS.

DAY 4

Perform BrdU ELISA as follows (all procedures are at room temperature):

a. Flick off medium from the assay plates and pat dry on paper towels.

b. Add 70 μl/well FixDenat (from Boehringer Mannheim) for 30 min.

c. Flick and pat as in a. above.

d. Add 100 μl/well 5% milk in PBS for 30 min.

e. Flick and pat as in a. above.

f. Add 80 μl 1:1000 (diluted in PBS+0.1% BSA) anti-BrdU (PharMingen) for 1 hour.

Lot to lot variability may require slightly different dilutions as recommended by the manufacturer (PharMingen)

g. Wash plates 3× in PBS.

h. Add 80 μl/well goat-anti-mouse horse-radish peroxidase for 1 hour; diluted 1:1000 in PBS+0.1% BSA. Tap plates gently to disperse liquid evenly in well. As in step f., lot to lot variability may require slightly different dilutions as recommended by the manufacturer (Southern Biotechnology).

i. Wash 3× in PBS.

j. Add 100 μl/well ABTS substrate solution for 15–30 min. Before use, add 2 μl H2O2 for every 10 m ABTS to be used. Tap plates gently to disperse liquid evenly in well. Read on the Dynatech MR5000 plate reader using BioCalc software and at 410 nm wavelength with 490 nm wavelength as reference.

The above-described assays are exemplary and not intended to limit the scope of the invention in any manner. Other assays known to those skilled in the art may be employed to ascertain the ability of the compounds of this invention. Those of skill in the art would appreciate that modifications can be made to the assays to develop equivalent assays that obtain the same result.

Thus, it will be appreciated that the compounds, of the present invention modulate the activity of protein tyrosine enzymes which mediate cellular signal transduction, in particular, protein tyrosine phosphatase, and therefore the invention encompasses the use of these as therapeutic agents against disorders associated with protein tyrosine enzyme related cellular signal transduction.

Although certain embodiments and examples have been used to describe the present invention, it will be apparent to those skilled in the art that changes to the embodiments and examples shown may be made without departing from the scope and spirit of this invention.

What is claimed:

1. A compound having the formula:

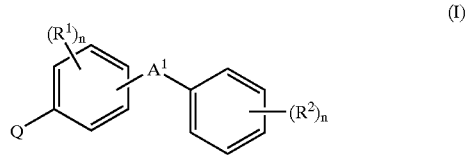

(I)

or a pharmaceutically acceptable salt or solvate thereof, wherein:

Q is $CF_3SO_2$, $CF_3SO_2NR^3$, $CF_3SO_2R^4$ or $CF_3SO_2N(R^3)$ $R^4$, wherein $R_3$ is H, alkoxy, acyl or $C_1$–$C_3$ alkyl, each of which may be substituted or unsubstituted, and $R^4$ is methylene which may be substituted or unsubstituted;

each $R^1$ is independently $C_1$–$C_3$ alkyl, $C_1$–$C_3$ haloalkyl, CN, (C=O)OR, (C=O)$R^5$, H, halo, O(C=O)R, OR, OH, NHR, NH(C=O)OR, NH(C=O)$R^5$, $NO_2$, $NHSO_2R^5$, $SO_2R^5$, $R^4SO_2CF_3$ or tetrazole, wherein $R^5$ is $CF_3$, $C_1$–$C_3$ alkyl, NHR and wherein R is H, $C_1$–$C_3$ alkyl, aryl or heteroaryl, which may be substituted or unsubstituted;

each $R^2$ is independently $C_1$–$C_3$ alkyl, $C_1$–$C_3$ haloalkyl, CN, (C=O)OR, (C=O)$R^5$, H, halo, O(C=O)R, OR, OH, NHR, NH(C=O)OR, NH(C=O)$R^5$, $NO_2$, $NHSO_2R^5$, $SO_2R^5$, tetrazole, or $X^1$—$R^6$—$X^2$, wherein $X^1$ is present or absent and if present is O, N, (C=O), (C=O)NH, NH(C=O), $SO_2NH$, $NHSO_2$, $R^6$ is $C_1$–$C_3$ alkylene which may be substituted or unsubstituted and $X^2$ is $CF_3$, (C=O)OR, (C=O)$R^5$, H, NH(C=O)$R^5$, NH(C=O)OR, $NHSO_2R^5$, $NRR^3$, O(C=O)R, OR, $SO_2R^5$, tetrazole; each n is independently from 0 to 3;

$A_1$ is a linkage in which the shortest path is 2–8 atoms in length wherein the atoms in the linkage are carbon which may be substituted or unsubstituted or the carbon replaced with a single nitrogen or oxygen, or combination of nitrogen, oxygen and sulfur provided no two heteroatoms are adjacently linked in a linear linkage;

the linkage may be an aryl, carbocyclic, or a phenyl ring, which may be directly in the linkage;

the linkage may contain, appended to the linkage, an aryl, carbocyclic, heteroaryl, heterocyclic or a phenyl ring;

the linkage may be acylalkyl, alkenylene, alkoxy, alkoxyalkyl, alkoxyamino, alkoxyarylalkoxy, alkoxyarylalkyl, alkoxyarylamino, alkoxyaryloxyalkyl, alkylamino, alkylaminoalkyl, alkylaminoarylaminoalkyl, alkylaryl, alkylarylalkyl, alkylarylamino, alkylaryloxy, alkylene, alkylenediamine, alkylenedioxy, alkyloxy, alkyloxyaryl, alkyloxyarylalkyloxy, alkyloxyaryloxyalkyl, $C_1$–$C_6$ alkylsulfonylamino, alkylthio, alkylthioalkyl, alkynylene, $C_1$–$C_6$ N-sulfonamido, $C_3$–$C_7$ N-amido, aminoalkyl, aminoalkylamino, aminoalkylarylalkyl, aminoalkylarylalkylamino, aminoalkylaryloxy, aminoalkyloxy, aminoaryl, aminoarylalkyl, aminoarylcarbonyl, aminoaryloxy, aminoaryloxyalkyl, aminoarylsulfonyl, aryl, arylamino, ortho or para aryldioxy, substituted meta-aryldioxy, aryldiamine, aryloxy, aryloxyalkyl, aryloxyamino, aryloxyaminoalkyl, aryloxycarbonyl, aryloxysulfonyl, $C_3$–$C_7$C-amido, carbonylarylamino, carbonylarylcarbonyl, carbonylaryloxy, cycloalkylene, haloalkyl, $C_2$–$C_6$ S-sulfonamido, sulfonylalkyl, sulfonylarylamino, sulfonylaryloxy, sulfonylarylsulfonyl and $C_3$–$C_6$ ureido, which may be substituted or unsubstituted.

2. The compound of claim 1, wherein Q is $CF_3SO_2$.
3. The compound of claim 1, wherein Q is $CF_3SO_2NR^3$.
4. The compound of claim 1, wherein Q is $CF_3SO_2R$.
5. The compound of claim 1, wherein Q is $CF_3SO_2N(R^3)R^4$.
6. The compound of claim 1, wherein $R^2$ is $SO_2R^5$, $NHSO_2R^5$ or $CF_3SO_2R^4$.
7. A compound having the formula:

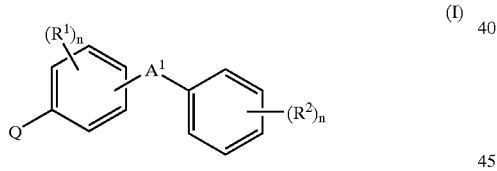

(I)

or a pharmaceutically acceptable salt or solvate thereof, wherein:

Q is $CF_3SO_2$;

each $R^1$ is independently $CF_3$, (C=O)OR, (C=O)$R^5$, H, halo, NHR, NH(C=O)OR, NH(C=O)$R^5$, NHSO$_2R^5$, NO$_2$, O(C=O)R, OH, OR, SO$_2R^5$ or tetrazole, wherein $R^5$ is $CF_3$, $C_1$–$C_3$ alkyl, NHR and wherein R is H, $C_1$–$C_3$ alkyl, aryl or heteroaryl, which may be substituted or unsubstituted;

each $R^2$ is independently (C=O)OR, (C=O)$R^5$, NH(C=O)OR, NH(C=O)$R^5$, NHR, NHSO$_2R^5$, NO$_2$, —$R^6$—(C=O)OR, —$R^6$—NRR$^3$, —$R^6$-tetrazole, or tetrazole and $R^6$ is $C_1$–$C_3$ alkylene which may be substituted or unsubstituted;

each n is independently from 0 to 2; and linkage $A^1$ is $C_2$–$C_4$ alkoxy, $C_2$–$C_4$ alkoxyalkyl, $C_2$–$C_4$ alkylenedioxy, $C_2$–$C_4$ alkylaminoalkyl, $C_2$–$C_4$ alkylenediamine, $C_3$–$C_4$C-amido, $C_3$–$C_4$ N-amido, $C_3$–$C_4$ ureido, $C_1$–$C_3$ N-sulfoamino $C_2$–$C_3$ S-sulfonamido, aryldioxy, aryldiamine, aryl, or alkylarylalkyl.

8. A compound having the formula:

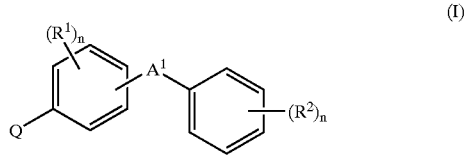

(I)

or a pharmaceutically acceptable salt or solvate thereof, wherein:

Q is $CF_3SO_2NR^3$, $CF_3SO_2R^4$ or $CF_3SO_2N(R^3)R^4$, wherein $R^3$ is H, alkoxy, acyl or $C_1$–$C_3$ alkyl each of which may be substituted or unsubstituted and $R^4$ is methylene which may be substituted or unsubstituted;

each $R^1$ is independently $CF_3$, (C=O)OR, (C=O)$R^5$, H, halo, NHR, NH(C=O)OR, NH(C=O)$R^5$, NHSO$_2R^5$, NO$_2$, O(C=O)R, OH, OR, SO$_2R^5$ or tetrazole, wherein $R^5$ is $CF_3$, $C_1$–$C_3$ alkyl, NHR and wherein R is H, $C_1$–$C_3$ alkyl, aryl or heteroaryl, which may be substituted or unsubstituted;

each $R^2$ is independently (C=O)OR, (C=O)$R^5$, NH(C=O)OR, NH(C=O)$R^5$, NHR, NHSO$_2R^5$, NO$_2$, SO$_2R^5$, —$R^6$—(C=O)OR, —$R^6$—NRR$^3$, —$R^6$-tetrazole, or tetrazole and $R^6$ is $C_1$–$C_3$ alkylene which may be substituted or unsubstituted;

each n is independently from 0 to 2; and linkage $A^1$ is $C_2$–$C_4$ alkoxy, $C_2$–$C_4$ alkoxyalkyl, $C_2$–$C_4$ alkylenedioxy, $C_2$–$C_4$ alkylaminoalkyl, $C_2$–$C_4$ alkylenediamine, $C_3$–$C_4$C-amido, $C_3$–$C_4$ N-amido, $C_3$–$C_4$ ureido, $C_1$–$C_3$ N-sulfonamino $C_2$–$C_3$ S-sulfonamido, aryldioxy, aryldiamine, aryl, and alkylarylalkyl.

9. A compound having the formula:

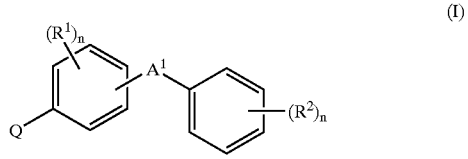

(I)

or a pharmaceutically acceptable salt or solvate thereof, wherein:

Q is $CF_3SO_2$;

each $R^1$ is independently H, NHR, NO$_2$ or OR;

each $R^2$ is independently (C=O)OR, NHSO$_2R^5$, or SO$_2R^5$;

each n is independently from 0 to 2; and the linkage $A^1$ is alkylarylalkyl, $C_2$–$C_4$ alkoxyalkyl, $C_2$–$C_4$ alkylenedioxy, aryl, aryldiamine, or aryldioxy, which may be substituted or unsubstituted or $A^1$ is unsubstituted or monosubstituted $C_2$–$C_4$ N-amido.

10. The compound of claim 8 having the formula:

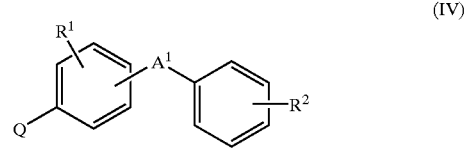

(IV)

or a pharmaceutically acceptable salt or solvate thereof, wherein:

$R^1$ is H or $NO^2$;

$R^2$ is (C=O)OR, $NHSO_2R^5$ or $SO_2R^5$; and the linkage $A^1$ is $C_2$–$C_4$ alkoxyalkyl, aryldioxy, aryl, or alkylarylalkyl.

11. A compound selected from the group consisting of:

Bis(4-Trifluoromethylsulfonylbenzyl) ether;
4-Trifluoromethylsulfonylbenzyl 4-trifluoromethylsulfonylphenyl ether;
N,N-Bis(4-triluoromethylsulfonylbenzyl)benzamide;
1,2-Bis(4-trifluoromethylsullfonylphenyl)ethane;
N-(4-Trifluoromethylsulfonylbenzyl)-4-trifluoromethylsulfonylbenzamide;
N-(4-Trifluoromethylsulfonylbenzyl)benzamide;
3,5-Bis-(4-trifluoromethanesulfonyl-phenoxy)-benzoic acid methyl ester;
[3,5-Bis-(2-nitro-4-trifluoromethanesulfonyl-phenoxy)-phenyl]-acetic acid methyl ester;
3,5-Bis-(2-nitro-4-trifluoromethanesulfonyl-phenoxy)-benzoic acid methyl ester;
1,3-Bis-(2-nitro-4-trifluoromethanesulfonyl-phenoxy)-cyclopentane;
4-Methyl-2,6-bis-(2-nitro-4-trifluoromethanesulfonyl-phenoxy)-benzoic acid methyl ester;
4-[2-(2-Nitro-4-trifluoromethanesulfonyl-phenoxy)-ethoxy]-benzoic acid methyl ester;
4-[3-(2-Nitro-4-trifluoromethanesulfonyl-phenoxy)-phenoxy]-benzoic acid;
{4-[4-(2-Nitro-4-trifluoromethanesulfonyl-phenoxy)-benzenesulfonyl]-phenoxy}-acetic acid ethyl ester;
4-[3-(4-Trifluoromethanesulfonyl-phenoxy)-phenoxy]-benzoic acid;
{4-[4-(4-Trifluoromethanesulfonyl-phenoxy)-benzenesulfonyl]-phenoxy}-acetic acid ethyl ester;
N-(3-Trifluoromethanesulfonyl-phenyl)-2-{2-[(3-trifluoromethanesulfonyl-phenylcarbamoyl)-methyl]-phenyl}-acetamide;
N-(3-Trifluoromethanesulfonyl-phenyl)-2-{3-[(3-trifluoromethanesulfonyl-phenylcarbamoyl)-methyl]-phenyl}-acetamide;
N-(3-Trifluoromethanesulfonyl-phenyl)-2-{4-[(3-trifluoromethanesulfonyl-phenylcarbamoyl)-methyl]-phenyl}-acetamide;
3,6-Bis-(morpholin-4-ylmethyl)-2,5-bis-(2-nitro-4-trifluoromethanesulfonyl-phenoxy)-benzene;
[2,3-Bis-(2-nitro-4-trifluoromethanesulfonyl-phenoxy)-propyl]-dimethyl-amine;
N-(2-Ethylamino-5-trifluoromethanesulfonyl-phenyl)-2-(4-methanesulfonyl-phenyl)-acetamide;
2-Hydroxy-5-(2-nitro-4-trifluoromethanesulfonyl-phenoxy)-terephthalic acid diethyl ester;
{2-[(3-Trifluoromethanesulfonyl-phenylcarbamoyl)-methyl]-phenyl}-acetic acid;
{3-[(3-Trifluoromethanesulfonyl-phenylcarbamoyl)-methyl]-phenyl}-acetic acid;
{4-[(3-Trifluoromethanesulfonyl-phenylcarbamoyl)-methyl]-phenyl}-acetic acid;
3,5-Bis-(2-nitro-4-trifluoromethanesulfonyl-phenoxy)-benzamide;
3,5-Bis-(4-trifluoromethanesulfonyl-phenoxy)-benzoic acid;
N-(4-Trifluoromethanesulfonyl-phenyl)-2-{2-[(4-trifluoromethanesulfonyl-phenylcarbamoyl)-methyl]-phenyl}-acetamide;
N-(4-Trifluoromethanesulfonyl-phenyl)-2-{3-[(4-trifluoromethanesulfonyl-phenylcarbamoyl)-methyl]-phenyl}-acetamide;
N-(4-Trifluoromethanesulfonyl-phenyl)-2-{4-[(4-trifluoromethanesulfonyl-phenylcarbamoyl)-methyl]-phenyl}-acetamide;
[2-(Benzoyl-butyl-amino)-2-(4-trifluoromethanesulfonyl-phenyl)-acetylamino]-acetic acid methyl ester;
N-Benzyl-N-[butylcarbamoyl-(4-trifluoromethanesulfonyl-phenyl)-methyl]-benzamide;
N-[Butylcarbamoyl-(4-trifluoromethanesulfonyl-phenyl)-methyl]-N-(2-hydroxy-ethyl)-benzamide;
[2-(Benzoyl-cyclohexyl-amino)-2-(4-trifluoromethanesulfonyl-phenyl)-acetylamino]-acetic acid ethyl ester;
N-Cyclohexyl-N-[(2,6-dimethyl-phenylcarbamoyl)-(4-trifluoromethanesulfonyl-phenyl)-methyl]-benzamide;
4-[2-(2-Nitro-4-trifluoromethanesulfonyl-phenoxy)-ethoxy]-benzoic acid;
2,5-Bis-(2-nitro-4-trifluoromethanesulfonyl-phenoxy)-terephthalic acid diethyl ester;
[2,3-Bis-(2-nitro-4-trifluoromethanesulfonyl-phenoxy)-propyl]-(2-nitro-phenyl)-amine;
1-(2-Nitro-phenylamino)-3-(2-nitro-4-trifluoromethanesulfonyl-phenoxy)-propan-2-ol;
[2,3-Bis-(2-nitro-4-trifluoromethanesulfonyl-phenoxy)-propyl]-(4-nitro-phenyl)-amine;
1-(4-Nitro-phenylamino)-3-(2-nitro-4-trifluoromethanesulfony-phenoxy)-propan-2-ol;
4-[2-Hydroxy-3-(2-nitro-4-trifluoromethanesulfonyl-phenoxy)-propylamino]-benzenesulfonamide;
4-[2,3-Bis-(2-nitro-4-trifluoromethanesulfonyl-phenoxy)-propylamino]-benzenesulfonamide;
1-[2,3-Bis-(2-nitro-4-trifluoromethanesulfonyl-phenoxy)-propyl]-piperidine; and
4-[2,3-Bis-(2-nitro-4-trifluoromethanesulfonyl-phenoxy)-propyl]-morpholine.

12. A compound selected from the group consisting of:

1,2-Bis(4-trifluoromethylsulfonamidophenyl)ethane;
1,2-Bis(2-methyl-4-trifluoromethylsulfonamidophenyl) ethane;
1,3-Bis(4-trifluoromethylsulfonamidophenoxy)-2,2-dimethylpropane;
1,3-Bis(4-trifluoromethylsulfonamidophenoxy)propane;
1,4-Bis(4-trifluoromethylsulfonamidophenoxy)butane;
1,4-Bis(4-trifluoromethylsulfonamidophenoxy)benzene;
1-(4-Aminophenoxy)-4-trifluoromethylsulfonamidophenoxy benzene;
1,3-Bis(4-trifluoromethylsulfonamidophenoxy)benzene; and
Bis(4-trifluoromethylsulfonamidophenyl)-1,4-diisopropylbenzene.

13. A pharmaceutical composition comprising a compound having the formula:

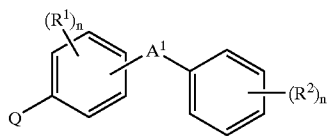

(I)

or a pharmaceutically acceptable salt or solvate thereof, wherein:

Q is $CF_3SO_2$, $CF_3SO_2NR^3$, $CF_3SO_2R^4$ or $CF_3SO_2N(R^3)R^4$, wherein $R^3$ is H, alkoxy, acyl or $C_1$–$C_3$ alkyl, each of which may be substituted or unsubstituted, and $R^4$ is methylene which may be substituted or unsubstituted;

each $R^1$ is independently $C_1$–$C_3$ alkyl, $C_1$–$C_3$ haloalkyl, CN, (C=O)OR, (C=O)$R^5$, H, halo, NHR, NH(C=O)OR, NH(C=O)$R^5$, $NO_2$, $NHSO_2R^5$, O(C=O)R, OR, OH, $SO_2R^5$, $R^4SO_2CF_3$ or tetrazole, wherein $R^5$ is $CF_3$, $C_1$–$C_3$ alkyl, NHR and wherein R is H, $C_1$–$C_3$ alkyl, aryl or heteroaryl, which may be substituted or unsubstituted;

each $R^2$ is independently $C_1$–$C_3$ alkyl, $C_1$–$C_3$ haloalkyl, CN, (C=O)OR, (C=O)$R^5$, H, halo, O(C=O)R, OR, OH, NHR, NH(C=O)OR, NH(C=O)$R^5$, $NO_2$, $NHSO_2R^5$, $SO_2R^5$, tetrazole, or $X^1$—$R^6$—$X^2$ wherein $X^1$ may be present or absent and if present is O, N, (C=O), (C=O)NH, NH(C=O), $SO_2NH$, $NHSO_2$;

$R^6$ is $C_1$–$C_3$ alkylene which may be substituted or unsubstituted;

$X^2$ is $CF_3$, (C=O)OR, (C=O)$R^5$, H, NH(C=O)$R^5$, NH(C=O)OR, $NHSO_2R^5$, $NRR^3$, O(C=O)R, OR, $SO_2R^5$, tetrazole;

easch n is independently from 0 to 3;

$A^1$ is a linkage in which the shortest path is 2–8 atoms in length wherein the atoms in the linkage are carbon which may be substituted or unsubstituted or the carbon replaced with a single nitrogen or oxygen, or combination of nitrogen, oxygen and sulfur provided no two heteroatoms are adjacently linked in a linear linkage;

the linkage may be an aryl, carbocyclic, or a phenyl ring, which may be directly in the linkage;

the linkage may contain, appended to the linkage, an aryl, carbocyclic, heteroaryl, heterocyclic or a phenyl ring;

the linkage may be acylalkyl, alkenylene, alkoxy, alkoxyalkyl, alkoxyamino, alkoxyarylalkoxy, alkoxyarylalkyl, alkoxyarylamino, alkoxyaryloxyalkyl, alkylamino, alkylaminoalkyl, alkylaminoarylaminoalkyl, alkylaryl, alkylarylalkyl, alkylarylamino, alkylaryloxy, alkylene, alkylenediamine, alkylenedioxy, alkyloxy, alkyloxyaryl, alkyloxyarylalkyloxy, alkyloxyaryloxyalkyl, $C_1$–$C_6$ alkylsulfonylamino, alkylthio, alkylthioalkyl, alkynylene, $C_1$–$C_6$ N-sulfonamido, $C_3$–$C_7$ N-amido, aminoalkyl, aminoalkylamino, aminoalkylarylalkyl, aminoalkylarylalkylamino, aminoalkylaryloxy, aminoalkyloxy, aminoaryl, aminoarylalkyl, aminoarylcarbonyl, aminoaryloxy, aminoaryloxyalkyl, aminoarylsulfonyl, aryl, arylamino, aryldioxy, aryldiamine, aryloxy, aryloxyalkyl, aryloxyamino, aryloxyaminoalkyl, aryloxycarbonyl, aryloxysulfonyl, $C_3$–$C_7$C-amido, carbonylarylamino, carbonylarylcarbonyl, carbonylaryloxy, cycloalkylene, haloalkyl, $C_2$–$C_6$ S-sulfonamido, sulfonylalkyl, sulfonylarylamino, sulfonylaryloxy, sulfonylarylsulfonyl, $C_3$–$C_6$ ureido, which may be substituted or unsubstituted.

14. The pharmaceutical composition of claim 13, wherein:

Q is $CF_3SO_2$ or $CF_3SO_2NH$;

each $R^1$ is independently $CF_3$, (C=O)OR, (C=O)$R^5$, H, halo, NHR, NH(C=O)OR, NH(C=O)$R^5$, $NHSO_2R^5$, $NO_2$, O(C=O)R, OH, OR, $SO_2R^5$ or tetrazole;

each $R^2$ is independently (C=O)OR, (C=O)$R^5$, NH(C=O)OR, NH(C=O)$R^5$, NHR, $NHSO_2R^5$, $NO_2$, $SO_2R^5$, —$R^6$—(C=O)OR, —$R^6$—$NRR_3$, —$R^6$-tetrazole or tetrazole;

each n is independently from 0 to 2; and linkage $A^1$ is $C_2$–$C_4$ alkoxy, $C_2$–$C_4$ alkoxyalkyl, $C_2$–$C_4$ alkylenedioxy, $C_2$–$C_4$ alkylaminoalkyl, $C_2$–$C_4$ alkylenediamine, $C_3$–$C_4$C-amido, $C_3$–$C_4$ N-amido, $C_3$–$C_4$ ureido, $C_1$–$C_3$ N-sulfoamido, $C_2$–$C_3$ S-sulfonamido, aryldioxy, aryldiamine, aryl, and alkylarylalkyl.

15. The pharmaceutical composition of claim 14, wherein the compound has the formula:

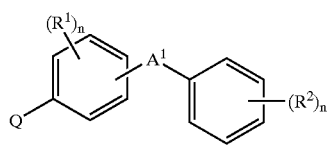

(I)

or a pharmaceutically acceptable salt or solvate thereof, wherein:

Q is $CF_3SO_2$ or $CF_3SO_2NH$;

each $R^1$ is independently H, NHR, $NO^2$ or OR;

each $R^2$ is independently (C=O)OR, or $NHSO_2R^5$ or $SO_2R^5$;

each n is independently from 0 to 2; and the linkage $A^1$ is alkylarylalkyl, $C_2$–$C_4$ alkoxyalkyl, $C_2$–$C_4$ alkylenedioxy, aryl, or aryldiamine.

16. A pharmaceutical composition comprising a compound having the formula:

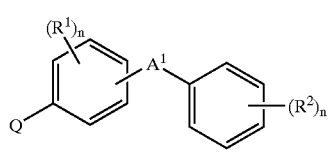

(I)

or a pharmaceutically acceptable salt or solvate thereof, wherein:

Q is $CF_3SO_2$, $CF_3SO_2NR^3$, $CF_3SO_2R^4$ or $CF_3SO_2N(R^3)R^4$, wherein $R^3$ is H, alkoxy, acyl or $C_1$–$C_3$ alkyl, each of which may be substituted or unsubstituted, and $R^4$ is methylene which may be substituted or unsubstituted;

each $R^1$ is independently $C_1$–$C_3$ alkyl, $C_1$–$C_3$ haloalkyl, CN, (C=O)OR, (C=O)$R^5$, H, halo, NHR, NH(C=O)OR, NH(C=O)$R^5$, $NO_2$, $NHSO_2R^5$, O(C=O)R, OR, OH, $SO_2R^5$, $R^4SO_2CF_3$ or tetrazole, wherein $R^5$ is $CF_3$, $C_1$–$C_3$ alkyl, NHR and wherein R is H, $C_1$–$C_3$ alkyl, aryl or heteroaryl, which may be substituted or unsubstituted;

each $R^2$ is independently $C_1$–$C_3$ alkyl, $C_1$–$C_3$ haloalkyl, CN, (C=O)OR, (C=O)$R^5$, H, halo, O(C=O)R, OR, OH, NHR, NH(C=O)OR, NH(C=O)$R^5$, $NO_2$, $NHSO_2R^5$, $SO_2R^5$, tetrazole, or $X^1$—$R^6$—$X^2$ wherein $X^1$ may be present or absent and if present is O, N, (C=O), (C=O)NH, NH(C=O), $SO_2$NH, $NHSO_2$;

$R^6$ is $C_1$-$C_3$ alkylene which may be substituted or unsubstituted;

$X^2$ is $CF_3$, (C=O)OR, (C=O)$R^5$, H, NH(C=O)$R^5$, NH(C=O)OR, $NHSO_2R^5$, $NRR^3$, O(C=O)R, OR, $SO_2R^5$, tetrazole;

easch n is independently from 0 to 3;

$A^1$ is a linkage in which the shortest path is 2–8 atoms in length wherein the atoms in the linkage are carbon which may be substituted or unsubstituted or the carbon replaced with a single nitrogen or oxygen, or combination of nitrogen, oxygen and sulfur provided no two nitrogen or oxygen atoms are adjacently linked in a linear linkage;

the linkage may be an aryl, carbocyclic, or a phenyl ring, which may be directly in the linkage;

the linkage may contain, appended to the linkage, an aryl, carbocyclic, heteroaryl, heterocyclic or a phenyl ring;

the linkage may be acylalkyl, alkenylene, alkoxy, alkoxyalkyl, alkoxyamino, alkoxyarylalkoxy, alkoxyarylalkyl, alkoxyarylamino, alkoxyaryloxyalkyl, alkylamino, alkylaminoalkyl, alkylaminoarylaminoalkyl, alkylaryl, alkylarylalkyl, alkylarylamino, alkylaryloxy, alkylene, alkylenediamine, alkylenedioxy, alkyloxy, alkyloxyaryl, alkyloxyarylalkyloxy, alkyloxyaryloxyalkyl, $C_1$–$C_6$ alkylsulfonylamino, alkylthio, alkylthioalkyl, alkynylene, $C_1$–$C_6$ N-sulfonamido, $C_3$–$C_7$ N-amido, aminoalkyl, aminoalkylamino, aminoalkylarylalkyl, aminoalkylarylalkylamino, aminoalkylaryloxy, aminoalkyloxy, aminoaryl, aminoaryialkyl, aminoarylcarbonyl, aminoaryloxy, aminoaryloxyalkyl, aminoarylsulfonyl, aryl, arylamino, aryldioxy, aryldiamine, aryloxy, aryloxyalkyl, aryloxyamino, aryloxyaminoalkyl, aryloxycarbonyl, aryloxysulfonyl, $C_3$–$C_7$ C-amido, carbonylarylamino, carbonylarylcarbonyl, carbonylaryloxy, cycloalkylene, haloalkyl, $C_2$–$C_6$ S-sulfonamido, sulfonylalkyl, sulfonylarylamino, sulfonylaryloxy, sulfonylarylsulfonyl, $C_3$–$C_6$ ureido, which may be substituted or unsubstituted.

17. The pharmaceutical composition according to claim 16, wherein the compound is bis(4-trifluoromethylsufonylphenyl)disulfide or bis(2-nitro-4-trifluoromethylsufonylphenyl)disulfide.

18. A pharmaceutical composition comprising the compound of claims 1–12 or a pharmaceutically acceptable salt or solvate thereof.

19. A method for treating type II diabetes in a mammal comprising administering to the mammal a therapeutically effective amount of the compound of claims 1–12.

20. A method for treating type II diabetes in a mammal which comprises administering to the mammal the pharmaceutical composition of claims 13–17.

* * * * *